United States Patent
Ryu et al.

(10) Patent No.: US 12,006,312 B2
(45) Date of Patent: Jun. 11, 2024

(54) BENZAZOLE DERIVATIVE HAVING HETEROARYL GROUP AND ORGANIC ELECTROLUMINESCENCE DEVICE INCLUDING THE SAME

(71) Applicant: LG Display Co., Ltd., Seoul (KR)

(72) Inventors: Daewon Ryu, Goyang-si (KR); Dohan Kim, Goyang-si (KR); Hyeseung Kang, Seoul (KR); Sang Bae Han, Yongin-si (KR); Seong-Shik Moon, Changwon-si (KR); Kyousic Kim, Seongnam-si (KR)

(73) Assignee: LG DISPLAY CO., LTD., Seoul (KR)

( * ) Notice: Subject to any disclaimer, the term of this patent is extended or adjusted under 35 U.S.C. 154(b) by 956 days.

(21) Appl. No.: 16/502,478

(22) Filed: Jul. 3, 2019

(65) Prior Publication Data

US 2020/0010460 A1    Jan. 9, 2020

(30) Foreign Application Priority Data

Jul. 5, 2018   (KR) .................. 10-2018-0078289

(51) Int. Cl.
*H10K 50/11*    (2023.01)
*C07D 413/04*    (2006.01)
(Continued)

(52) U.S. Cl.
CPC ......... *C07D 413/10* (2013.01); *C07D 413/04* (2013.01); *C07D 413/14* (2013.01);
(Continued)

(58) Field of Classification Search
CPC .. C07D 417/10; C07D 417/04; C07D 413/10; C07D 413/14; C07D 413/04; C07D 417/14; H01L 51/0069; H10K 85/656
See application file for complete search history.

(56) References Cited

U.S. PATENT DOCUMENTS 8,138,347 B2   3/2012   Knight et al.
8,404,837 B2   3/2013   Adams et al.
(Continued)

FOREIGN PATENT DOCUMENTS

JP   H08-036236 A    2/1996
JP   2000-299186 A   10/2000
(Continued)

OTHER PUBLICATIONS

Korean Office Action dated Feb. 2, 2023 issued in Patent Application No. 10-2018-0078289 w/English Translation (19 pages).

*Primary Examiner* — Sean M DeGuire
(74) *Attorney, Agent, or Firm* — POLSINELLI PC

(57) ABSTRACT

Disclosed is a benzazole derivative having a heteroaryl group, wherein the benzazole derivative having the heteroaryl group is represented by Chemical Formula 1. Also disclosed is an organic electroluminescence device including an organic layer containing the benzazole derivative having the heteroaryl group:

<Chemical Formula 1>

(Continued)

wherein, each of Z1, X1, X2, X3, Ar1, Ar2, Ar3, m1, m2 and q is the same as defined in the specification.

1 Claim, 4 Drawing Sheets

(51) Int. Cl.

| | |
|---|---|
| *C07D 413/10* | (2006.01) |
| *C07D 413/14* | (2006.01) |
| *C07D 417/04* | (2006.01) |
| *C07D 417/10* | (2006.01) |
| *C07D 417/14* | (2006.01) |
| *C09K 11/06* | (2006.01) |
| *H10K 50/15* | (2023.01) |
| *H10K 50/16* | (2023.01) |
| *H10K 50/17* | (2023.01) |
| *H10K 85/60* | (2023.01) |
| *H10K 101/10* | (2023.01) |

(52) U.S. Cl.
CPC ......... *C07D 417/04* (2013.01); *C07D 417/10* (2013.01); *C07D 417/14* (2013.01); *C09K 11/06* (2013.01); *H10K 50/11* (2023.02); *H10K 50/15* (2023.02); *H10K 50/16* (2023.02); *H10K 50/171* (2023.02); *H10K 85/654* (2023.02); *H10K 85/656* (2023.02); *H10K 85/6572* (2023.02); *C09K 2211/1033* (2013.01); *C09K 2211/1048* (2013.01); *C09K 2211/1051* (2013.01); *C09K 2211/1062* (2013.01); *C09K 2211/1066* (2013.01); *C09K 2211/1074* (2013.01); *C09K 2211/1077* (2013.01); *C09K 2211/1081* (2013.01); *H10K 2101/10* (2023.02)

(56) References Cited

U.S. PATENT DOCUMENTS

| | | |
|---|---|---|
| 8,633,187 B2 | 1/2014 | Knight et al. |
| 8,785,433 B2 | 7/2014 | Knight et al. |
| 10,431,766 B2 | 10/2019 | Ito et al. |
| 11,316,124 B2 | 4/2022 | Ito et al. |
| 2009/0270410 A1 | 10/2009 | Herz et al. |
| 2012/0165321 A1 | 6/2012 | Adams et al. |
| 2014/0100234 A1 | 4/2014 | Knight et al. |
| 2020/0251659 A1 | 8/2020 | Lee et al. |
| 2021/0070717 A1* | 3/2021 | Li .................. C07D 413/00 |
| 2022/0209136 A1 | 6/2022 | Kawakami et al. |

FOREIGN PATENT DOCUMENTS

| | | |
|---|---|---|
| JP | 2001-261664 A | 9/2001 |
| KR | 2010-0017852 A | 2/2010 |
| KR | 10-2014-0094408 A | 7/2014 |
| KR | 10-2015-0126756 A | 11/2015 |
| KR | 10-1847347 B1 | 4/2018 |
| WO | 2016022312 A1 | 2/2016 |

* cited by examiner

BENZAZOLE DERIVATIVE HAVING HETEROARYL GROUP AND ORGANIC ELECTROLUMINESCENCE DEVICE INCLUDING THE SAME

CROSS REFERENCE TO RELATED APPLICATION

This application claims priority from Korean Patent Application No. 10-2018-0078289 filed on Jul. 5, 2018, in the Korean Intellectual Property Office, the disclosure of which is incorporated herein by reference in its entirety.

BACKGROUND

Field of the Disclosure

The present disclosure relates to a benzazole derivative having a heteroaryl group and an organic electroluminescence device containing the same.

Description of the Background

An organic electroluminescence device is a self-light-emission device that converts electrical energy into light energy using an organic material. Generally, in the organic electroluminescence device, an organic material layer is disposed between an anode and a cathode.

When a voltage is applied between the anode and the cathode, holes are injected from the anode into the organic material layer, and electrons are injected into the organic material layer from the cathode. When the injected holes and electrons encounter each other, excitons are formed. Light emission may occur when the exciton falls to a ground state.

In order to increase efficiency and stability of the organic electroluminescence device, the organic material layer may have a multi-layered structure composed of different materials. For example, the organic material layer may include a hole injection layer, a hole transport layer, a light-emission layer, an electron transport layer, and an electron injection layer.

In order for the organic electroluminescence device to exhibit excellent characteristics, an organic material having an organic material layer, for example, a hole injection material, a hole transport material, a light-emission material, an electron transport material, and an electron injection material should be stable and efficient. However, development of stable and efficient organic materials for the organic electroluminescence device has not been sufficient yet. Therefore, development of novel stable and efficient organic materials for the organic electroluminescence device is continuously required.

SUMMARY

One purpose of the present disclosure is to provide a benzazole derivative having a heteroaryl group that is excellent in electron transportability and durability.

Another purpose of the present disclosure is to provide an organic electroluminescence device with improved light-emission efficiency and improved life-span.

The purposes of the present disclosure are not limited to the above-mentioned purposes. Other purposes and advantages of the present disclosure, not mentioned above, may be understood from the following descriptions and more clearly understood from aspects of the present disclosure. Further, it will be readily appreciated that the objects and advantages of the present disclosure may be realized by features and combinations thereof as disclosed in the claims.

One implementation of the present disclosure provides a benzazole derivative having a heteroaryl group, wherein the benzazole derivative includes a compound represented by Chemical Formula 1:

<Chemical Formula 1>

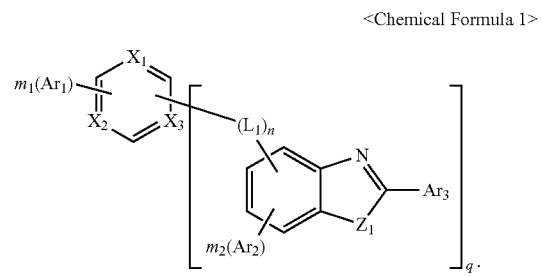

In Chemical Formula 1, each of Z1, X1, X2, X3, Ar1, Ar2, Ar3, m1, m2 and q is defined as follows.

Z1 represents O or S.

L1 represents either a substituted or unsubstituted C6 to C15 arylene or a substituted or unsubstituted C2 to C15 heteroarylene.

In (L1)n, n is 0 or 1. When n is 0, this indicates a single bond.

Each of X1, X2 and X3 independently represents N or CH, and at least one of X1, X2 and X3 is N.

Each of Ar1, Ar2 and Ar3 independently represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

Each of m1 and m2 denotes an integer of 1 or 2.

The q denotes an integer of 1, 2 or 3.

In one example, the benzazole derivative having the heteroaryl group is a compound represented by Chemical Formula 2-1, a compound represented by Chemical Formula 2-2, or a compound represented by Chemical Formula 2-3:

<Chemical Formula 2-1>

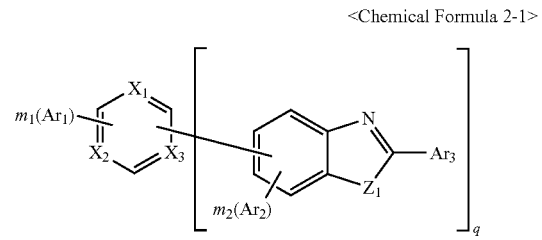

<Chemical Formula 2-2>

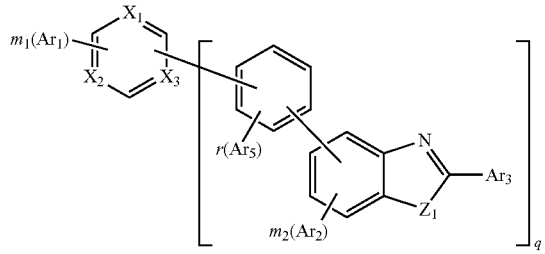

-continued

<Chemical Formula 2-3>

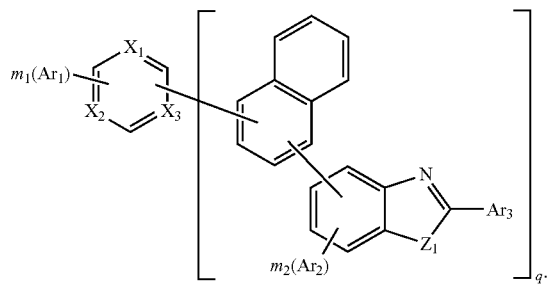

In each of Chemical Formula 2-1, Chemical Formula 2-2, and Chemical Formula 2-3, each of Z1, X1, X2, X3, Ar1, Ar2, Ar3, m1, m2 and q is the same as defined with reference to Chemical Formula 1.

In each of Chemical Formula 2-1, Chemical Formula 2-3, and Chemical Formula 2-3, each of Ar5 or r is defined as follows.

Ar5 represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

The r denotes an integer of 1 or 2.

The benzazole derivative having the heteroaryl group may be used as an organic material for an organic electroluminescence device.

Another implementation of the present disclosure provides an organic electroluminescence device including an organic layer, wherein the organic layer contains the benzazole derivative having the heteroaryl group as defined above.

Details of other aspects are contained in Detailed Descriptions and drawings.

According to one effect of the present disclosure, the benzazole derivative having the heteroaryl group which may include the compound as represented by Chemical Formula 1 which may have an excellent electron transporting ability and an excellent durability may be realized.

According to another effect of the present disclosure, the benzazole derivative with the heteroaryl group has a structure in which the heteroaryl group as an electron-attracting group is directly coupled to a 6-membered ring of the benzazole derivative, or is coupled via a linker to a 6-membered ring of the benzazole derivative. The benzazole derivative with the heteroaryl group has high triplet energy.

The benzazole derivative with the heteroaryl group may have the high triplet energy. This may improve light-emission efficiency and life-span characteristics of a resulting organic electroluminescence device.

According to still another effect of the present disclosure, the organic electroluminescence device with improved light-emission efficiency and life-span characteristics may be realized due to a fact that the device includes an organic layer containing the benzazole derivative with the heteroaryl group as defined above.

Further specific effects of the present disclosure as well as the effects as described above will be described in conduction with illustrations of specific details for carrying out the present disclosure.

BRIEF DESCRIPTION OF DRAWINGS

FIG. 1 is a graph showing a relationship between current density and driving voltage. FIG. 1 shows that the organic electroluminescence devices according to the Examples are driven at lower driving voltages than those of the organic electroluminescence devices according to the Comparative Examples, at the same current density.

FIG. 2 is a graph showing a relationship between luminance and light-emission efficiency. FIG. 2 shows that the organic electroluminescence devices according to the Examples exhibit relatively higher light-emission efficiencies than those of the organic electroluminescence devices according to the Comparative Examples, at the same luminance.

FIG. 3 is a graph showing a relationship between luminance and external quantum efficiency. FIG. 3 shows that the organic electroluminescence devices according to the Examples exhibit relatively higher external quantum efficiencies than those of the organic electroluminescence devices according to the Comparative Examples, at the same luminance.

FIG. 4 is a graph of a relationship between driving duration and a ratio L/L0. The L/L0 refers to a ratio of current luminance (L) to initial luminance (L0). FIG. 4 shows that the organic electroluminescence devices according to the Examples have improved life-spans compared to those of the organic electroluminescence devices according to the Comparative Examples.

DETAILED DESCRIPTIONS

Figure 1:
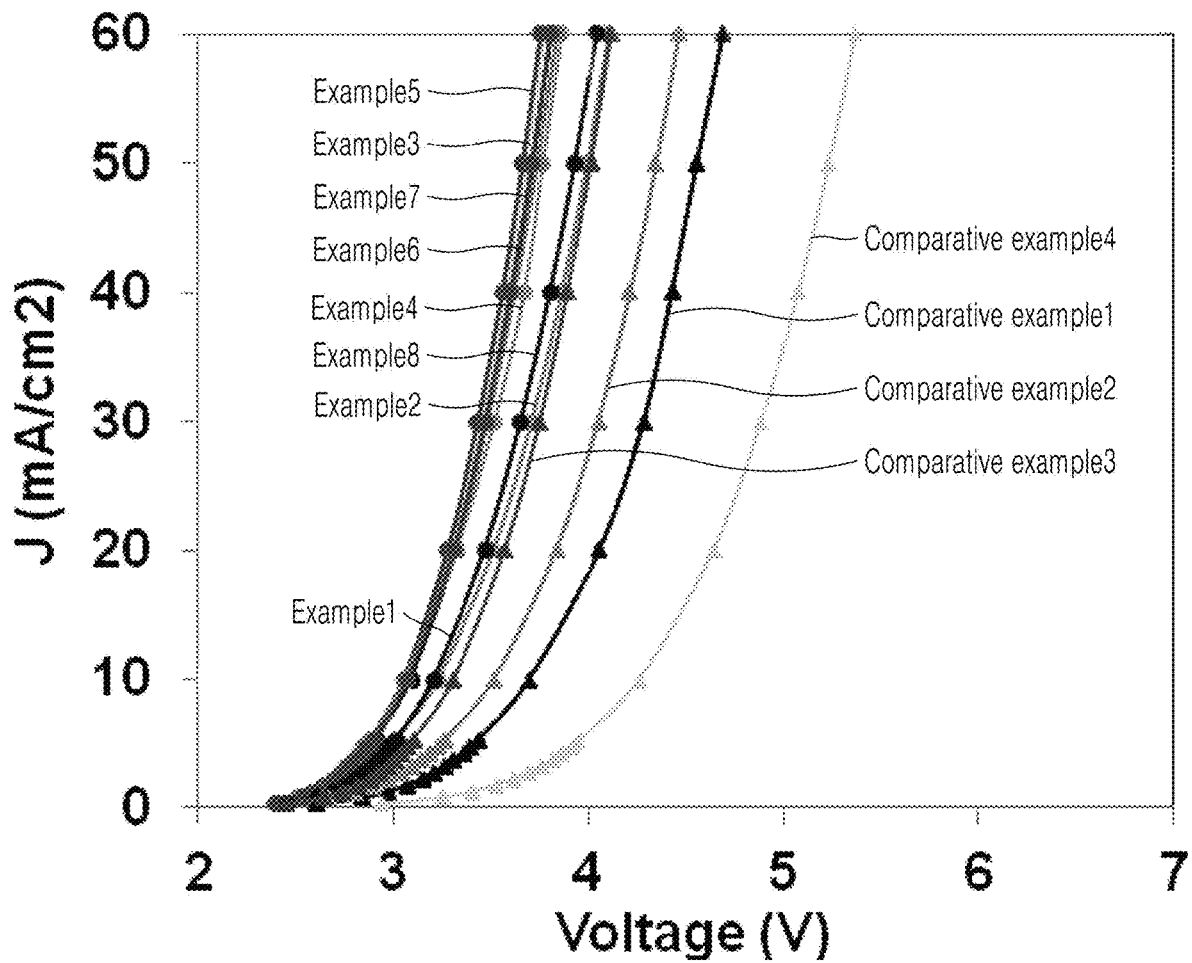
FIG. 1 to FIG. 4 show comparison experiment results between organic electroluminescence devices according to Examples and organic electroluminescence devices according to Comparative Examples.

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various aspects are illustrated and described further below. It will be understood that the description herein is not intended to limit the claims to the specific aspects described. On the contrary, it is intended to cover alternatives, modifications, and equivalents as may be included within the spirit and scope of the present disclosure as defined by the appended claims.

The terminology used herein is for the purpose of describing particular aspects only and is not intended to be limiting of the present disclosure. As used herein, the singular forms "a" and "an" are intended to include the plural forms as well, unless the context clearly indicates otherwise. It will be further understood that the terms "has", "having", "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of"

when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a "Ca to Cb" hydrocarbon group is defined as a hydrocarbon group or a hydrocarbon derivative group having a carbon number of "a" inclusive to "b" inclusive. A phase "a to b" is defined as being a or greater and b or smaller. As used herein, a phase "a and/or b" means "a" or "b" or "a and b".

As used herein, in a phase "substituted" or "unsubstituted", the term "substituted" means that at least one hydrogen of a hydrocarbon compound or hydrocarbon derivative is redisposed with a hydrocarbon group, a hydrocarbon derivative group, halogen or a cyano group (—CN). The term "unsubstituted" means that at least one hydrogen of a hydrocarbon compound or hydrocarbon derivative is not redisposed with a hydrocarbon group, a hydrocarbon derivative group, halogen or a cyano group (—CN). Examples of the hydrocarbon group or the hydrocarbon derivative group may include C1 to C20 alkyl, C2 to C20 alkenyl, C2 to C20 alkynyl, C6 to C20 aryl, C1 to C20 alkyl C6 to C20 aryl, C6 to C20 aryl C1 to C20 alkyl, C1 to C20 alkylamino, C6 to C20 arylamino, C1 to C20 alkylidene or the like, but may not be limited thereto.

One implementation of the present disclosure provides a benzazole derivative having a heteroaryl group.

The benzazole derivative refers to a condensed ring compound in which a 6-membered aromatic ring is bonded to a hetero five-membered ring. The benzazole derivative is electrochemically more stable, has improved electron transport ability and higher thermal stability compared with a 6-membered heterocyclic structure. Further, the heteroaryl group may act as an electron attracting group, which may further enhance the electron transport capability of the benzazole derivative. The benzazole derivative with the heteroaryl group may exhibit superior electron transport ability and superior durability compared to a compound that does not contain the benzazole derivative or compared to a benzazole derivative that does not contain the heteroaryl group.

The benzazole derivative having the heteroaryl group is a compound represented by the following Chemical Formula 1. The heteroaryl group is bonded to a 6-membered aromatic ring of the benzazole derivative. Because the benzazole derivative with the heteroaryl group has a high triplet energy, the benzazole derivative with the heteroaryl group may improve the light-emission efficiency and life-span characteristics of the organic electroluminescence device containing the benzazole derivative having the heteroaryl group.

<Chemical Formula 1>

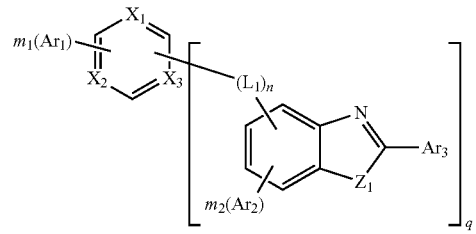

In Chemical Formula 1, each of Z1, X1, X2, X3, Ar1, Ar2, Ar3, m1, m2 and q is defined as follows.

Z1 represents O or S.

L1 represents either a substituted or unsubstituted C6 to C15 arylene or a substituted or unsubstituted C2 to C15 heteroarylene.

In (L1)n, n is 0 or 1.

Each of X1, X2 and X3 independently represents N or CH, and at least one of X1, X2 or X3 is N.

Each of Ar1, Ar2 and Ar3 independently represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

Each of m1 and m2 denotes an integer of 1 or 2.

The q denotes an integer of 1, 2 or 3.

In Chemical Formula 1, the benzazole derivative refers to a condensed ring compound in which a hetero five-membered ring containing two different heteroatoms is coupled to a six-membered aromatic ring. One of the two different heteroatoms is N, while the other thereof is S or O.

In Chemical Formula 1, the heteroaryl group is bonded to the 6-membered aromatic ring of the benzazole derivative. The heteroaryl group may include pyridine, pyrimidine or triazine. In Chemical Formula 1, when one of X1, X2 and X3 is N, the heteroaryl group includes pyridine. In Chemical Formula 1, when two of X1, X2 and X3 are N, the heteroaryl group includes pyrimidine. In Chemical Formula 1, when all of X1, X2 and X3 are N, the heteroaryl group include triazine.

In Chemical Formula 1, the heteroaryl group may be bonded directly to the 6-membered aromatic ring of the benzazole derivative. In Chemical Formula 1, when n is 0, the heteroaryl group may be bonded directly to the 6-membered aromatic ring of the benzazole derivative.

In Chemical Formula 1, the heteroaryl group may be coupled via a linker to the 6-membered aromatic ring of the benzazole derivative. In Chemical Formula 1, when n is 1, the heteroaryl group may be bonded via L1 to the 6-membered aromatic ring of the benzazole derivative.

The present inventors have confirmed that an organic electroluminescence device containing the compound of Chemical Formula 1 where Z1 is O or S could be driven at a lower driving voltage, and has improved light-emission efficiency, external quantum efficiency and life-span, compared to an organic electroluminescence device containing the compound of Chemical Formula 1 where Z1 is N. This will be demonstrated by the comparison experimental results as described below and FIG. 1 to FIG. 4.

In Chemical Formula 1, each of Ar1, Ar2, and Ar3 independently represents one selected from a group consisting of hydrogen, a methyl group, an ethyl group, an isopropyl group, an isobutyl group, a t-butyl group, a trimethylsilyl group, a triphenylsilyl group, a trifluoromethyl group, a substituted or unsubstituted phenyl group, a substituted or unsubstituted biphenyl group, a substituted or unsubstituted naphthyl group, a substituted or unsubstituted phenanthrene group, a substituted or unsubstituted pyridine, a substituted or unsubstituted quinoline group, a substituted or unsubstituted benzoquinoline group, a substituted or unsubstituted phenanthridine group, a substituted or unsubstituted dibenzothiophene group, and a substituted or unsubstituted dibenzofuran group.

In one example, the benzazole derivative having the heteroaryl group may include at least one of a compound represented by Chemical Formula 2-1, a compound represented by Chemical Formula 2-2, or a compound represented by Chemical Formula 2-3:

<Chemical Formula 2-1>

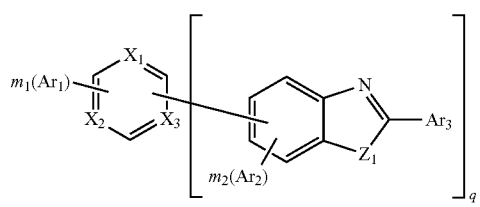

<Chemical Formula 2-2>

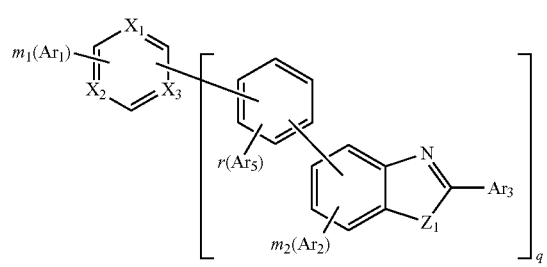

<Chemical Formula 2-3>

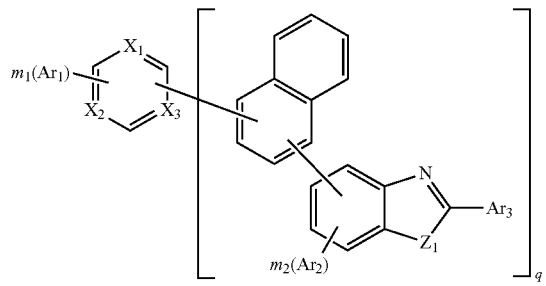

In each of Chemical Formula 2-1, Chemical Formula 2-2, and Chemical Formula 2-3, each of Z1, X1, X2, X3, Ar1, Ar2, Ar3, m1, m2 and q is the same as defined above with reference to Chemical Formula 1.

The compound represented by Chemical Formula 2-1 may refer to the compound of Chemical Formula 1 where n is 0, and the heteroaryl group is directly bonded to the 6-membered aromatic ring of the benzazole derivative.

The compound represented by Chemical Formula 2-2 may refer to the compound of Chemical Formula 1 where n is 1, and L1 is phenylene, and, thus, the heteroaryl group is bonded via phenylene as a linker to the six-membered aromatic ring of the benzazole derivative.

The compound represented by Chemical Formula 2-3 may refer to the compound of Chemical Formula 1 where n is 1, and L1 is naphthalenediyl, and, thus, the heteroaryl group is bonded via naphthalenediyl as a linker to the six-membered aromatic ring of the benzazole derivative.

In each of Chemical Formula 2-1, Chemical Formula 2-2 and Chemical Formula 2-3, Ar5 represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

In each of Chemical Formula 2-1, Chemical Formula 2-2, and Chemical Formula 2-3, Ar5 represents one selected from a group consisting of hydrogen, a methyl group, an ethyl group, an isopropyl group, an isobutyl group, a t-butyl group, a trimethylsilyl group, a triphenylsilyl group, a trifluoromethyl group, a substituted or unsubstituted phenyl group, a substituted or unsubstituted biphenyl group, a substituted or unsubstituted naphthyl group, a substituted or unsubstituted phenanthrene group, a substituted or unsubstituted pyridine, a substituted or unsubstituted quinoline group, a substituted or unsubstituted benzoquinoline group, a substituted or unsubstituted phenanthridine group, a substituted or unsubstituted dibenzothiophene group, and a substituted or unsubstituted dibenzofuran group.

In each of Chemical Formula 2-1, Chemical Formula 2-2 and Chemical Formula 2-3, r denotes an integer of 1 or 2.

In one example, the benzazole derivative having the heteroaryl group may include at least one of compounds represented by following structural formulas:

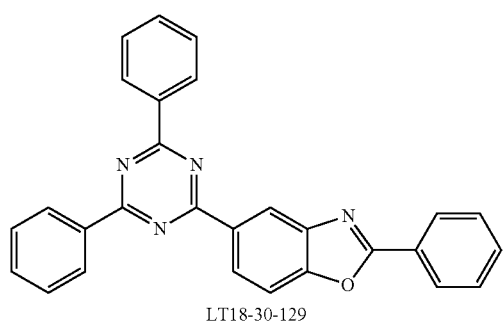
LT18-30-129
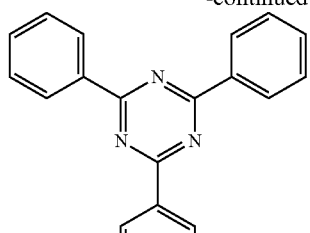
LT18-30-022
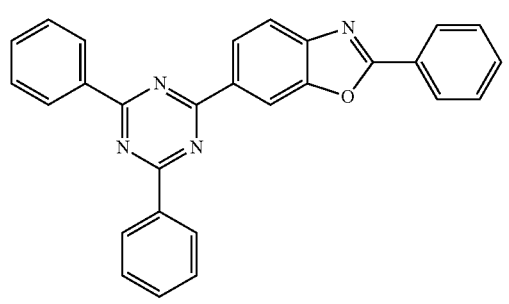
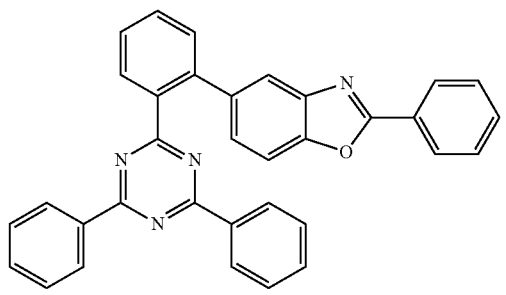
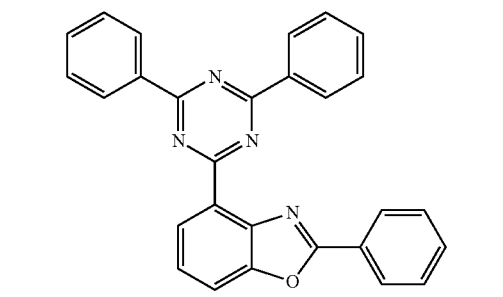
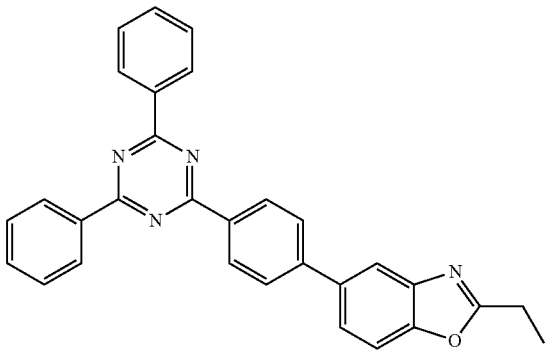
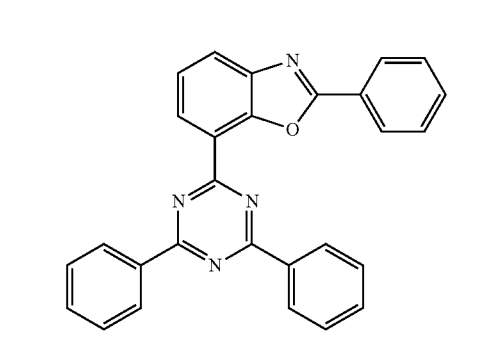
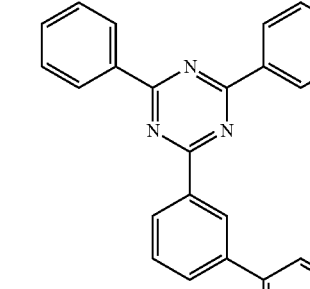

LT18-30-033

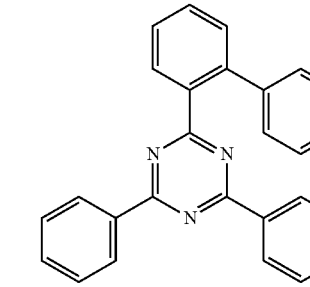

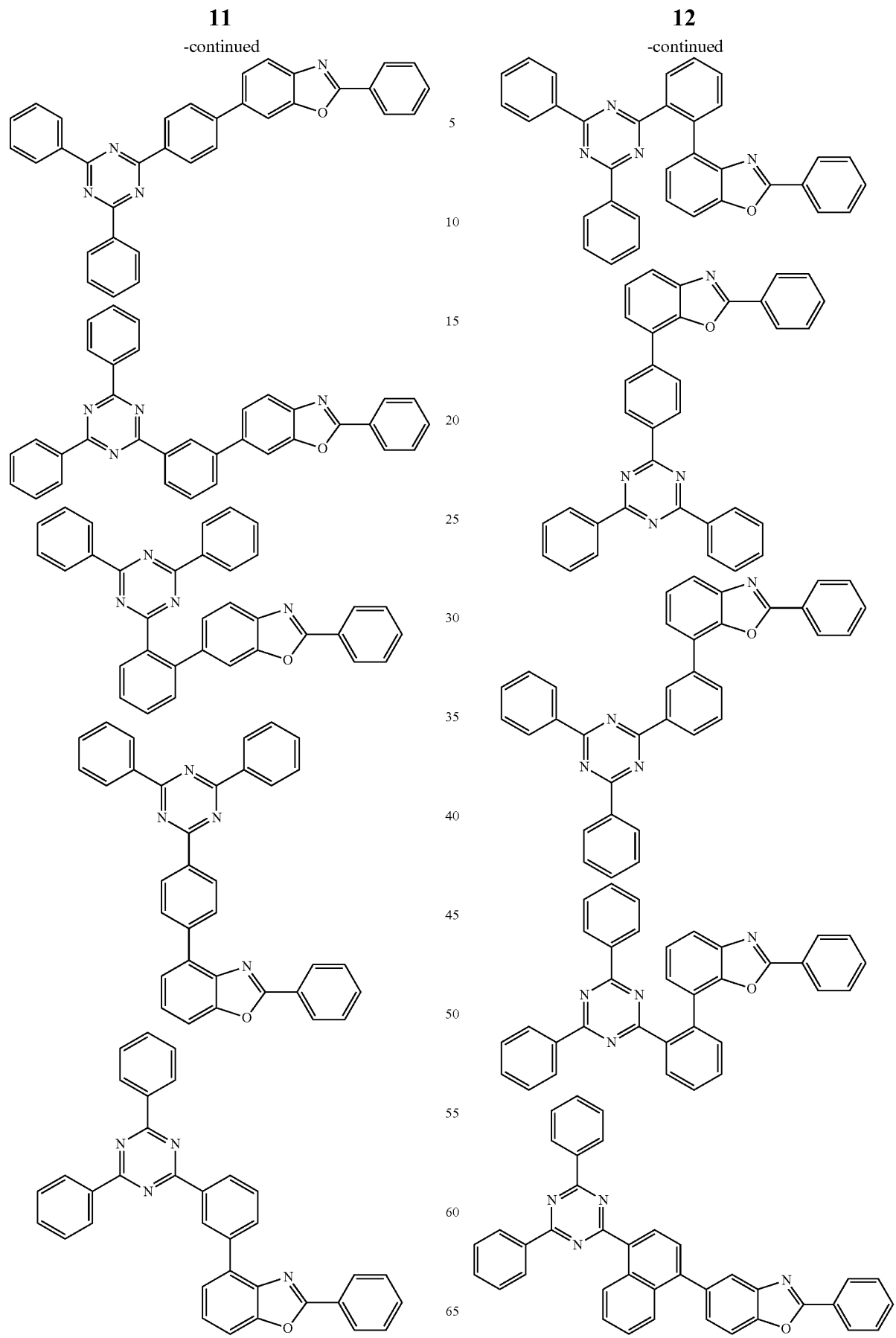

-continued
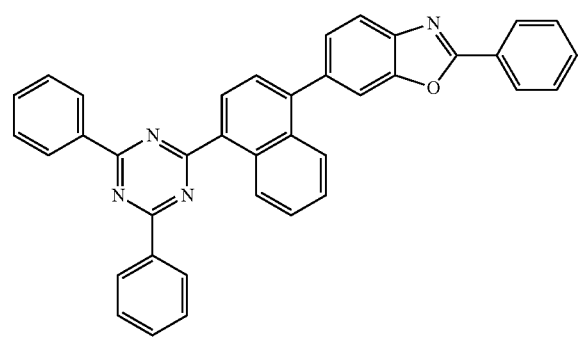
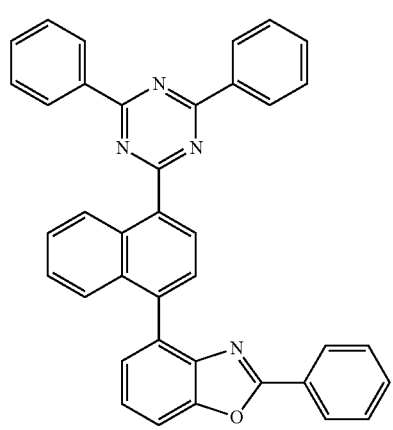
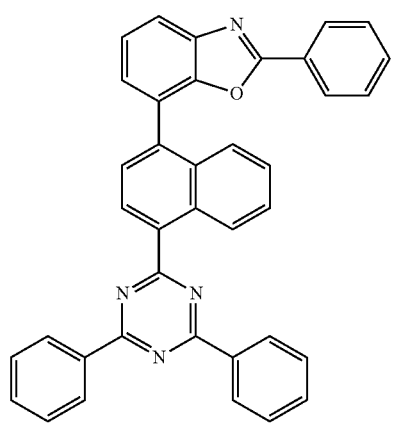
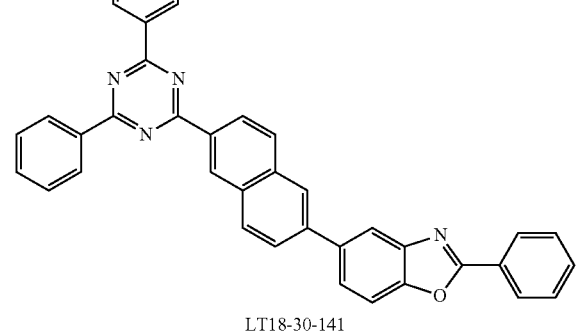
-continued
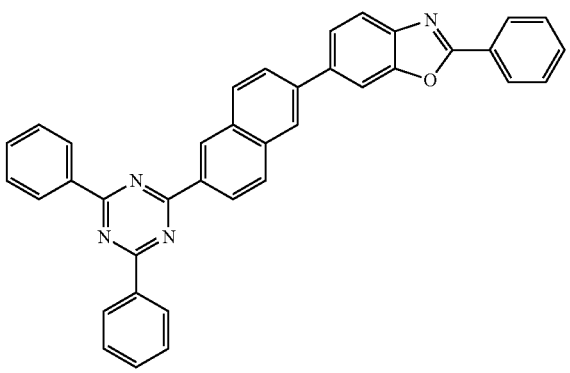
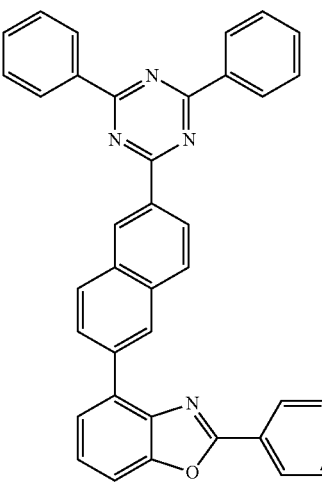
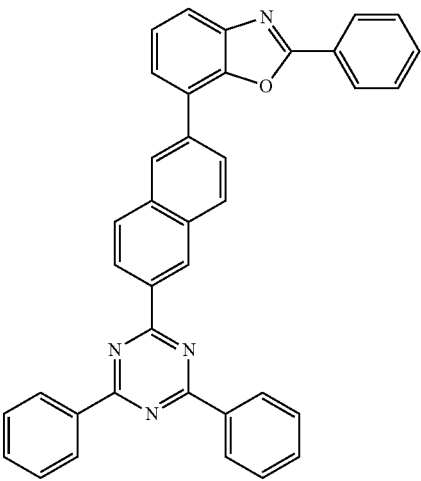

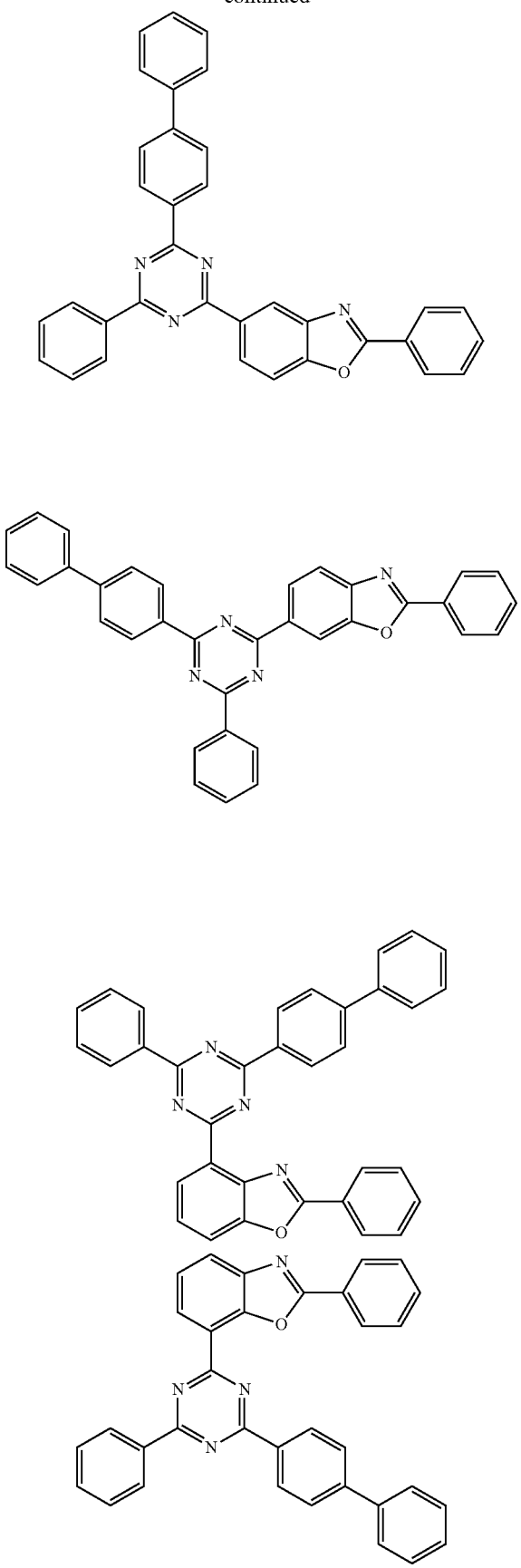
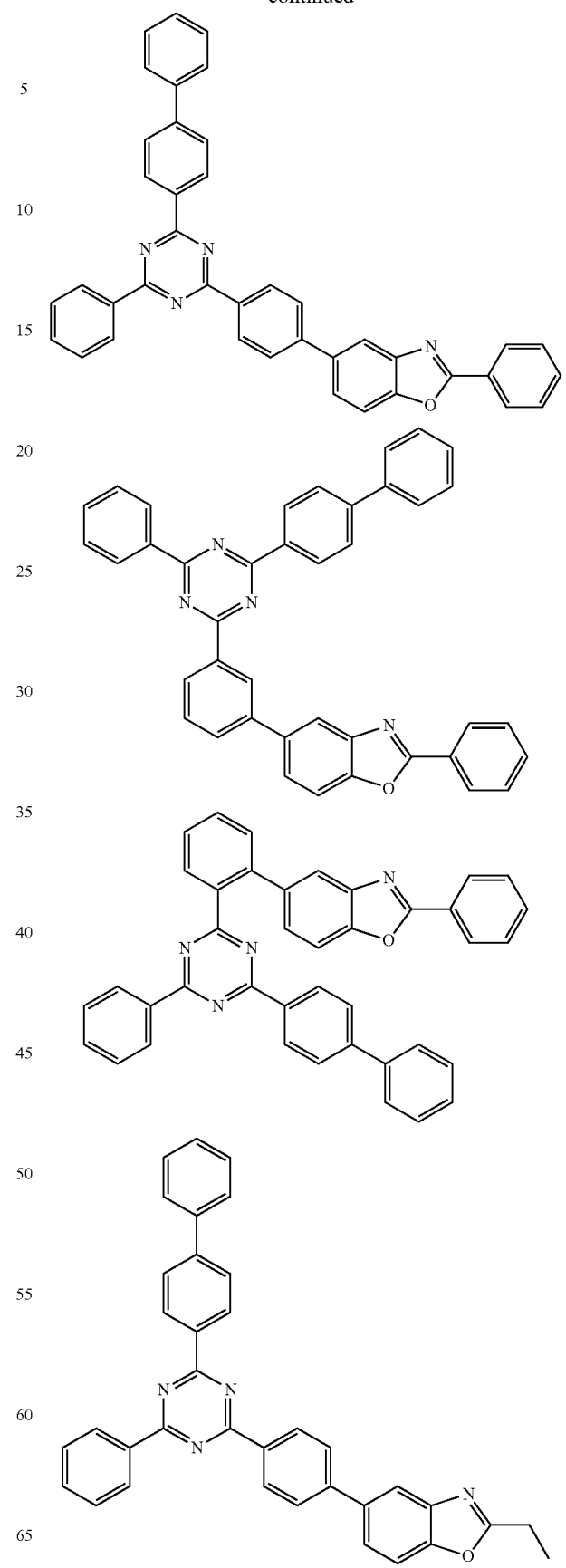

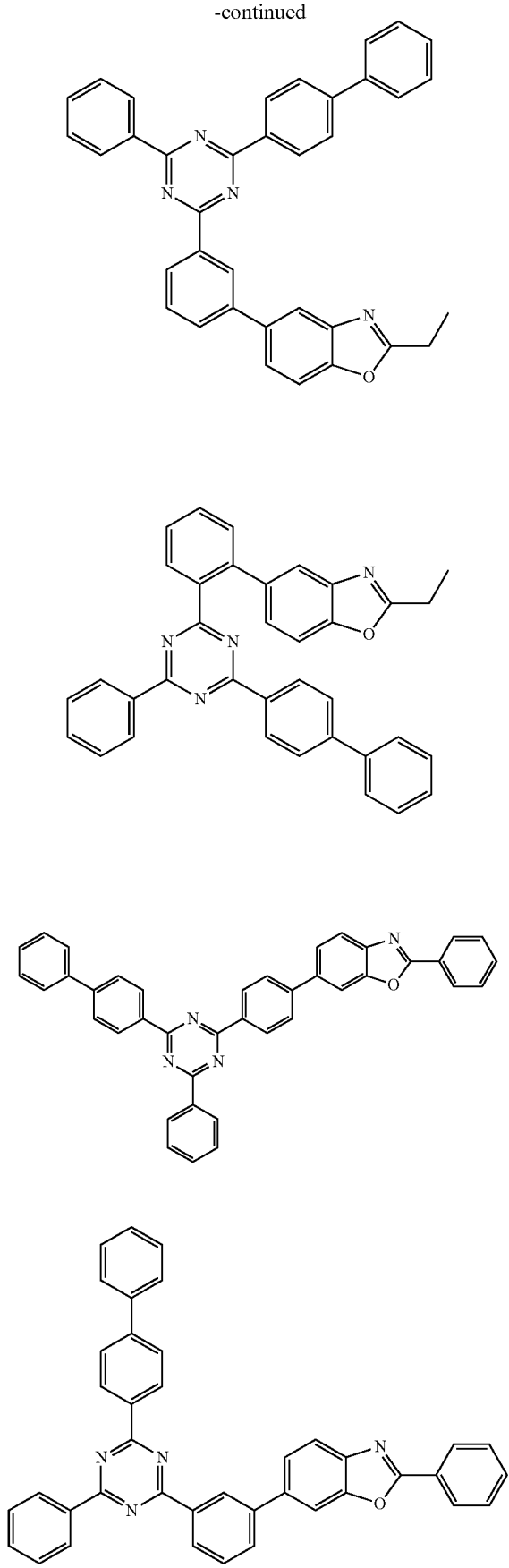

-continued
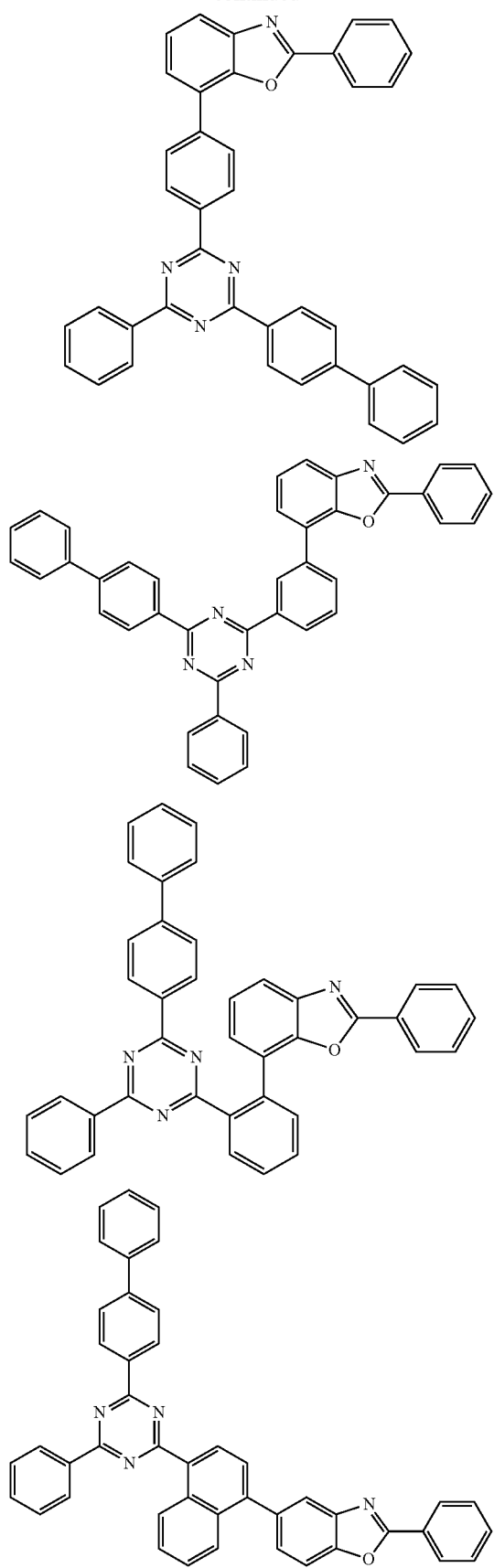
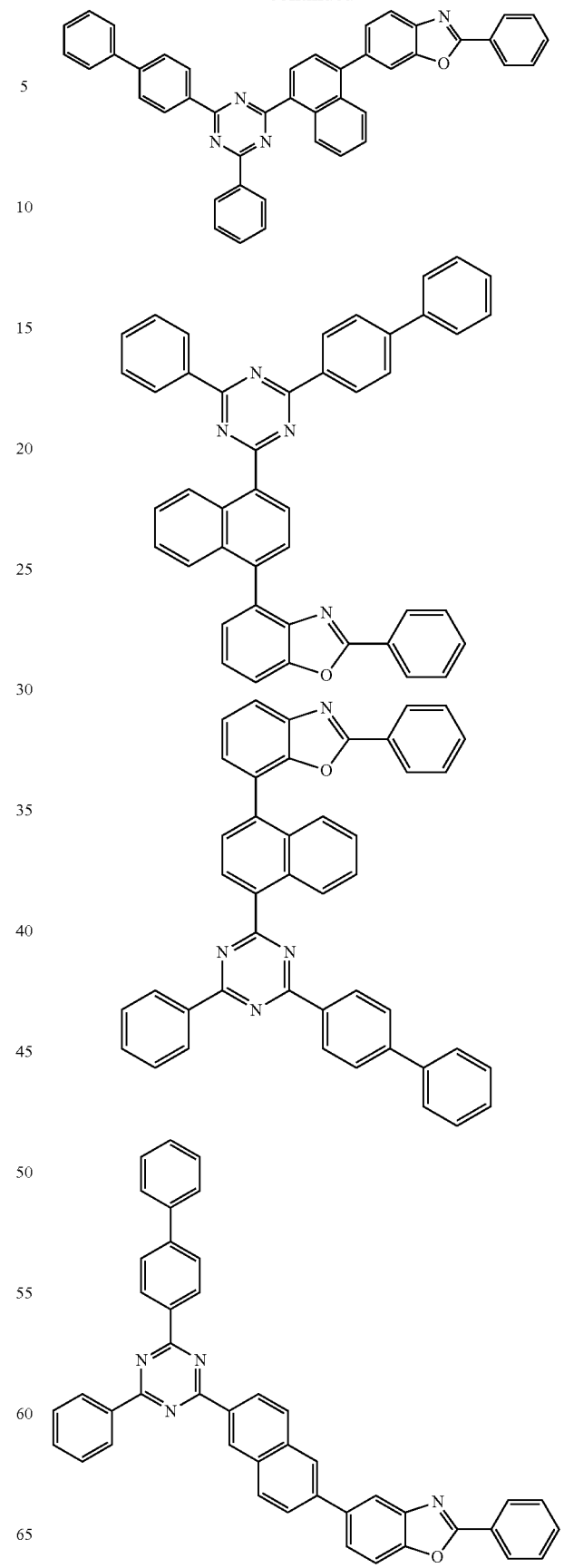

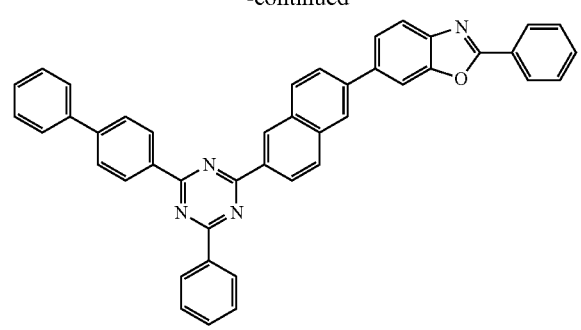
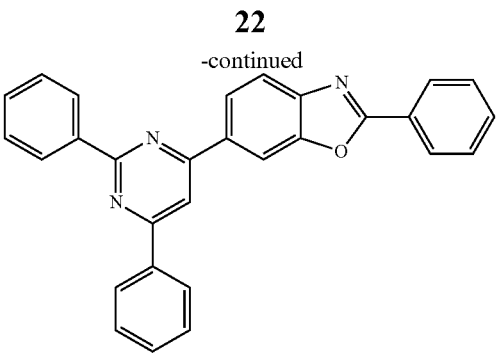
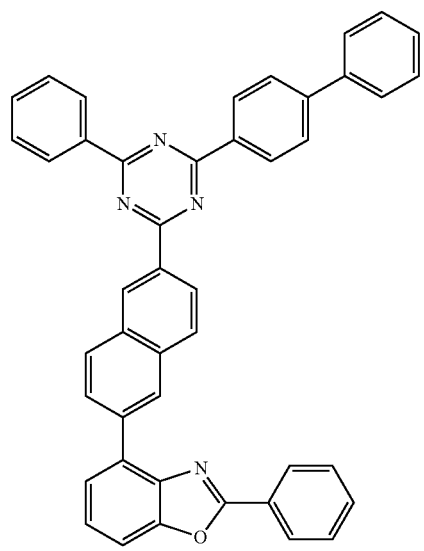
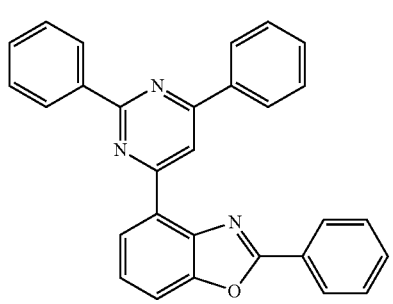
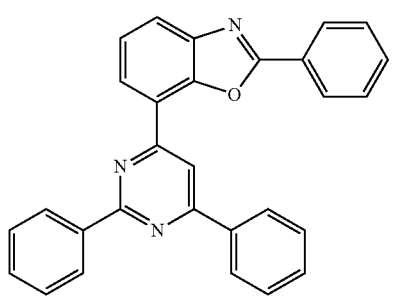
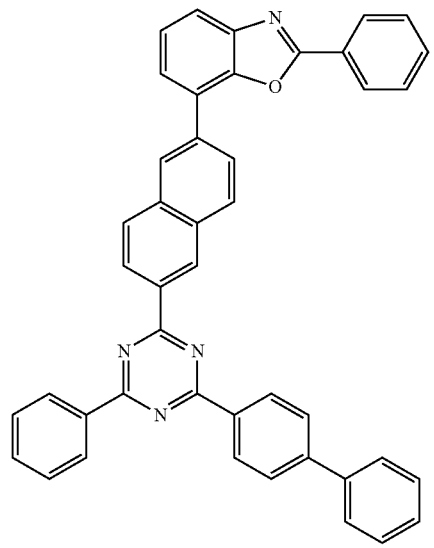
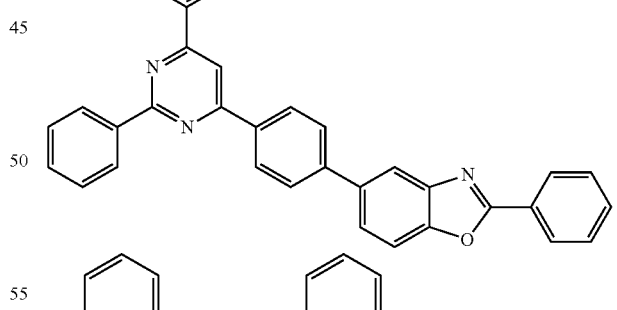
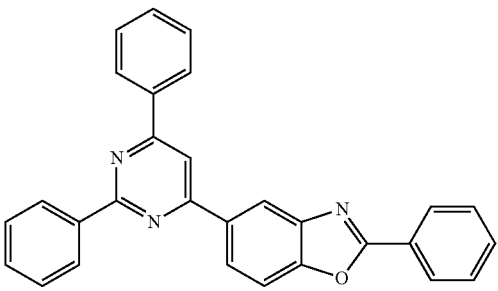
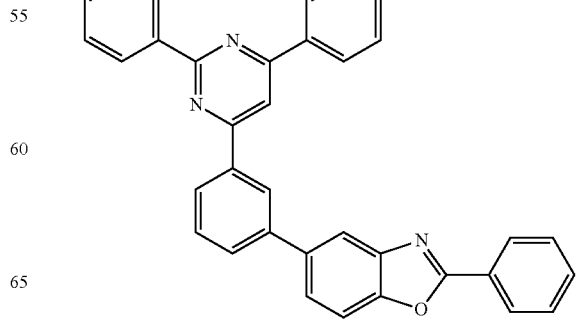

23
-continued
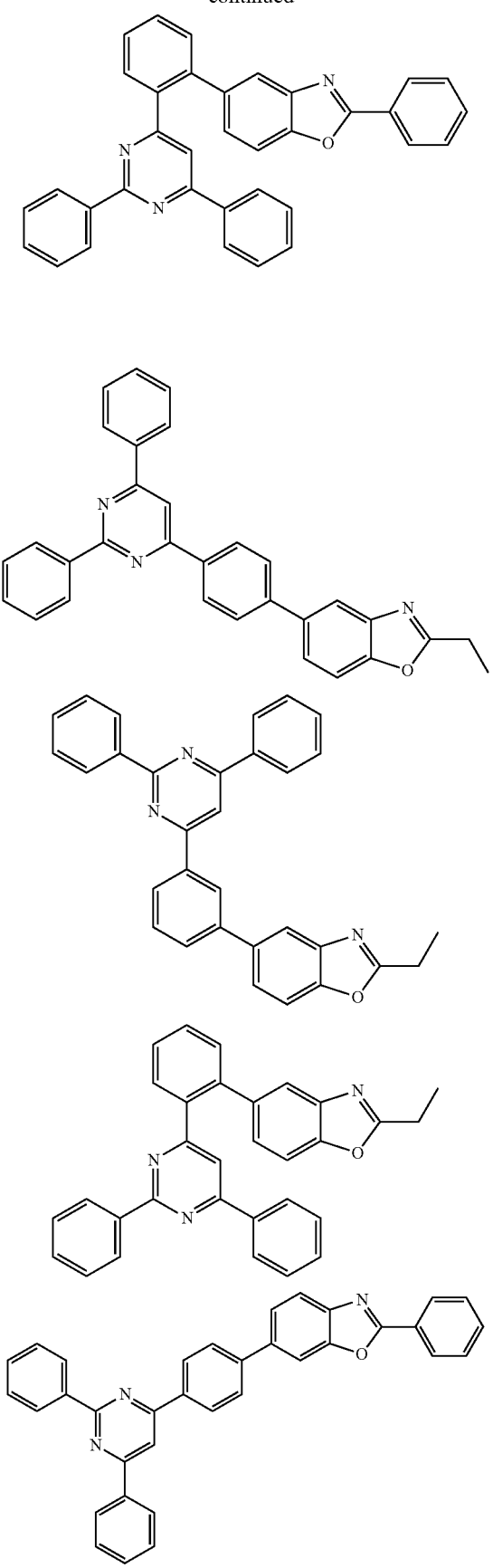
24
-continued
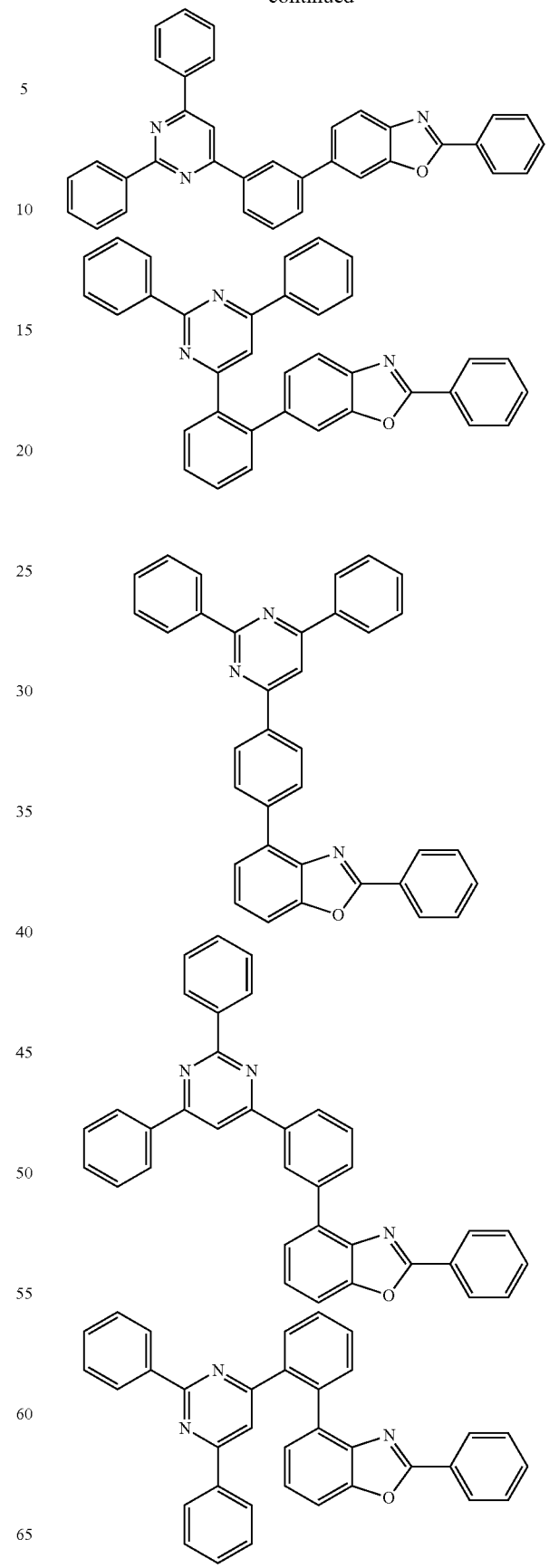

25
-continued
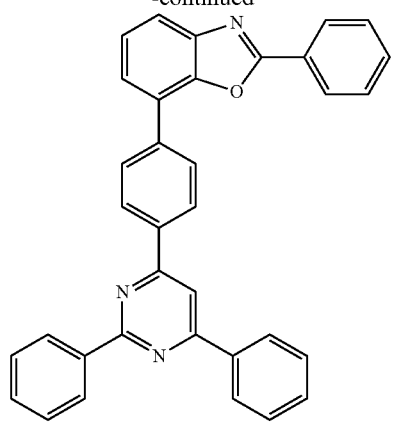
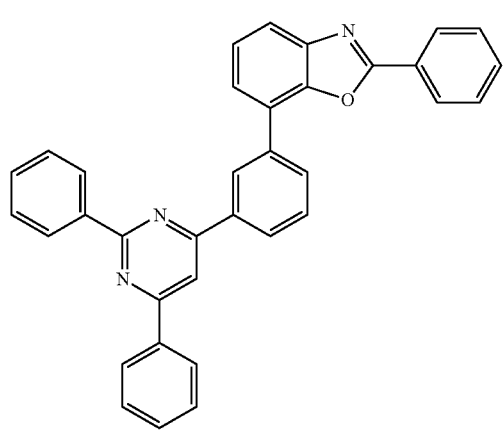
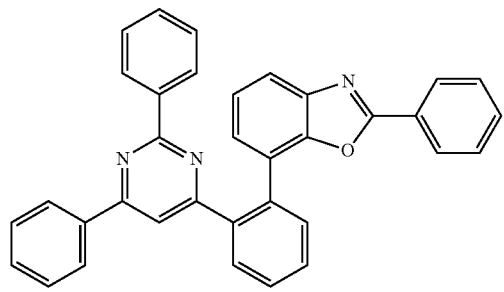
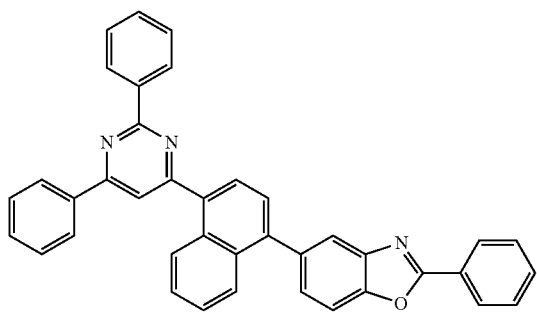
26
-continued
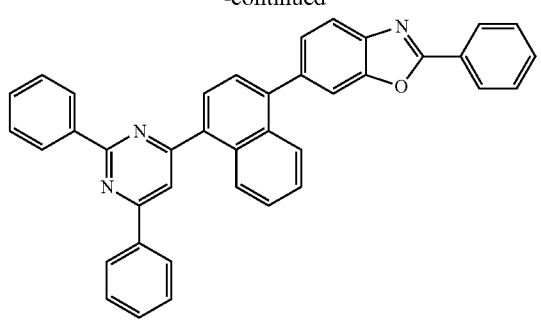
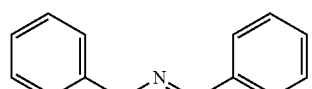
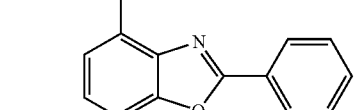
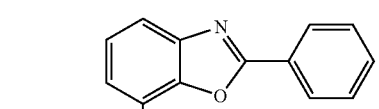
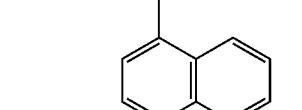
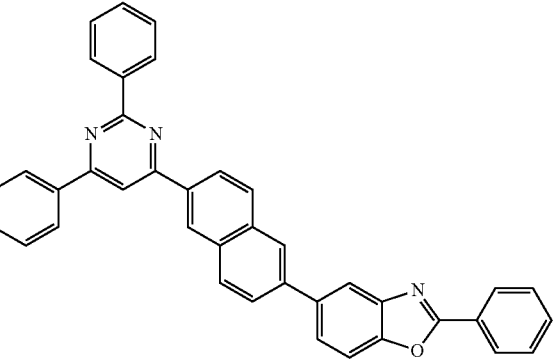

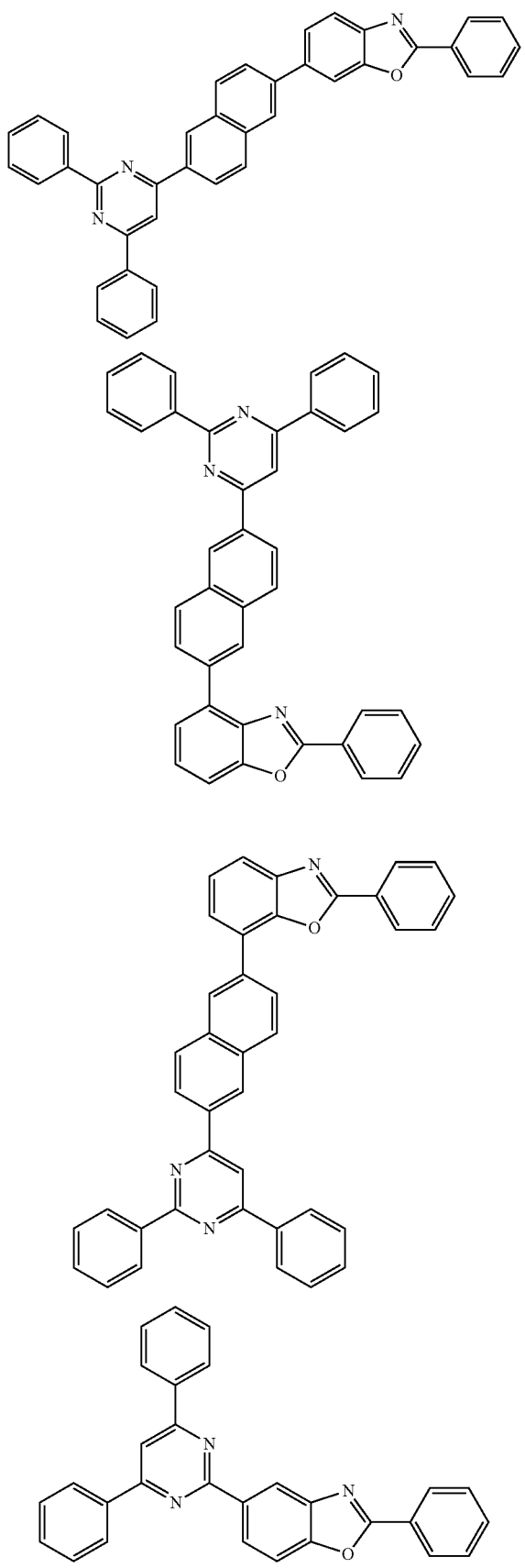
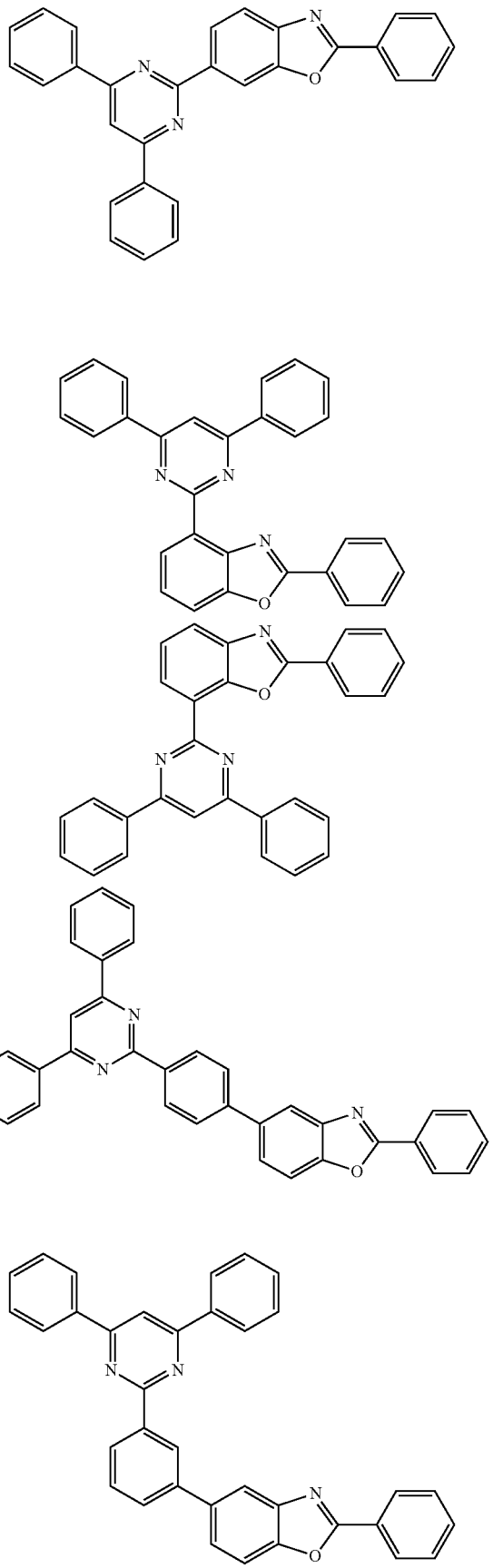

-continued
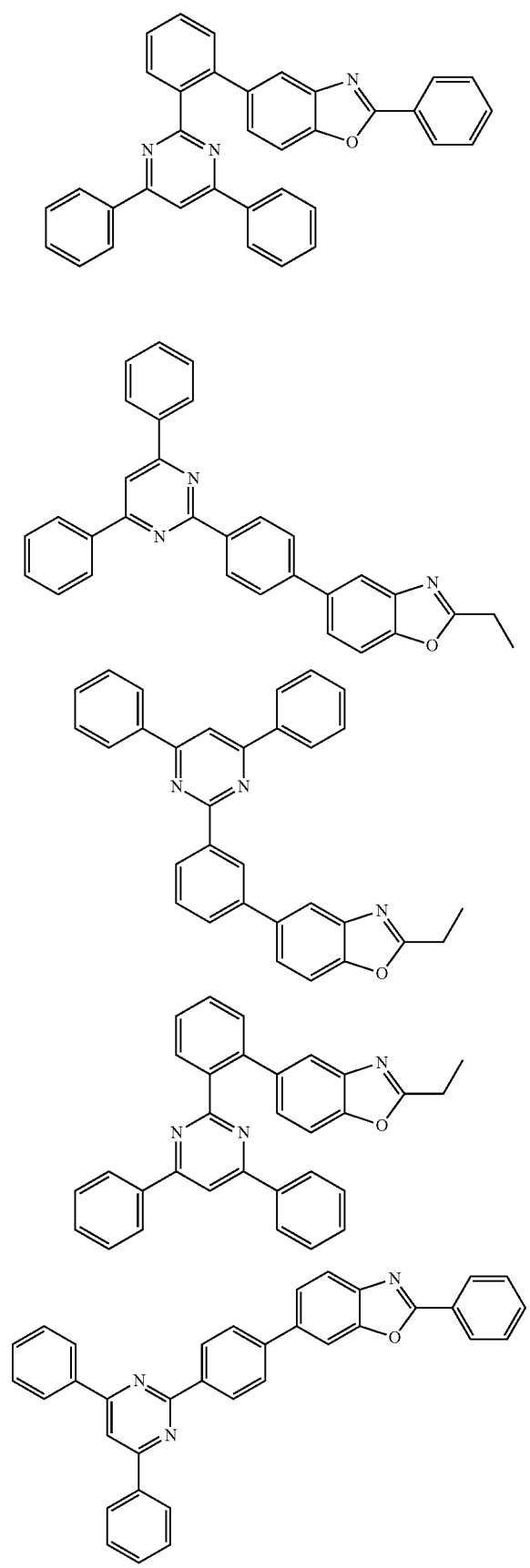
-continued
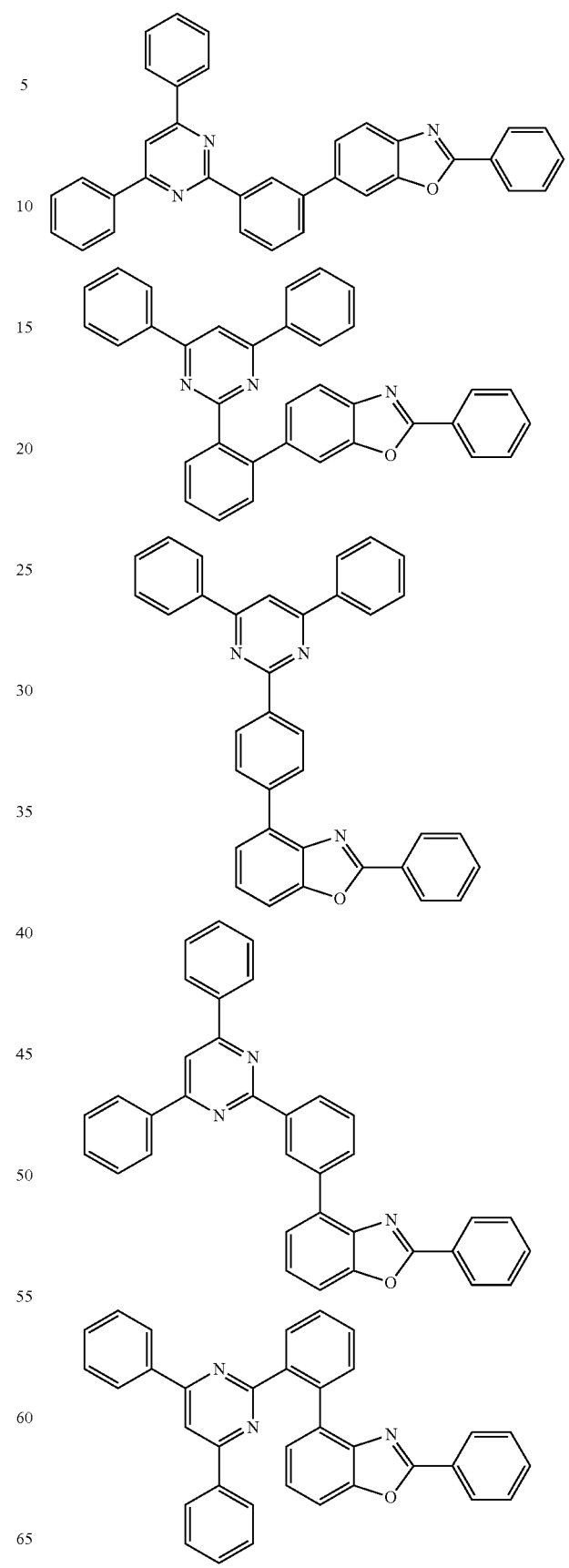

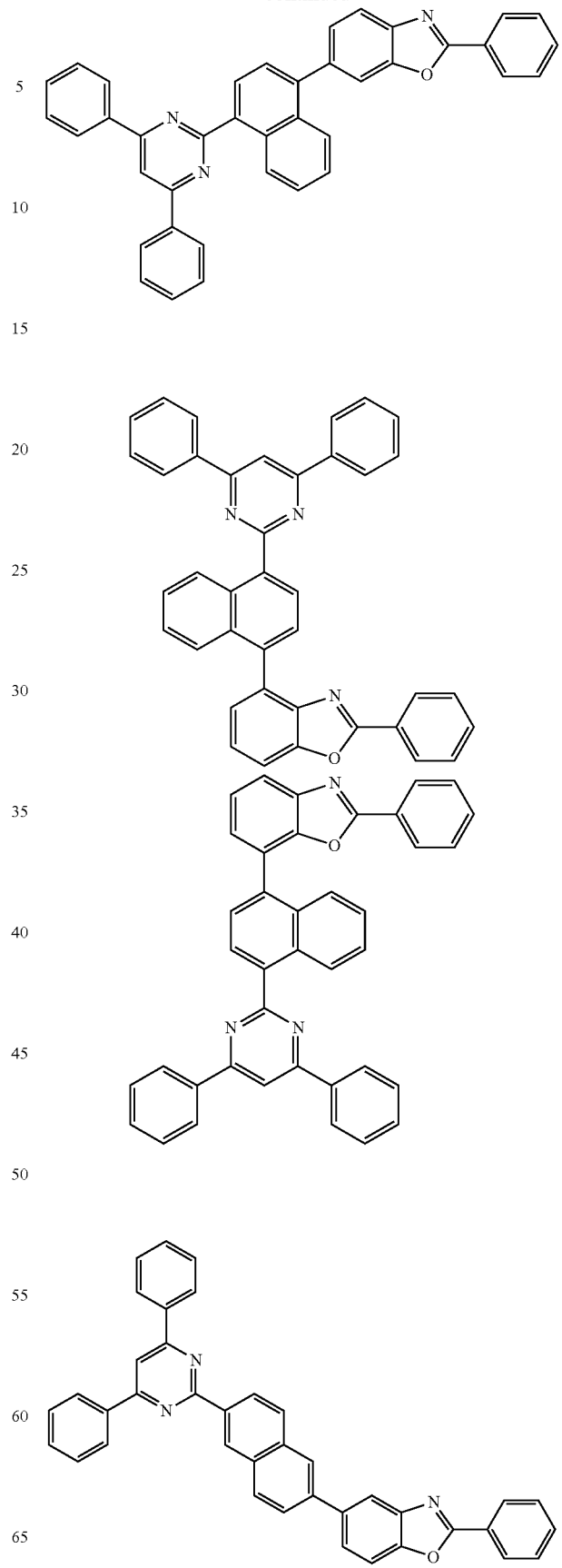

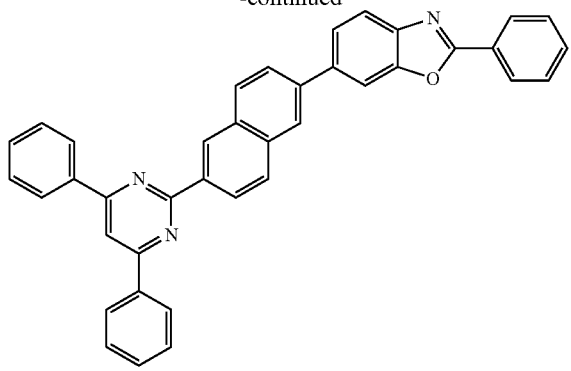
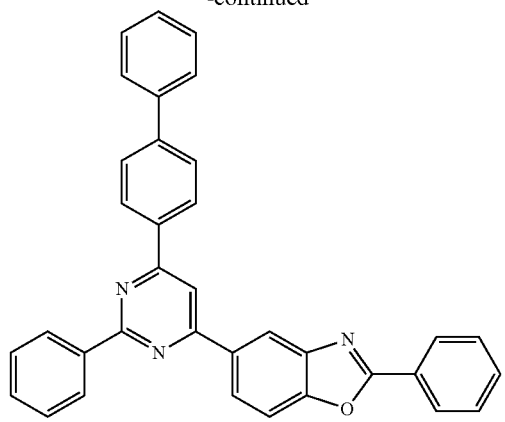
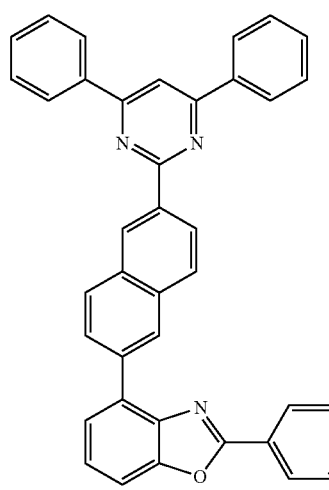
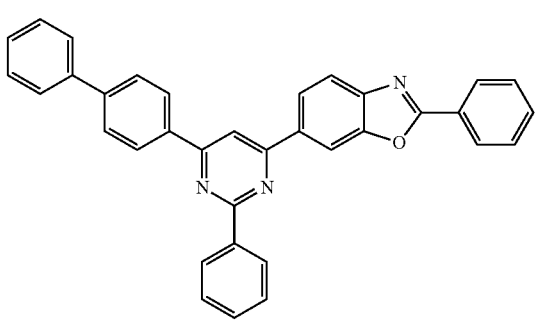
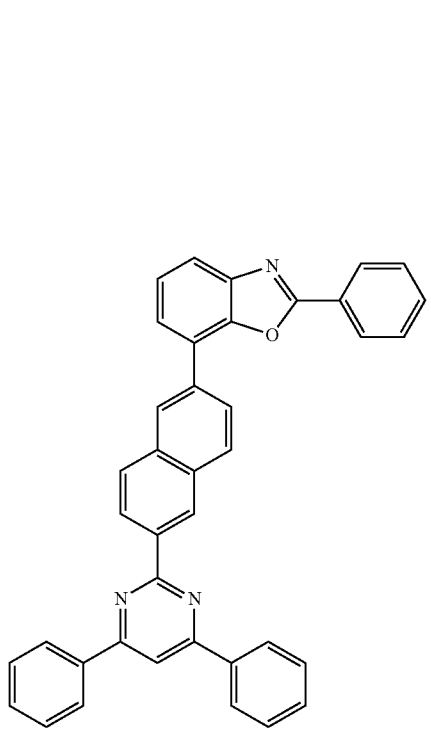
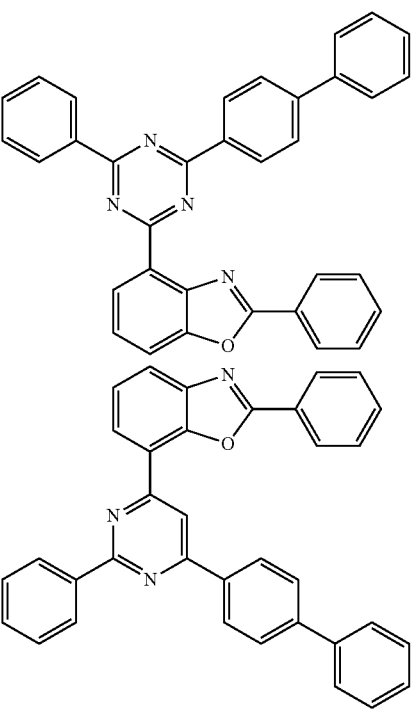

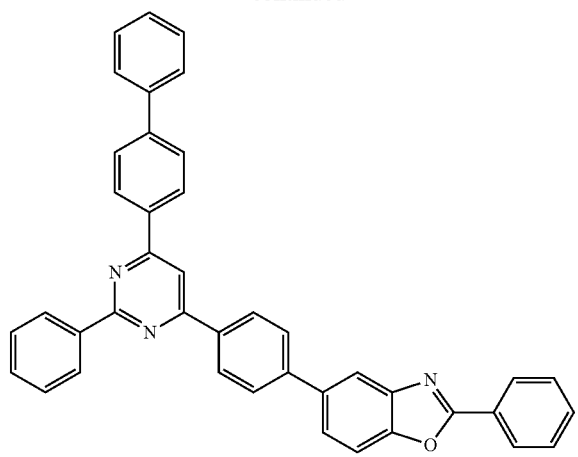
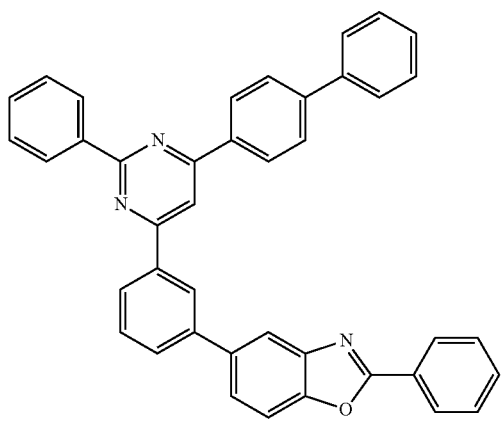
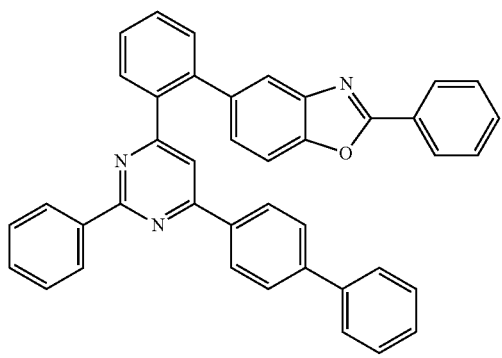
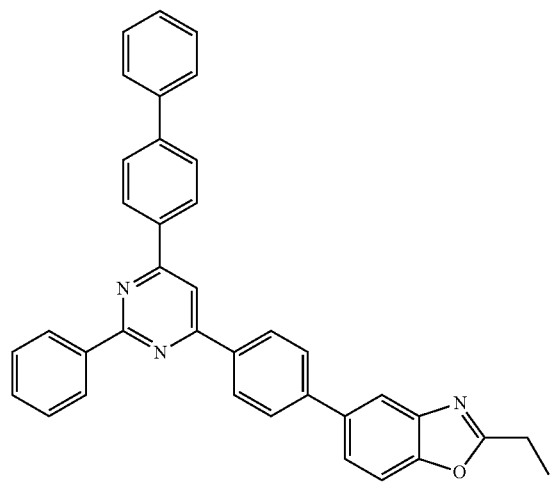
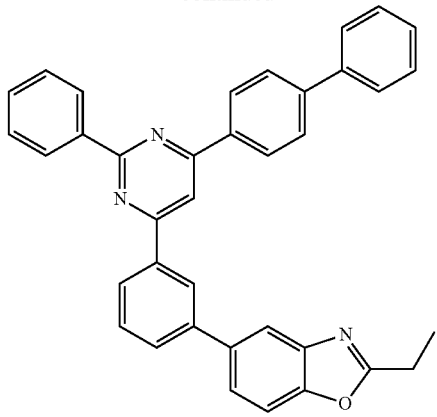
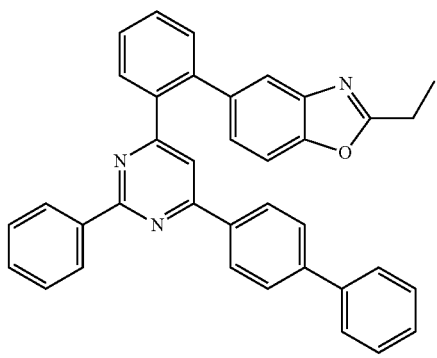
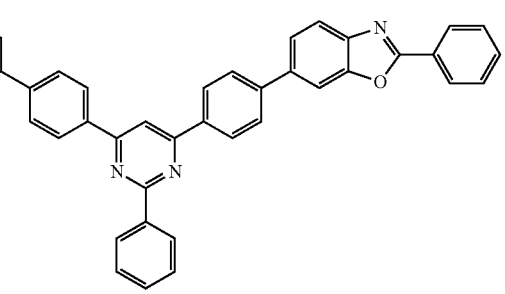
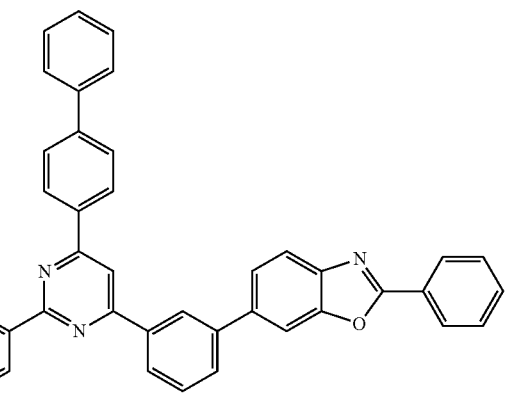

37
-continued
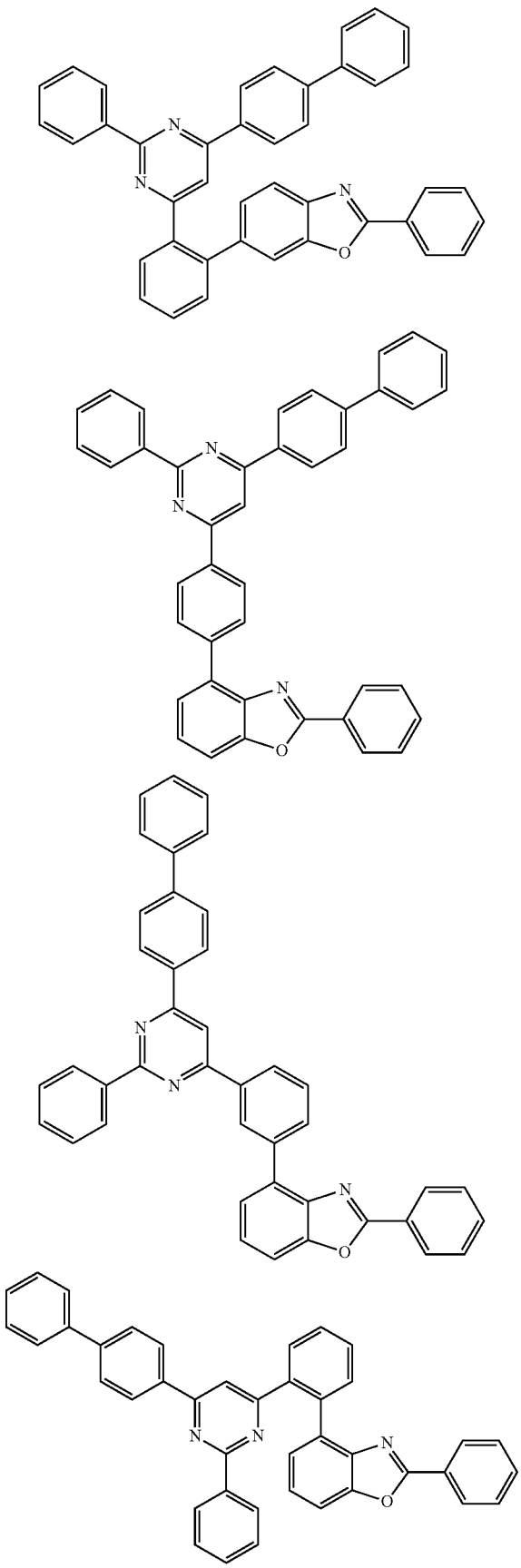
38
-continued
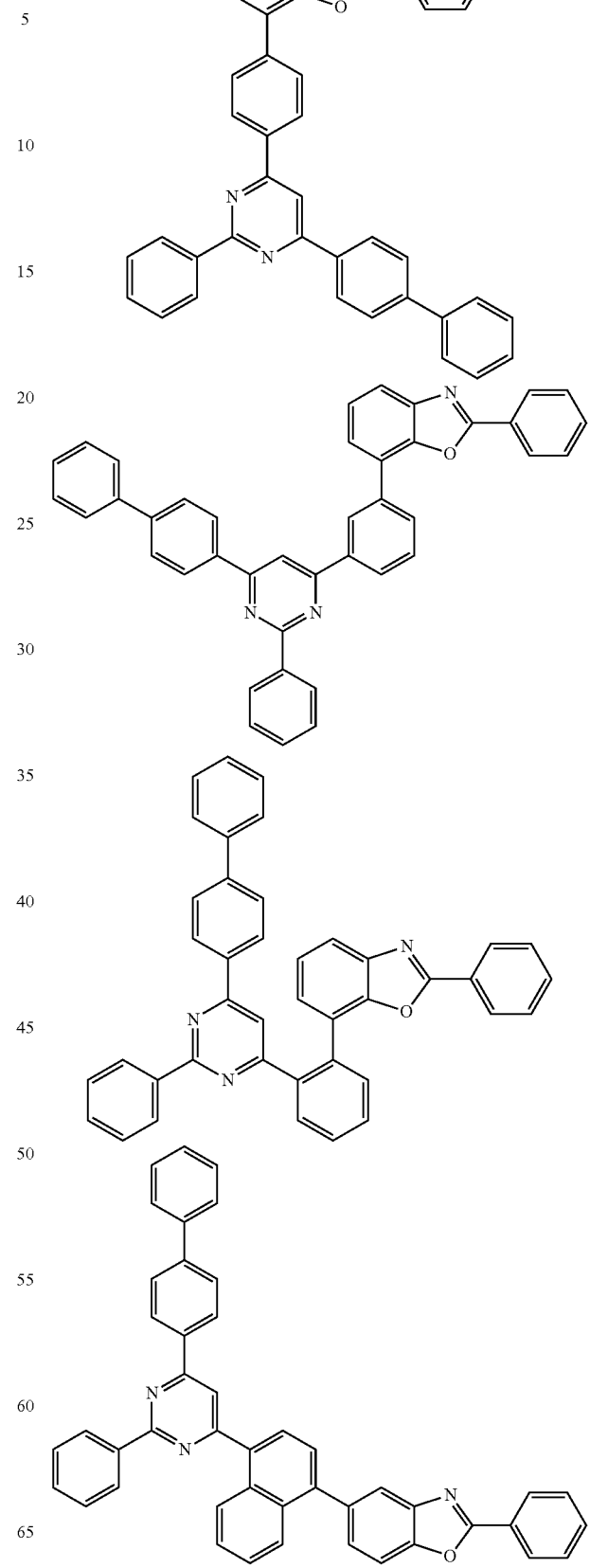

39
-continued
40
-continued
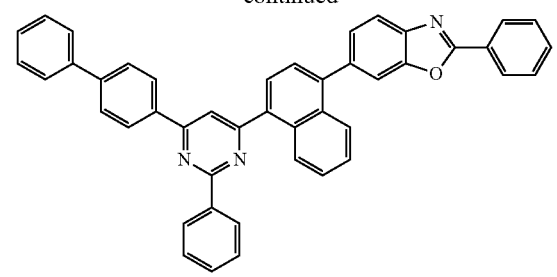
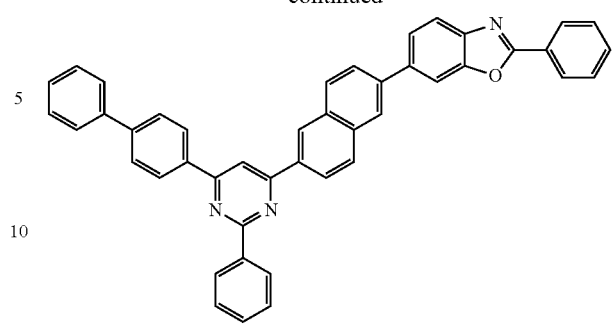

41
-continued
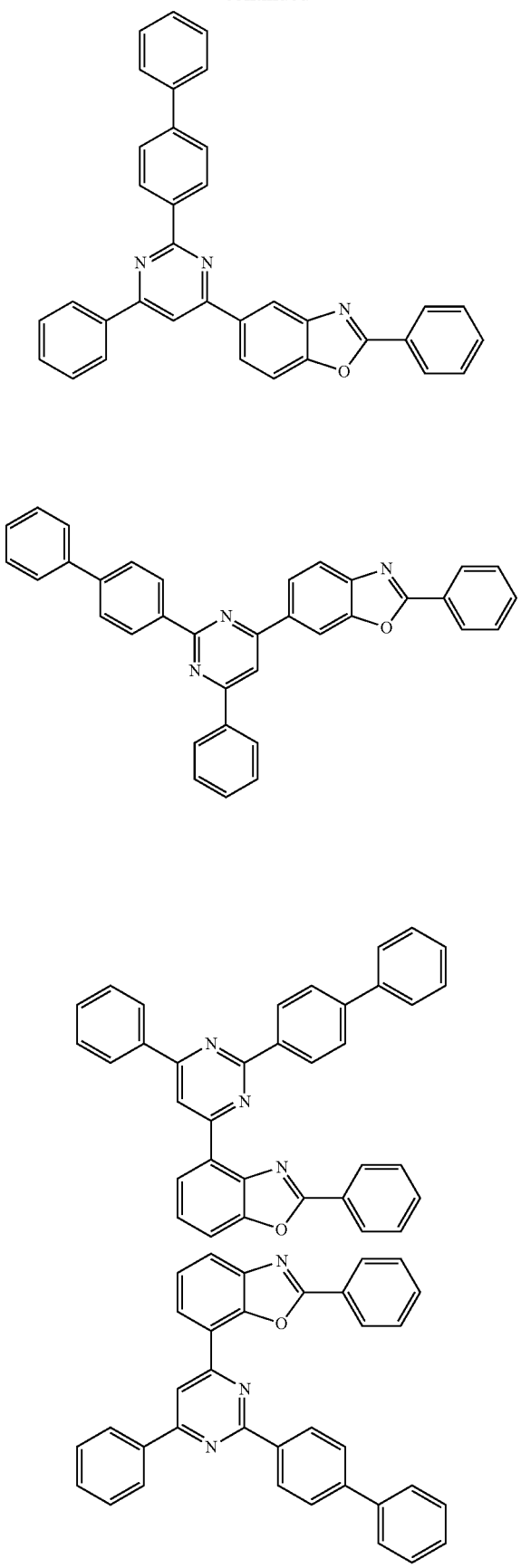
42
-continued
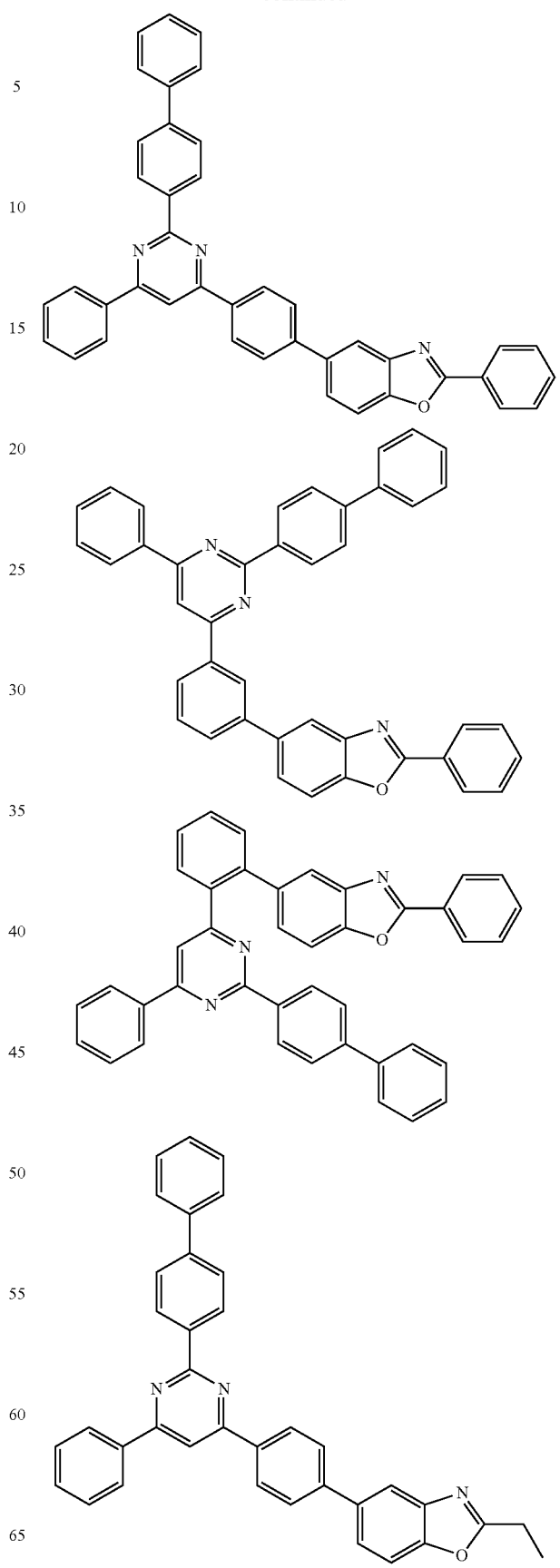

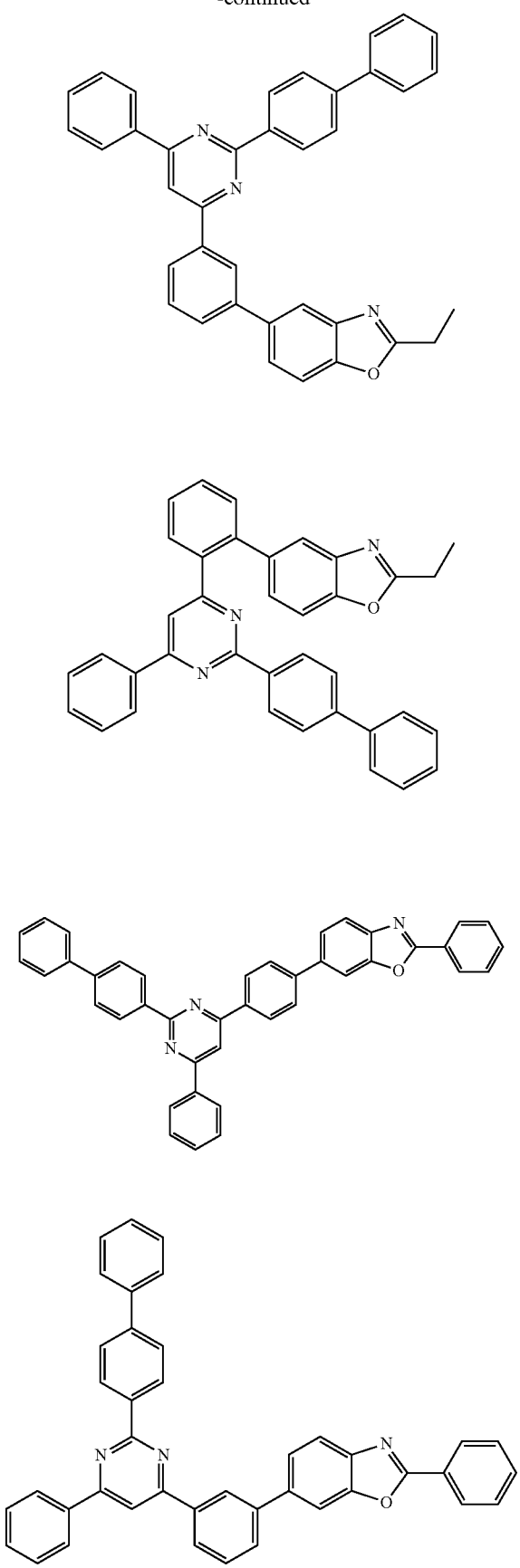

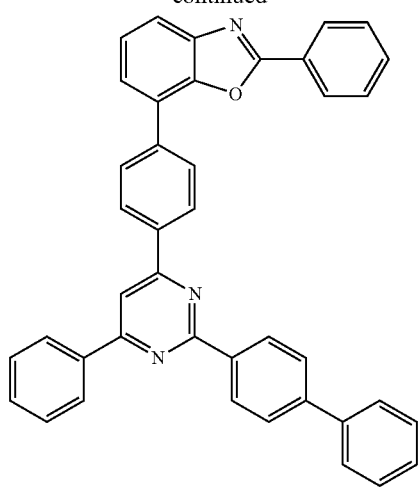
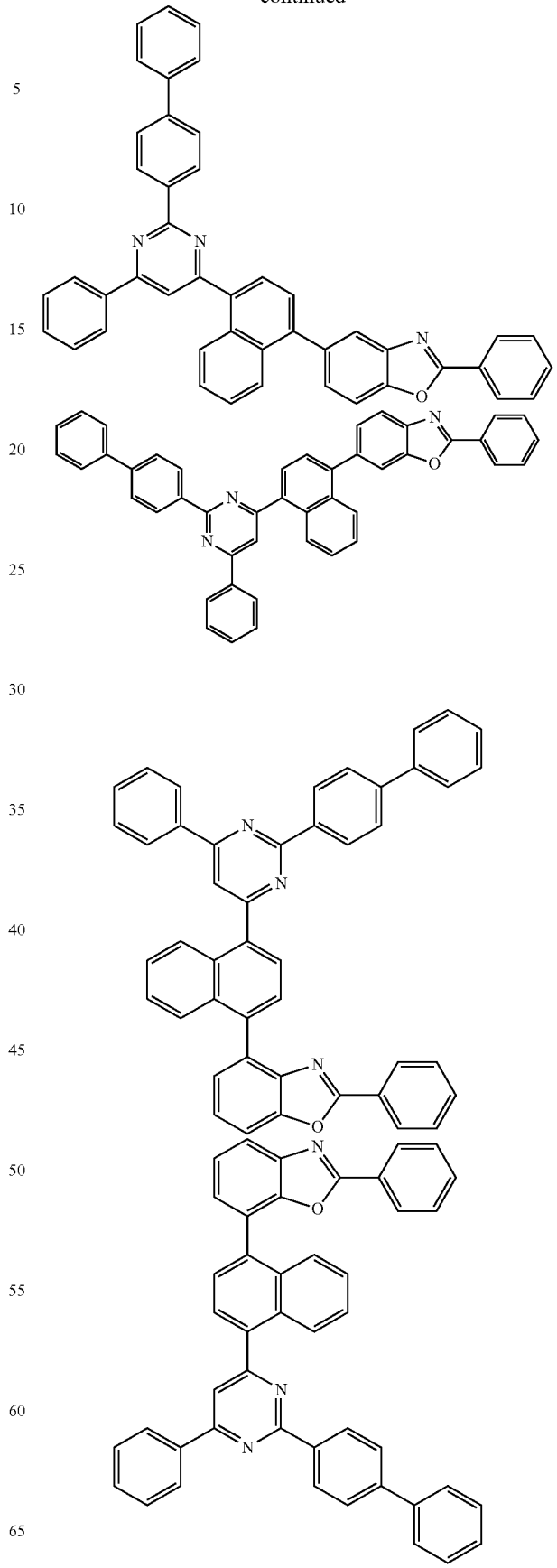

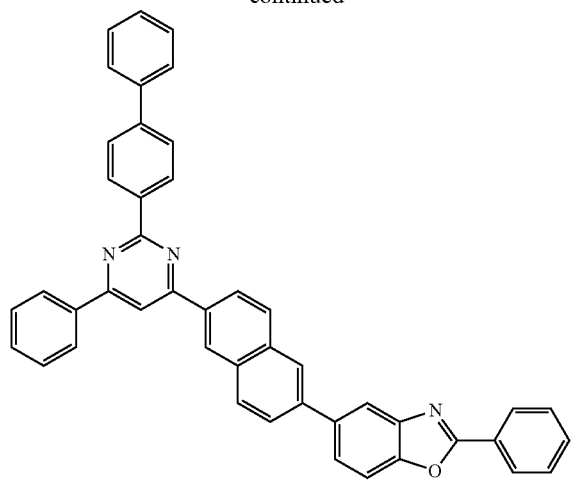
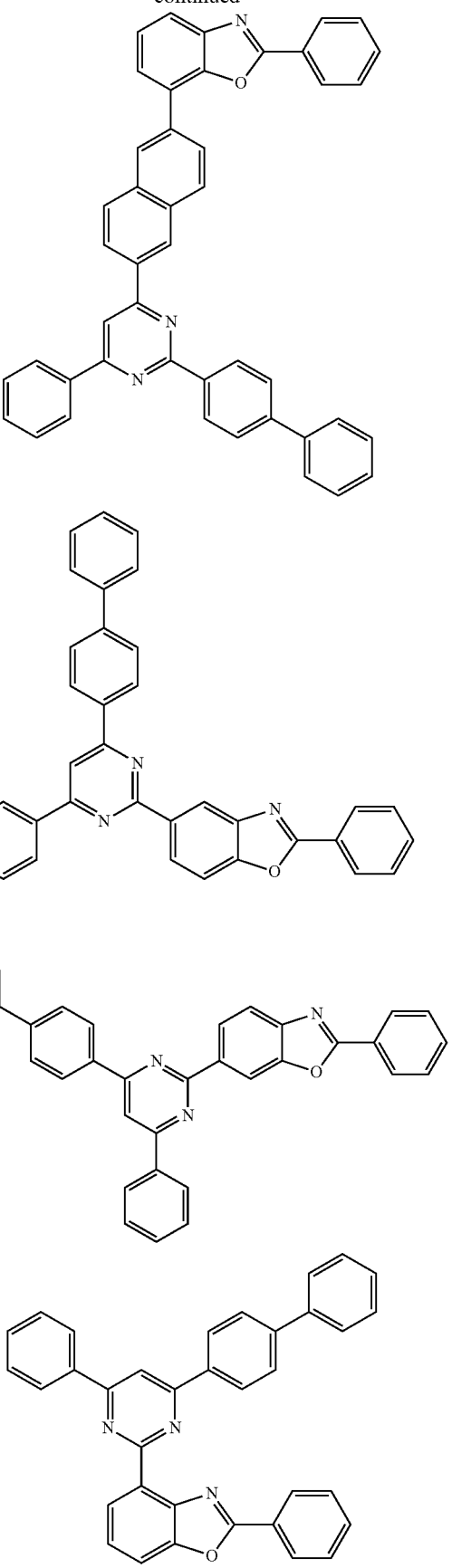

49
-continued
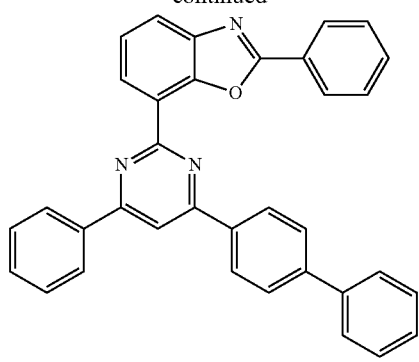
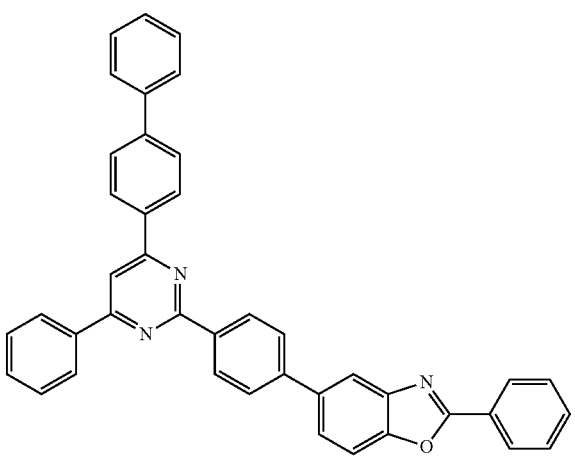
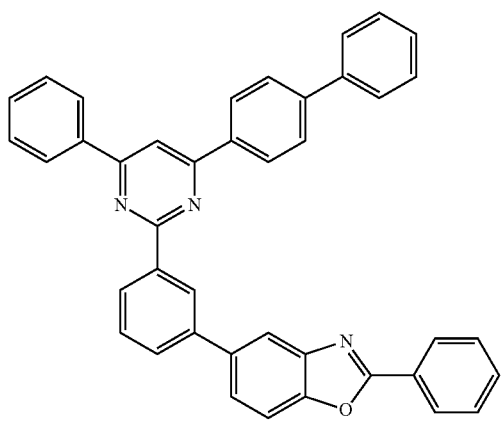
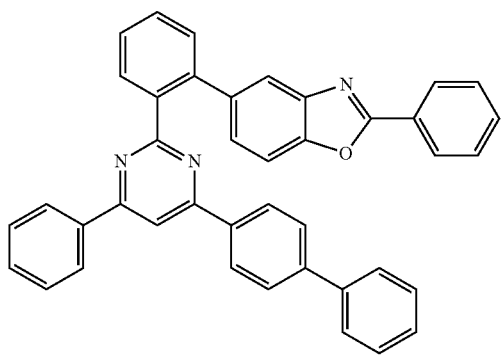
50
-continued
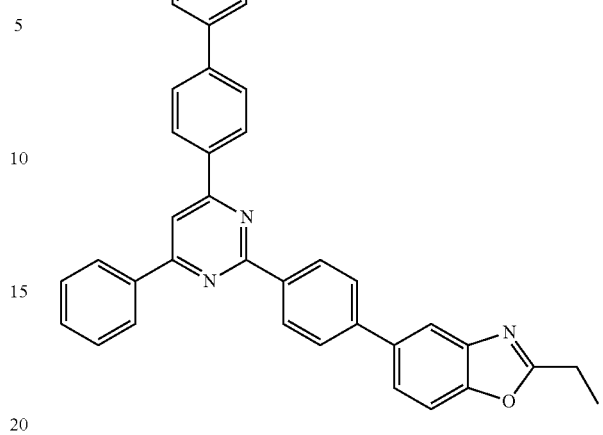
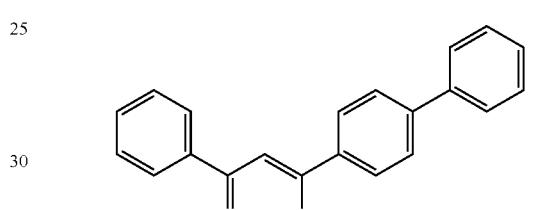
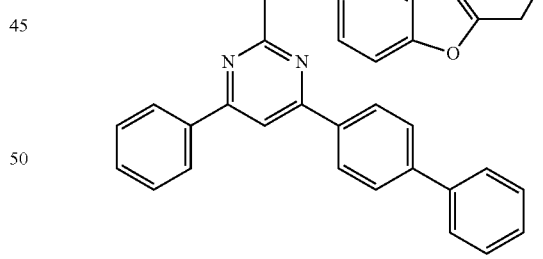
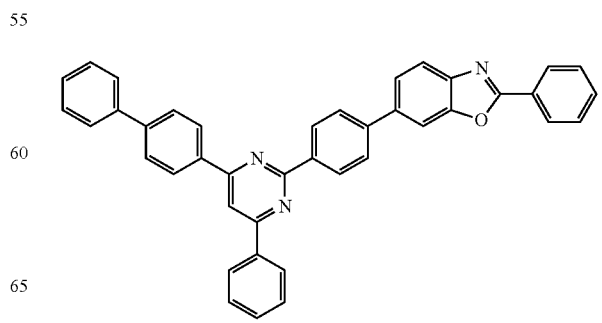

51
-continued
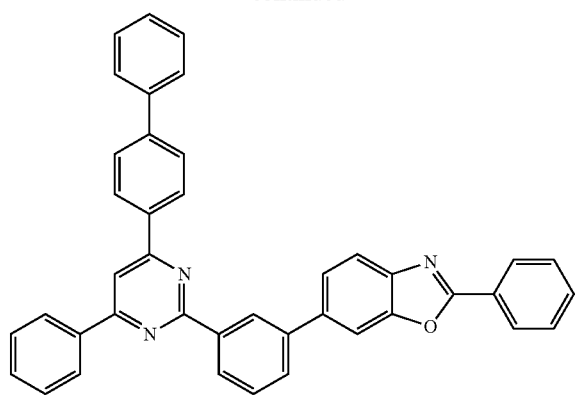
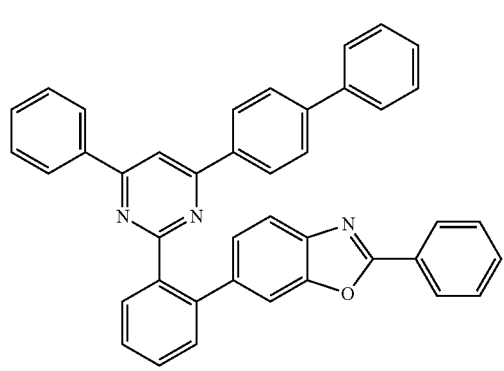
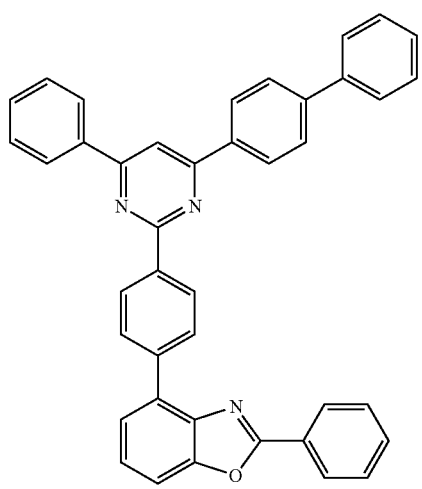
52
-continued
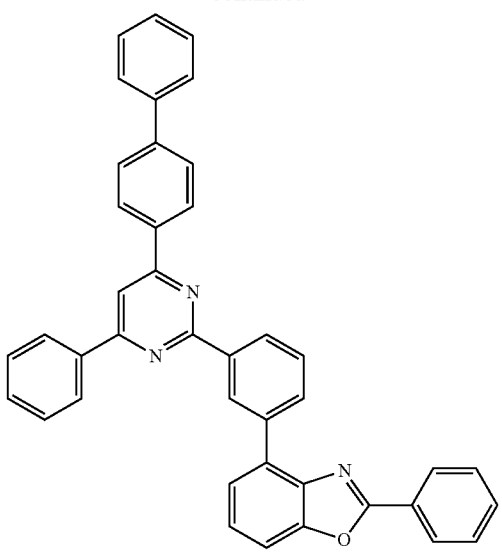
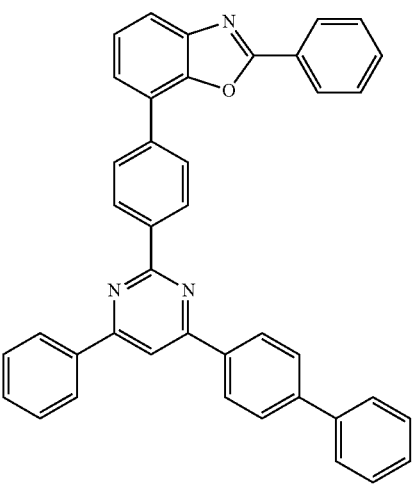

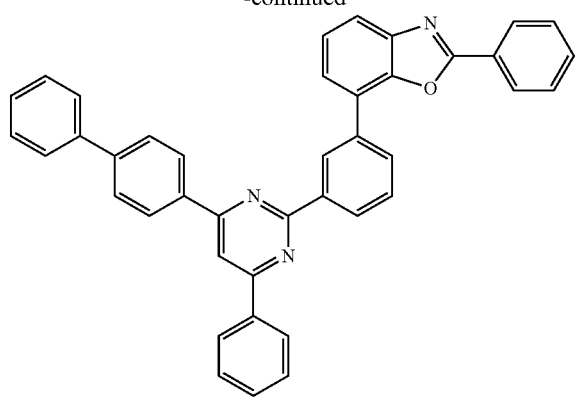
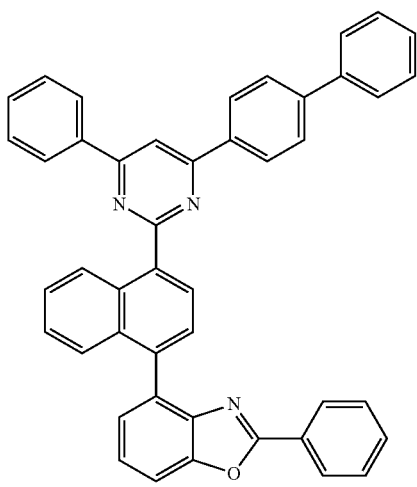
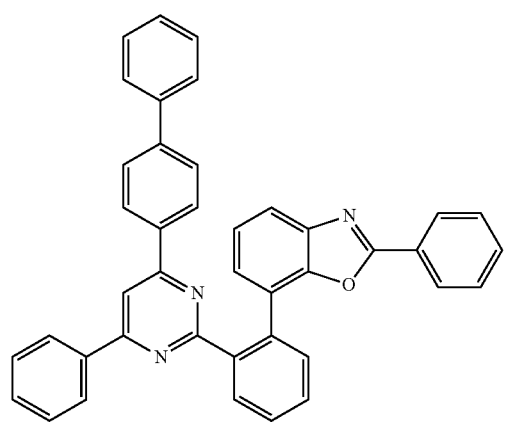
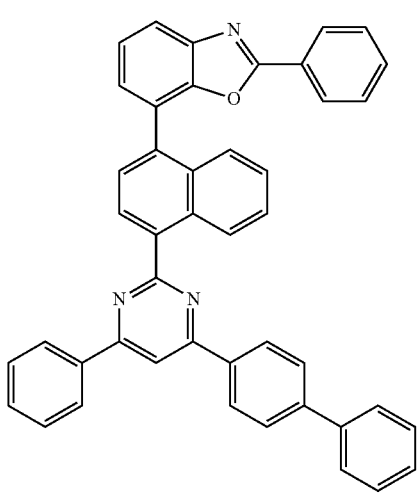
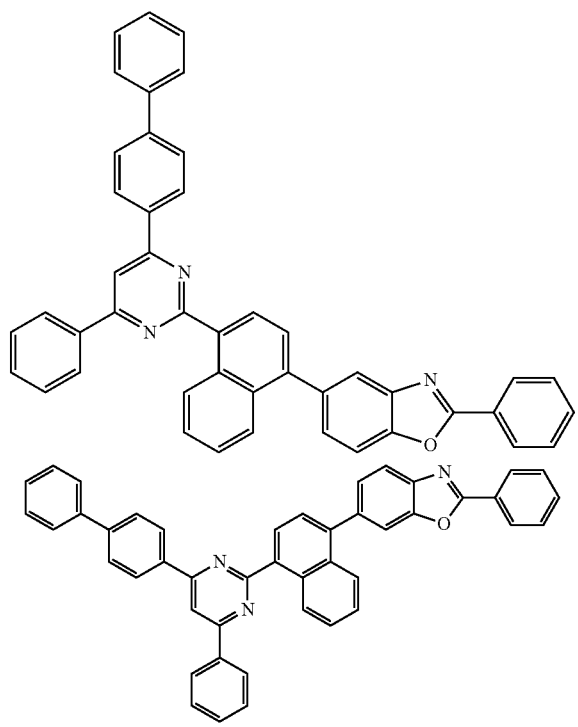

-continued
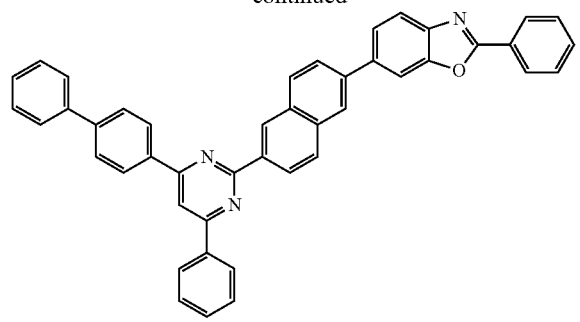
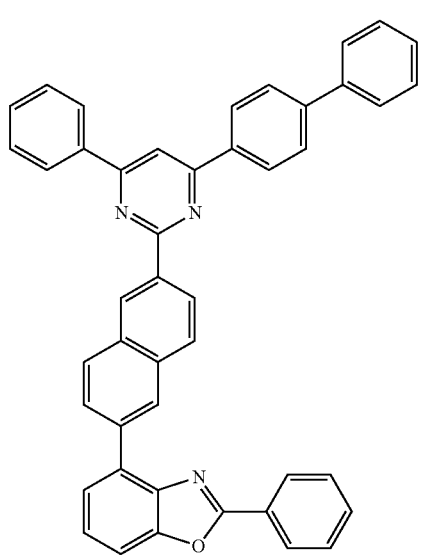
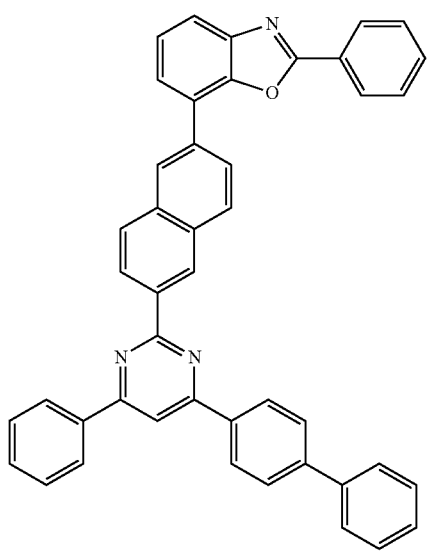
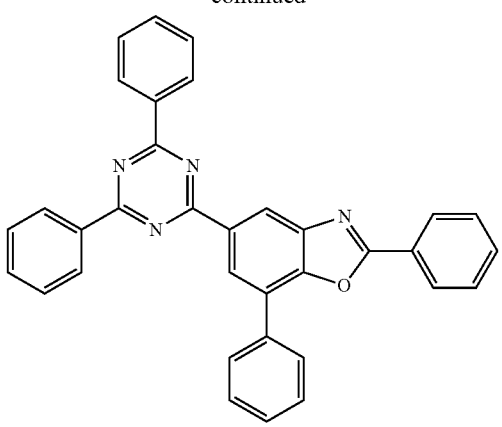

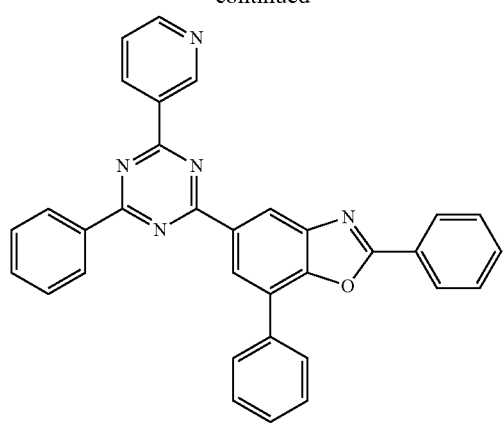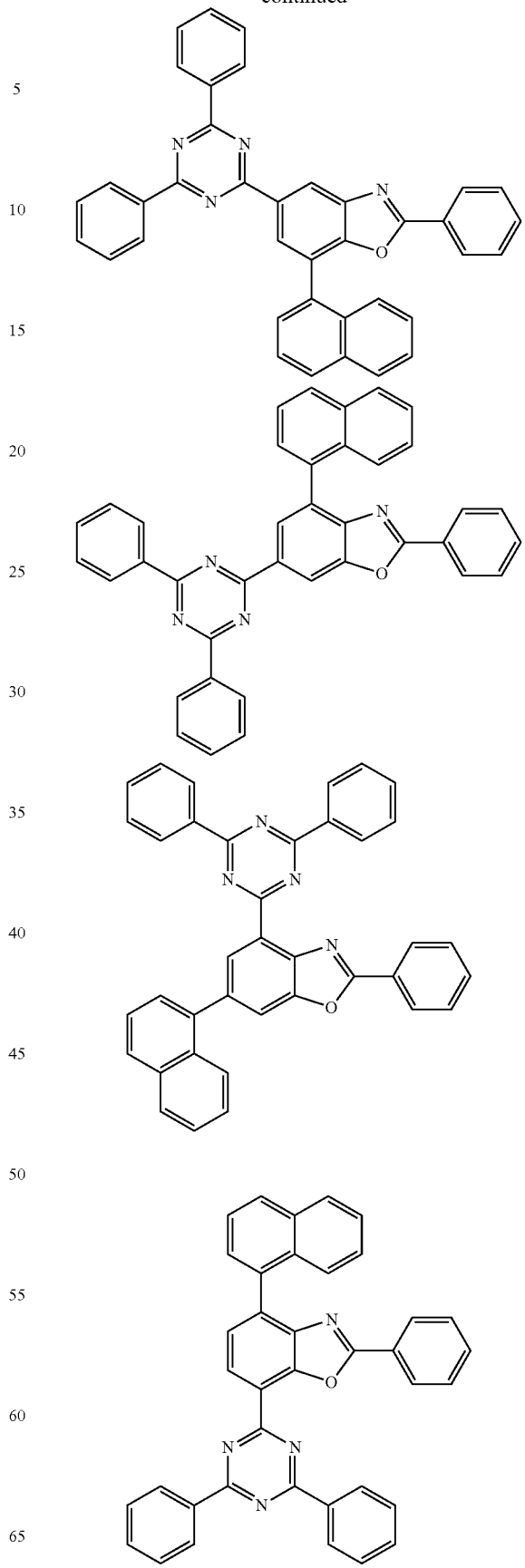

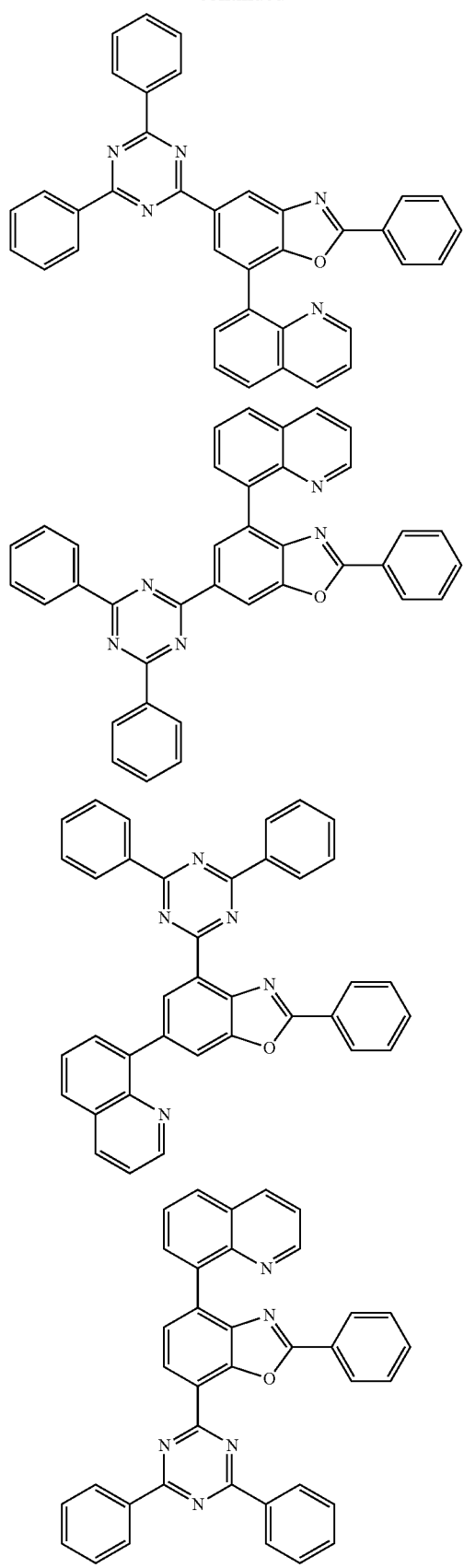

61
-continued
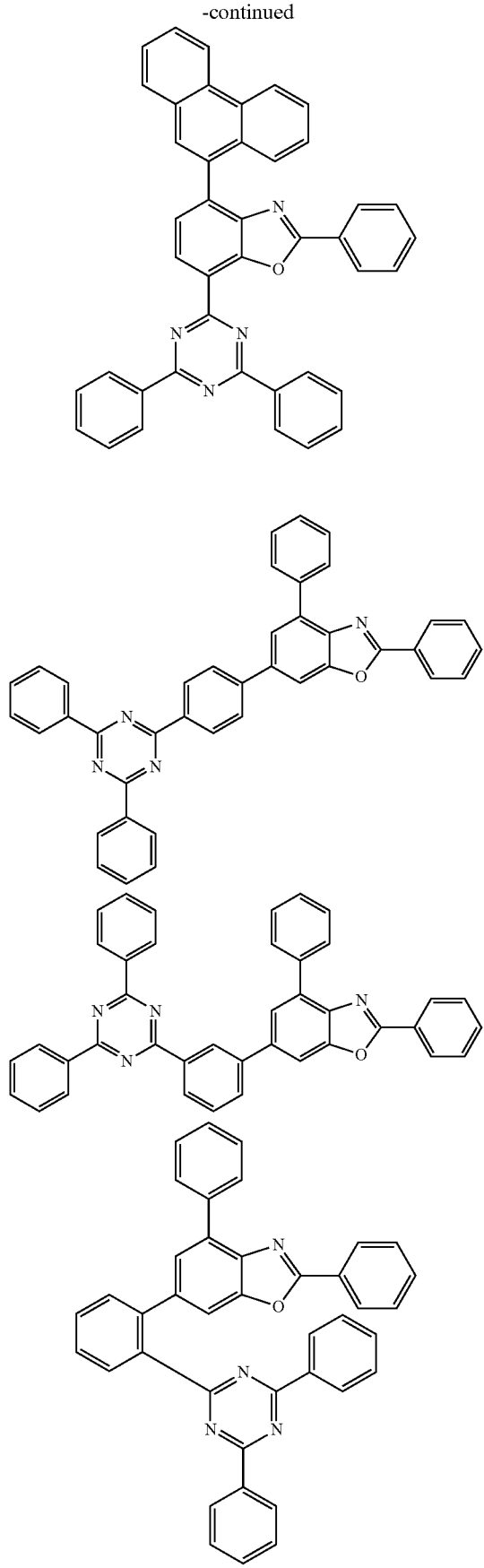
62
-continued
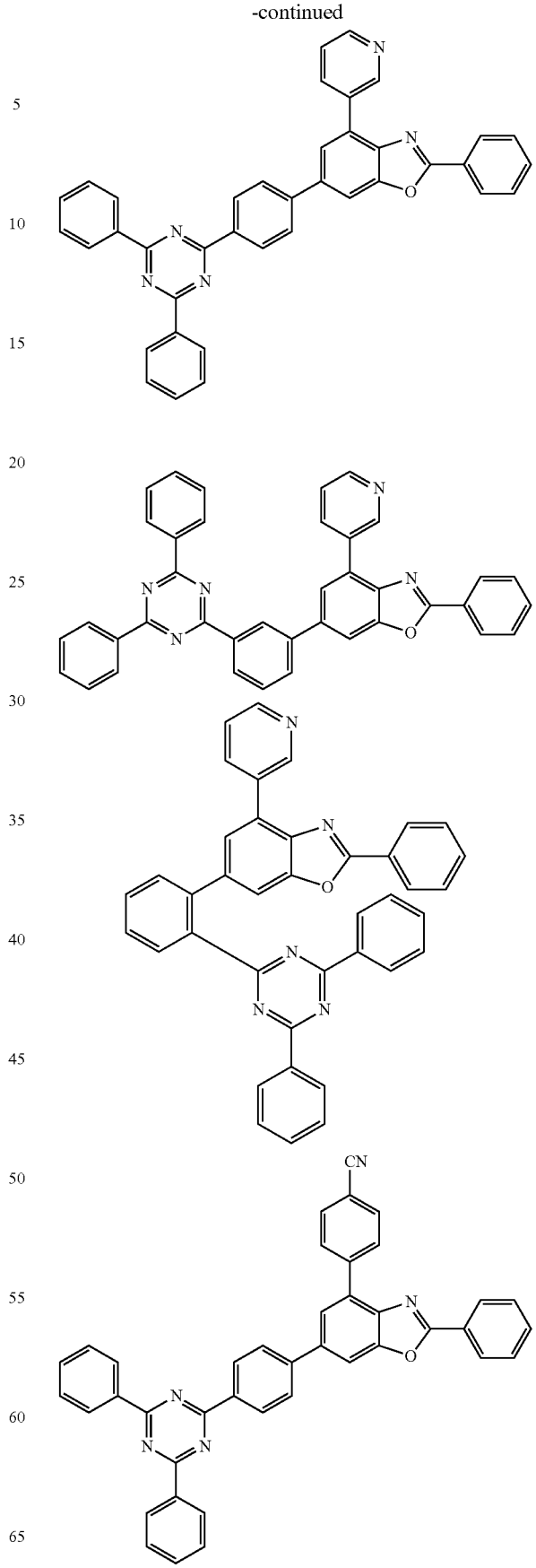

-continued
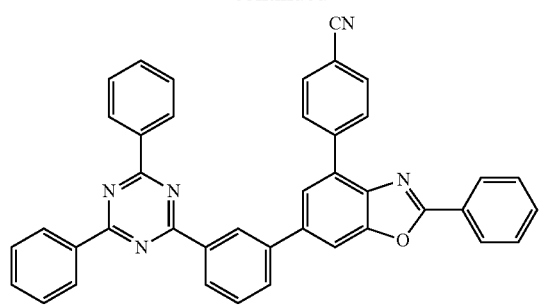
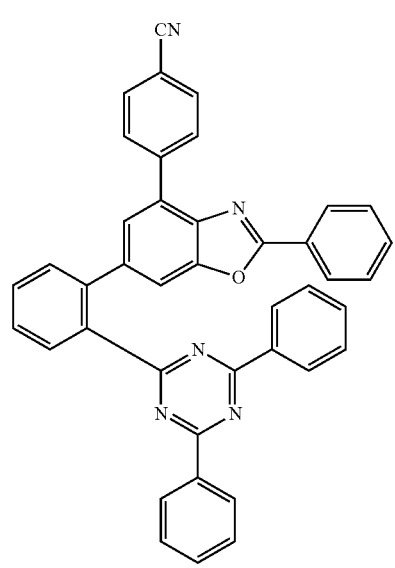
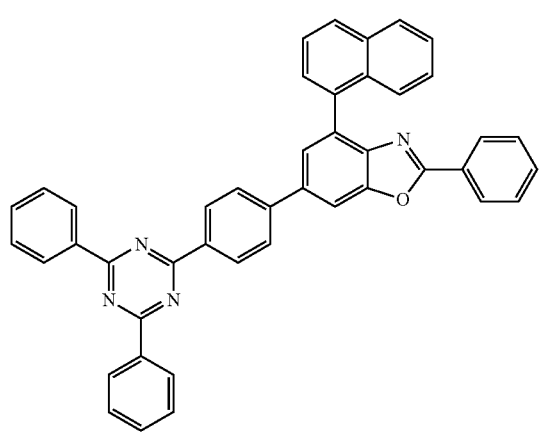
LT18-30-065
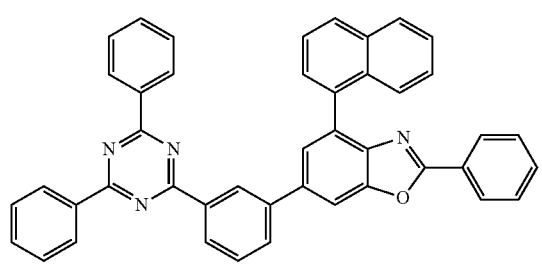
-continued
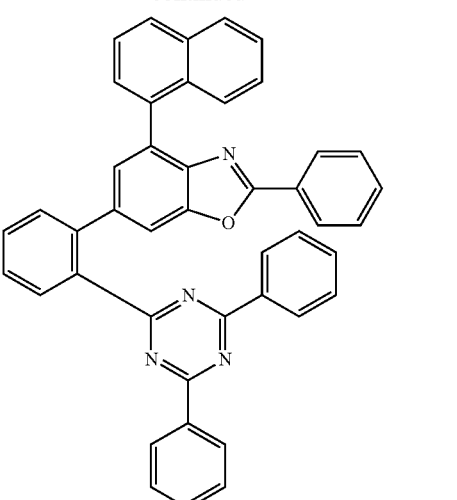
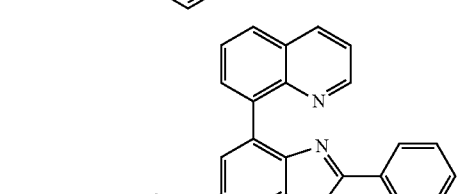
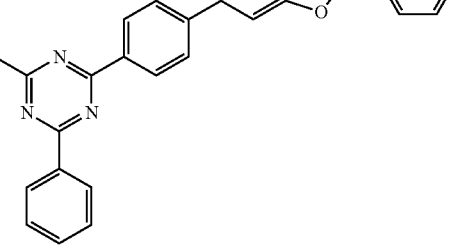
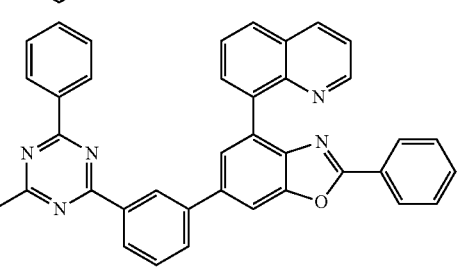
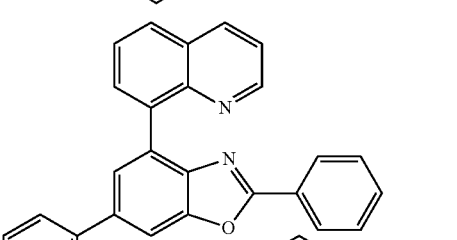
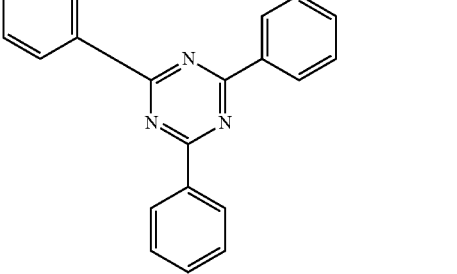

-continued
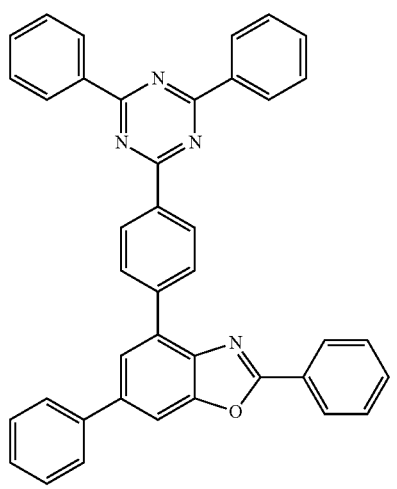
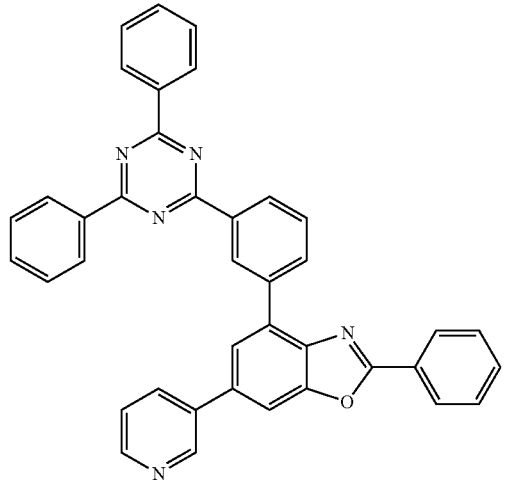
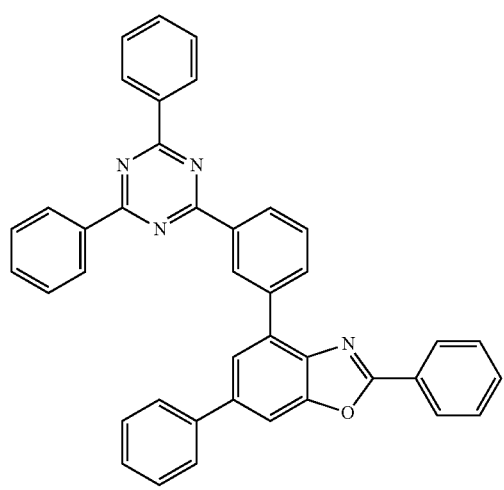
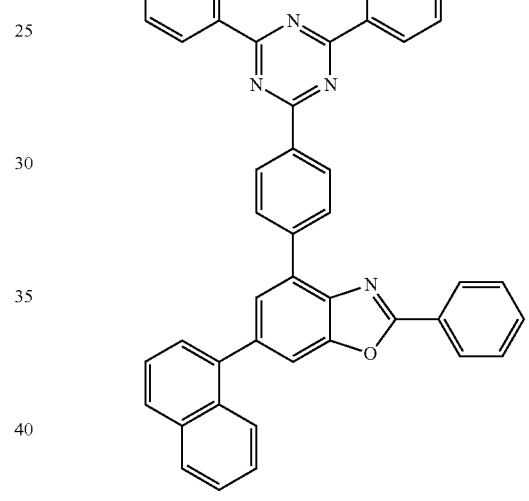
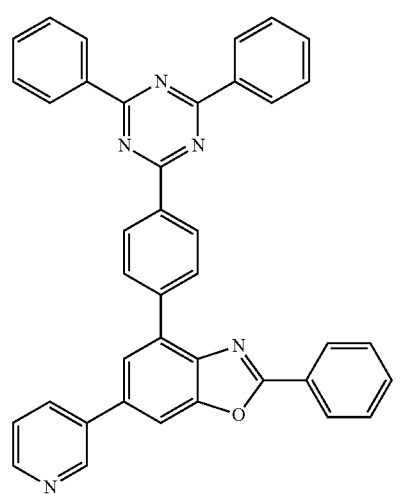
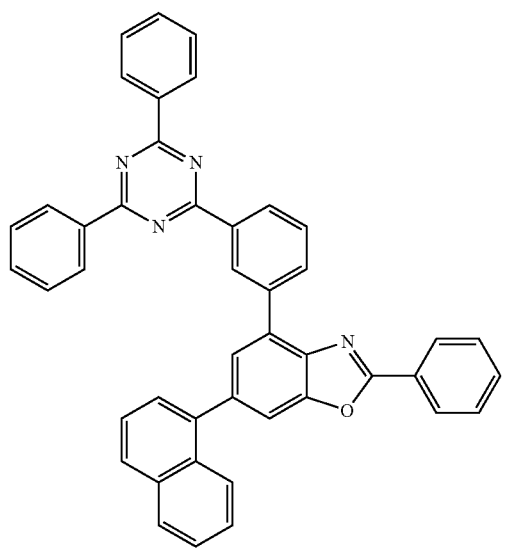

67
-continued
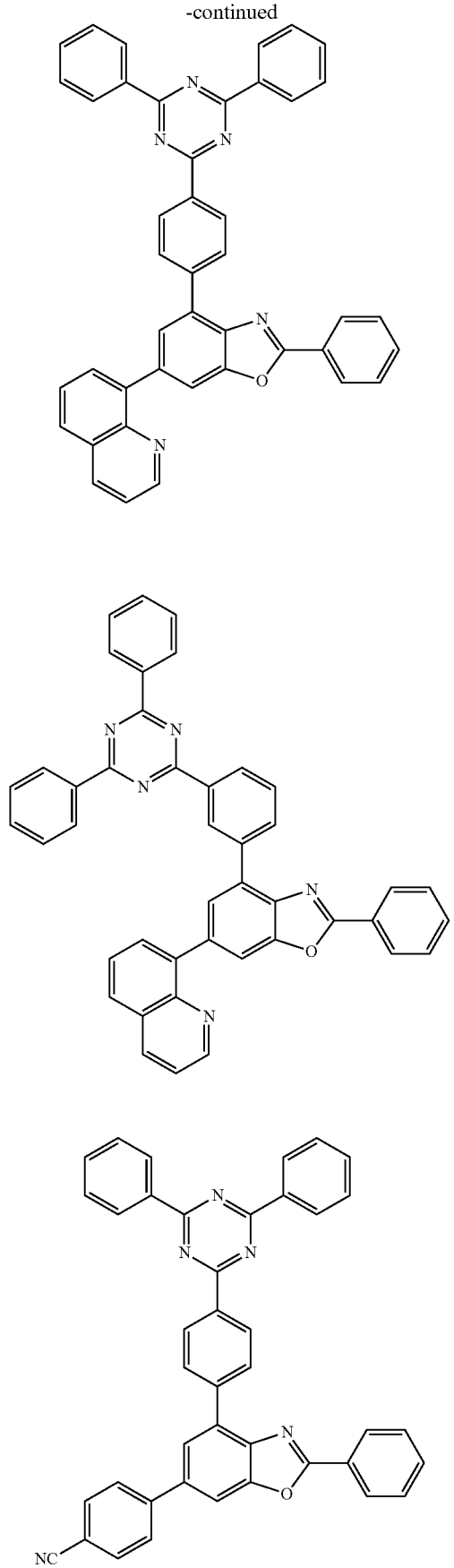
68
-continued
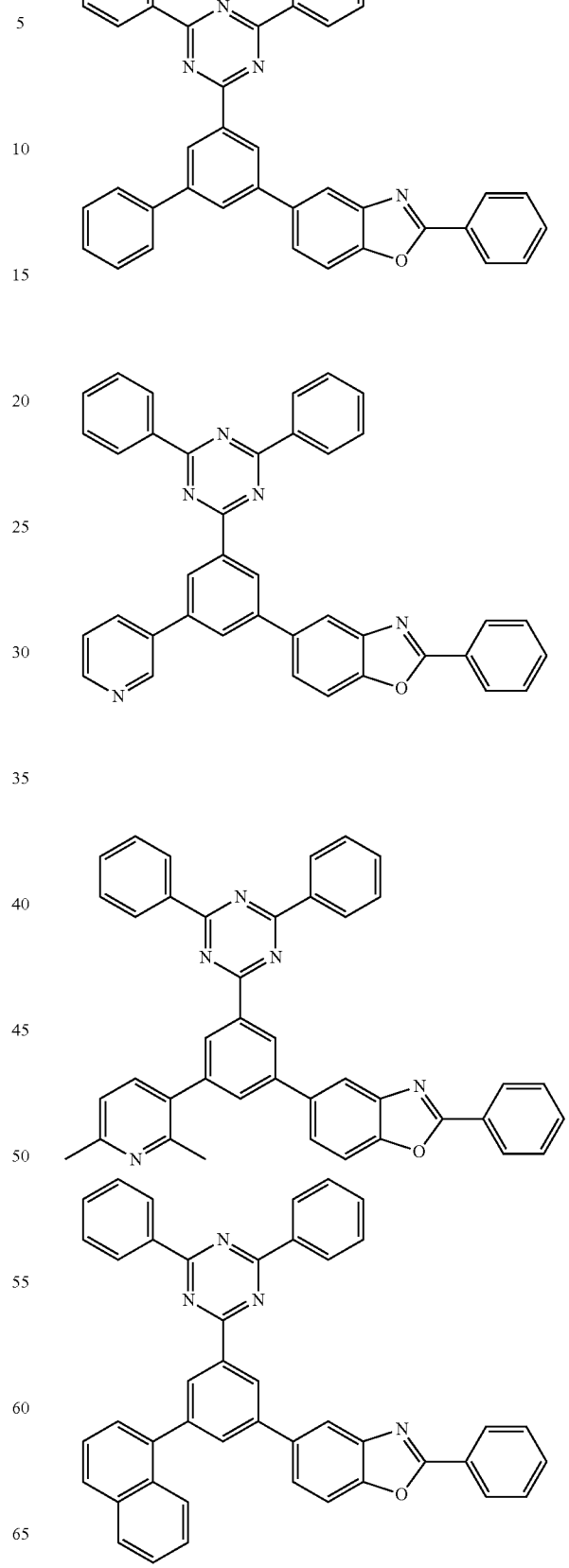

69
-continued
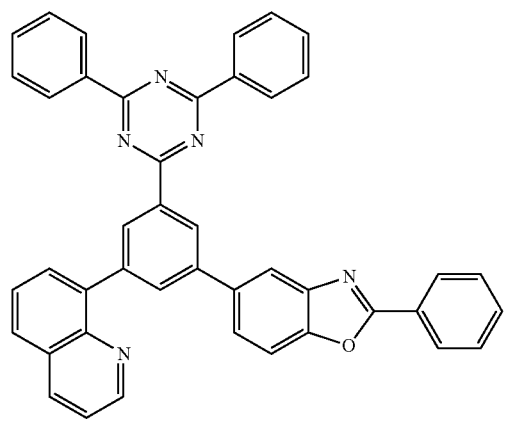
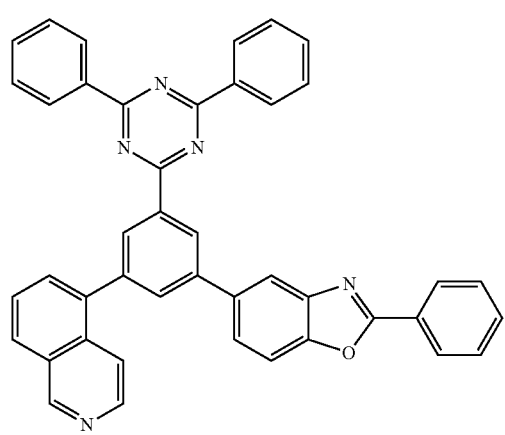
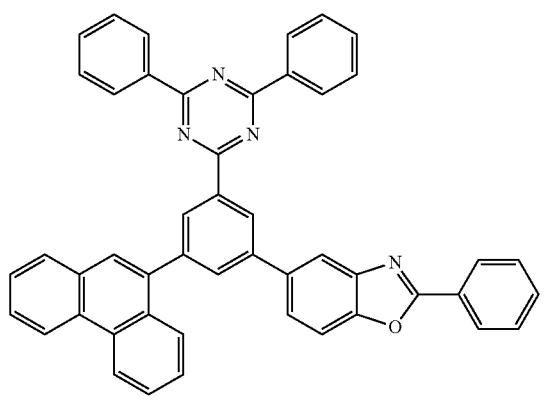
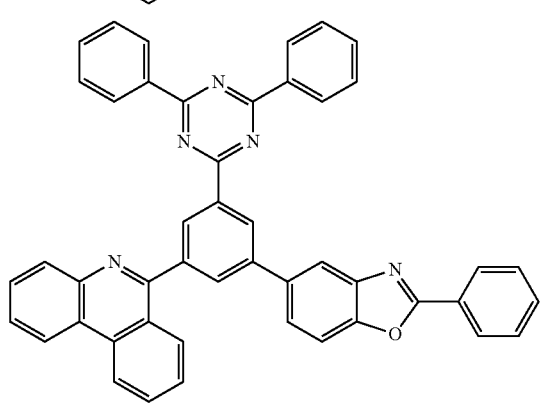
70
-continued
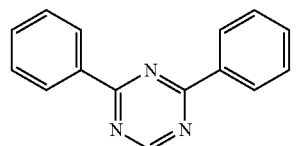
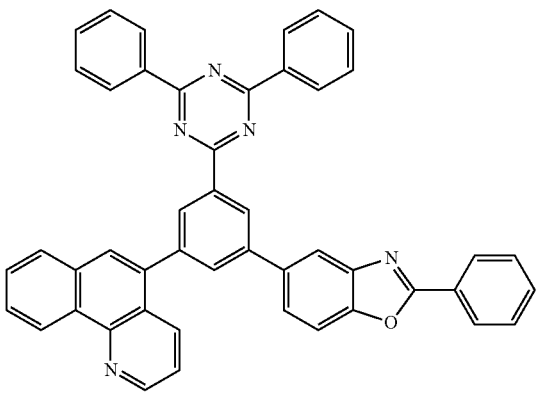
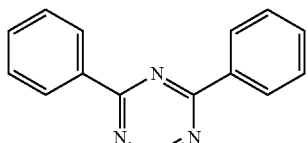
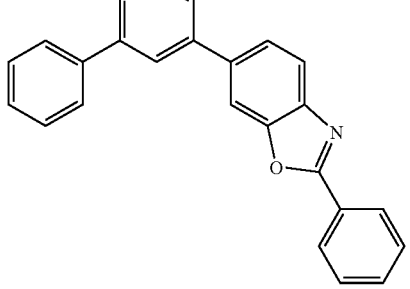
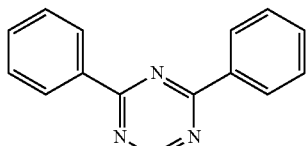
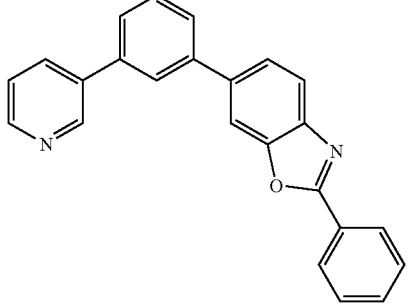

71
-continued
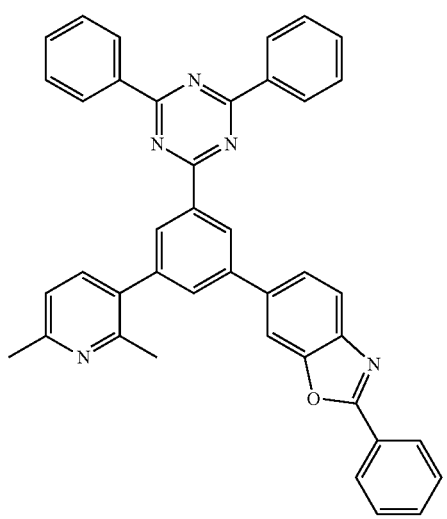
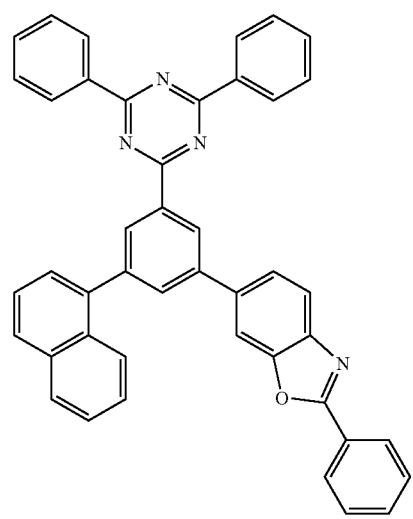
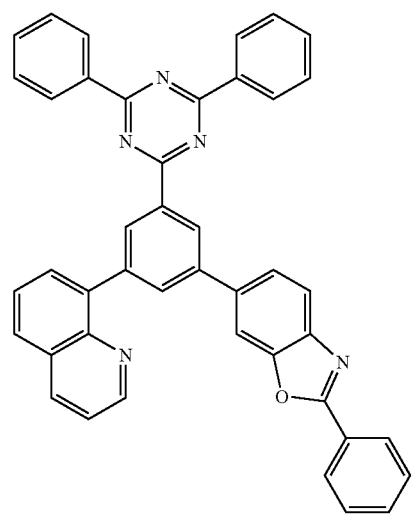
72
-continued
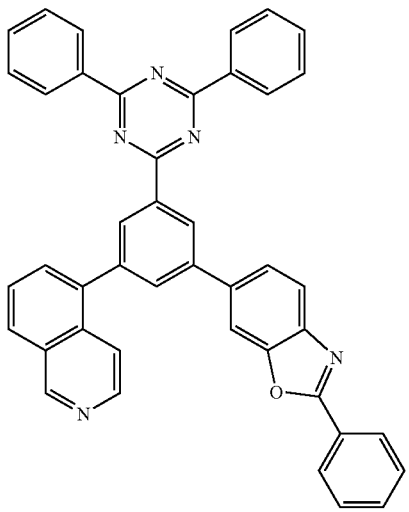
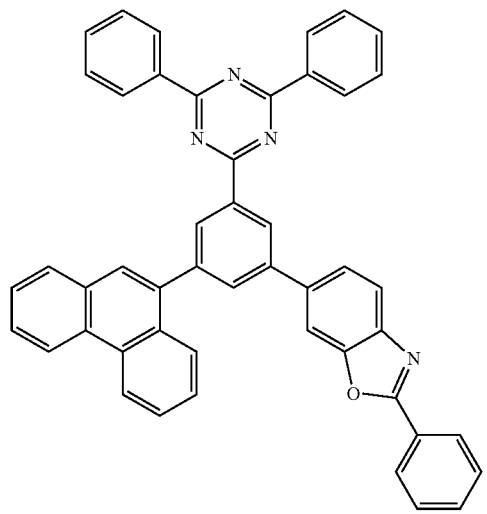
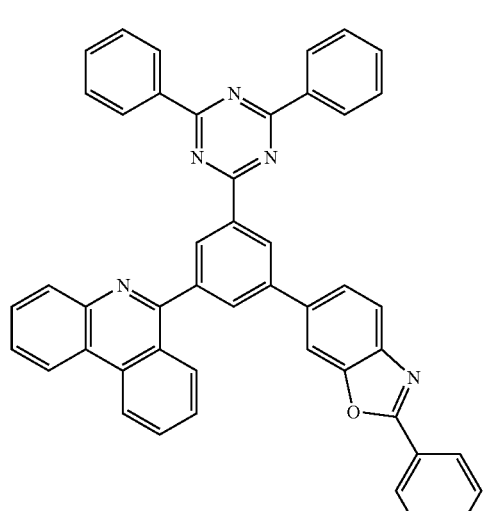

73
-continued
74
-continued
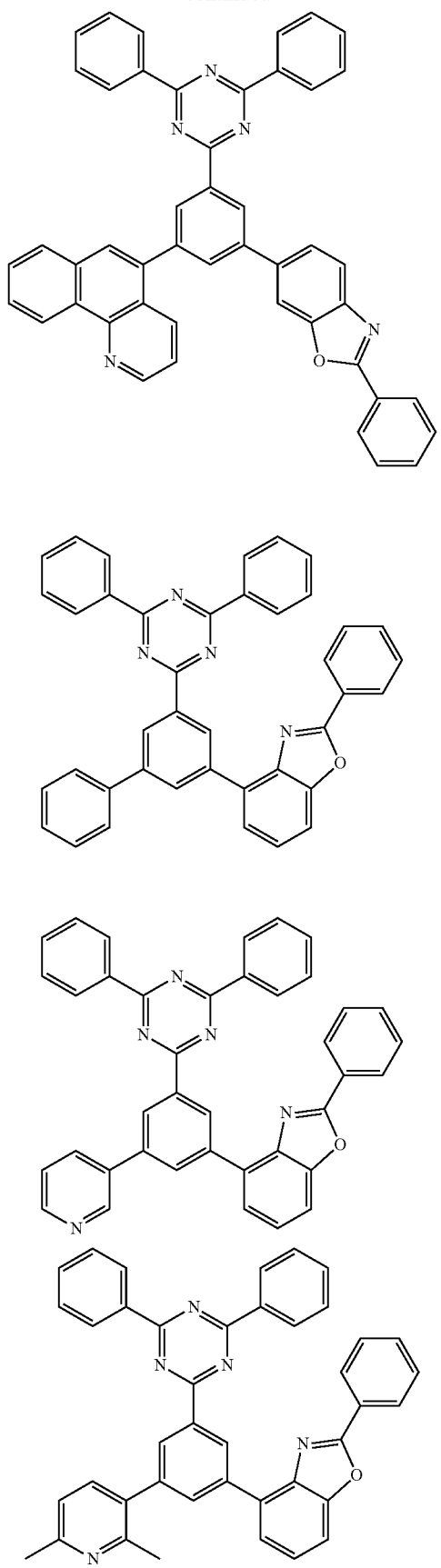
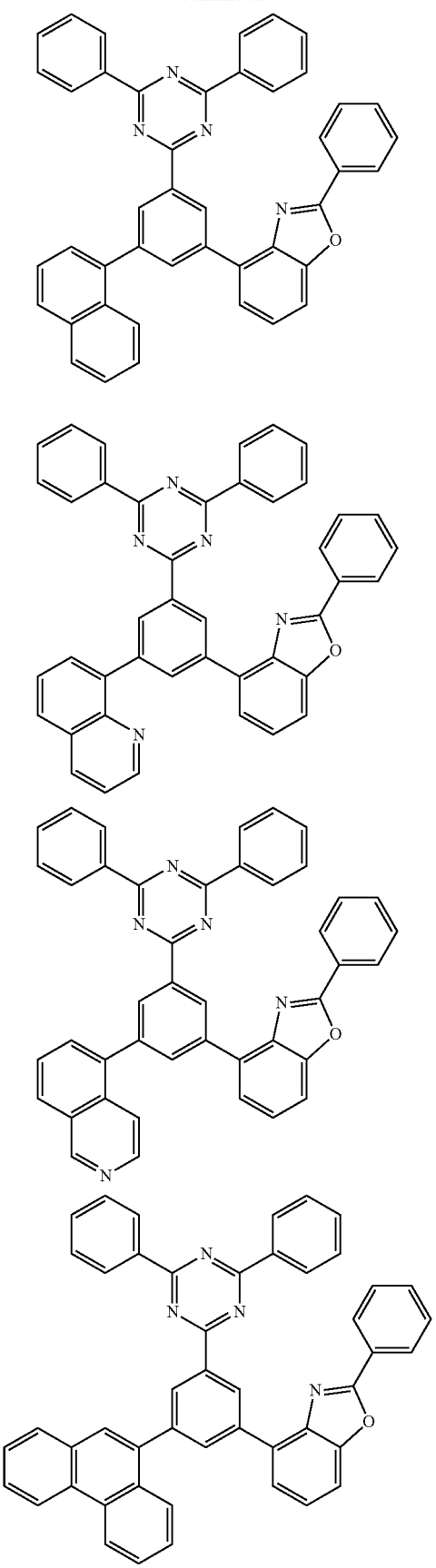

75
-continued
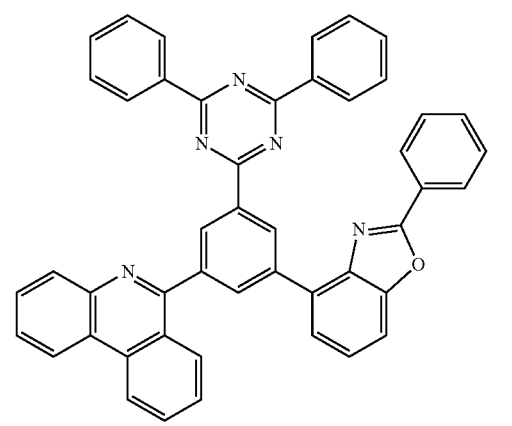
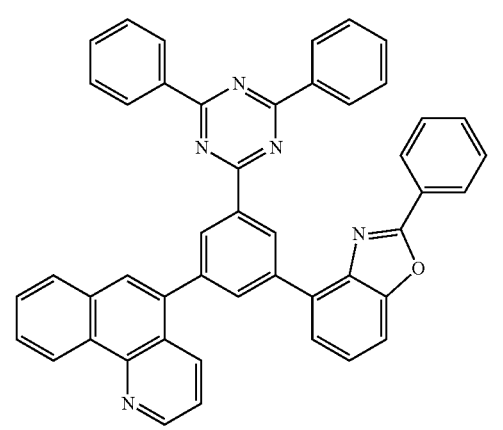
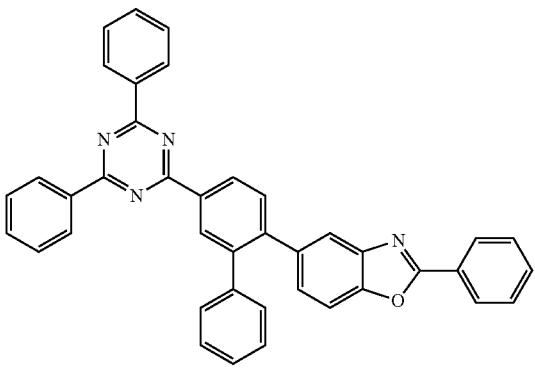
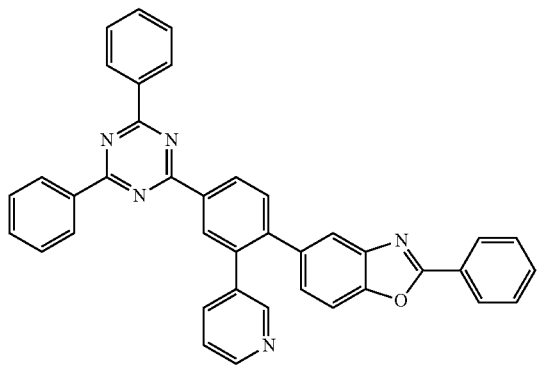
76
-continued
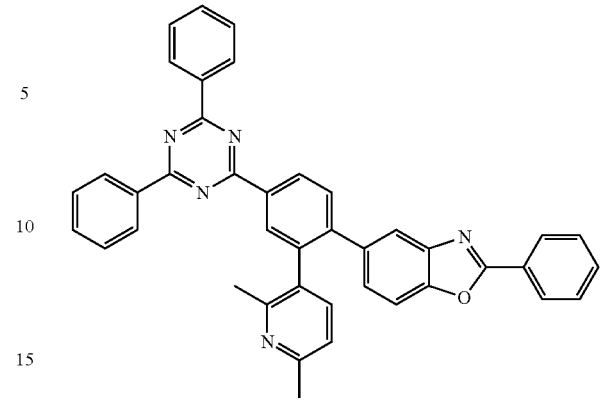
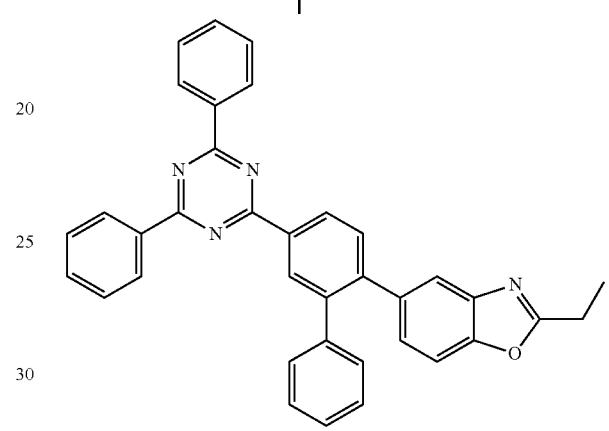
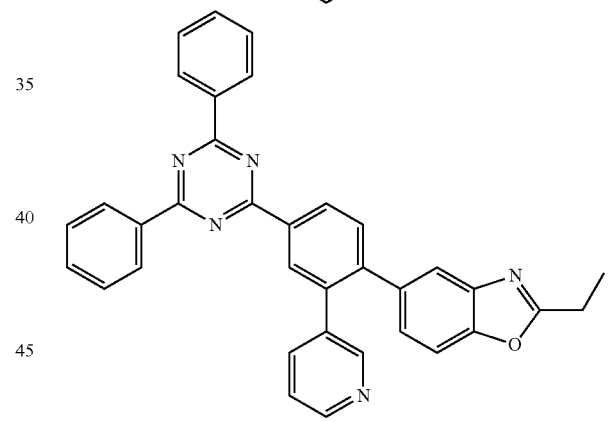
LT18-30-201
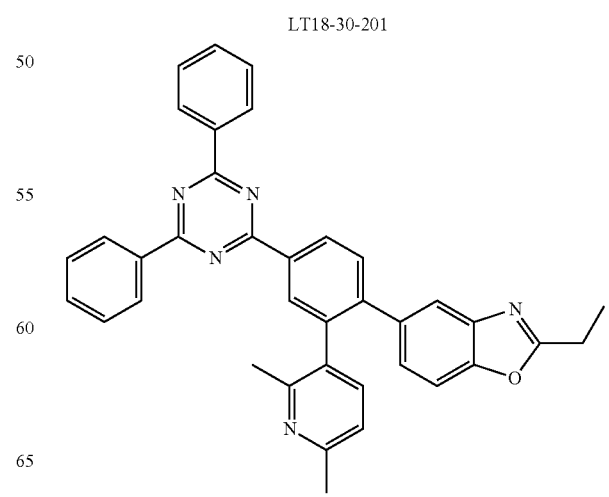

77
-continued
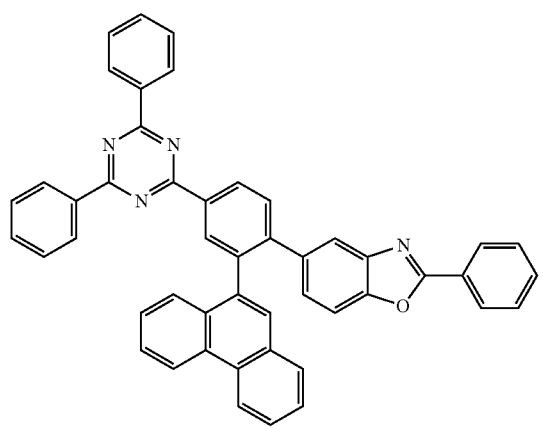
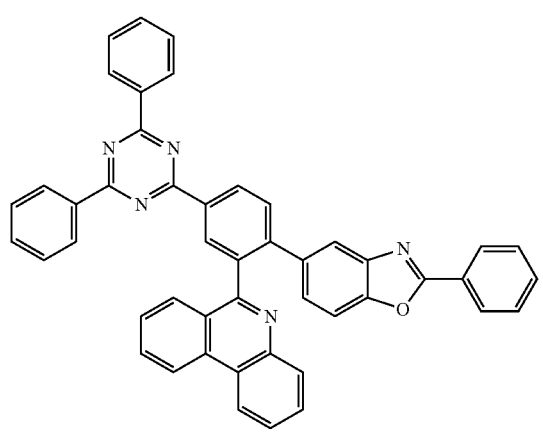
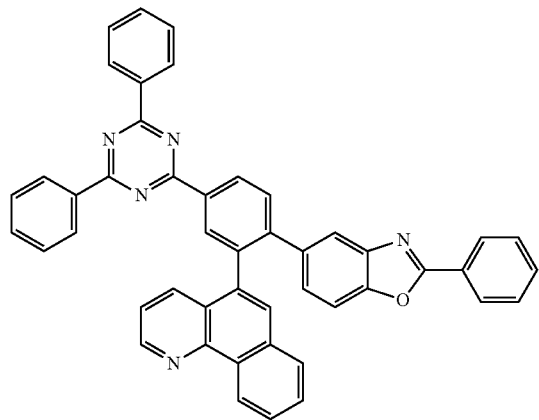
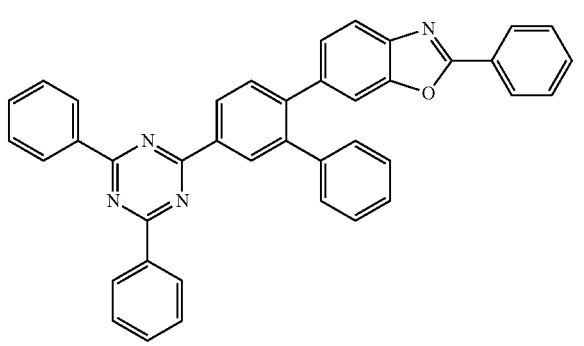
78
-continued
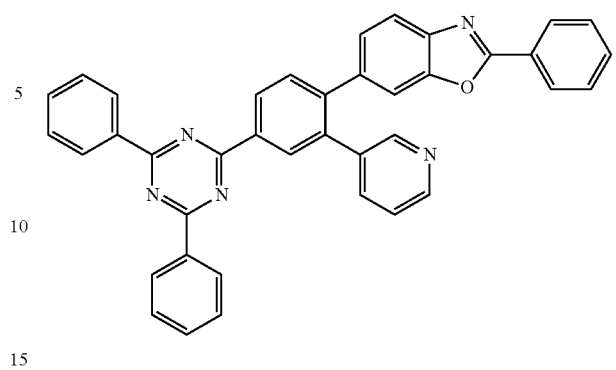
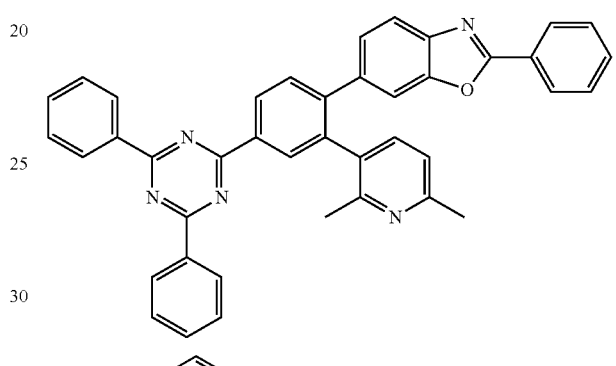
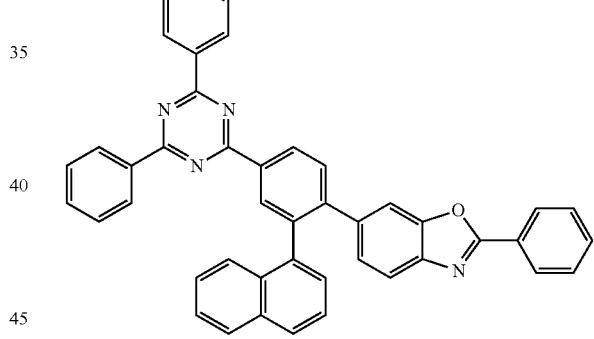
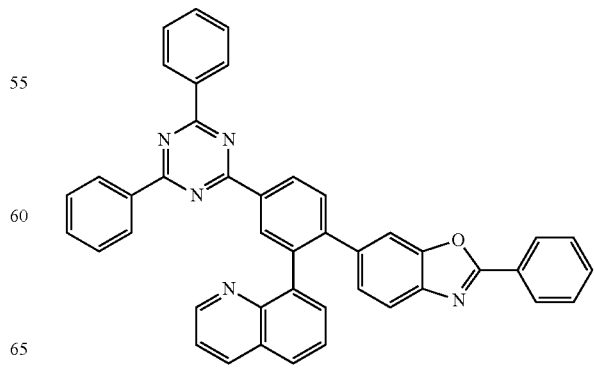

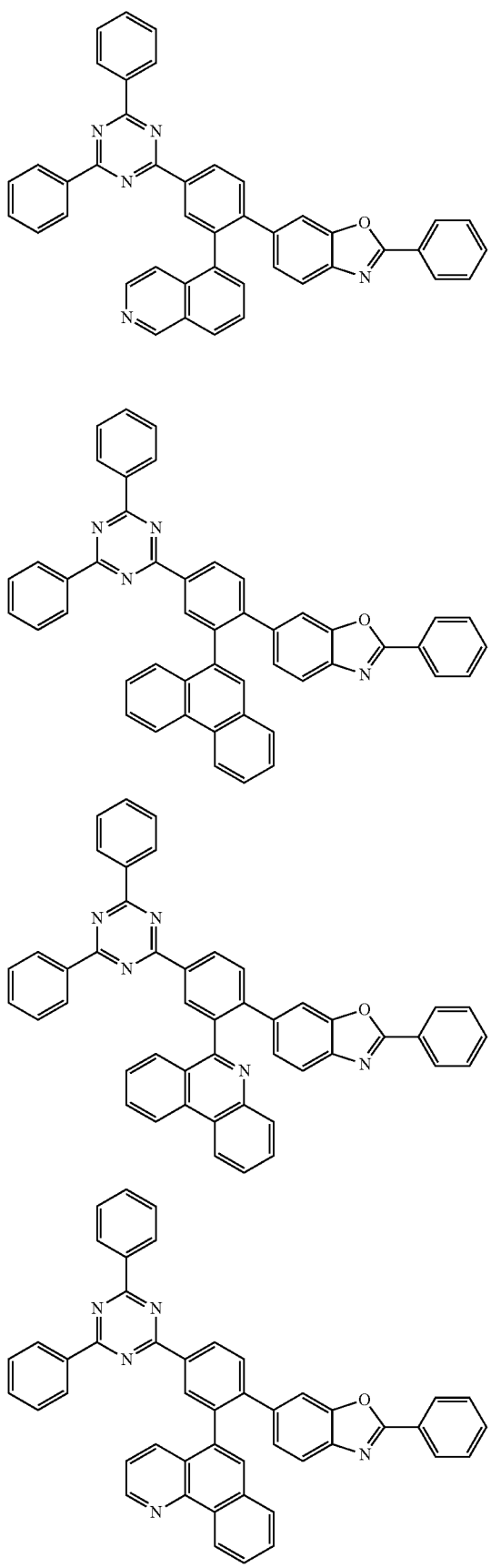
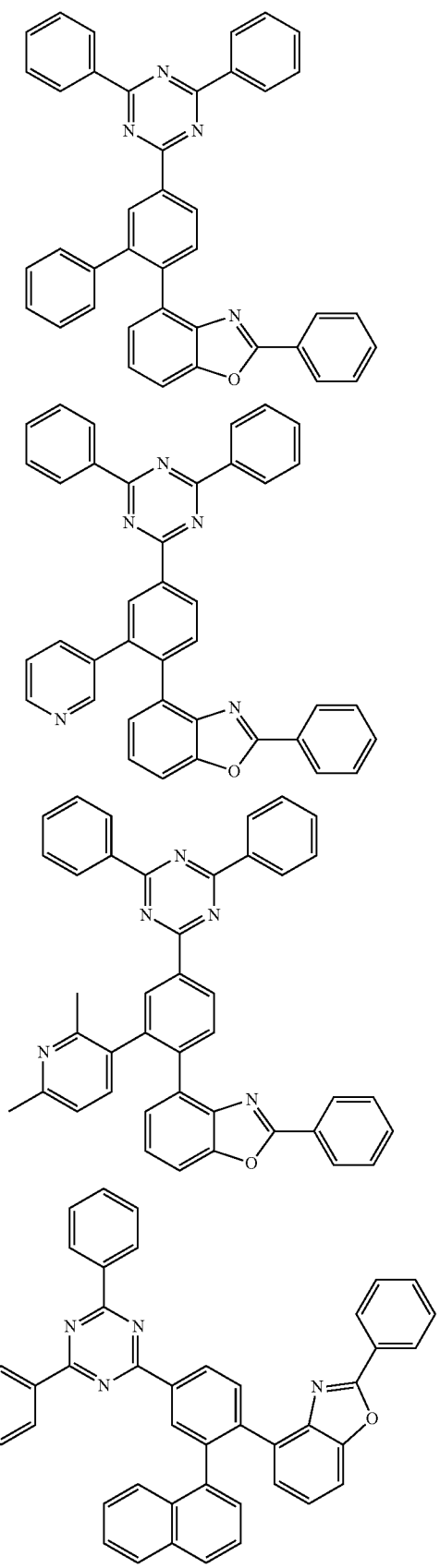

-continued
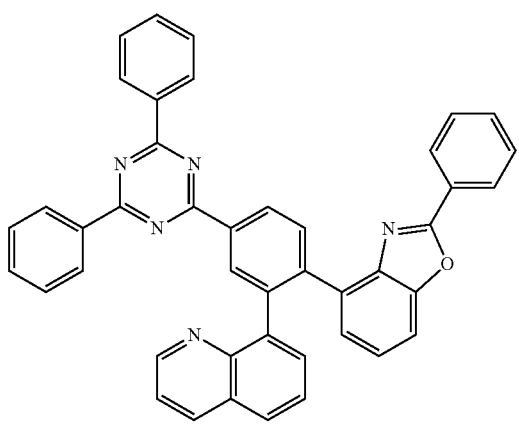
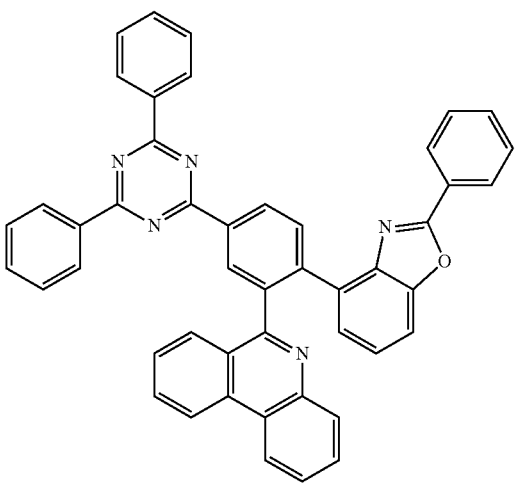
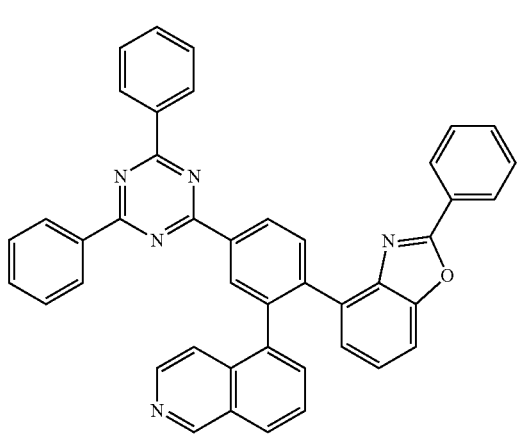
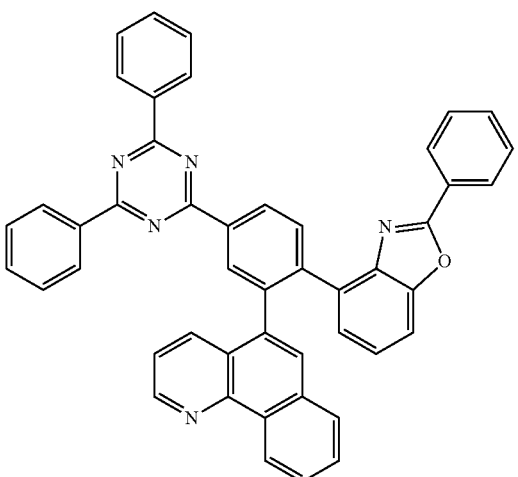
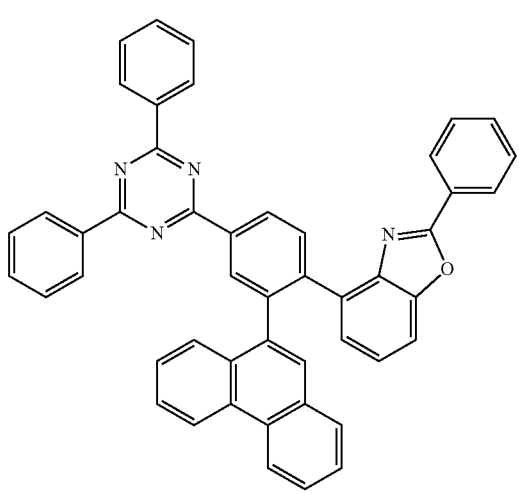
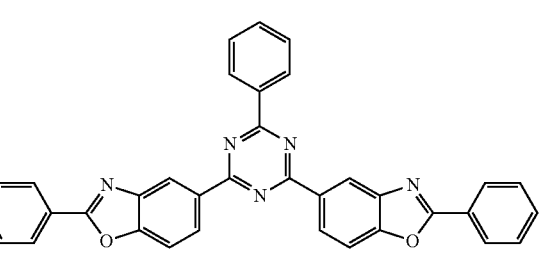

-continued
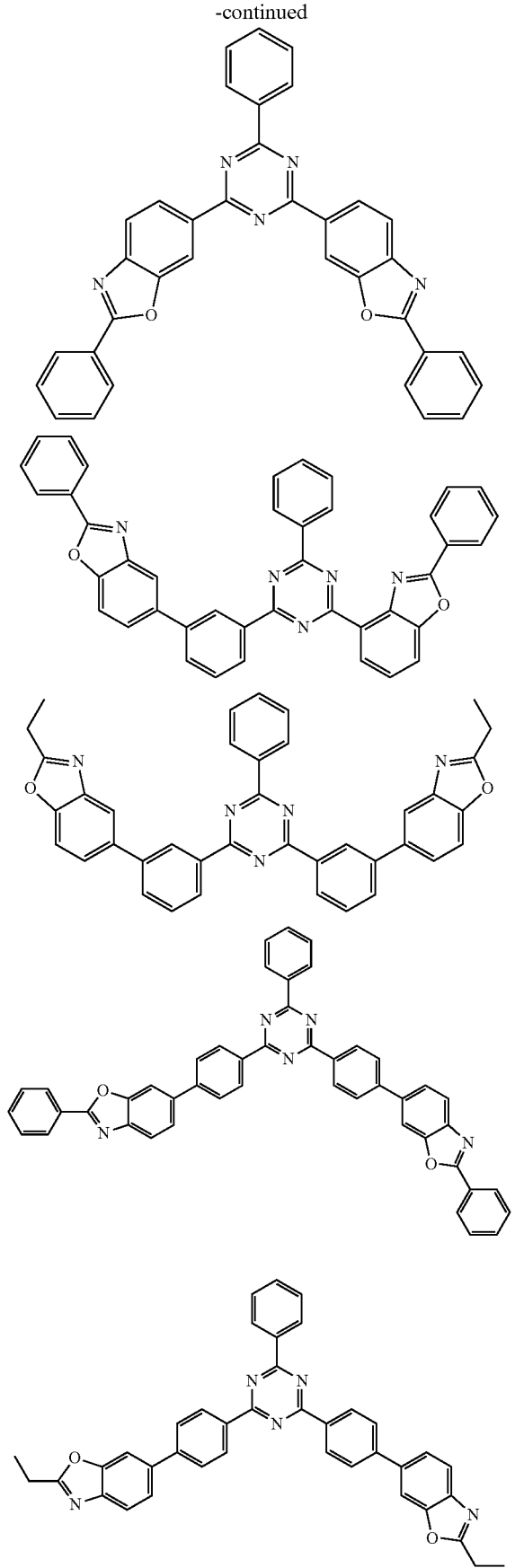
-continued
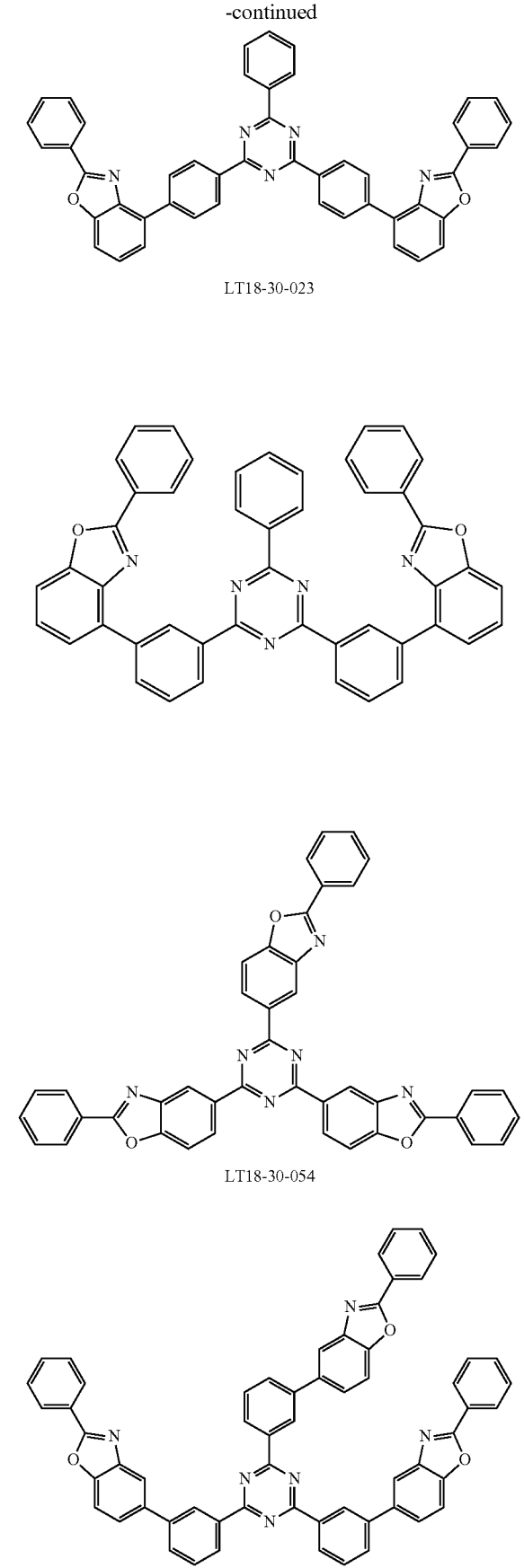
LT18-30-023
LT18-30-054

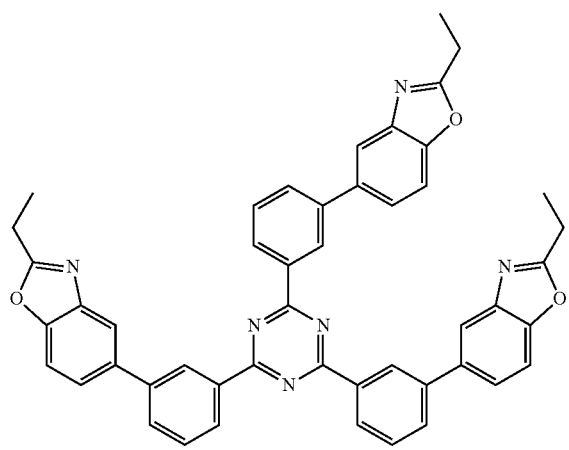
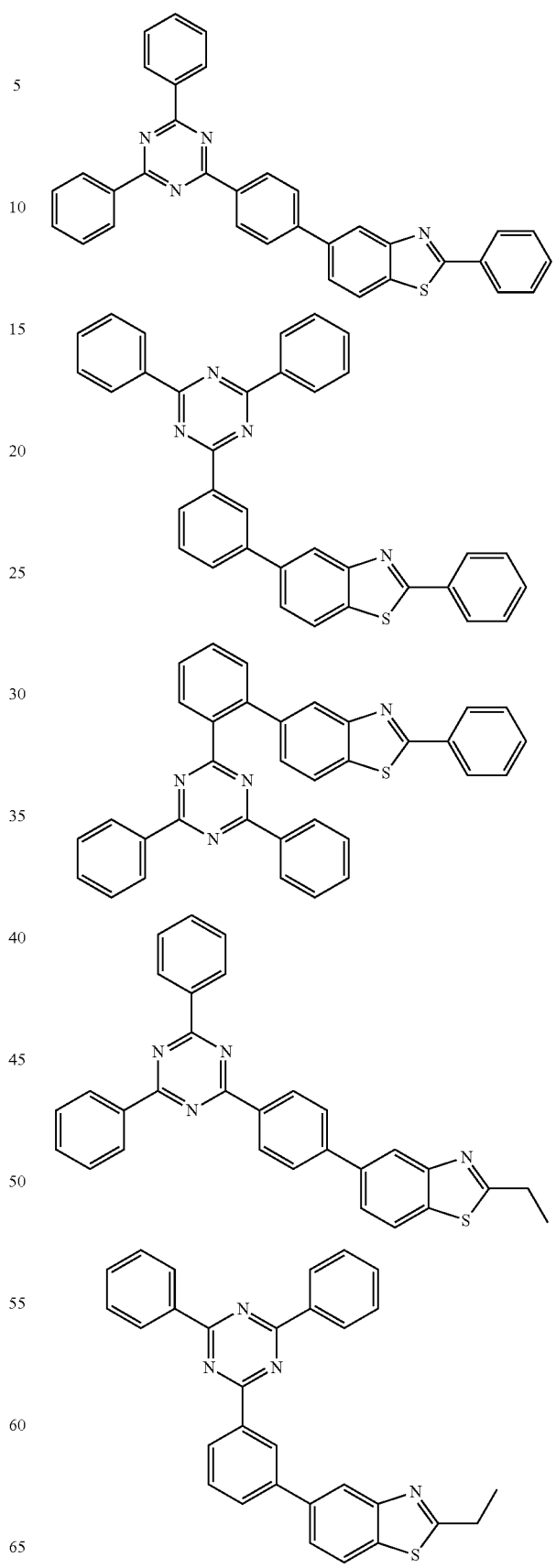

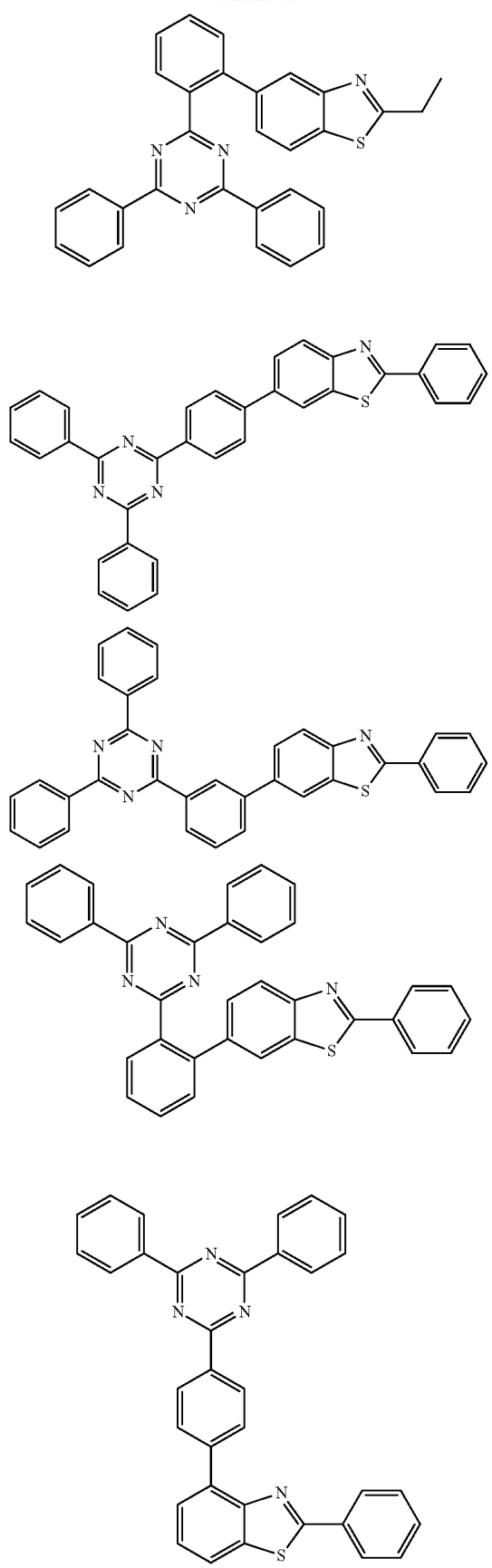

89
-continued
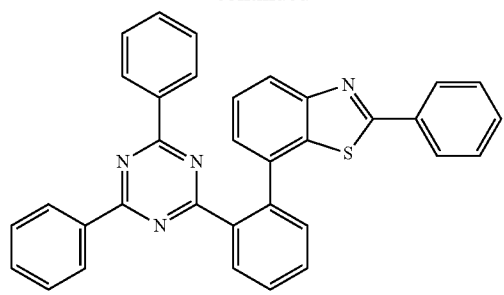
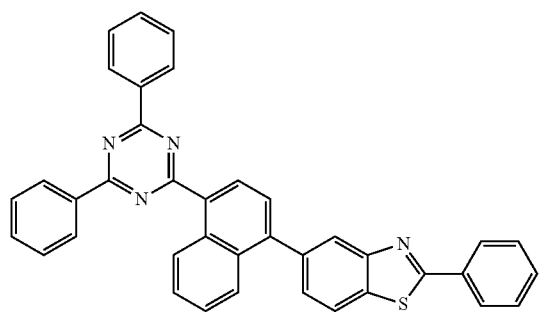
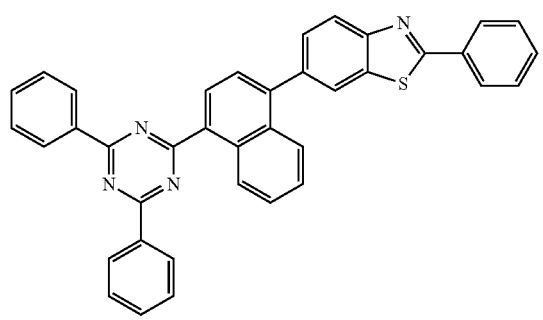
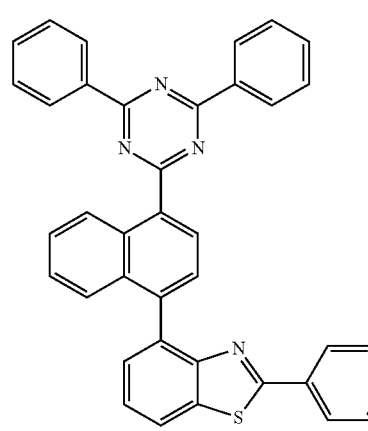
90
-continued
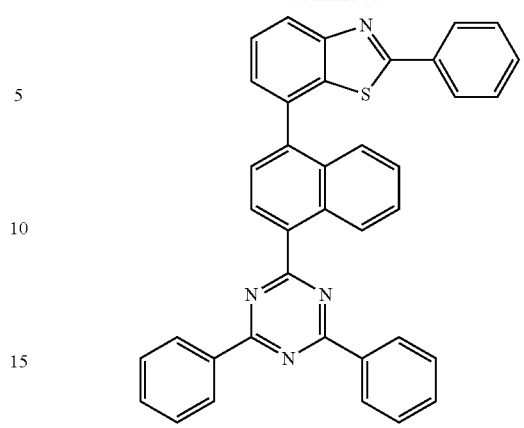
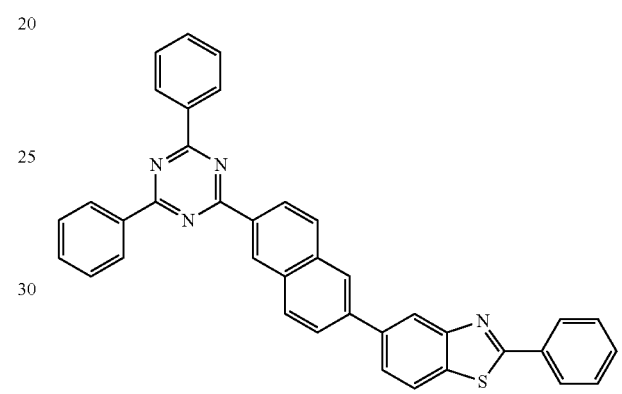
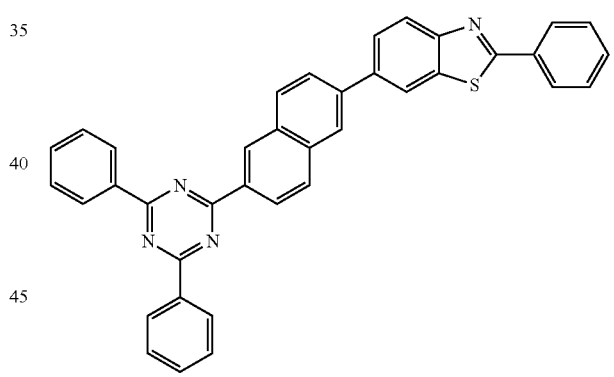
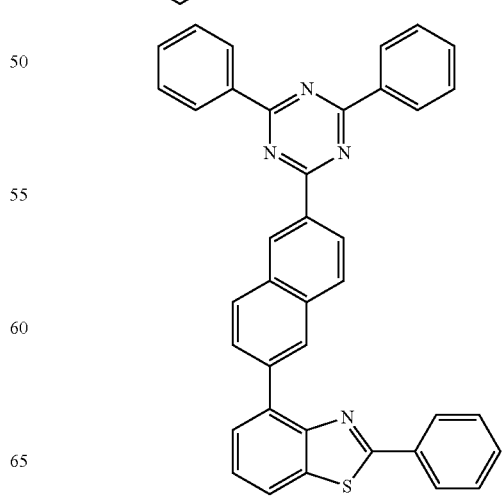

-continued
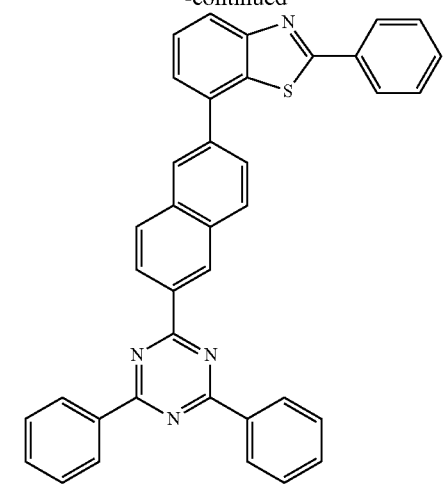
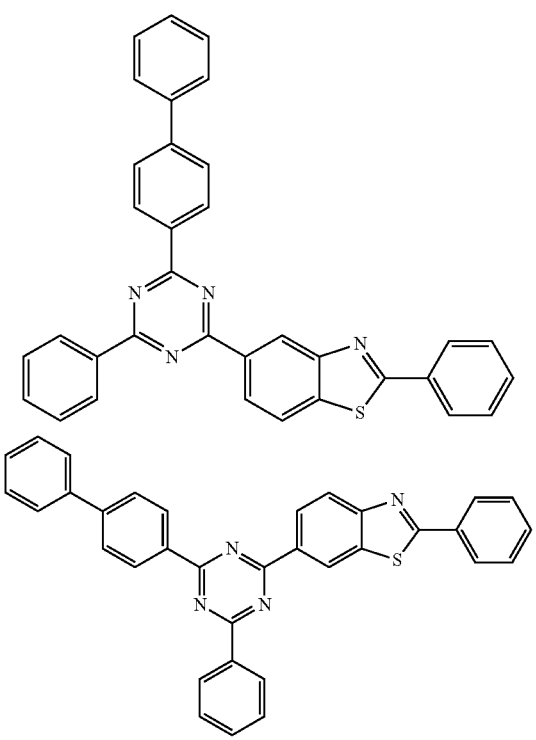
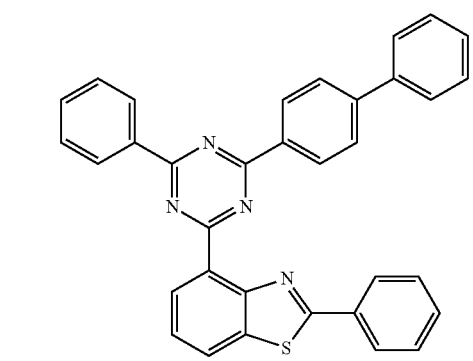
-continued
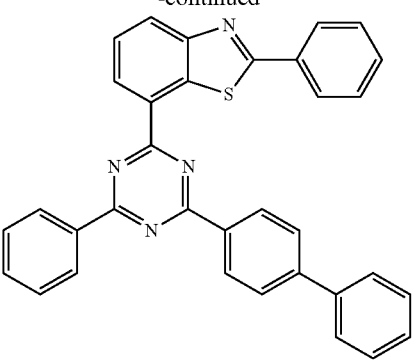
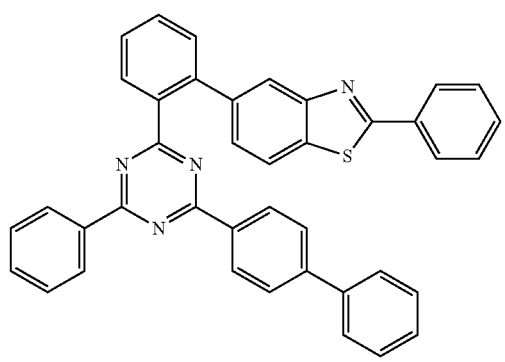

93
-continued
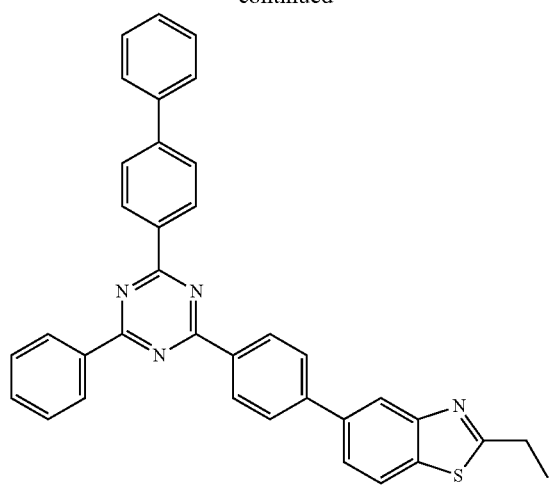
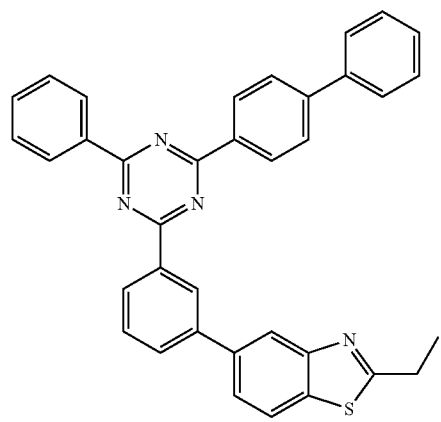
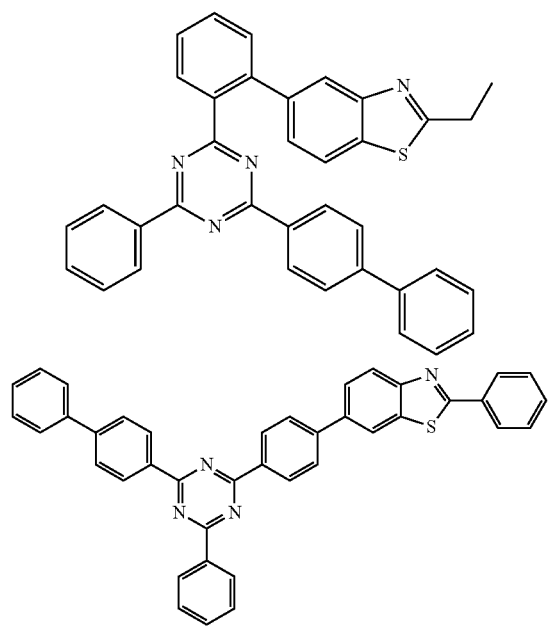
94
-continued
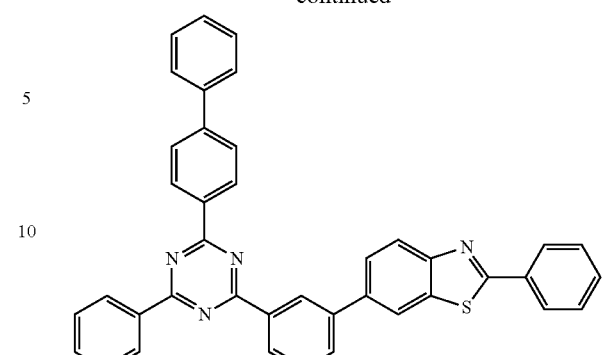
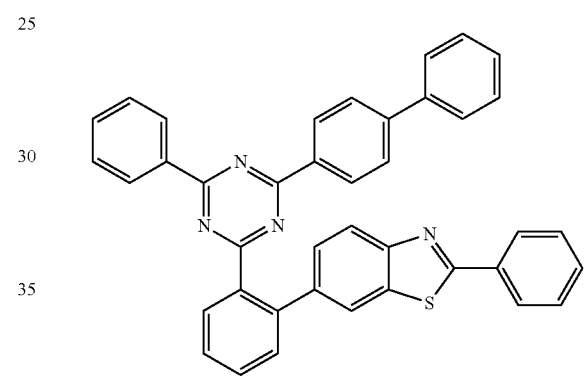
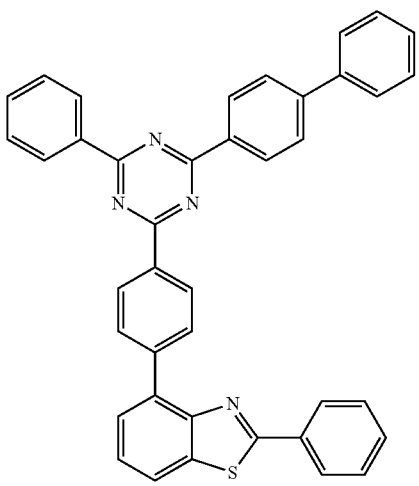

95
-continued
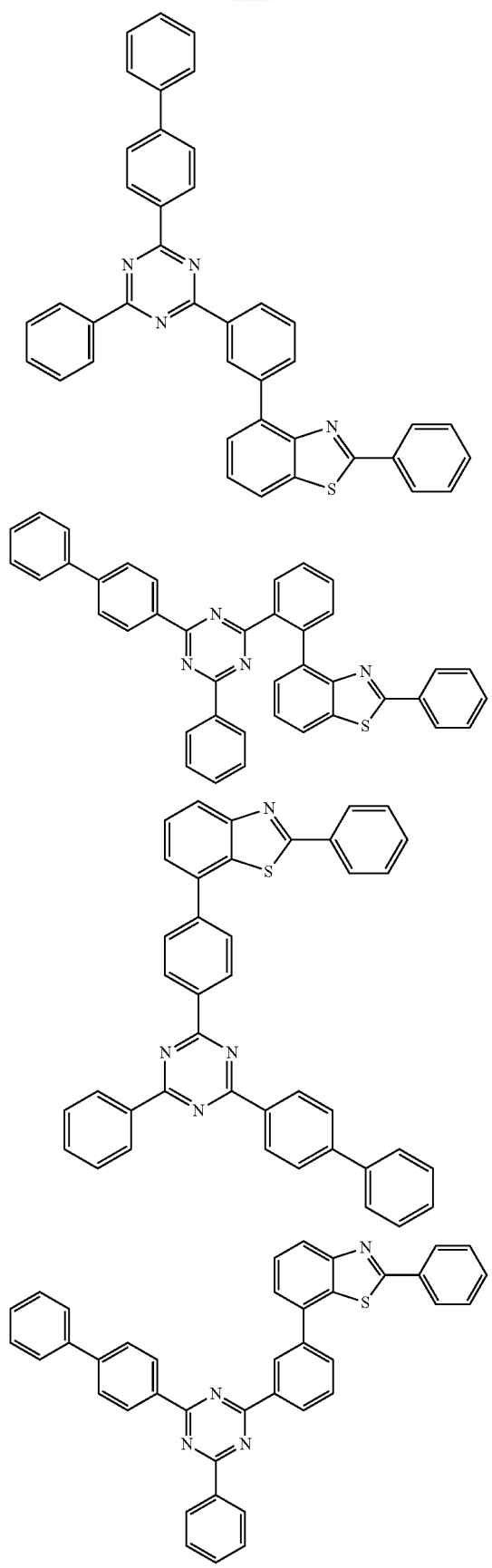
96
-continued
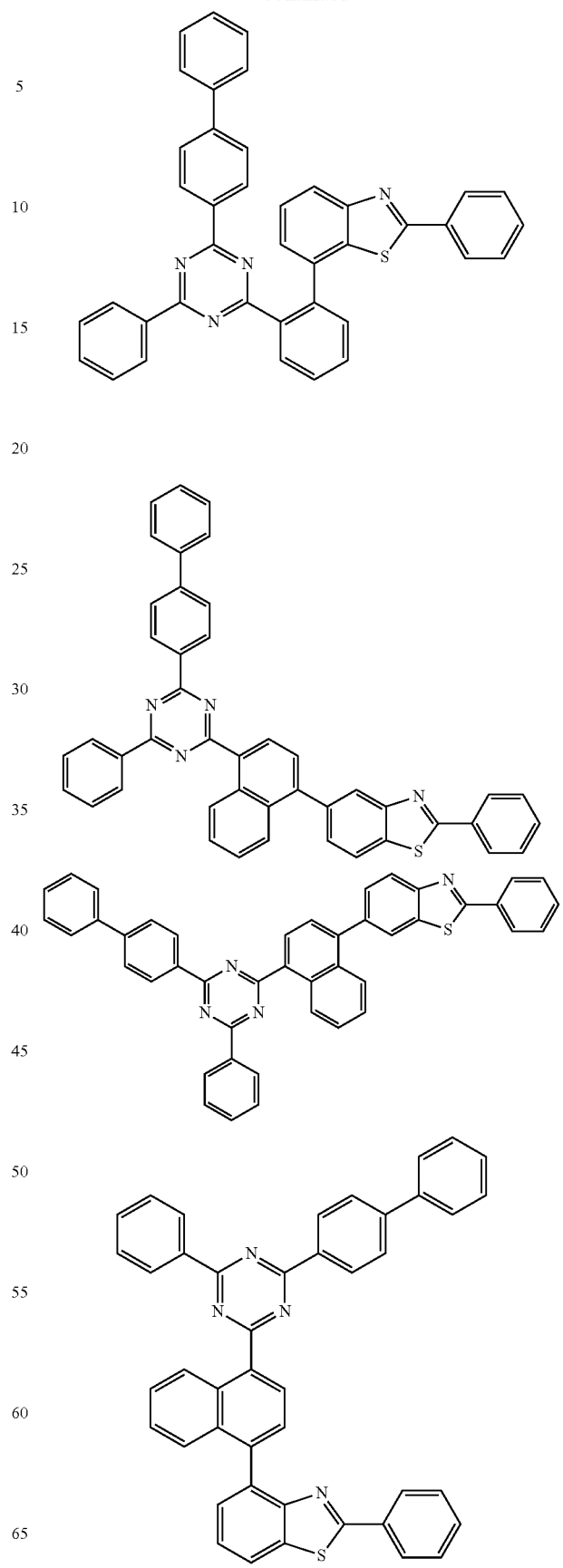

97
-continued
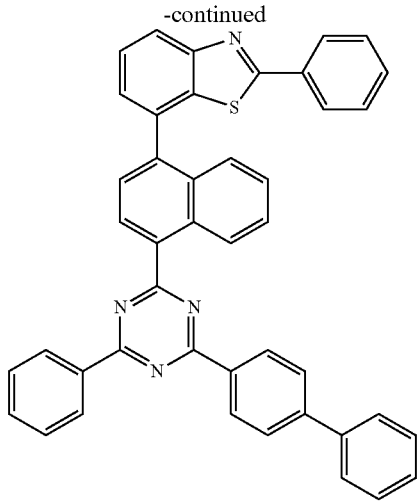
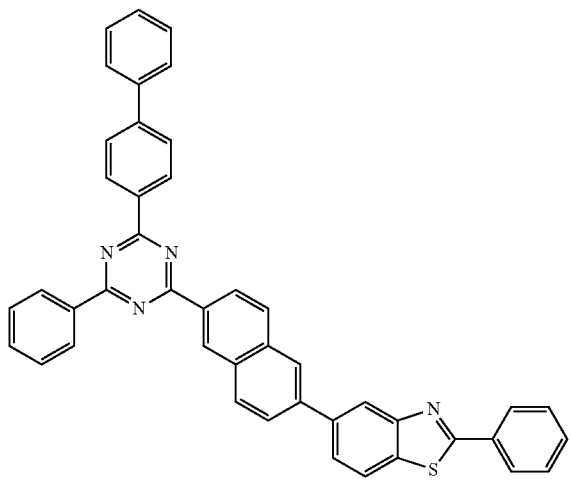
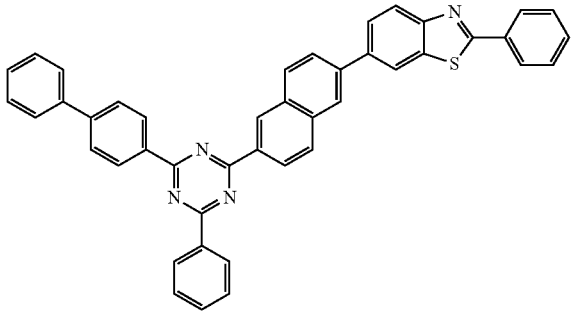
98
-continued
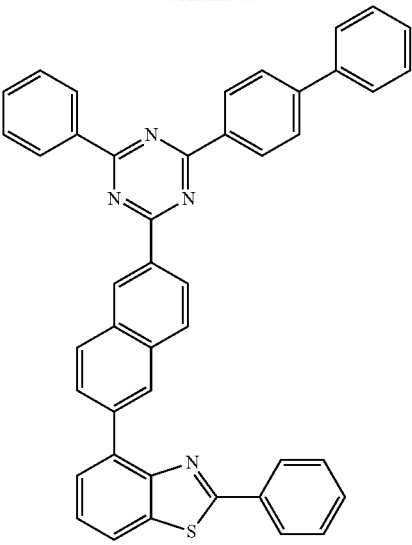
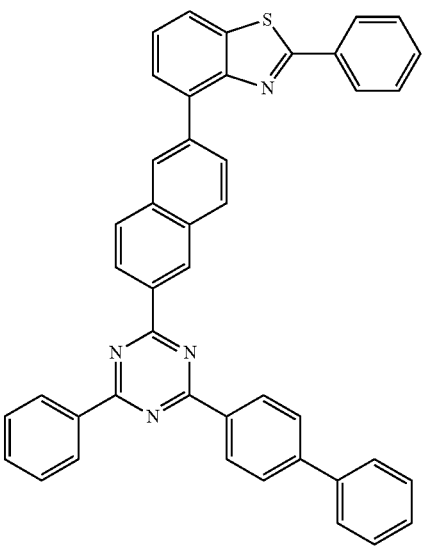
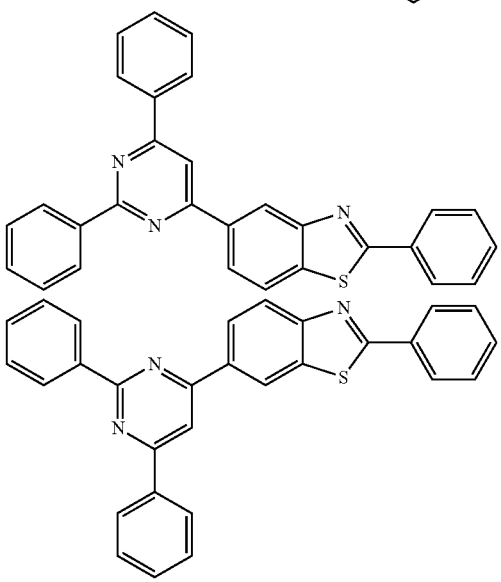

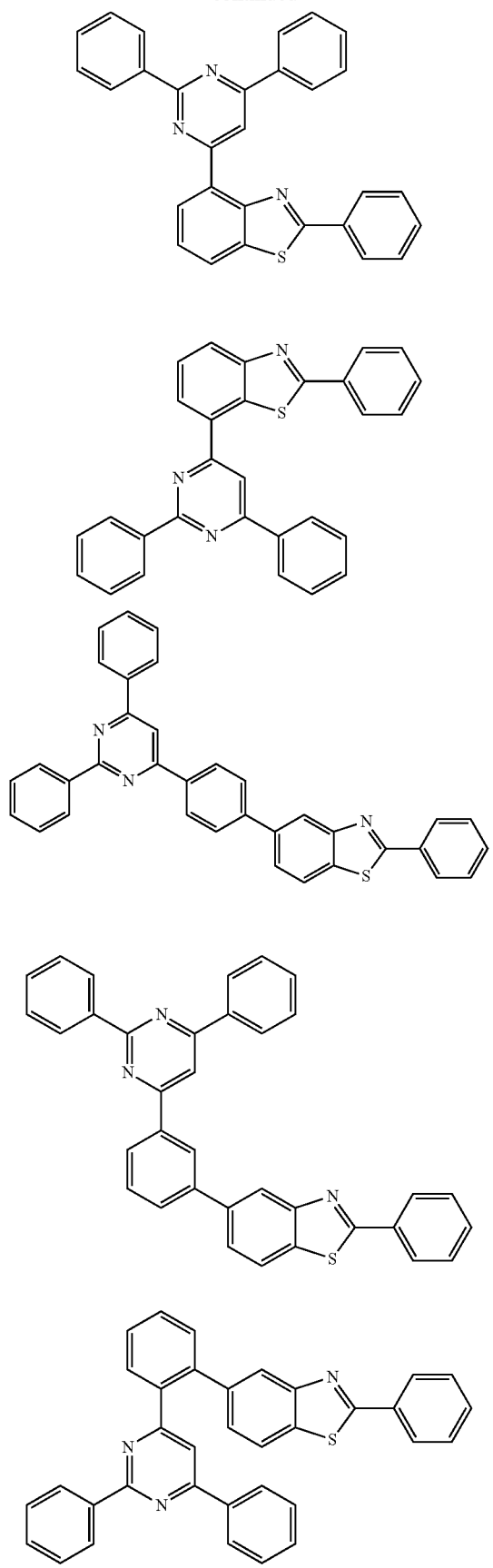

101
-continued
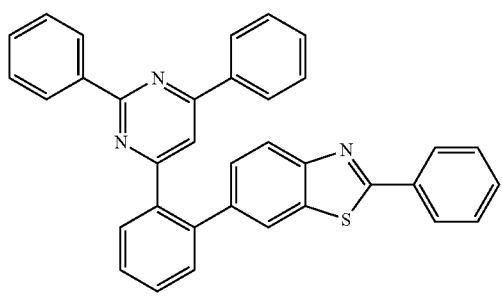
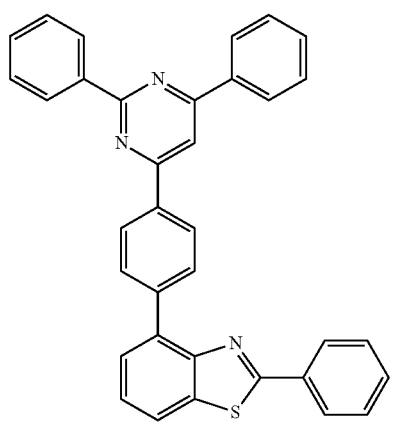
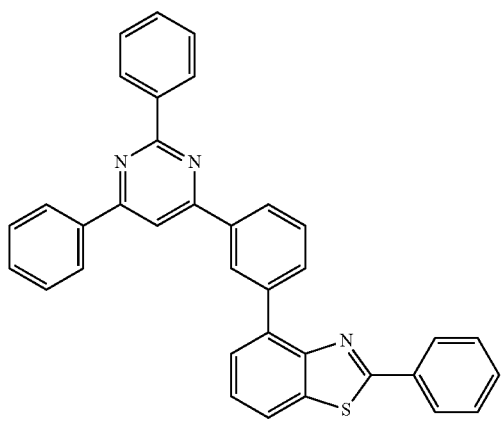
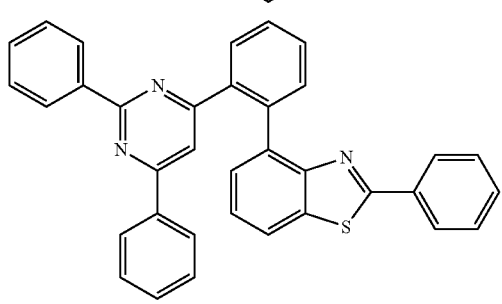
102
-continued
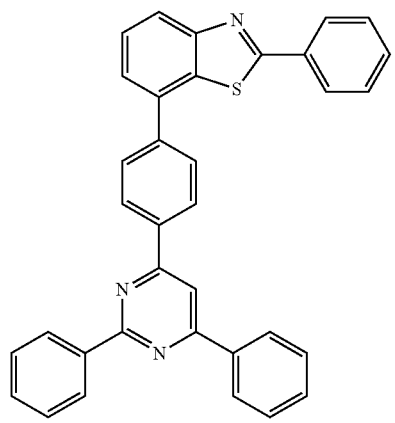
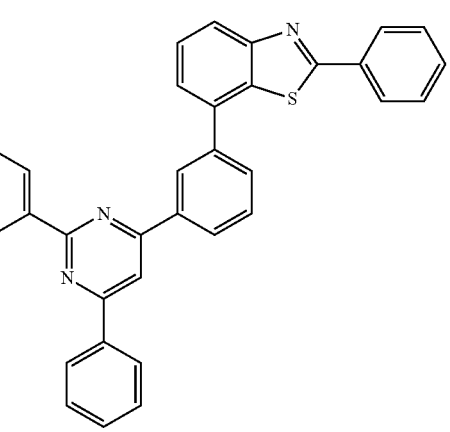
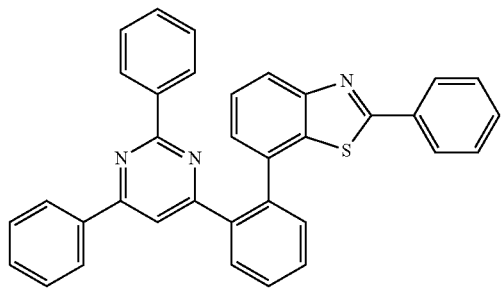
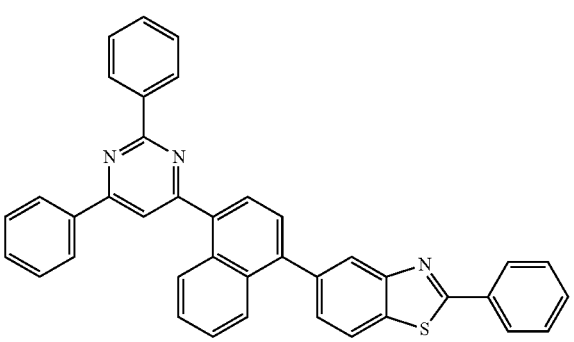

103
-continued
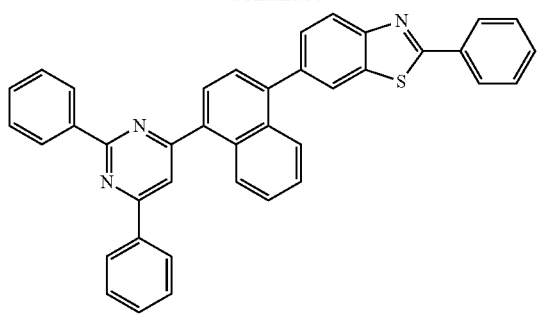
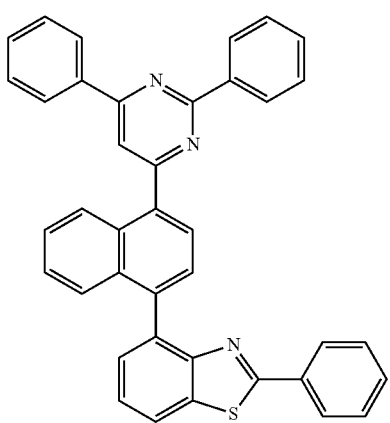
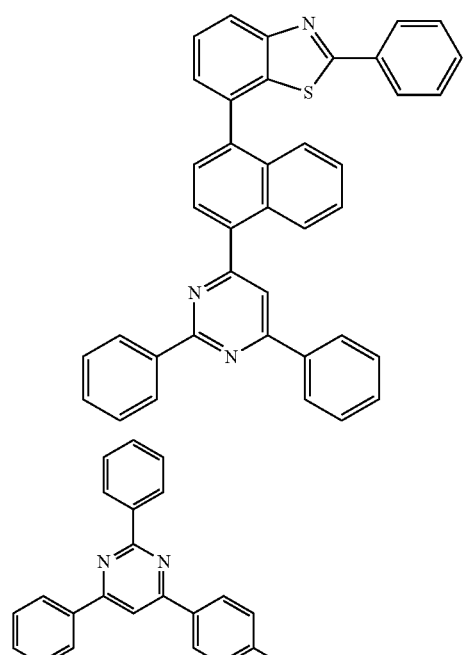
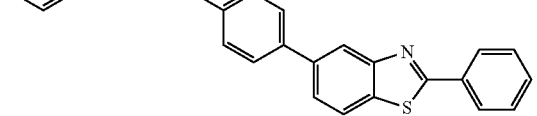
104
-continued
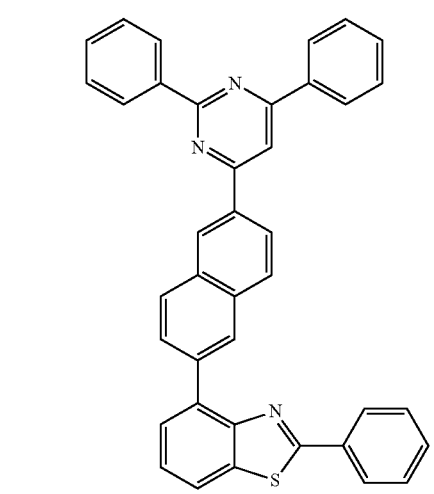
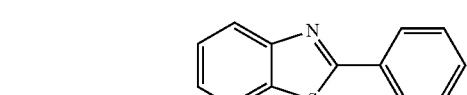
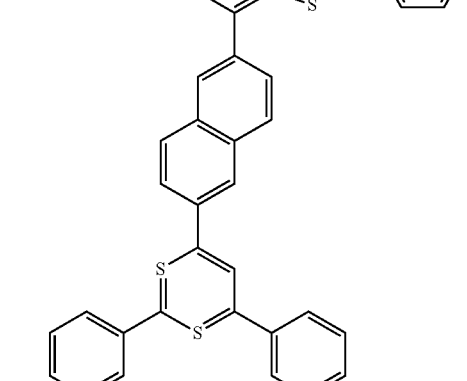
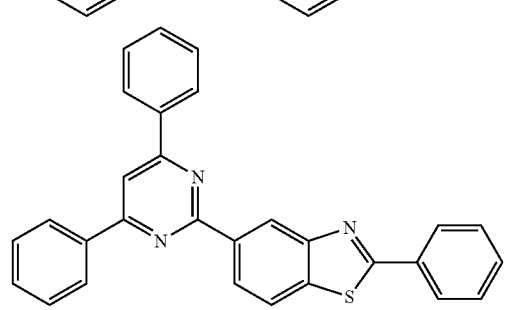

105
-continued
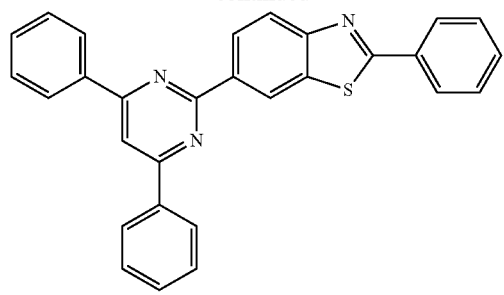
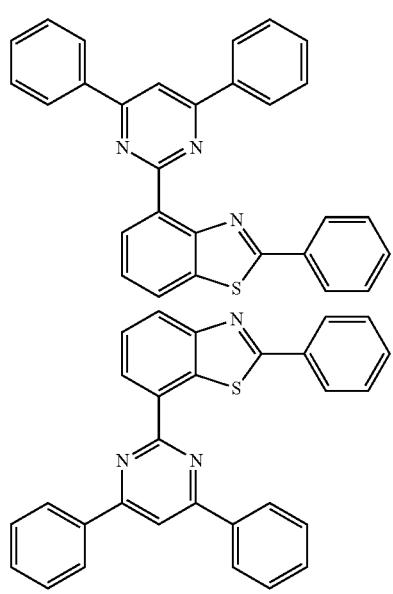
106
-continued
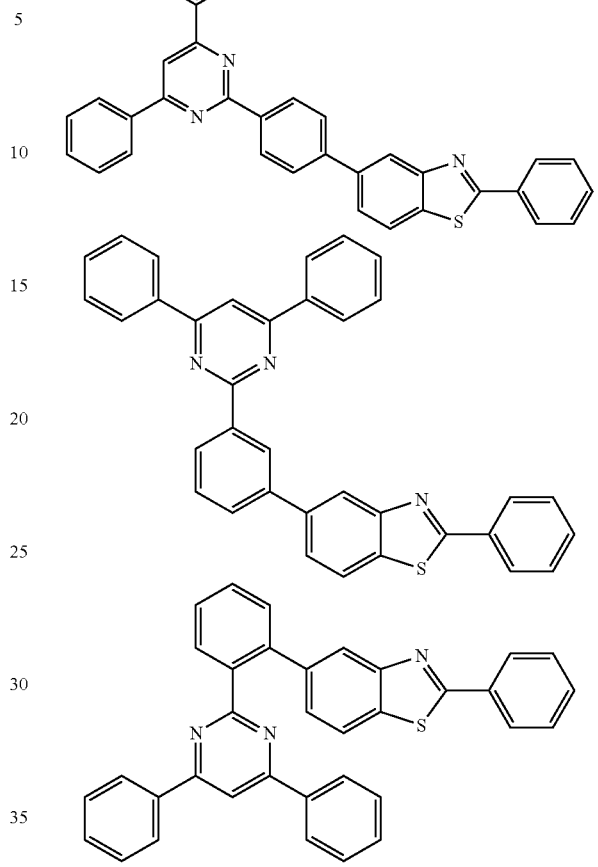
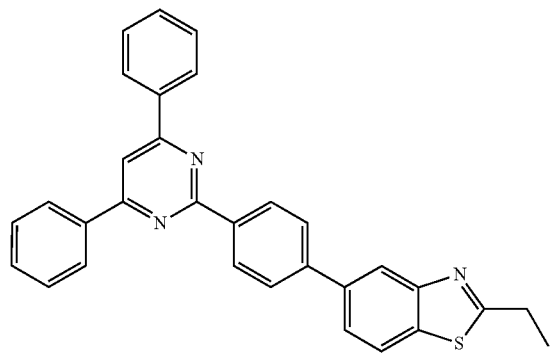
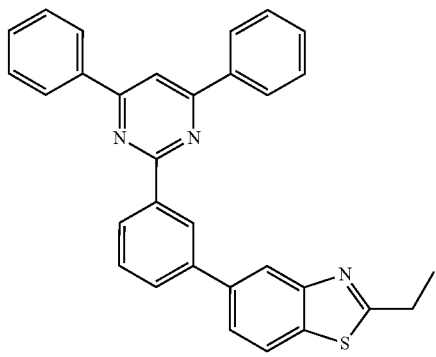

-continued
107
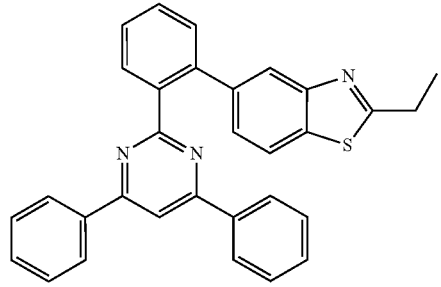
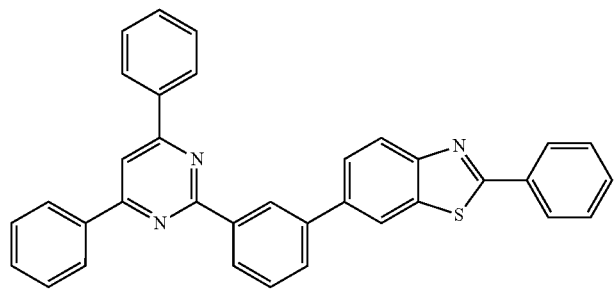
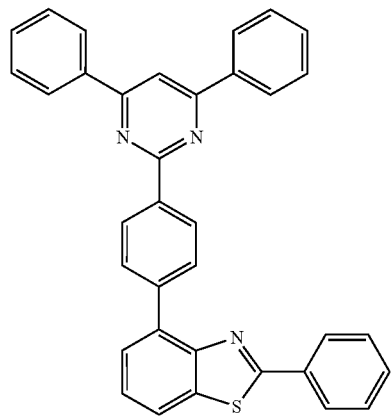
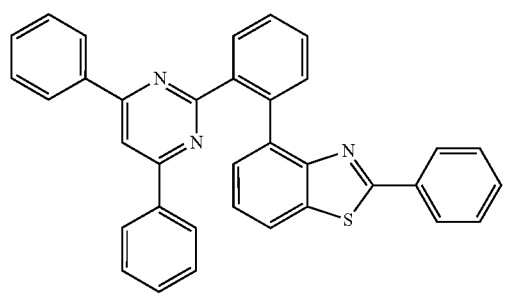
108
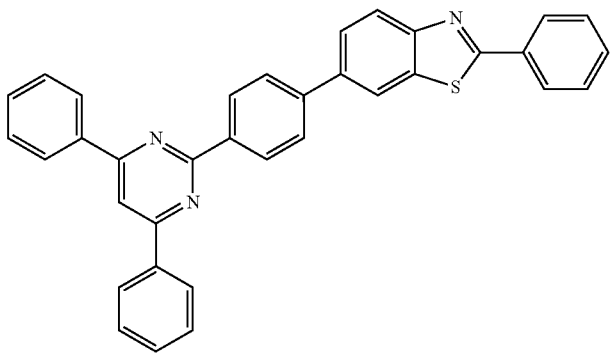
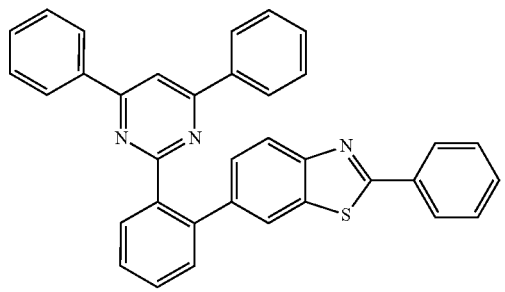
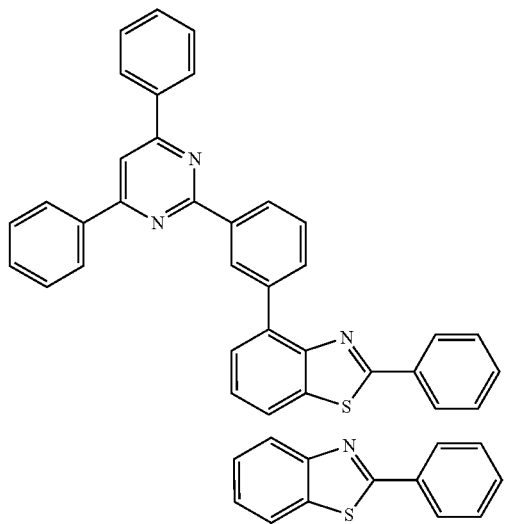
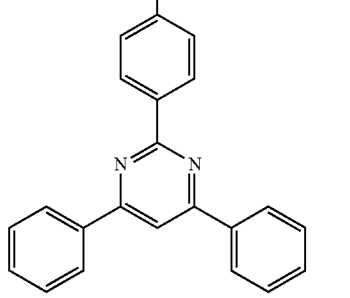

-continued
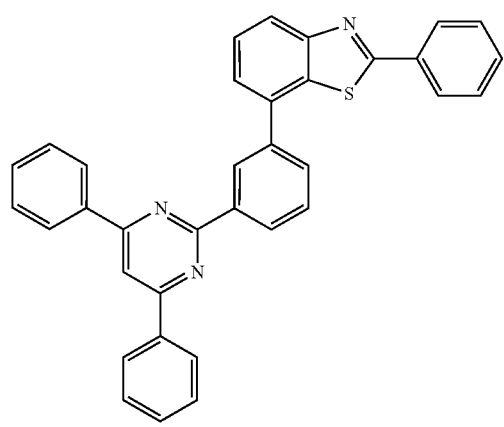
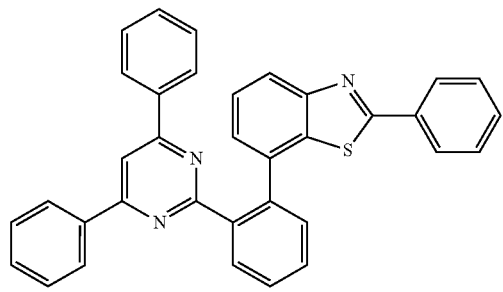
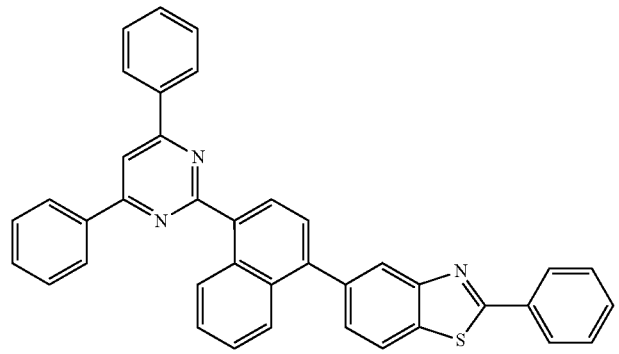
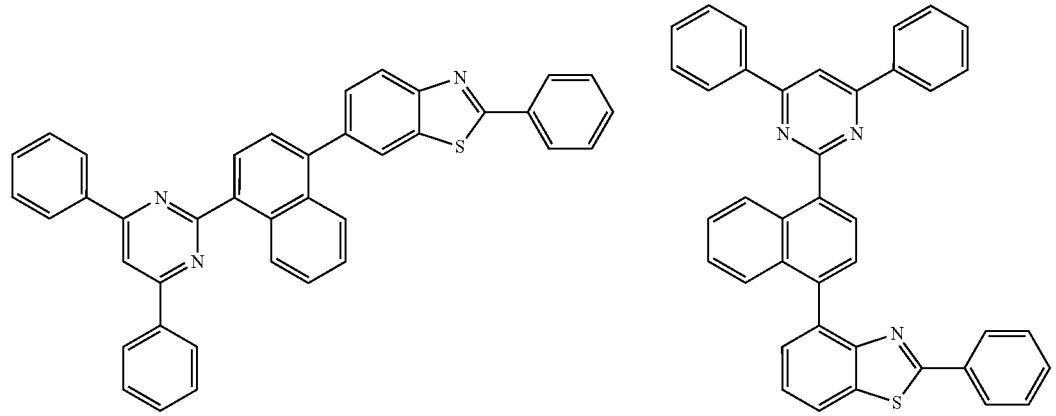
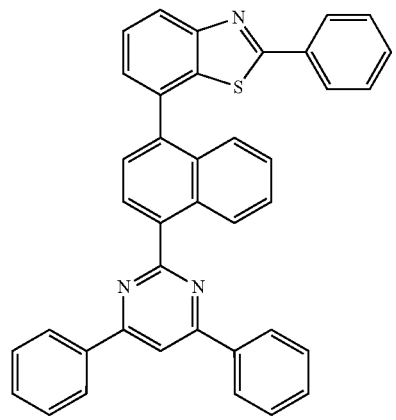
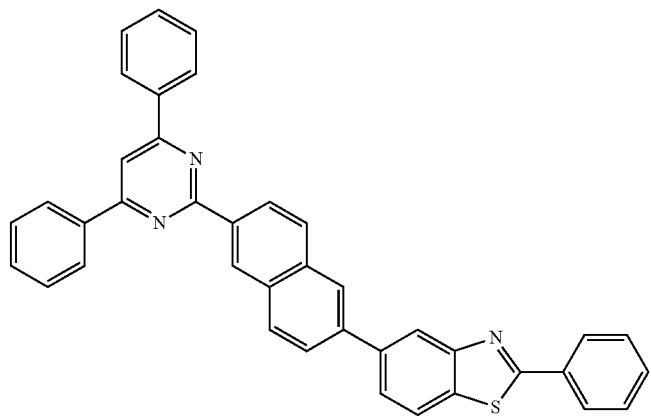

-continued
111
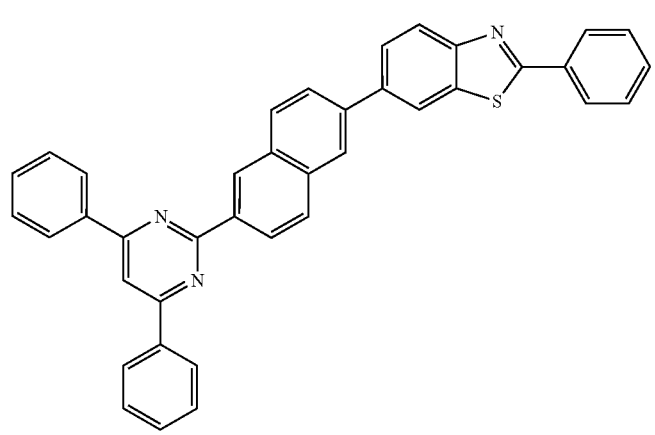
112
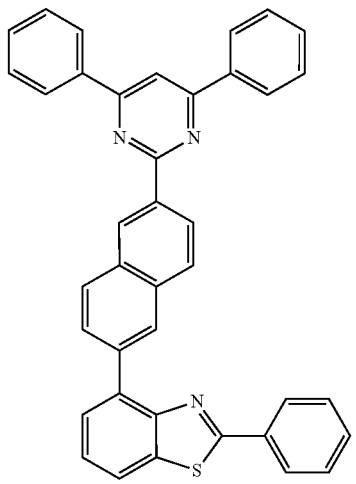
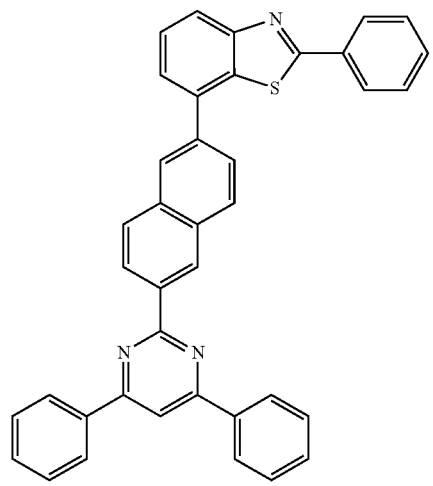
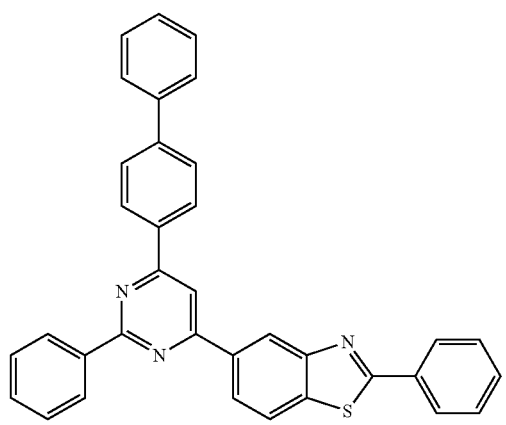
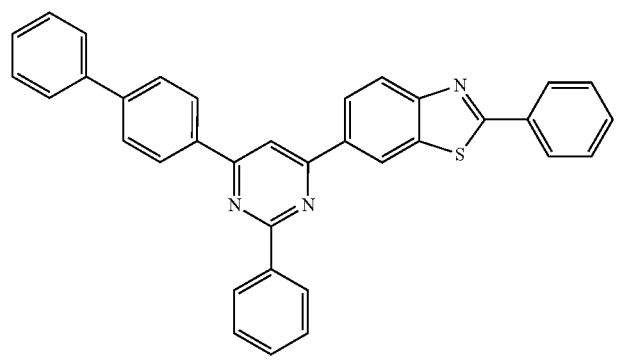
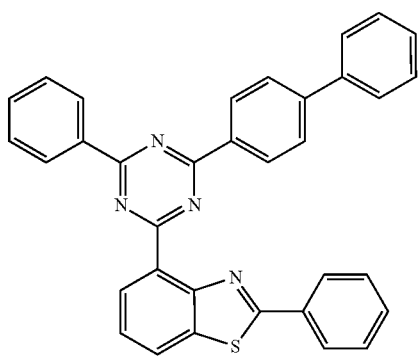

-continued
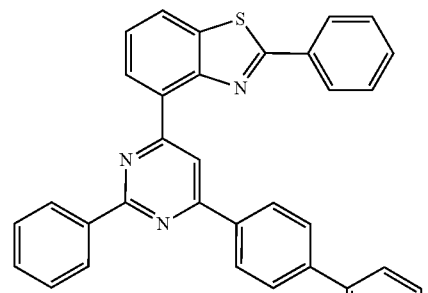
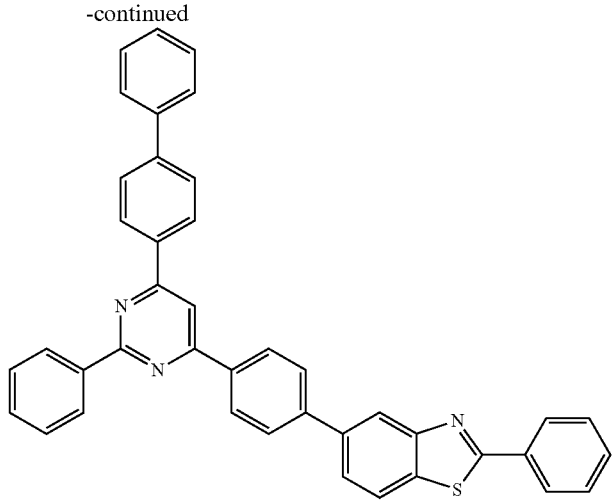
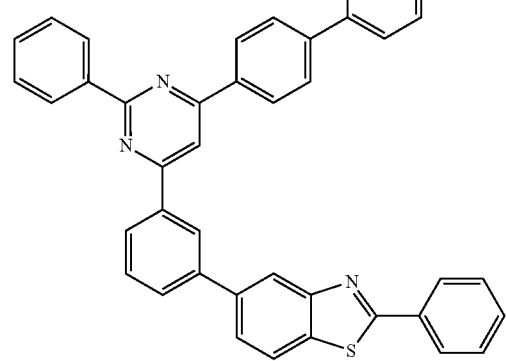
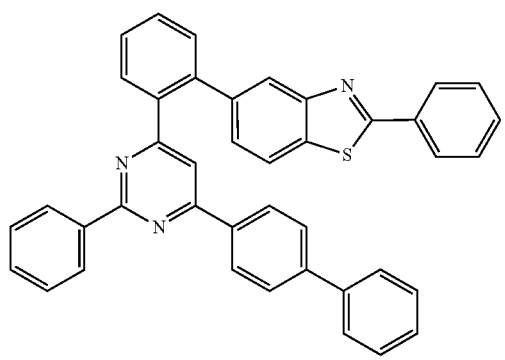
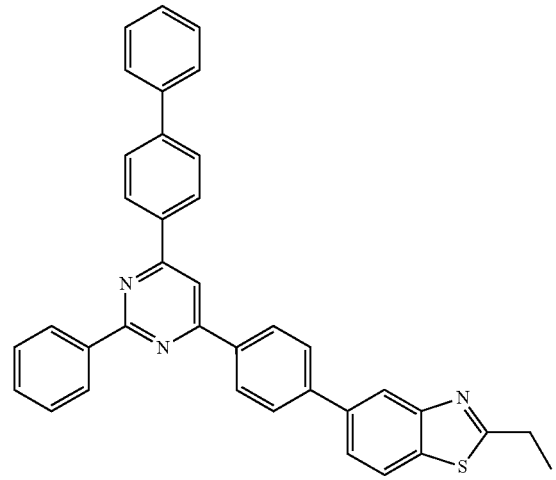
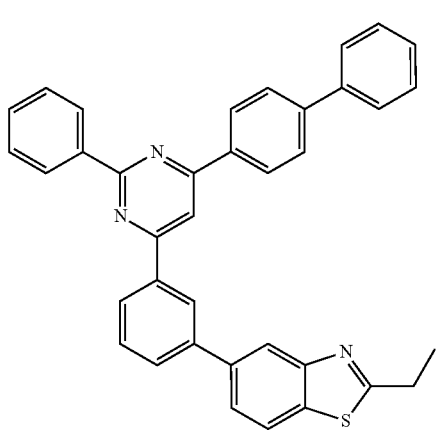
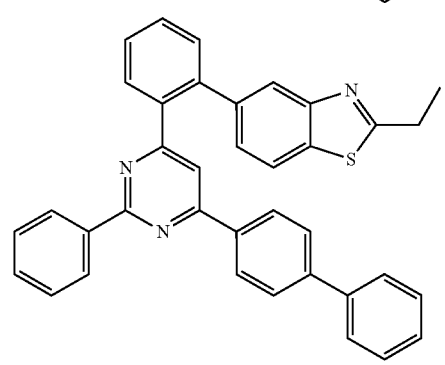
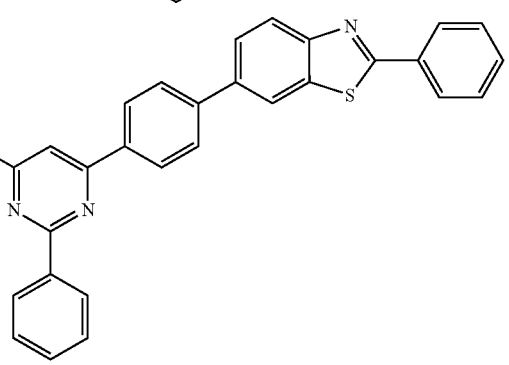

115 116
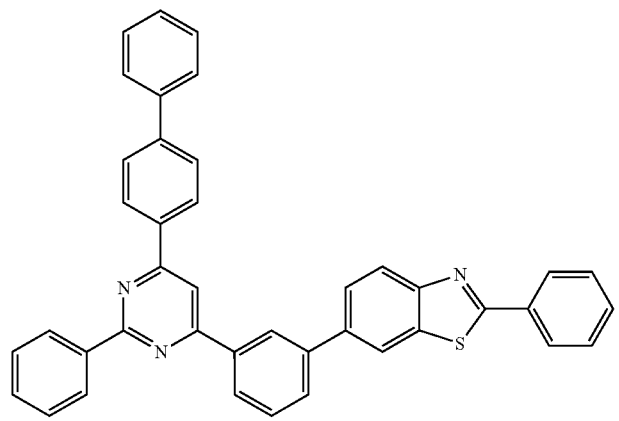
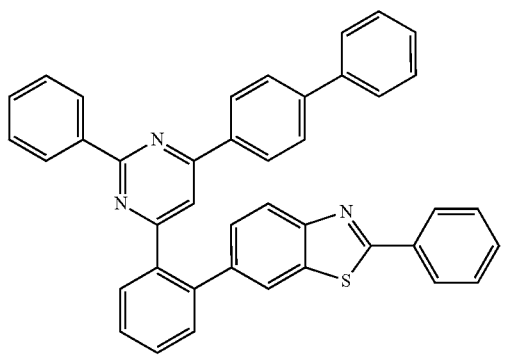
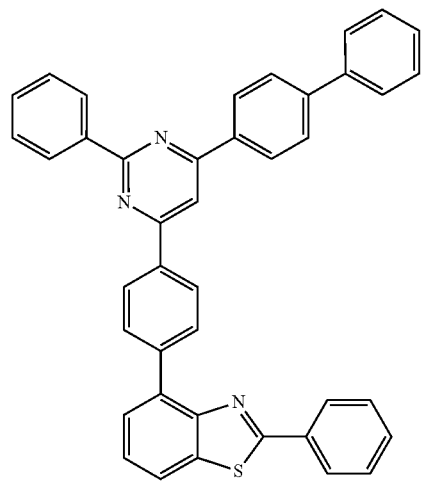
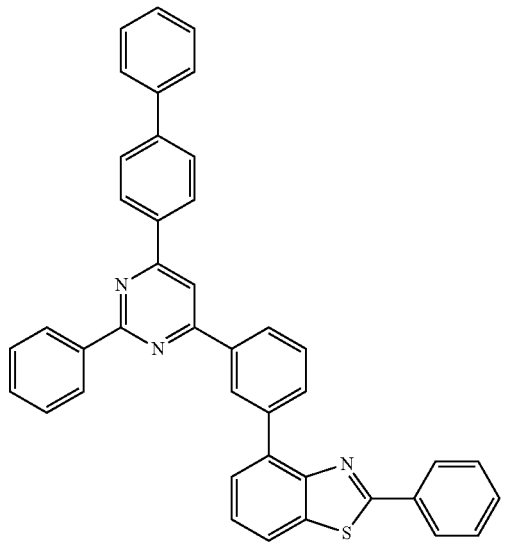
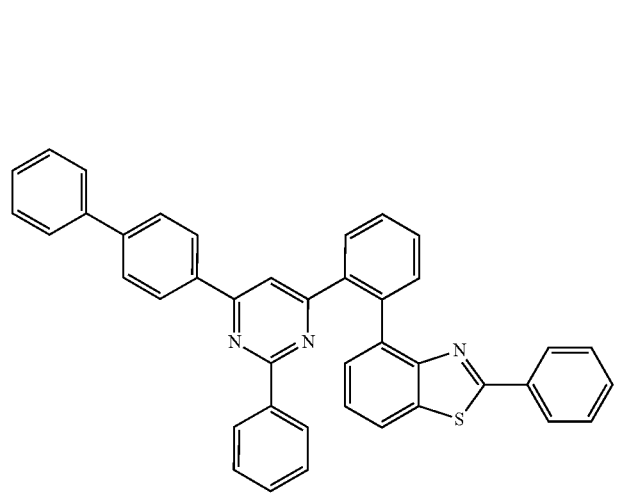
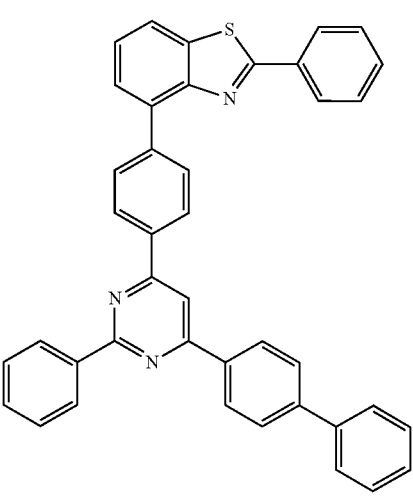

117
-continued
118
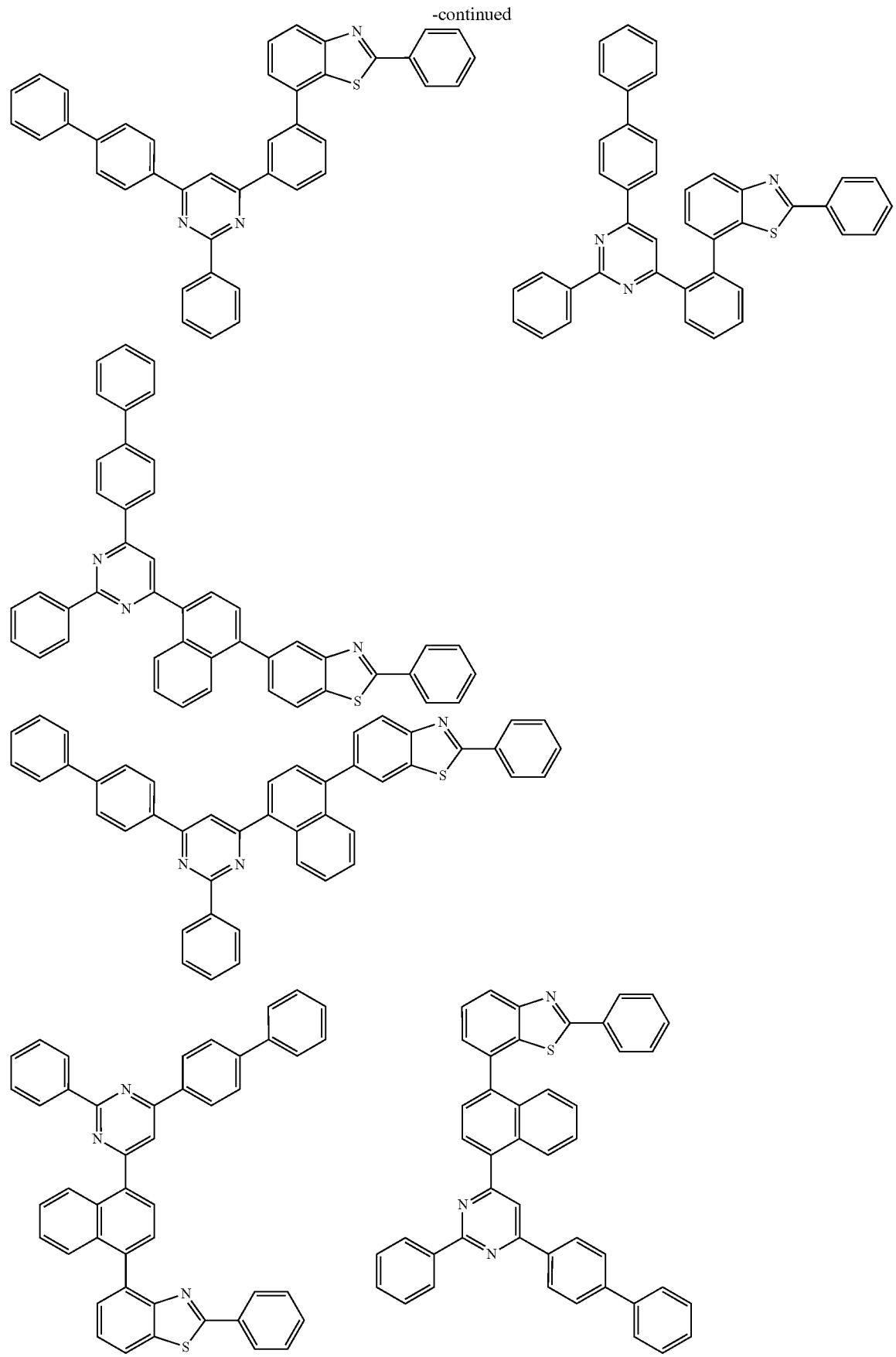

-continued
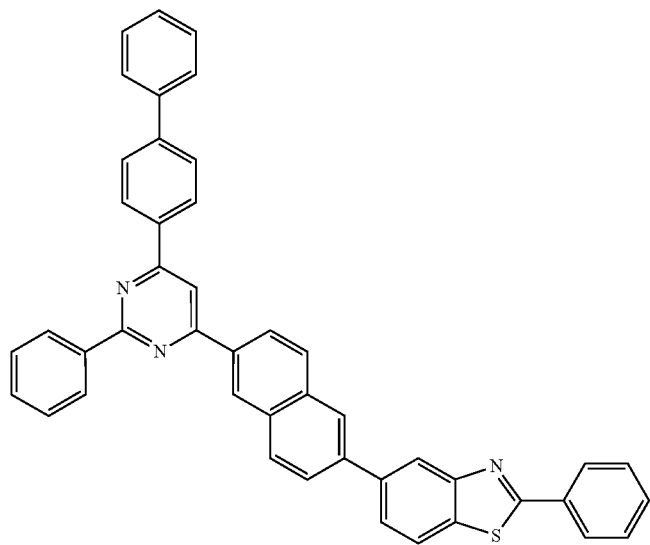
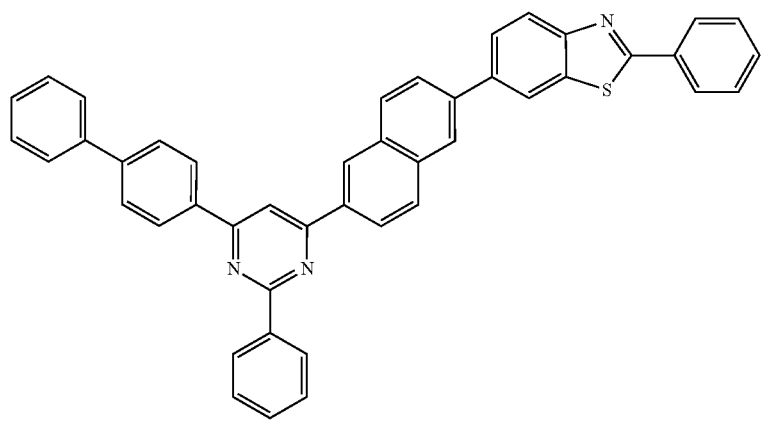
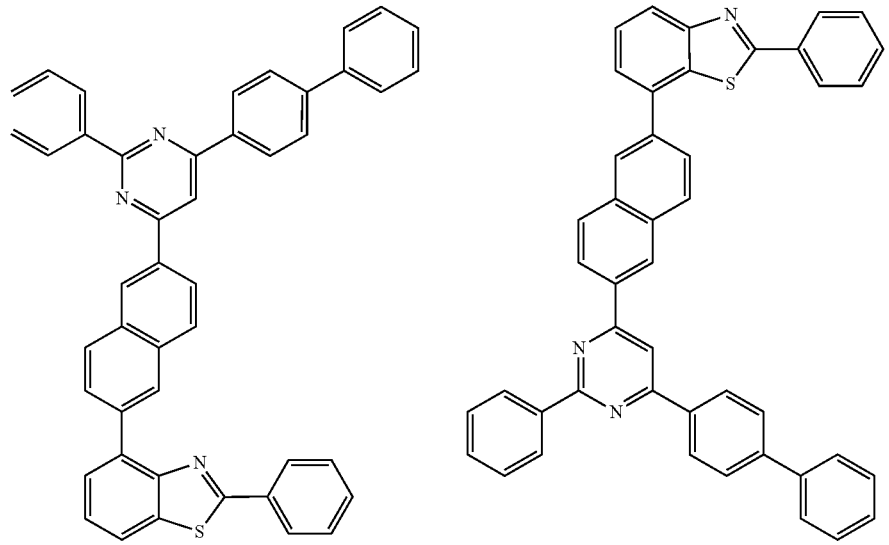

-continued
121
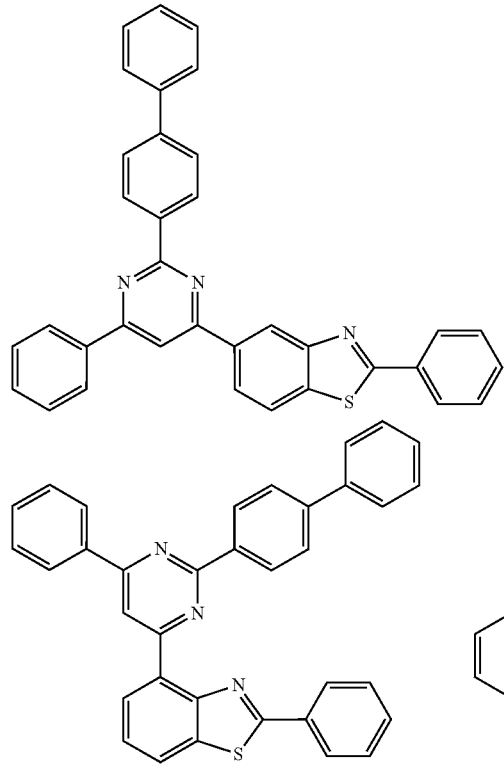
122
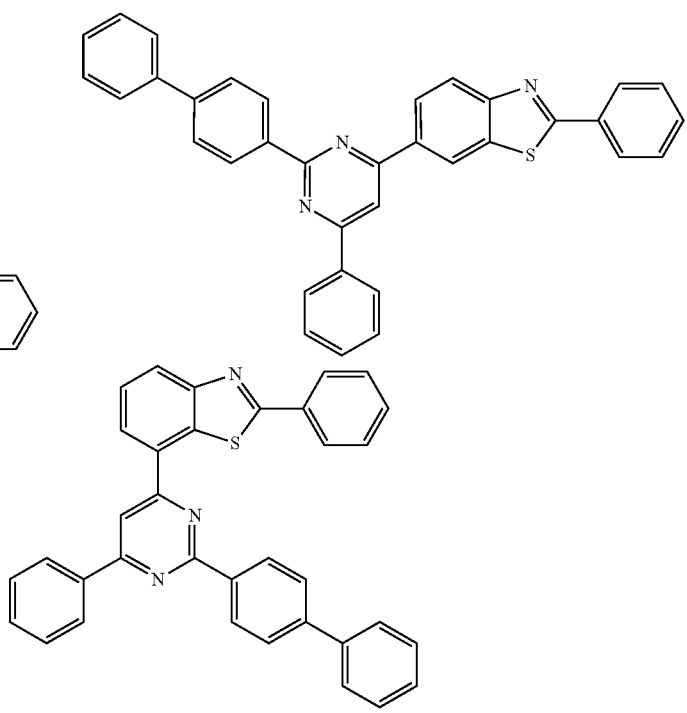
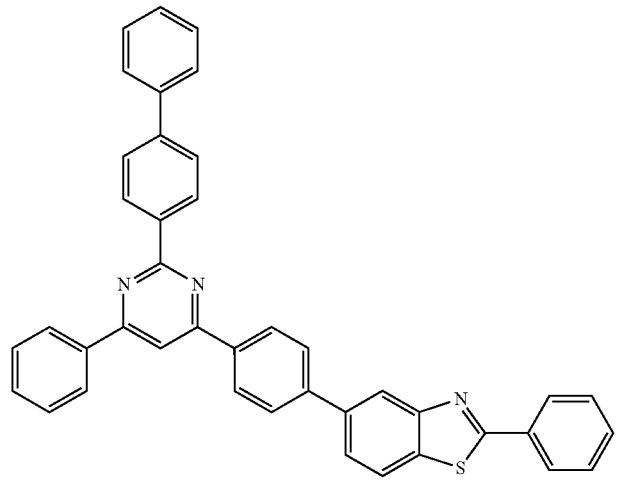
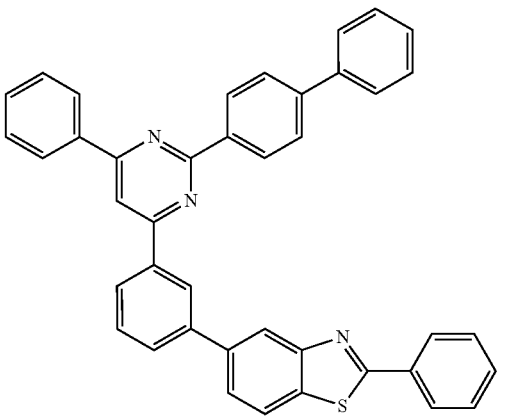
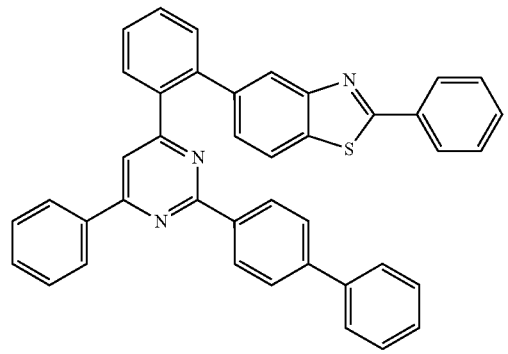
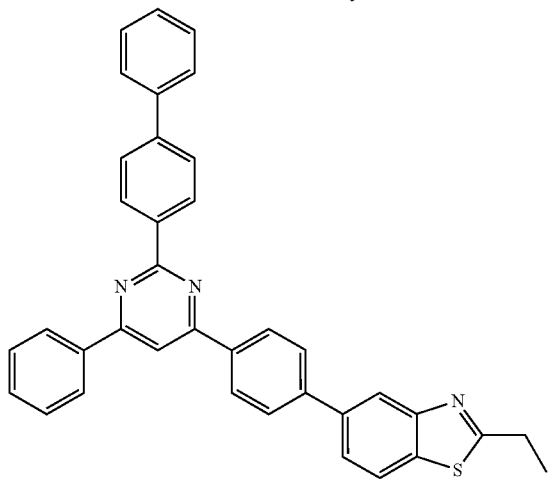

-continued
123
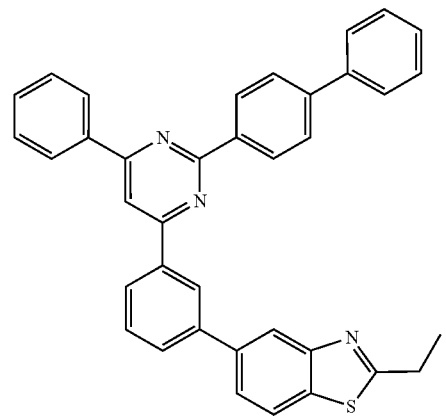
124
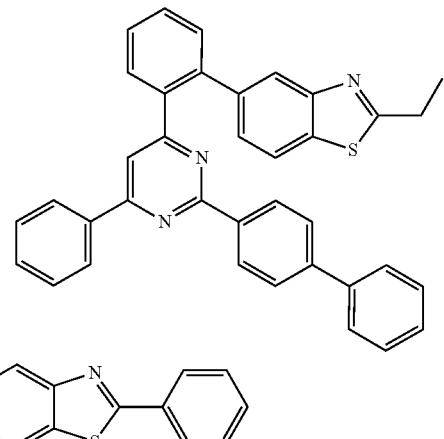
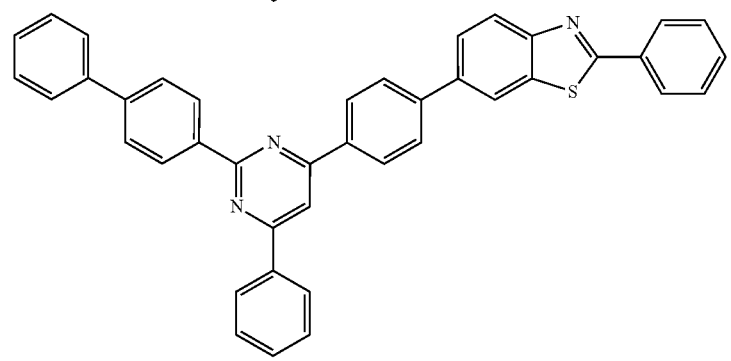
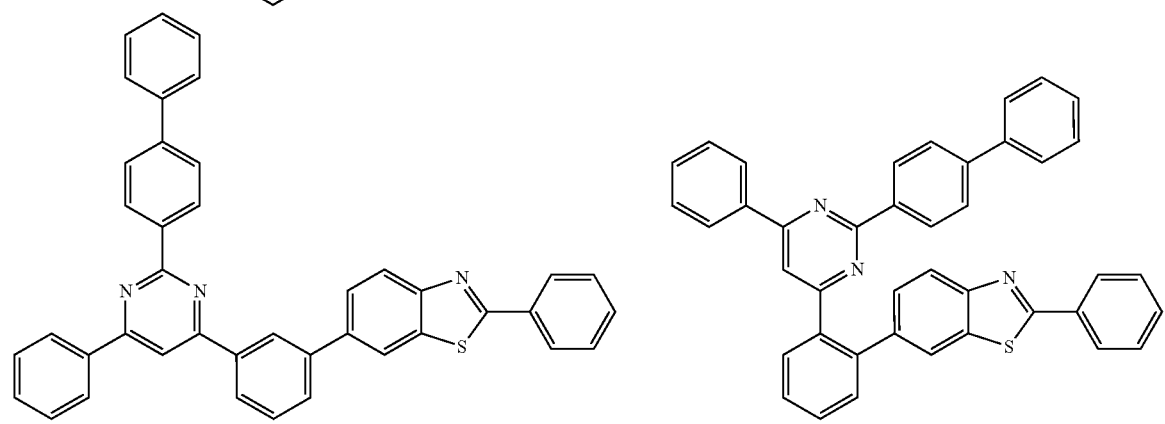
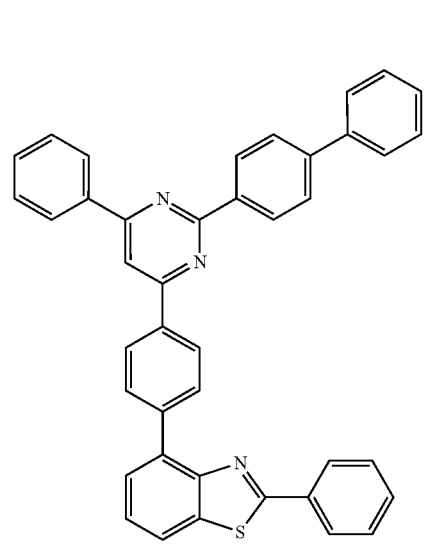
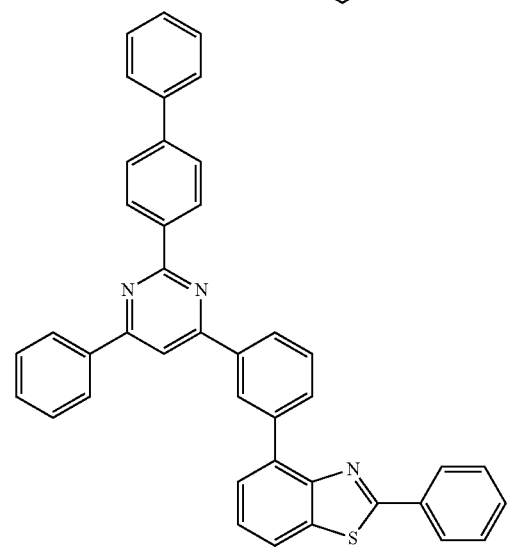

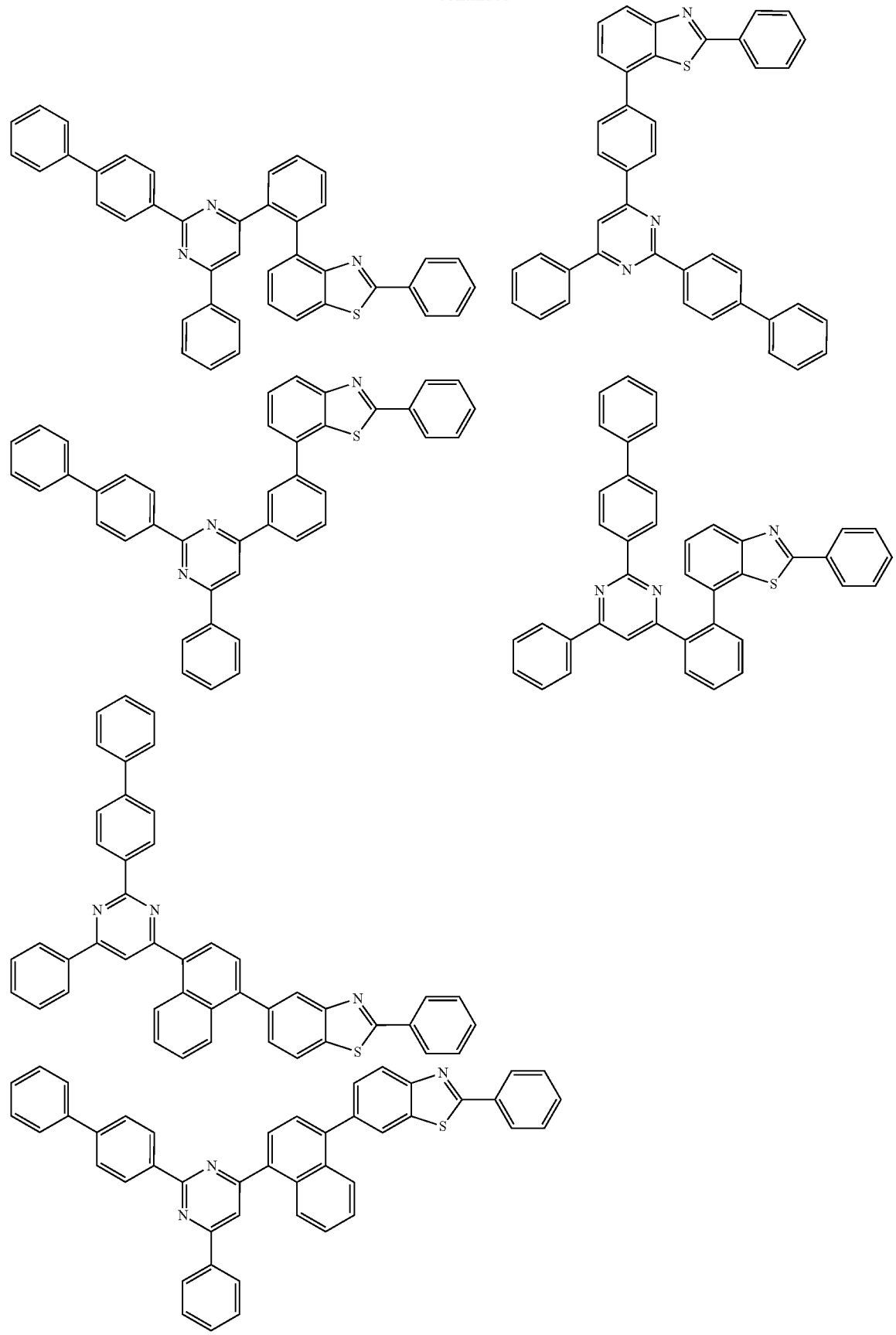

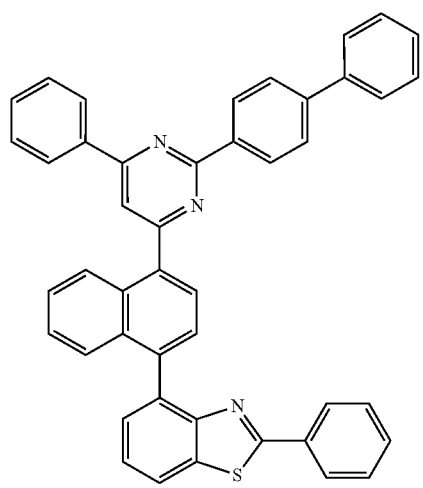
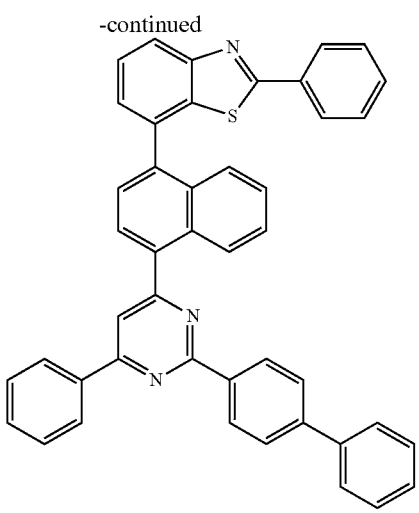
-continued
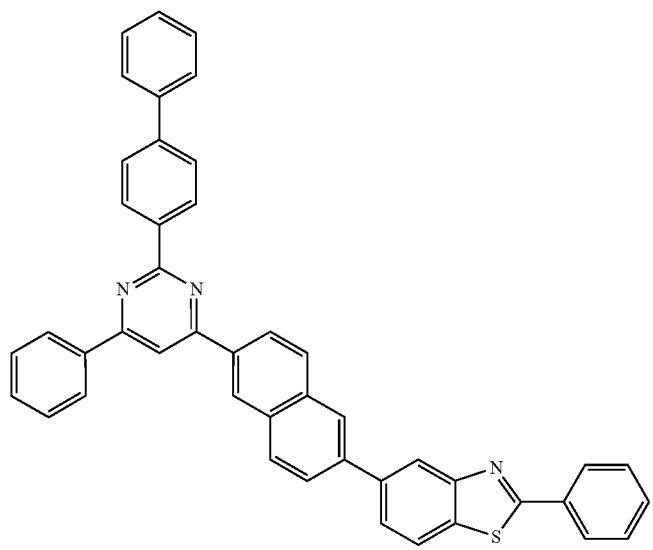
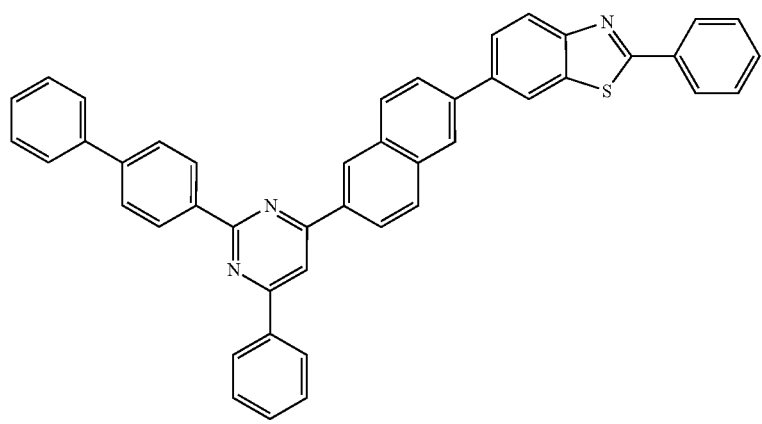

129
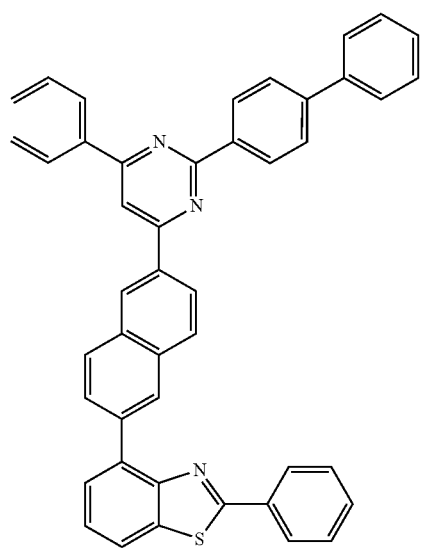
130
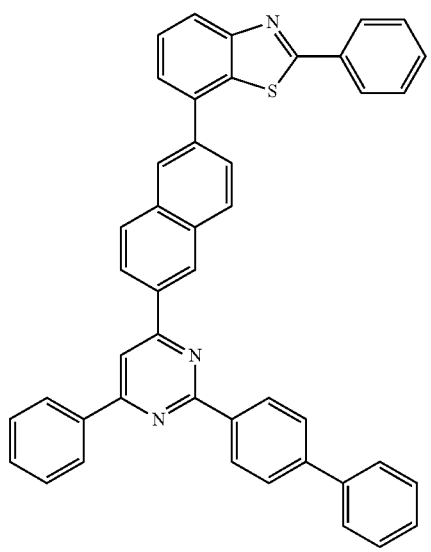
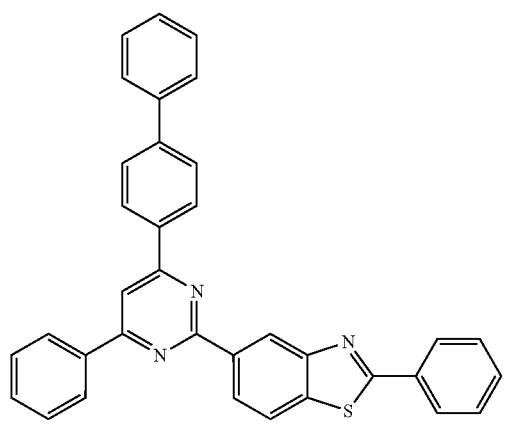
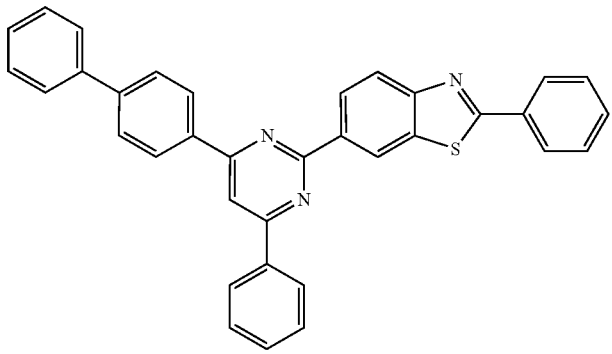
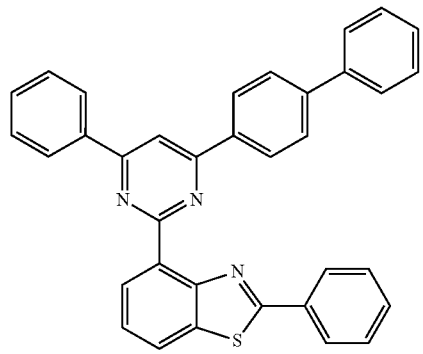
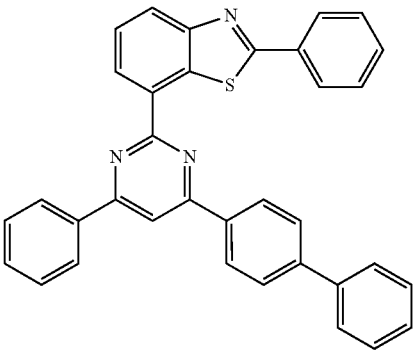

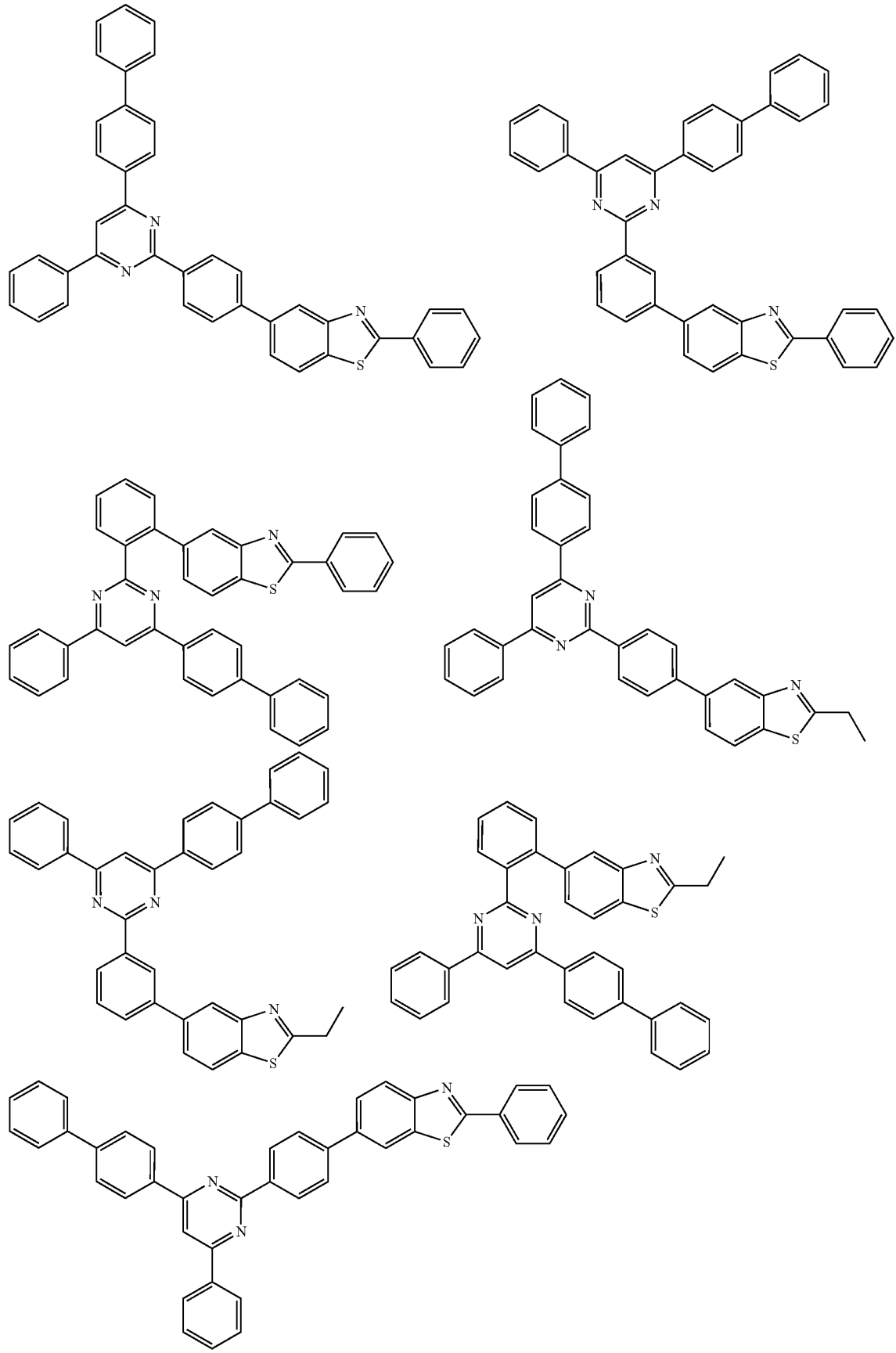

-continued
133
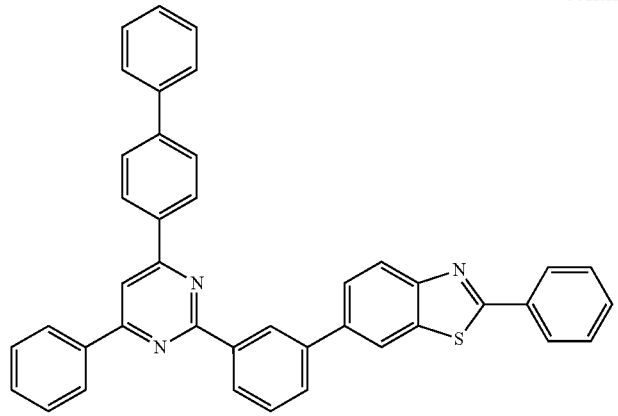
134
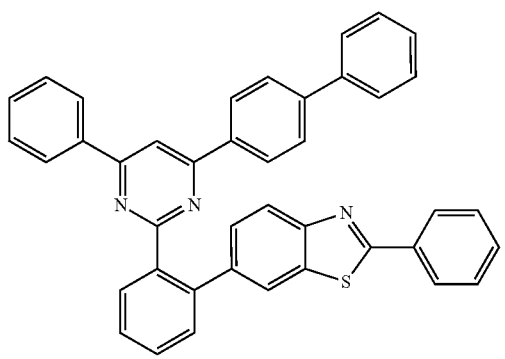
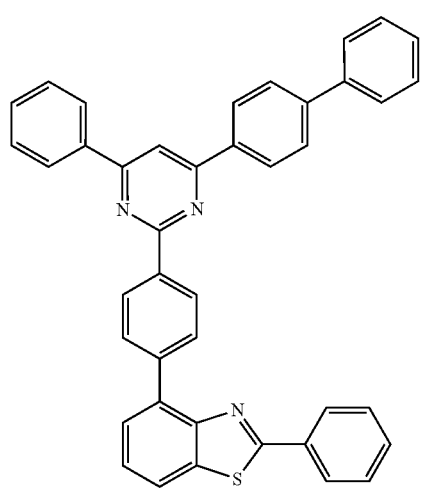
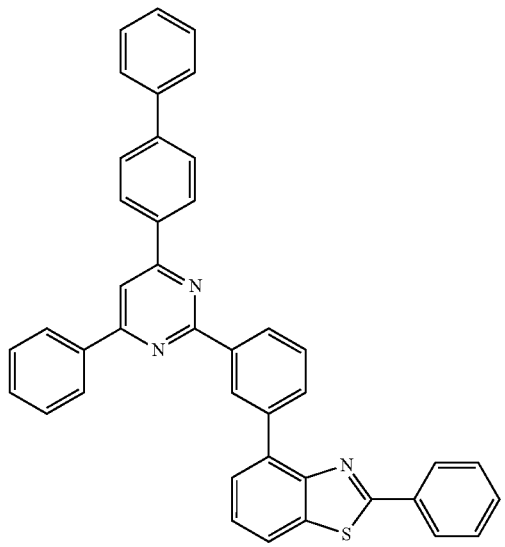
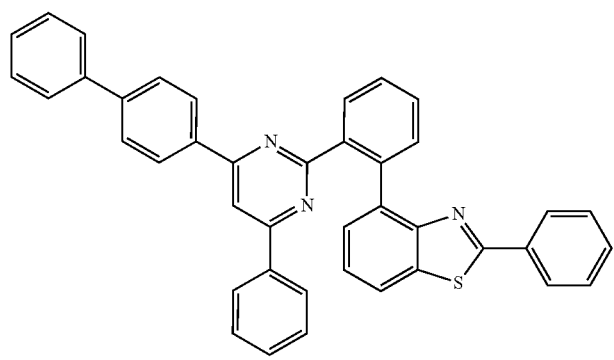
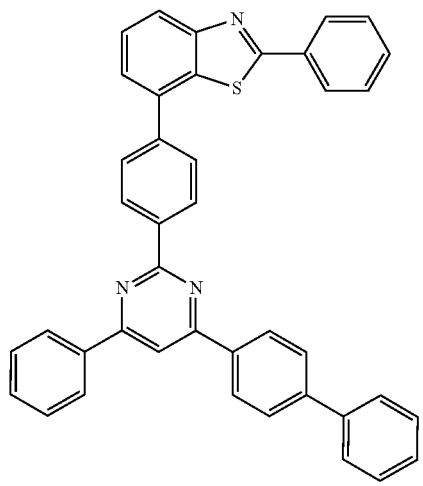

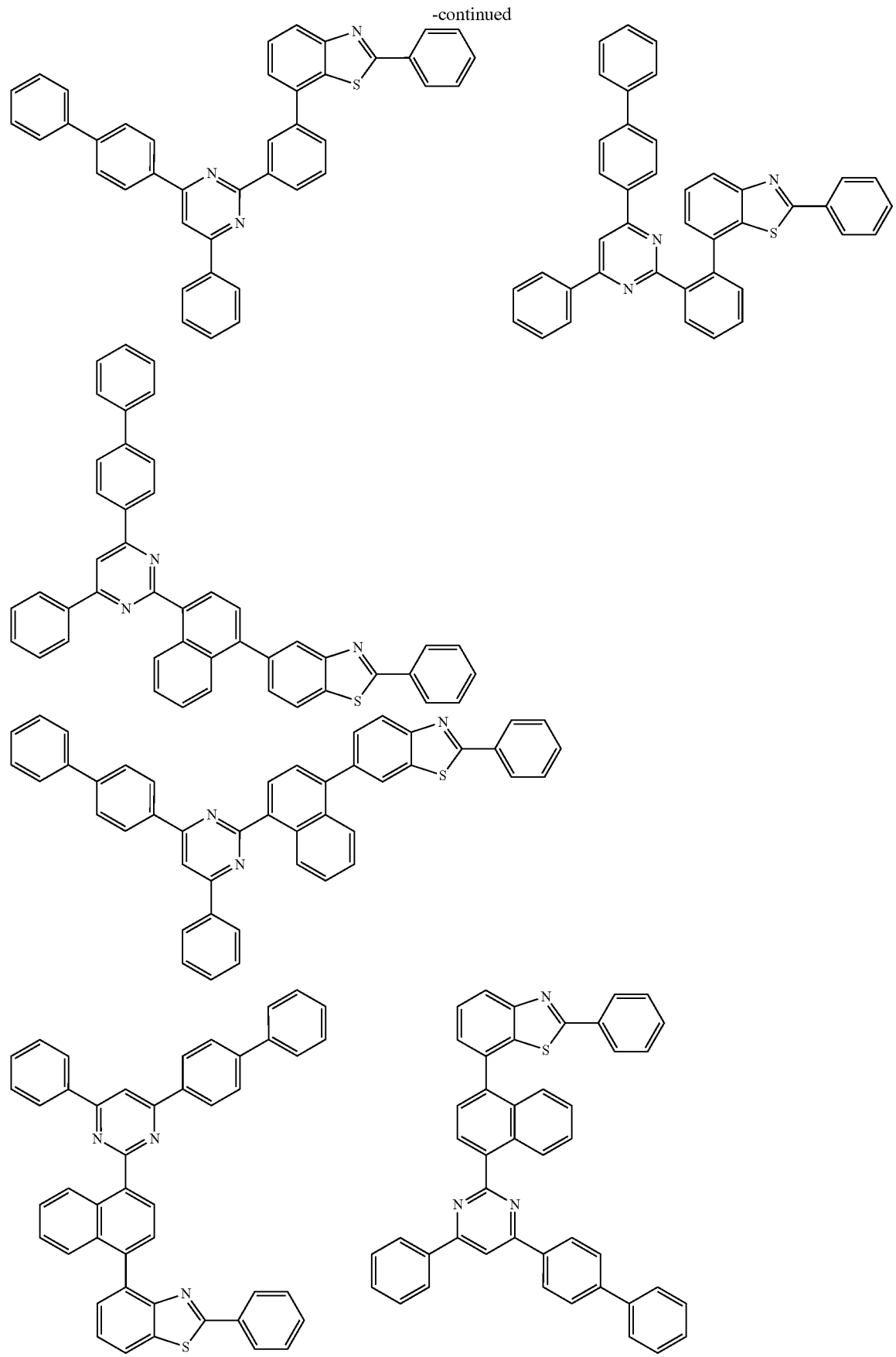

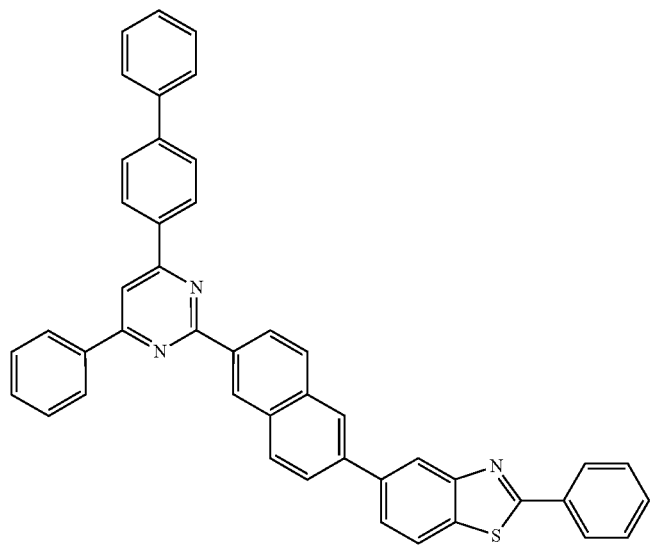
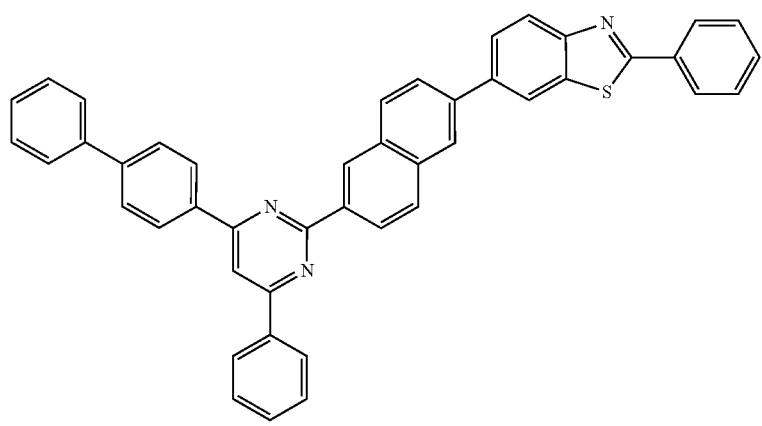
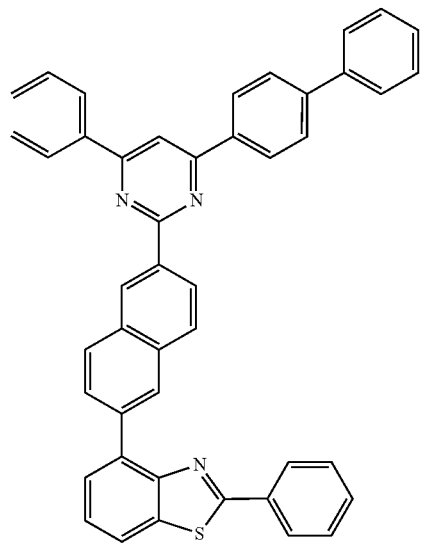
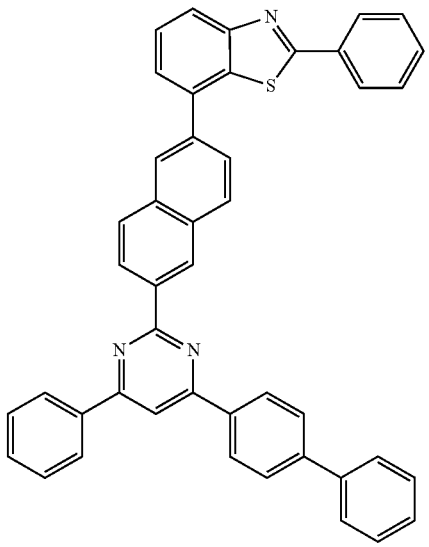

-continued
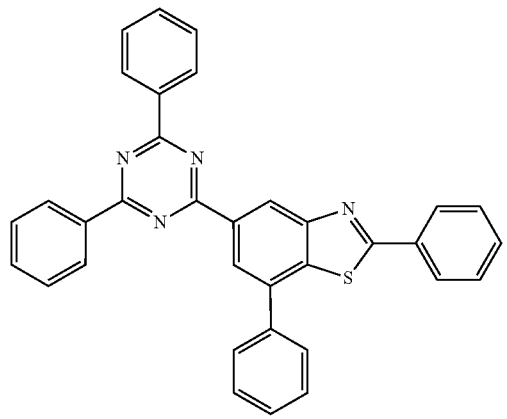
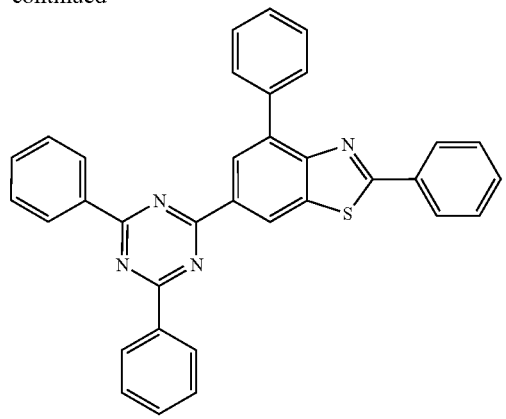
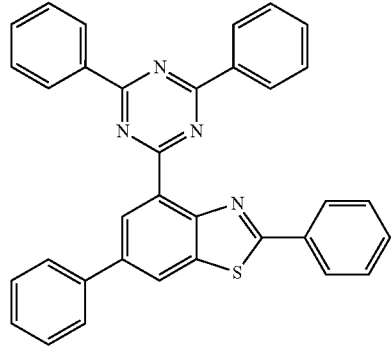
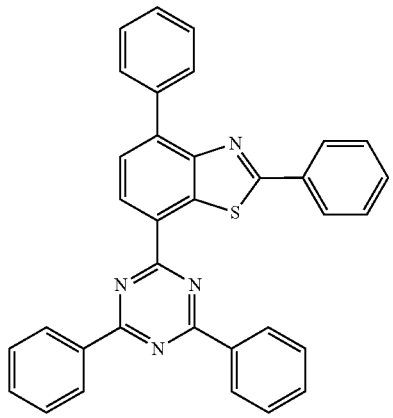
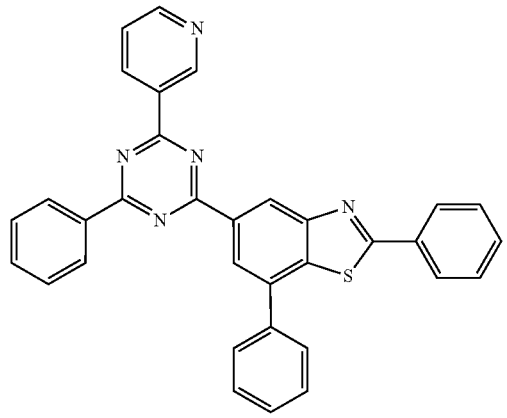
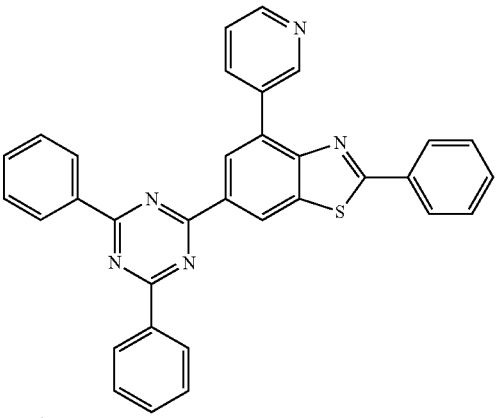
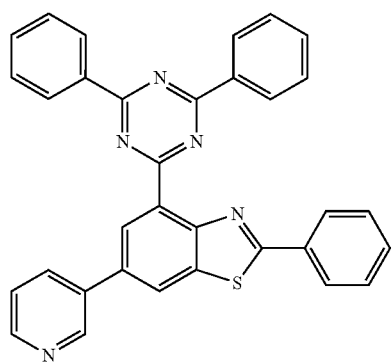
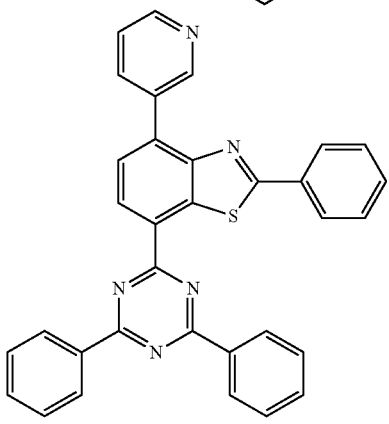

141
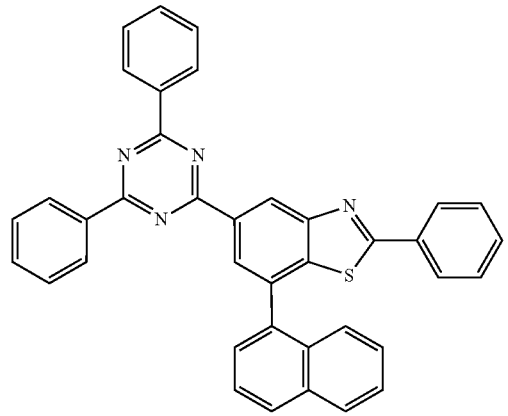
142
-continued
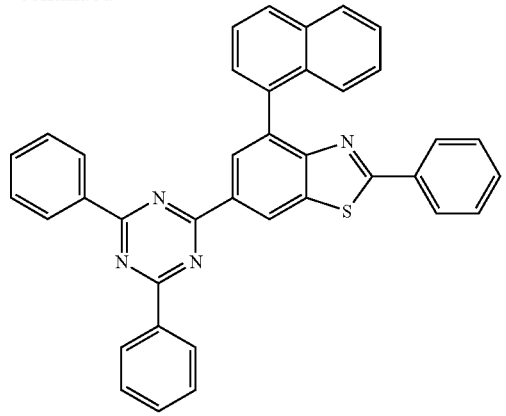
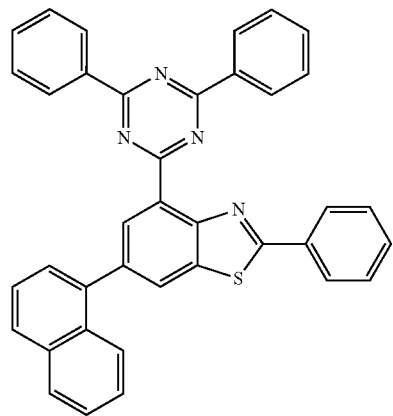
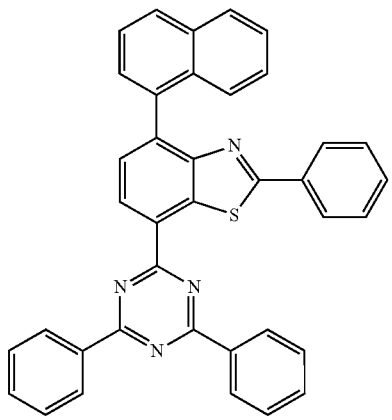
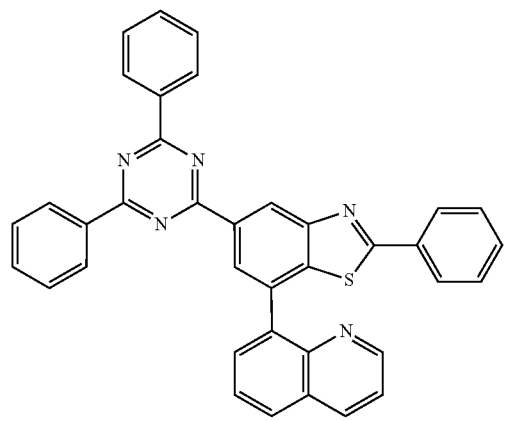
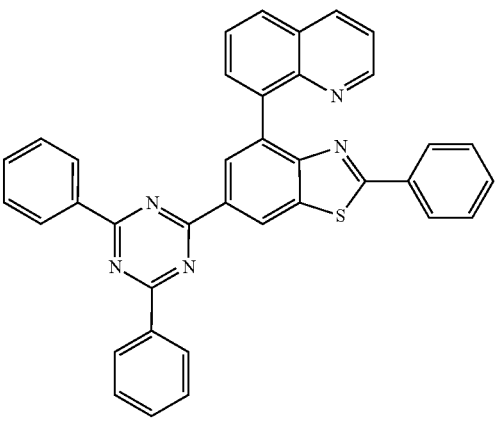
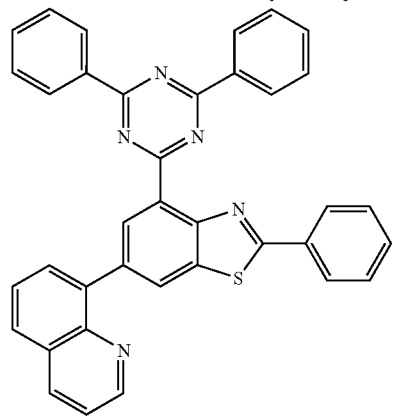
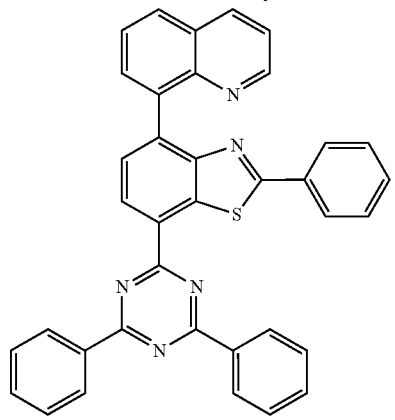

143
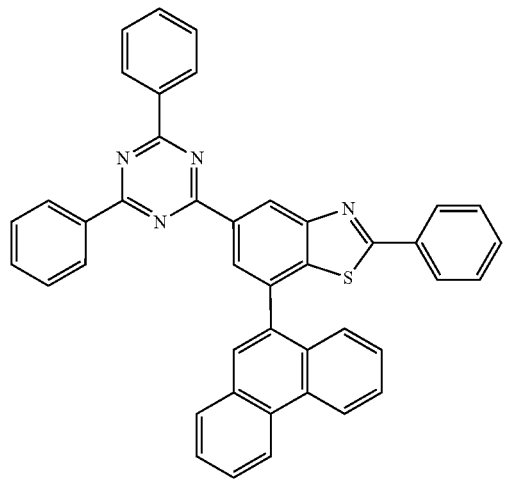
-continued
144
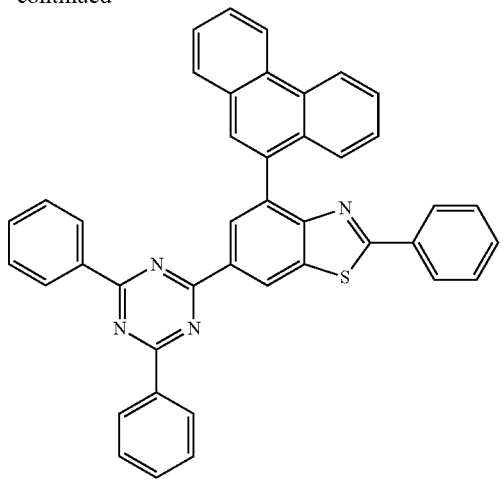
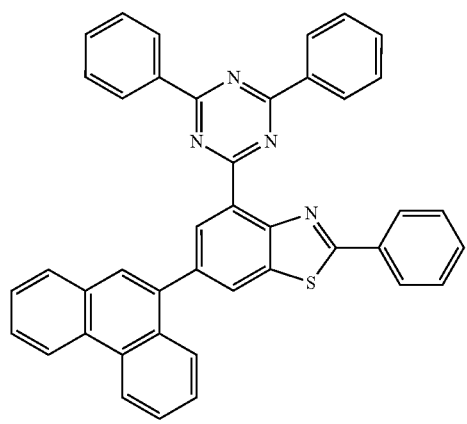
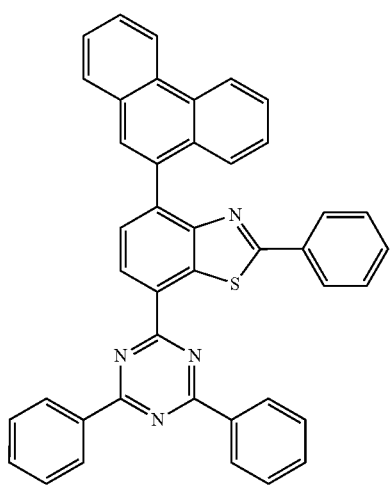
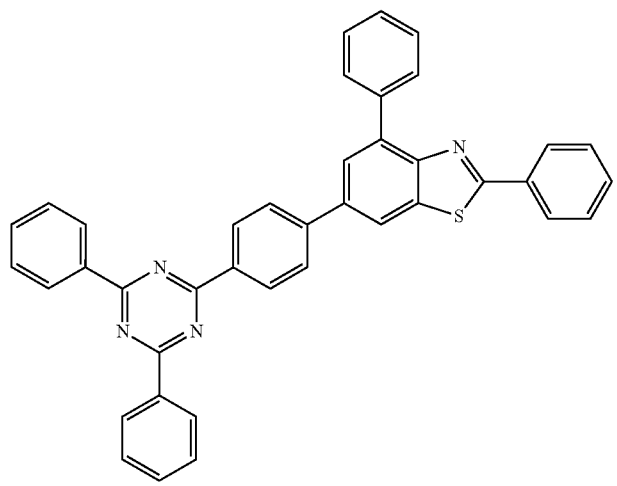

145
146
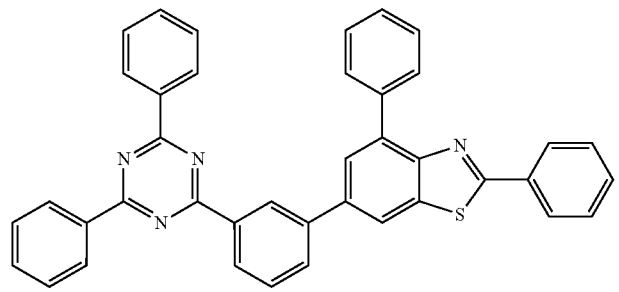
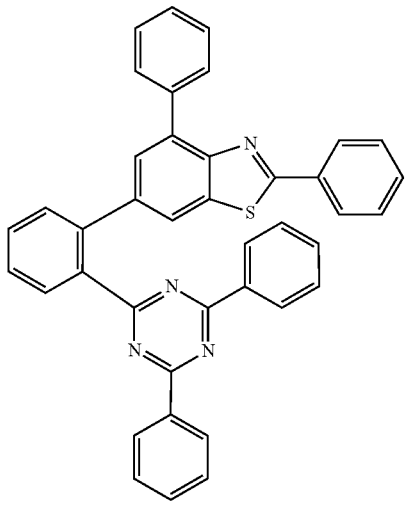
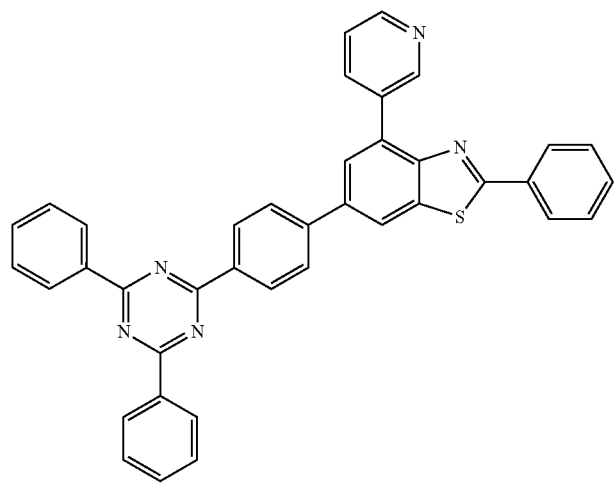
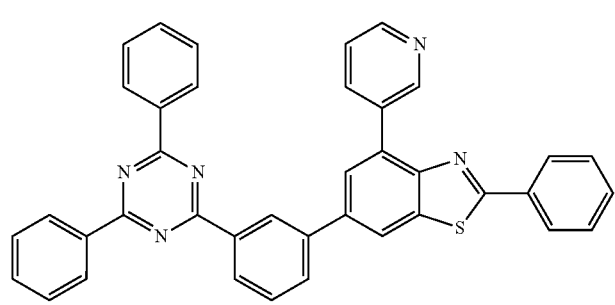
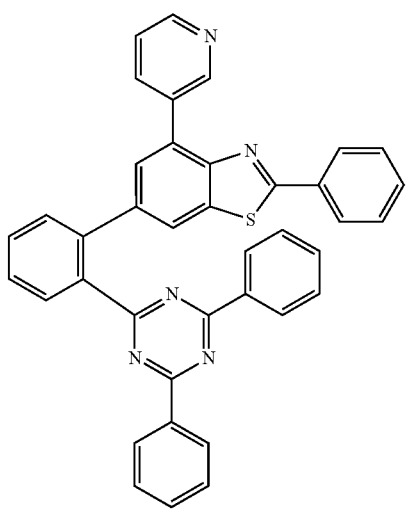

-continued
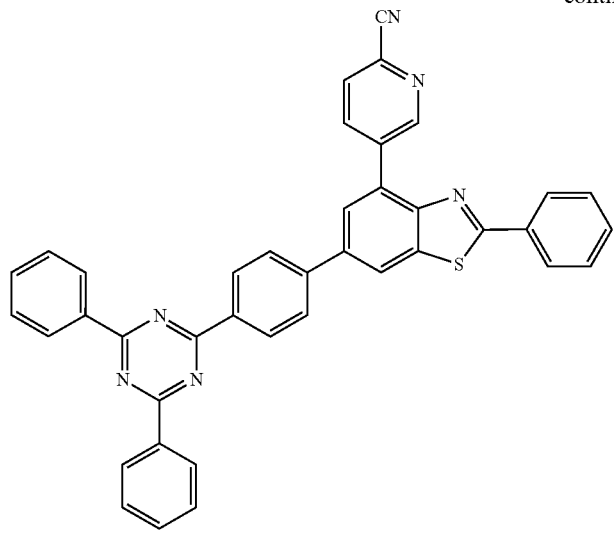
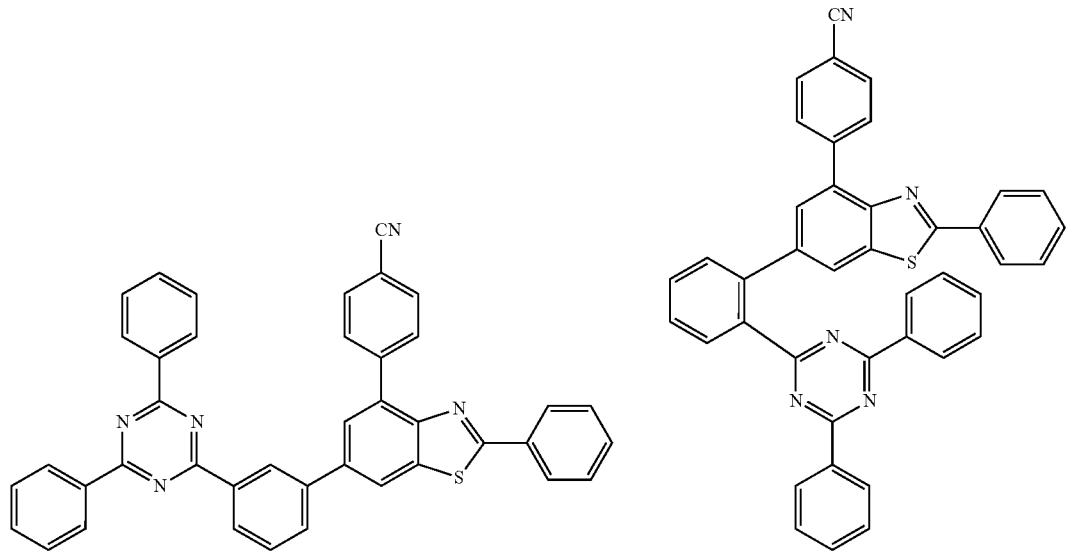
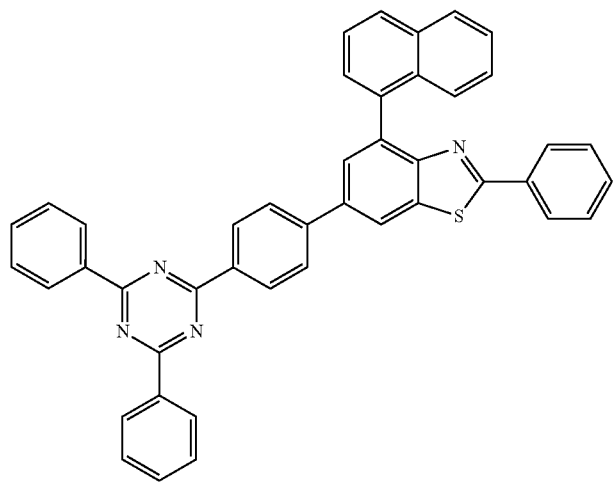

149
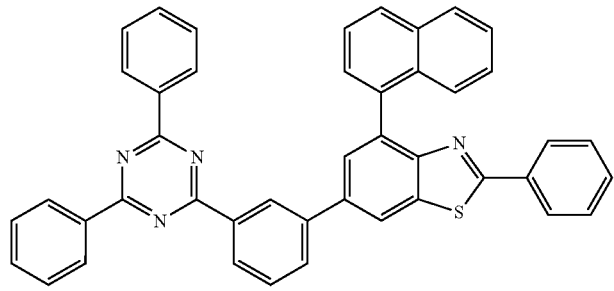
150
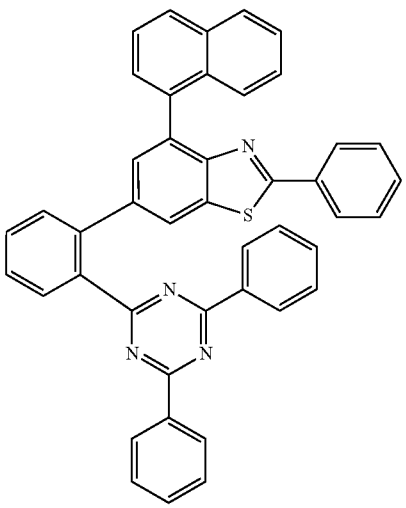
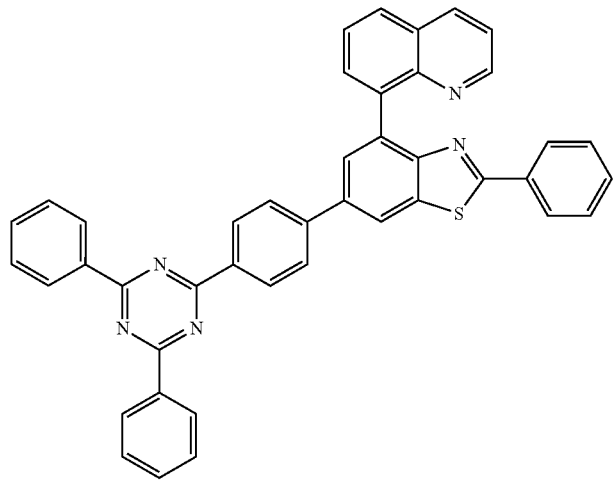
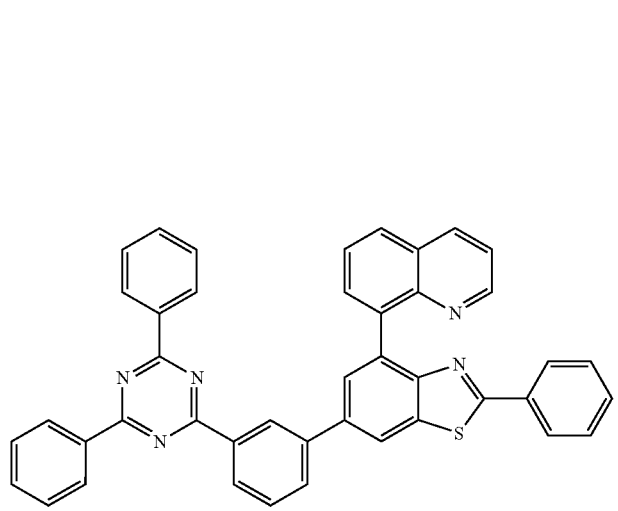
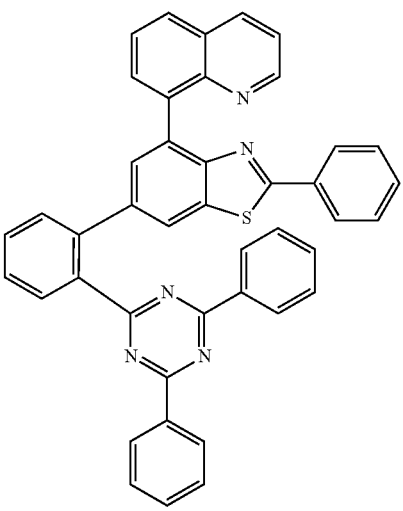

-continued
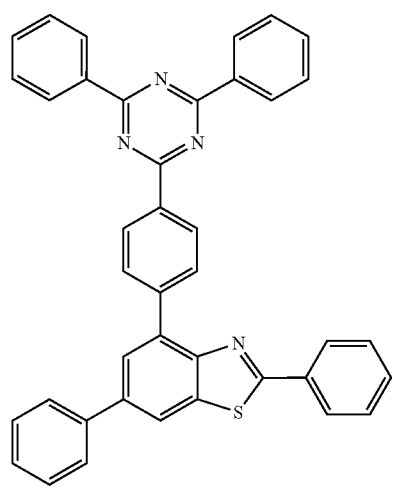
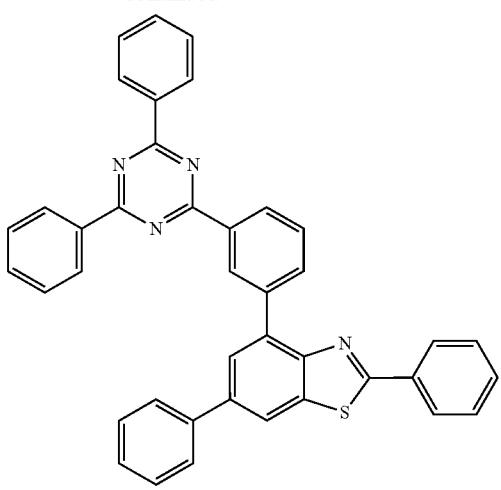
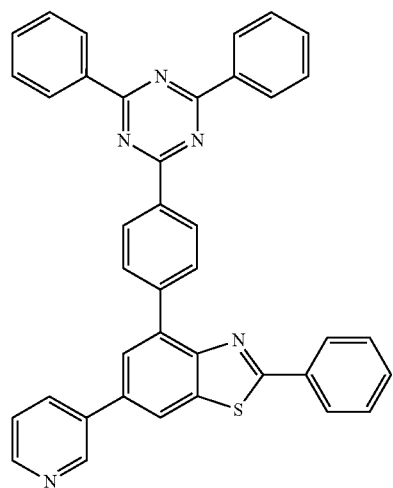
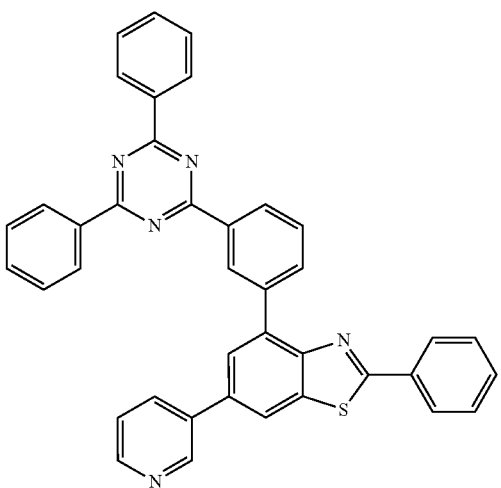
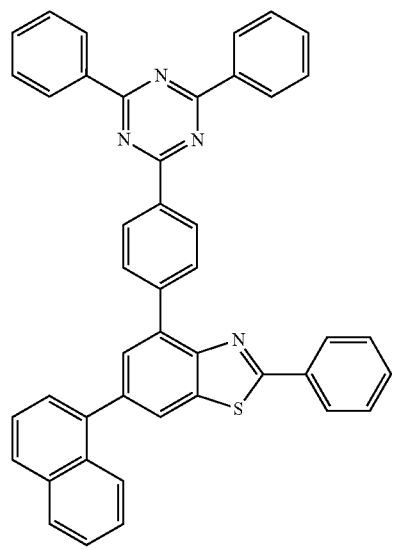
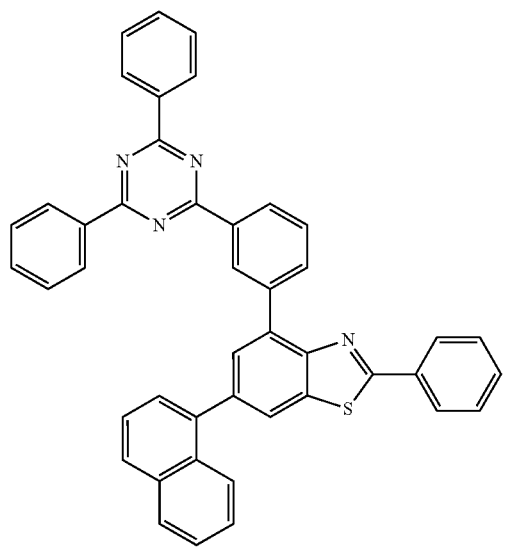

153
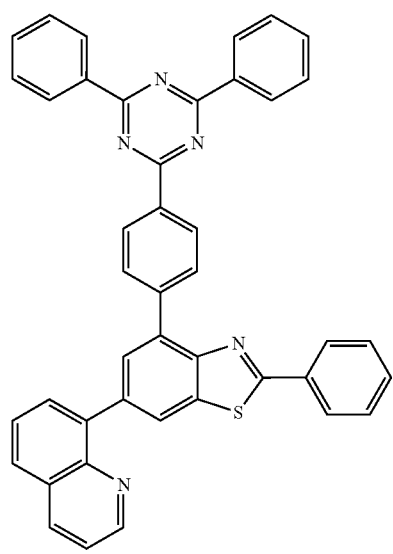
154
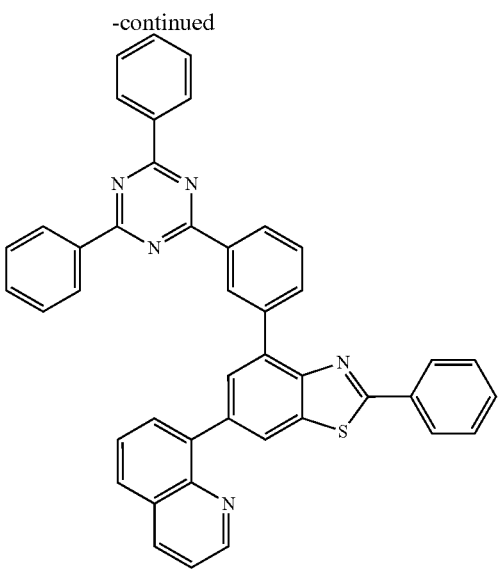
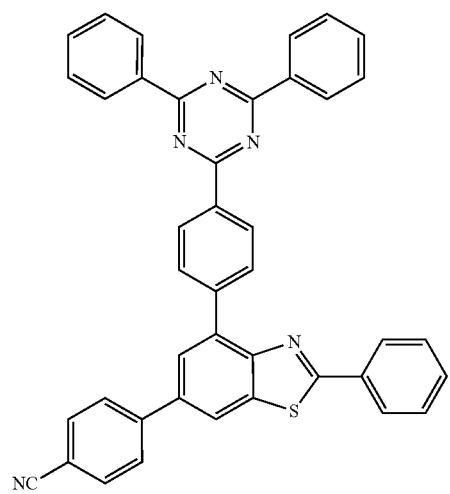
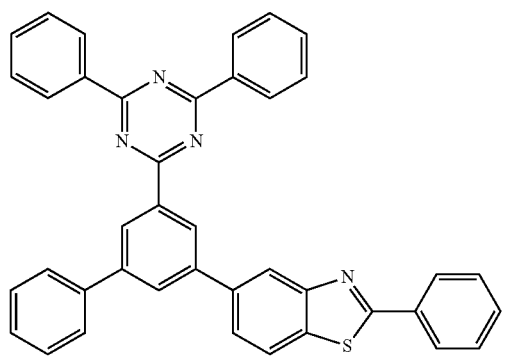
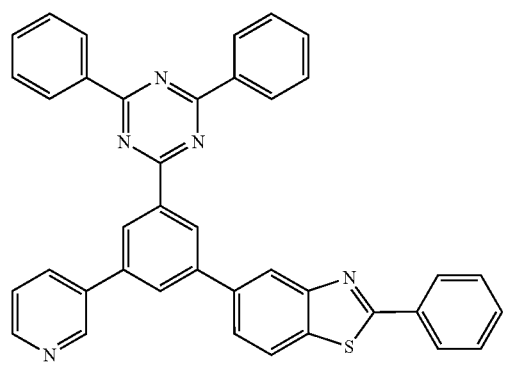
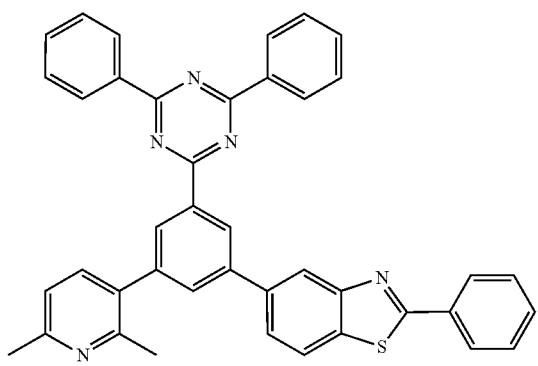

-continued
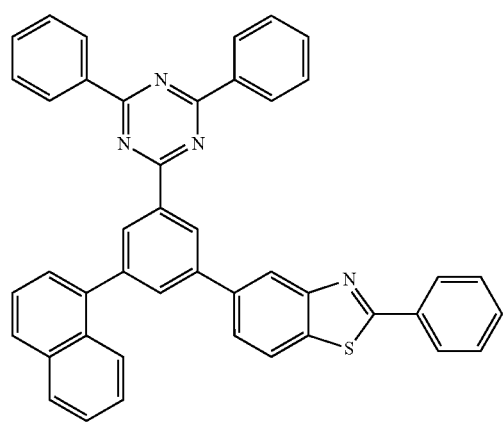
155
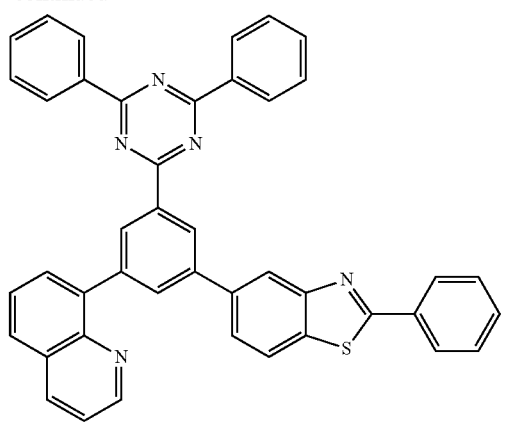
156
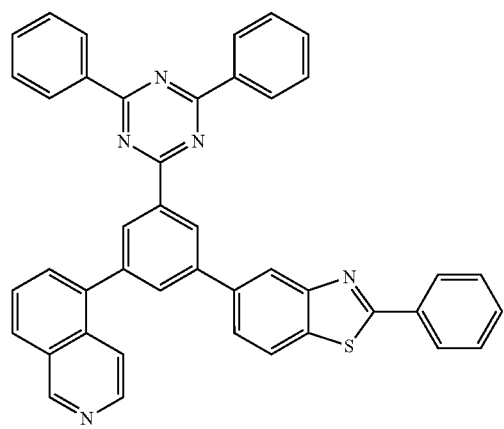
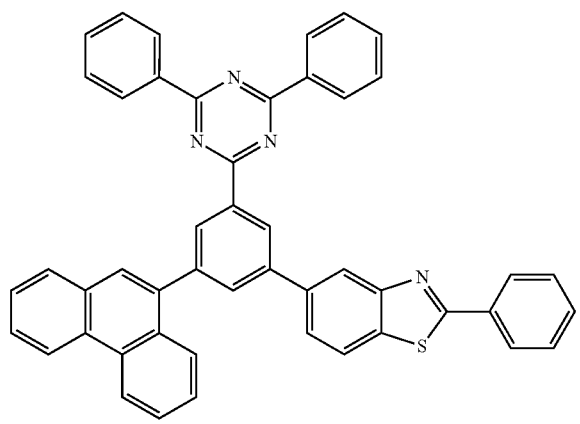
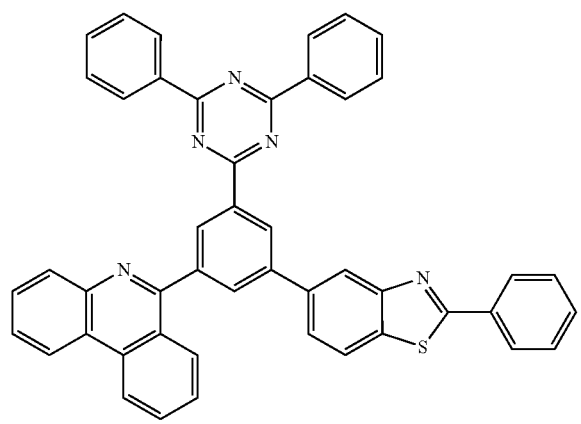
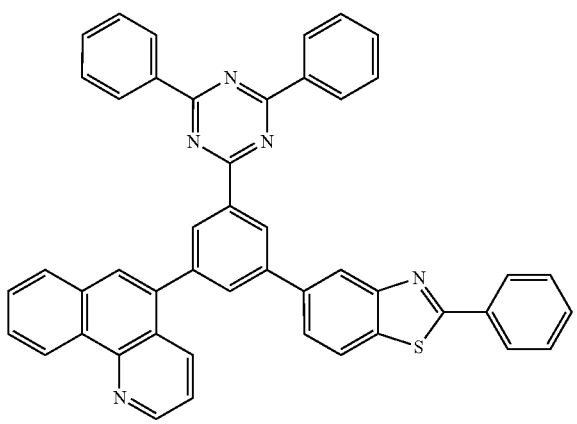

-continued
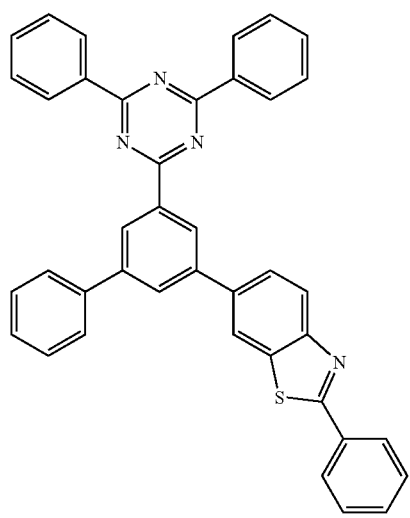
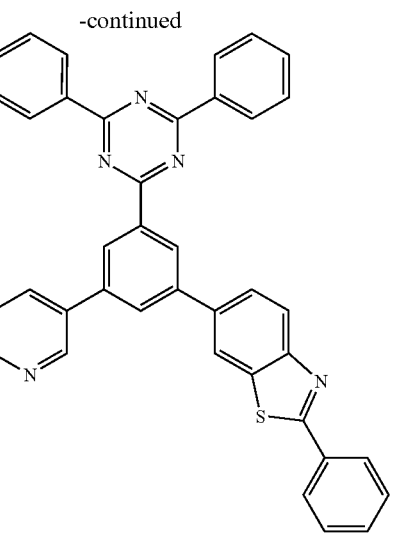
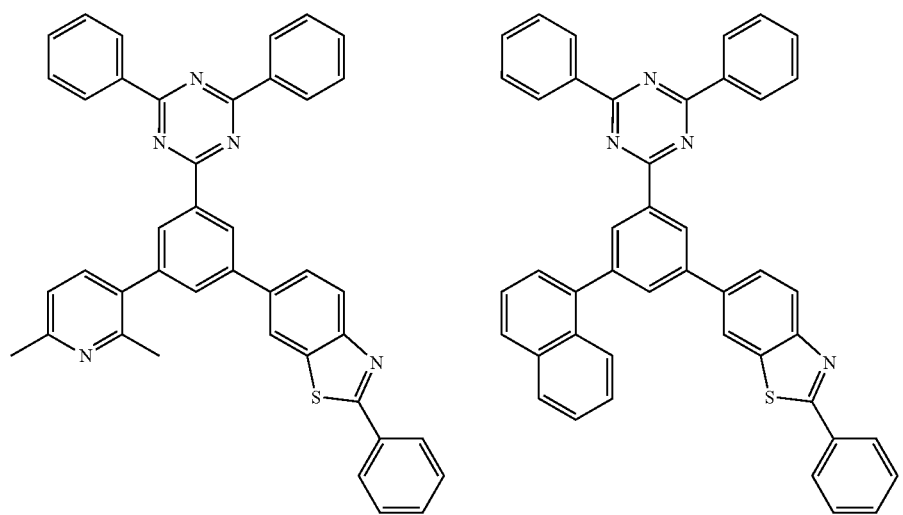
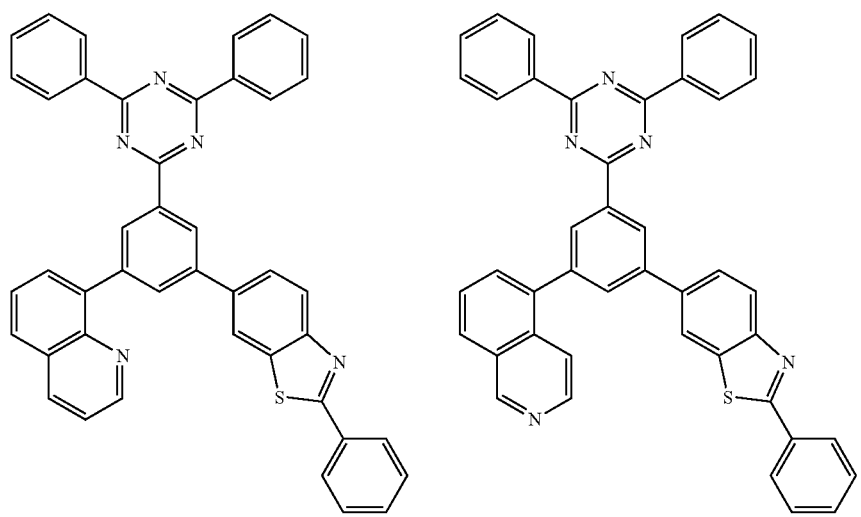

159
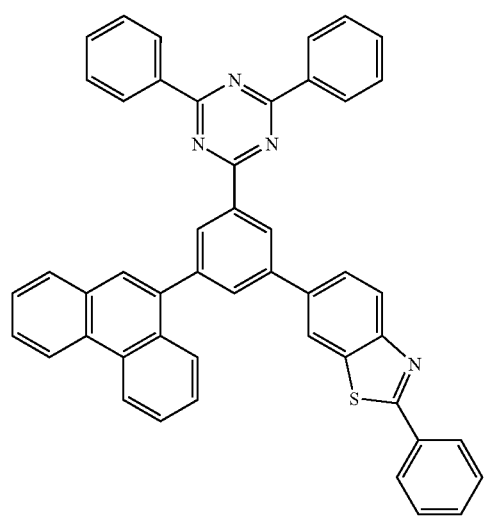
160
-continued
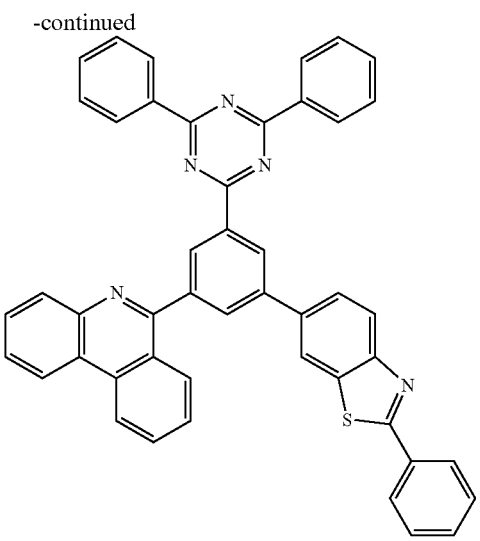
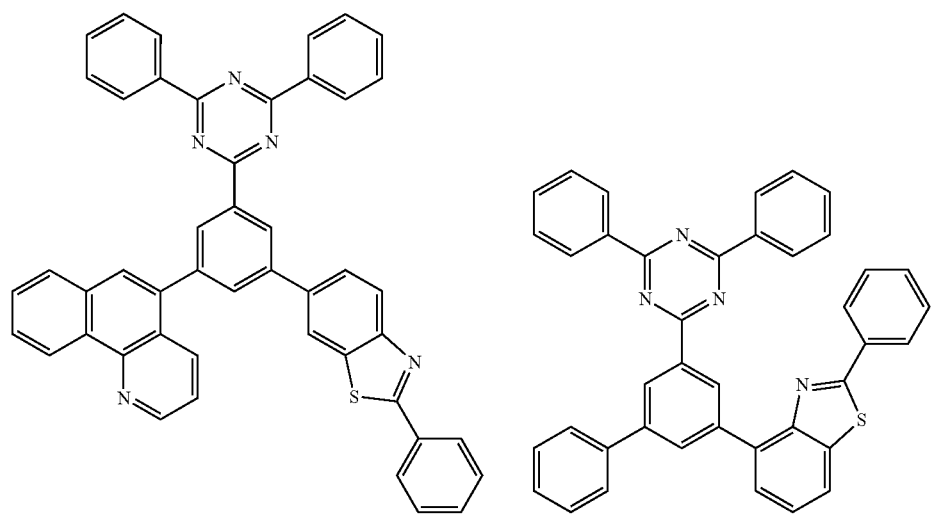
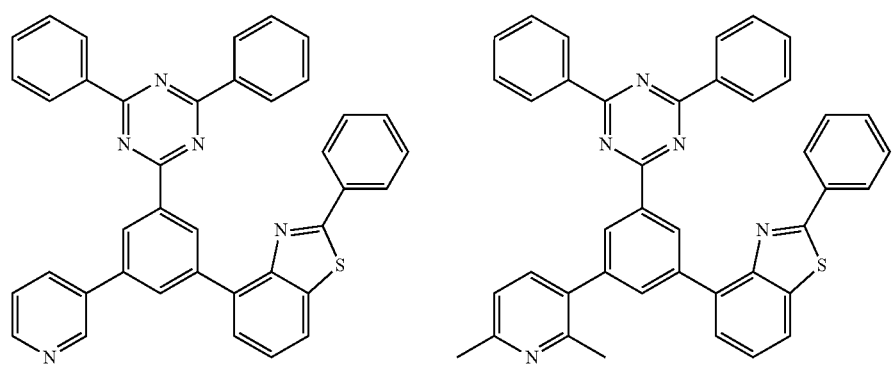

-continued
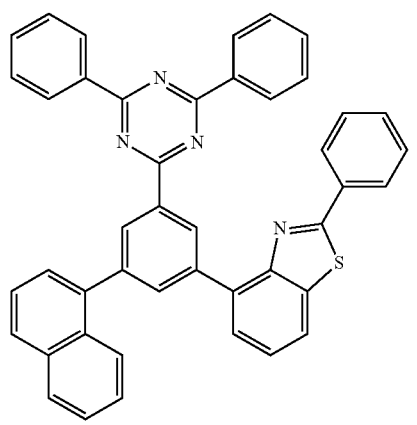
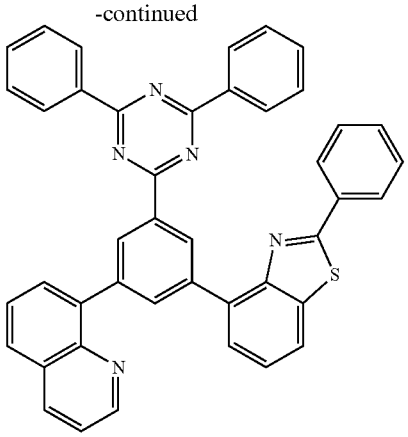
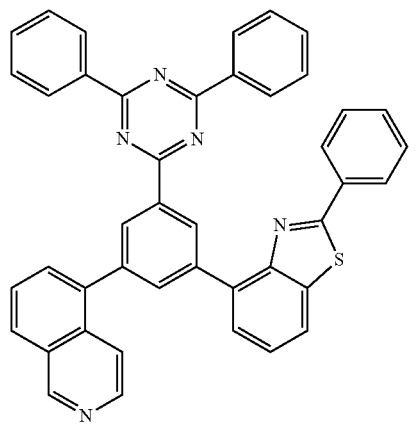
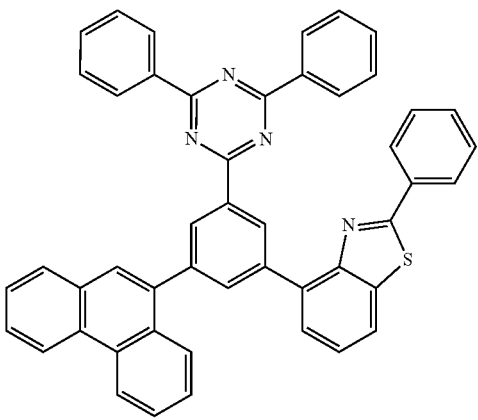
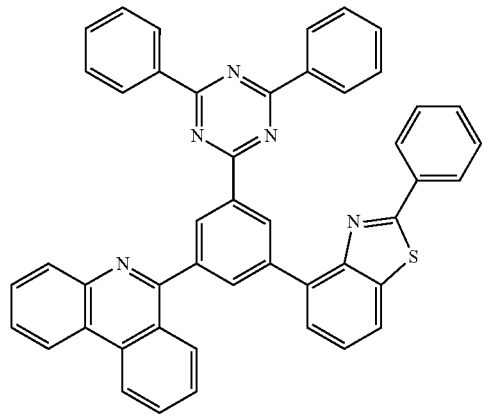
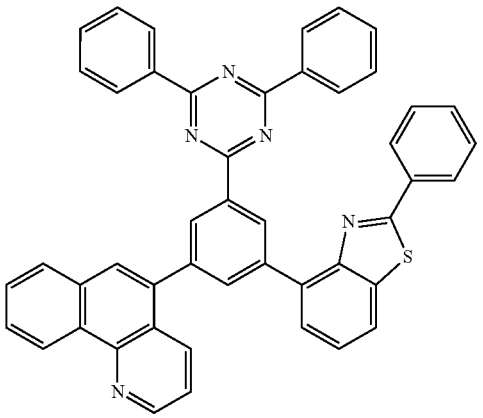
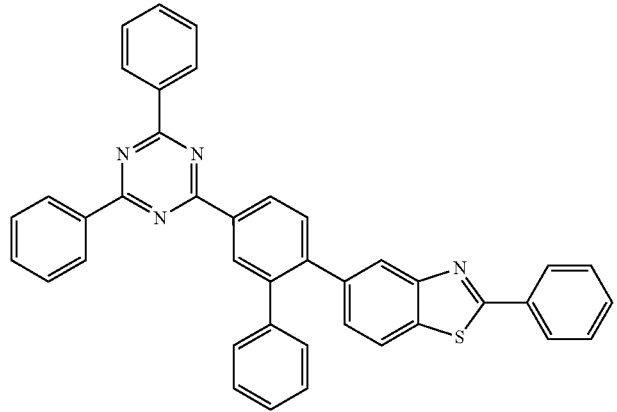

163
-continued
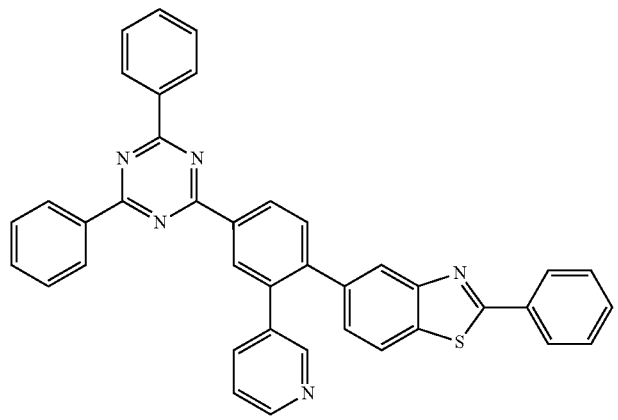
164
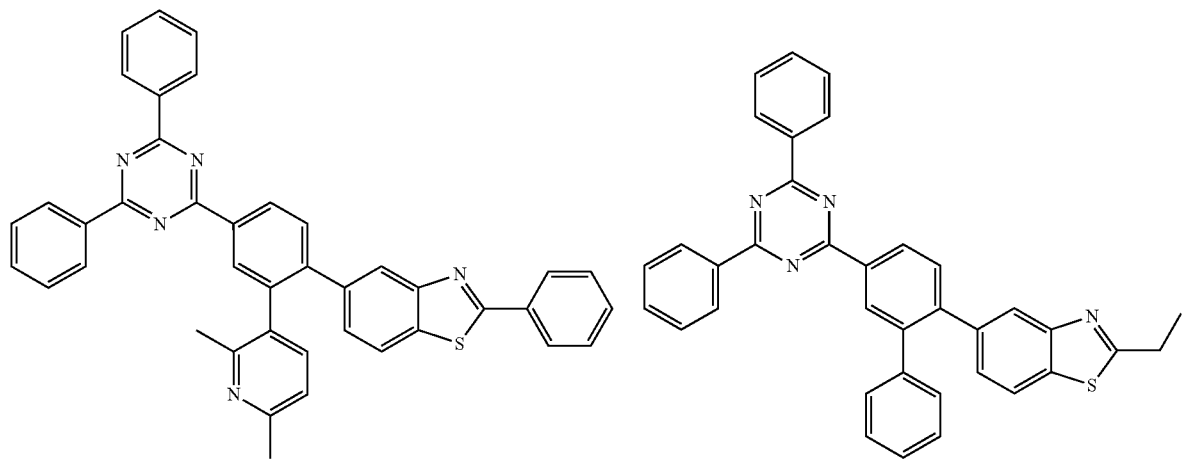
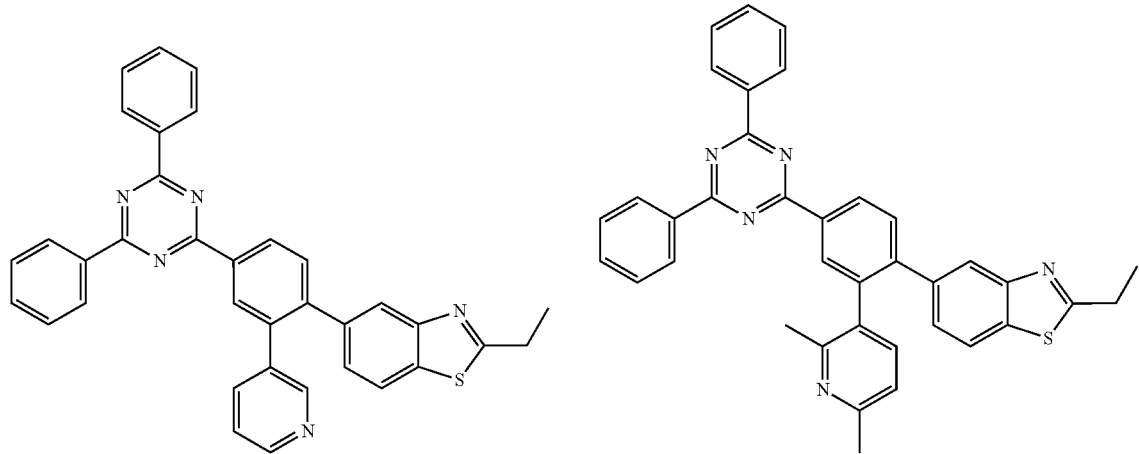

-continued
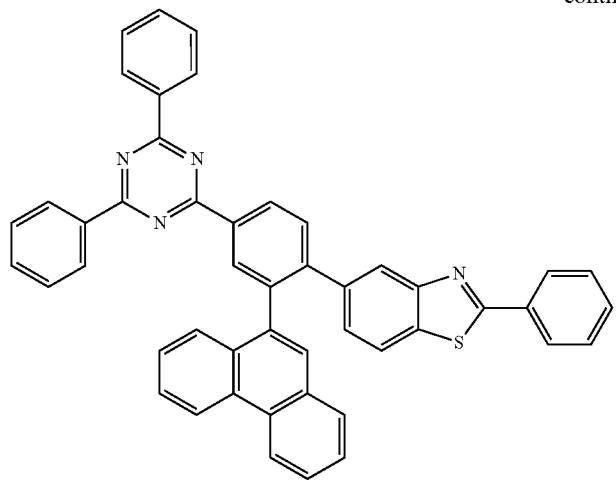
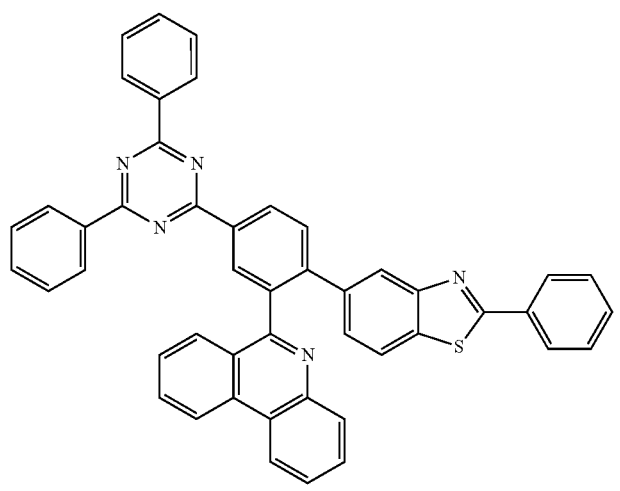
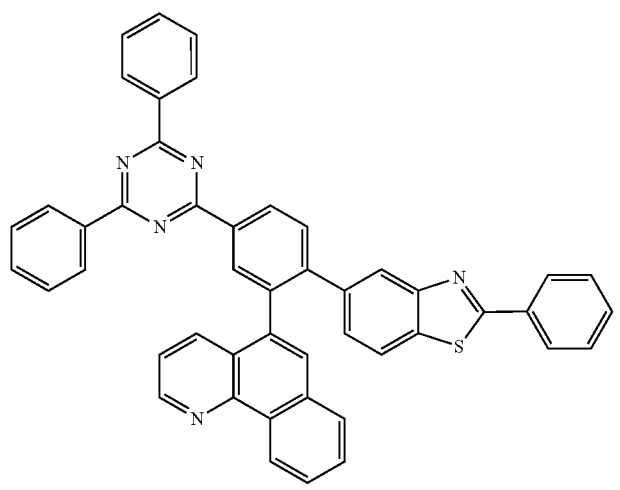

-continued
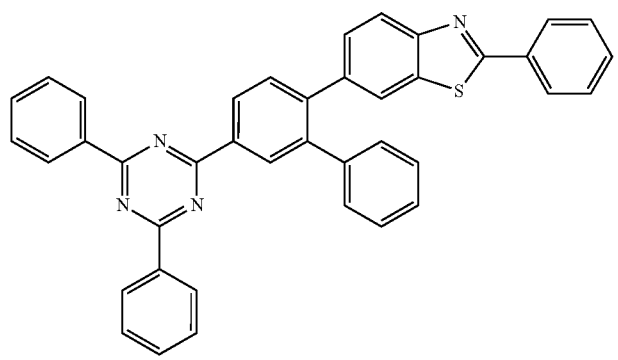
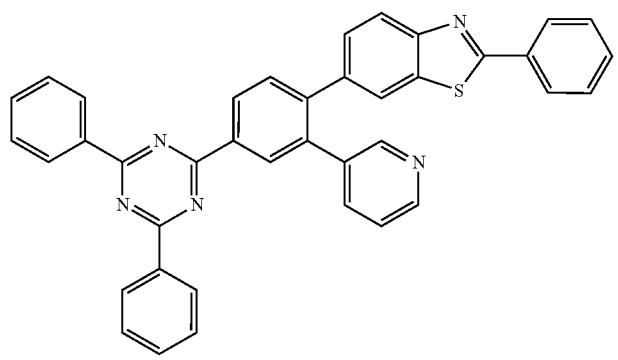
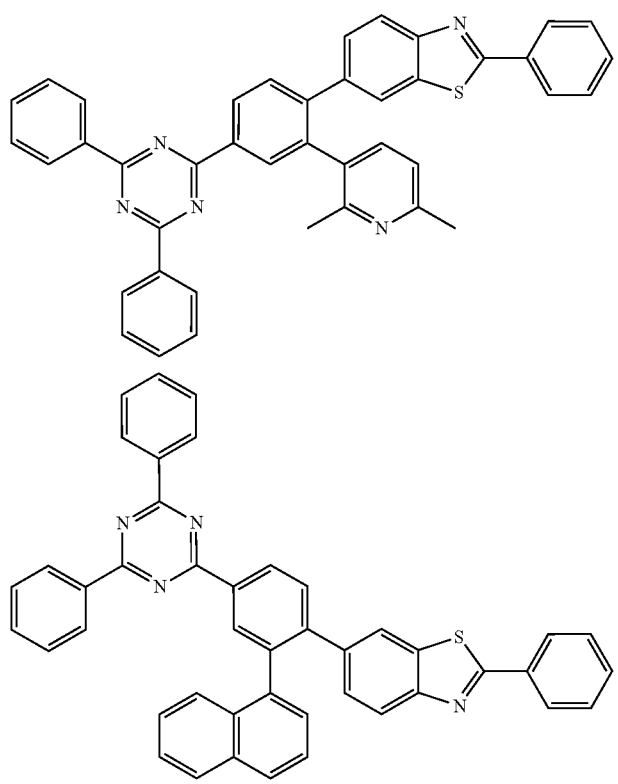

-continued
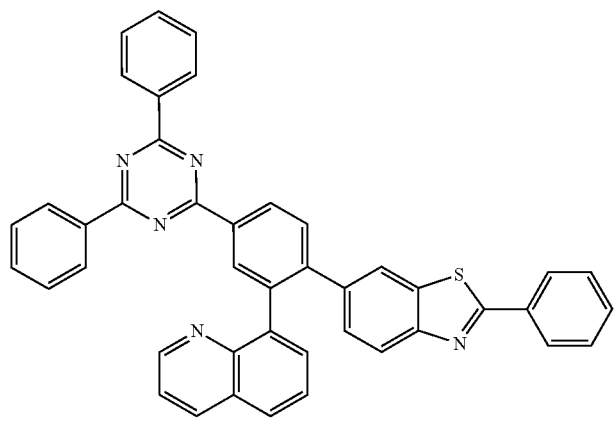
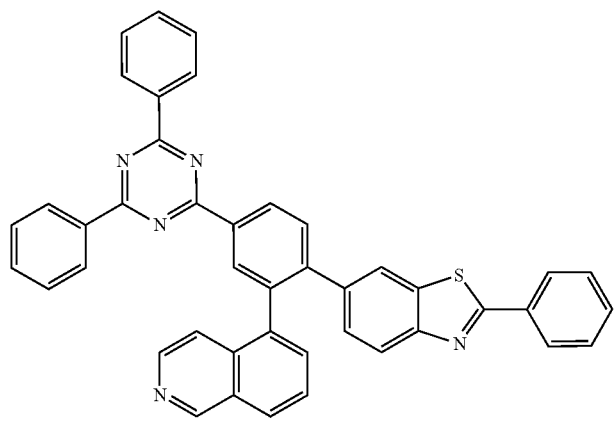
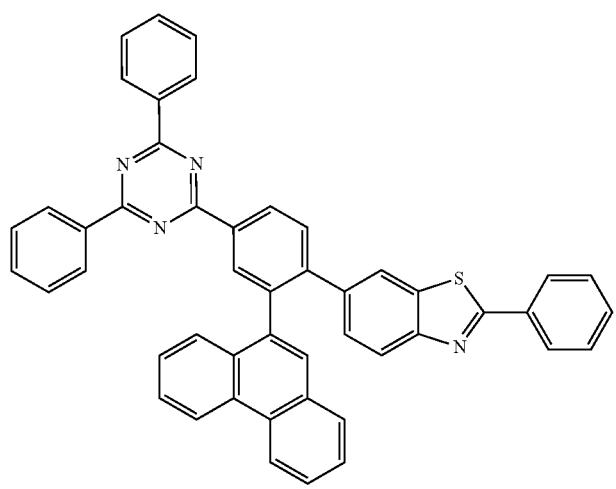

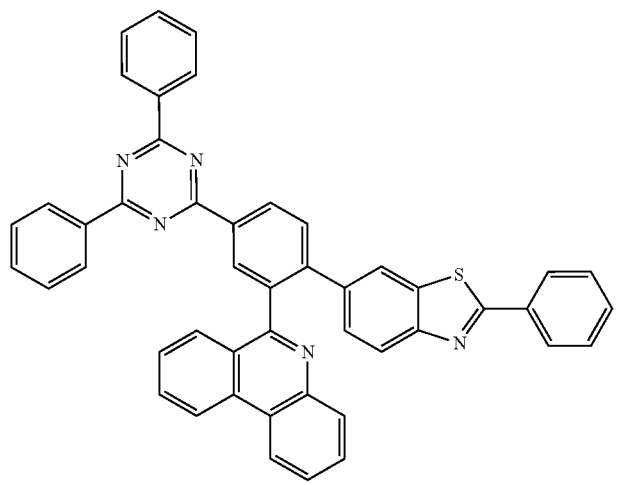
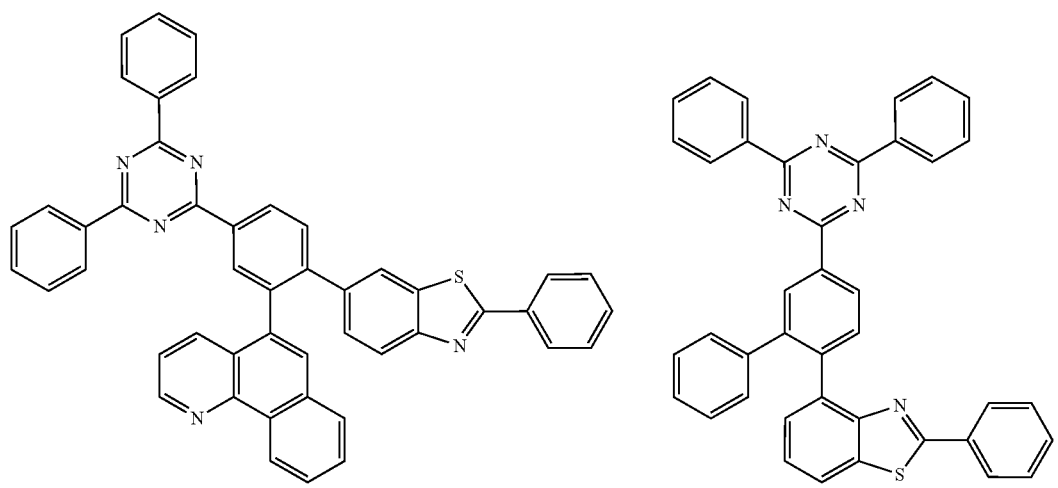
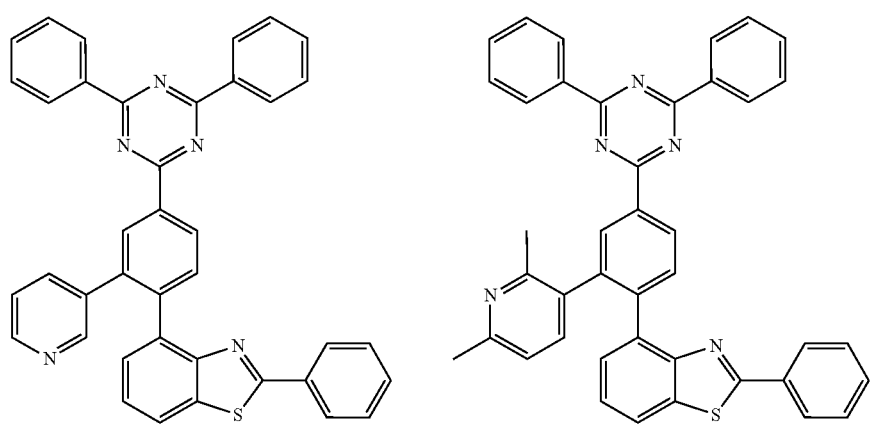

-continued
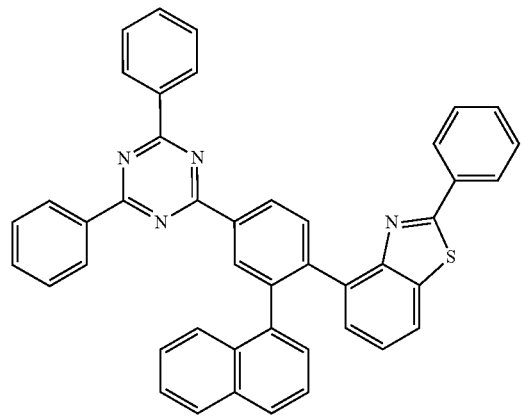
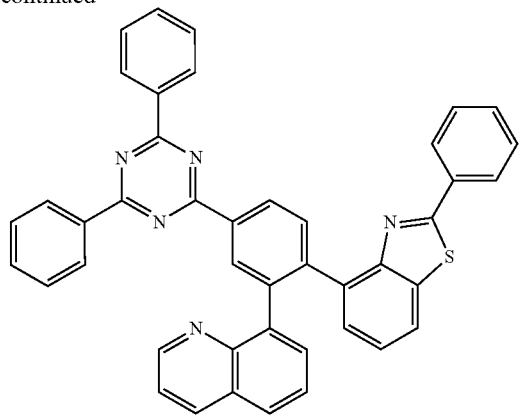
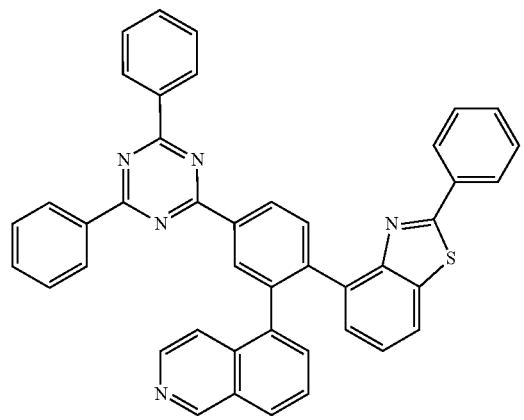
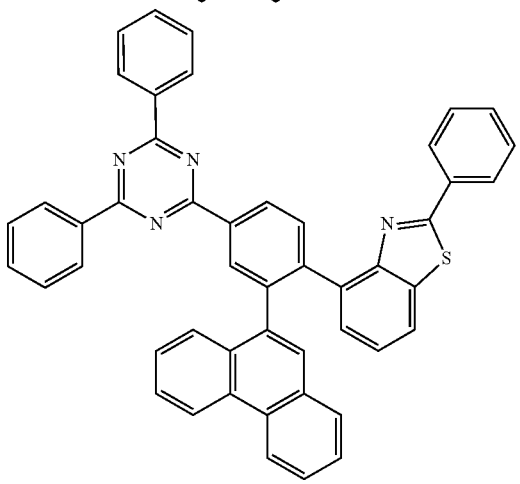
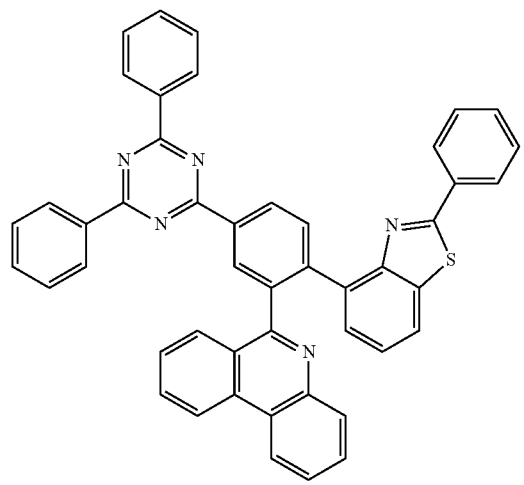
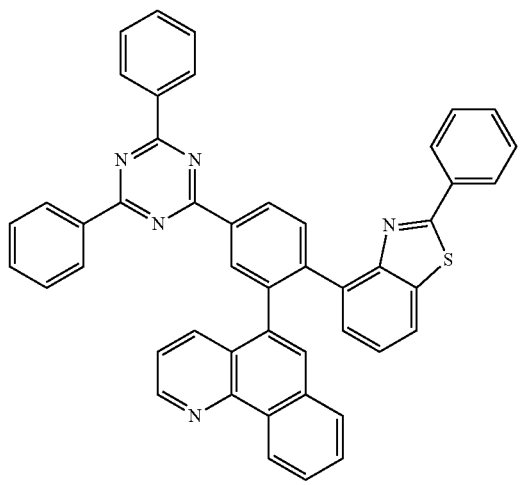
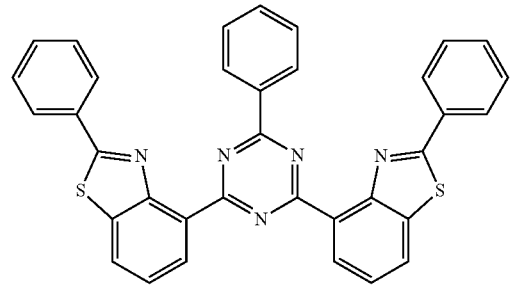
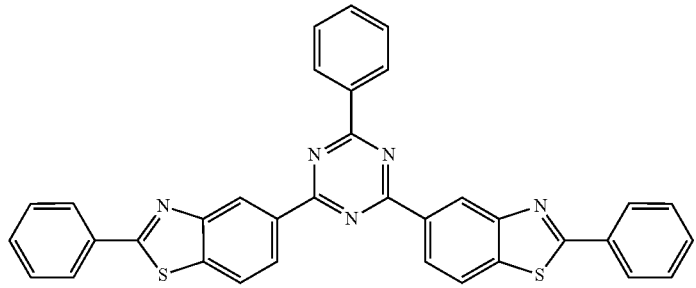

-continued
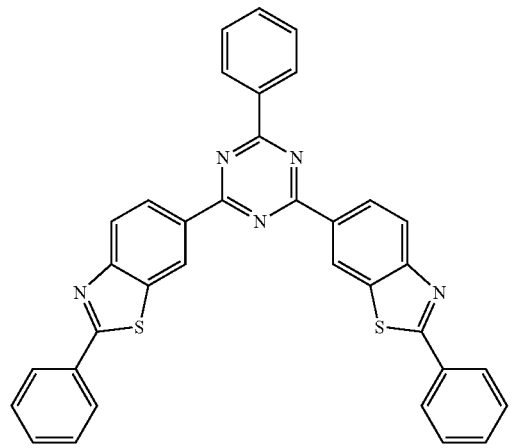
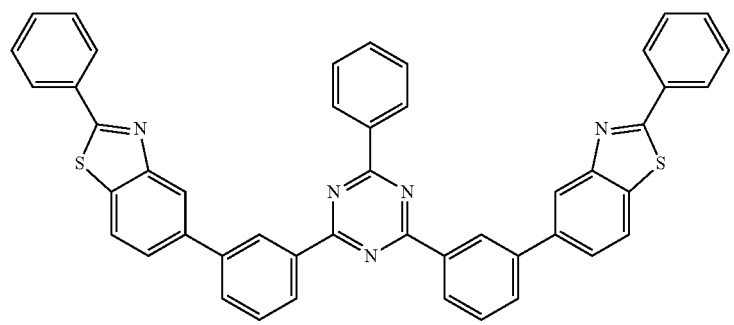
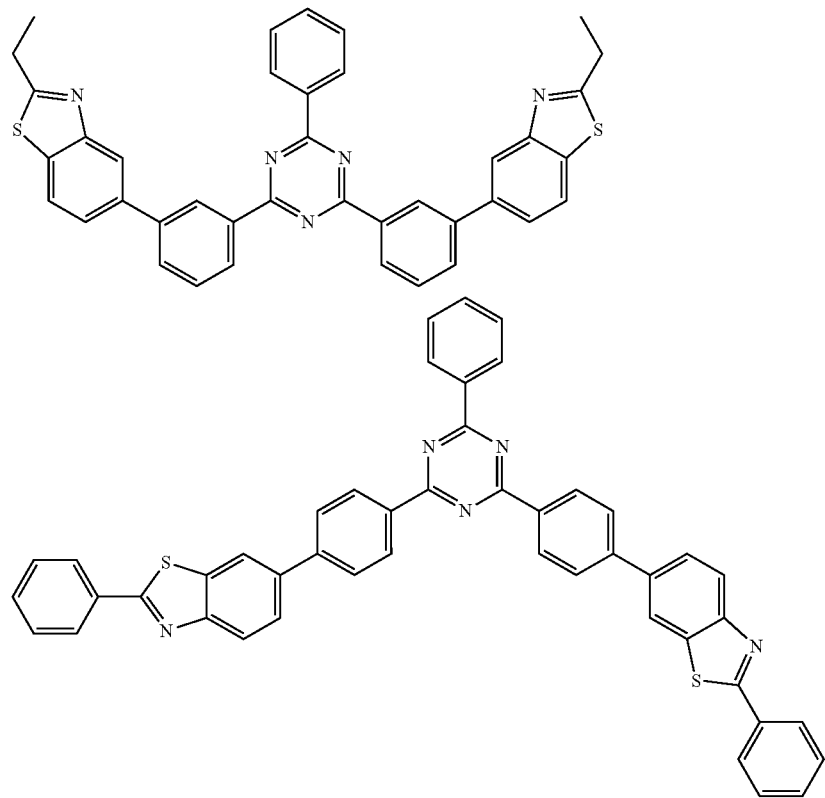

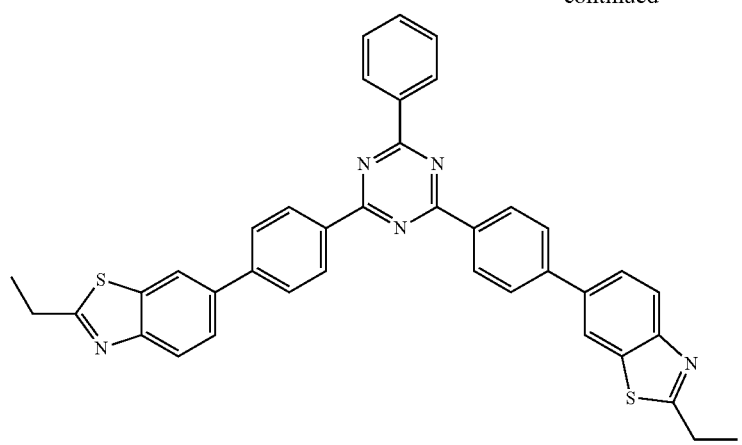
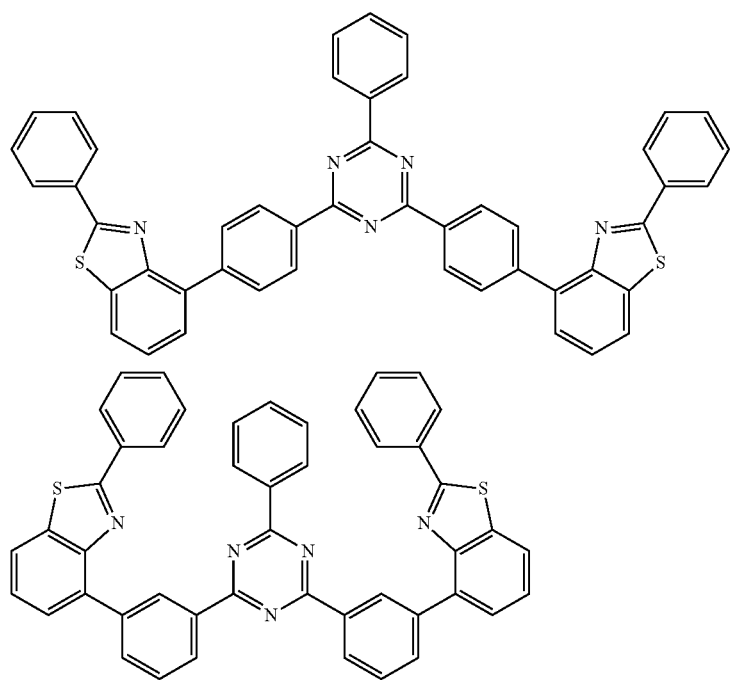
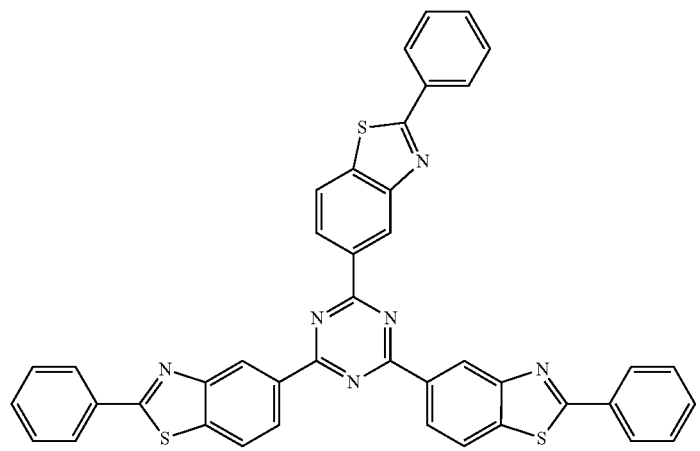

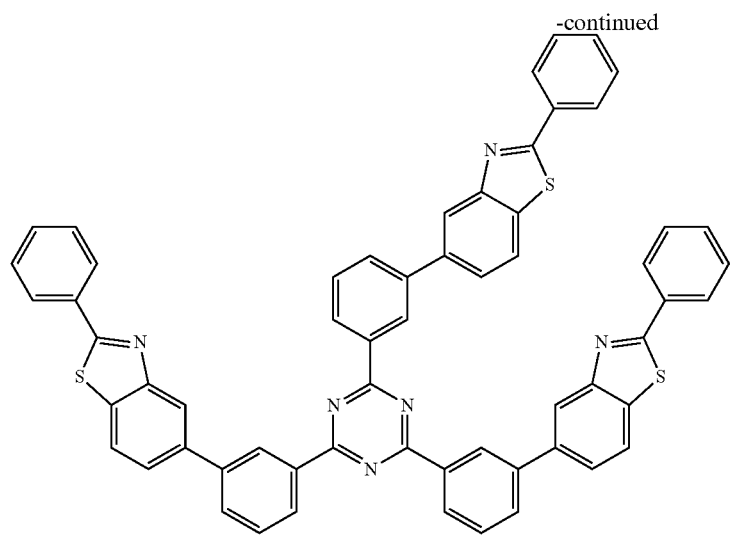

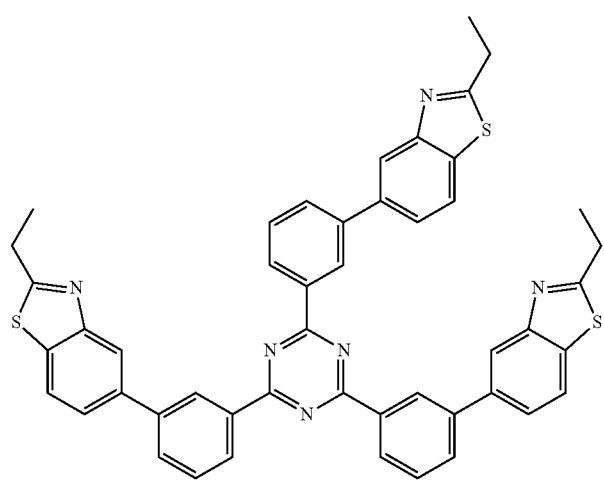

Hereinafter, examples of a synthesis method for obtaining the benzazole derivative having the heteroaryl group will be set forth below. The following examples refer to Synthesis Examples of some (LT18-30-129, LT18-30-033, LT18-30-022, LT18-30-141, LT18-30-065, LT18-30-201, LT18-30-023, and LT18-30-054) of the compounds as listed above. The following Synthesis Examples are provided to help understand the present disclosure, and should not limit the scope of the present disclosure thereto.

SYNTHESIS EXAMPLE

Intermediate Synthesis Example 1: Intermediate 3 Synthesis

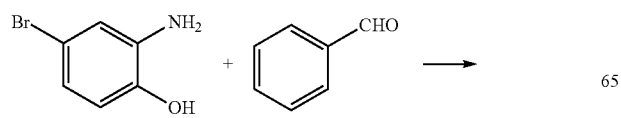

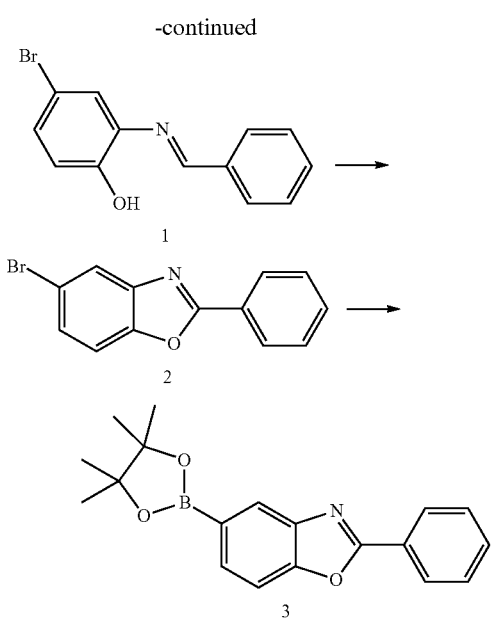

(Intermediate 2 Synthesis)

30.0 g (0.16 mol) of 2-amino-4-bromophenol, 16.2 mL (0.16 mol) of benzaldehyde and 200 mL of ethanol were put into a 1-necked 2 L flask. The mixture was stirred at room temperature for 12 hours. After completion of the reaction, the reaction product was subjected to distillation under reduced pressure to remove the solvent from the reaction product, to obtain an intermediate 1. Then, the intermediate 1 was dissolved into 800 mL of dichloromethane, to which, in turn, 36.0 g (0.176 mol) of 2,3-dichloro-5,6-dicyano-1,4-benzoquinone (DDQ) was slowly added at room temperature. Then, the mixed solution was stirred at the room temperature for 2 hours. After completion of the reaction, the reaction product was purified using short silica gel-based column chromatography (dichloromethane) and, then, the purified product was solidified with methanol, to obtain a solid compound (intermediate 2) 41.0 g (yield: 93.2%).

(Intermediate 3 Synthesis)

Then, the intermediate 2 20.0 g (72.96 mmol), bis(pinacolato)diboron 20.4 g (80.26 mmol), Pd(dppf)Cl2·CH2Cl2 2.98 g (3.65 mmol), potassium acetate (KOAc) 14.3 g (145.92 mmol), and dioxane 730 mL were input into a 1-neck 1 L flask to obtain a mixture. Then, the mixture was refluxed and stirred at 90 degrees C. for 12 hours. The resulting product was purified using silica gel column chromatography, to prepare a white solid compound (intermediate 3) 20.5 g (yield: 87.6%).

Intermediate Synthesis Example 2: Intermediate 4 Synthesis

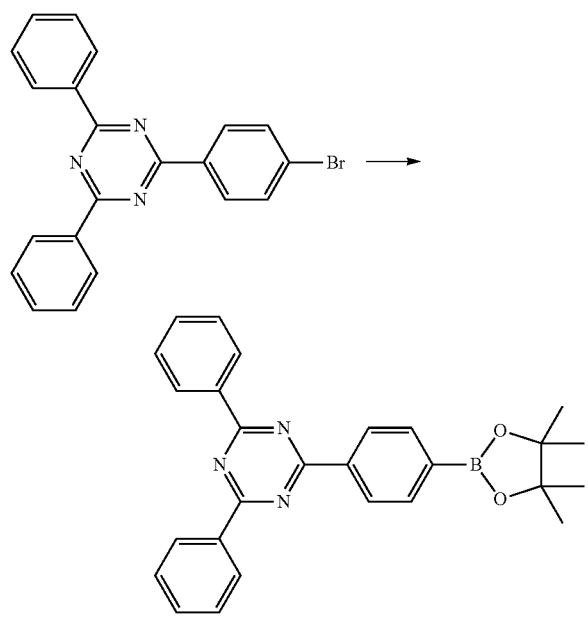

4

(Intermediate 4 Synthesis)

2-(4-bromophenyl)-4,6-diphenyl-1,3,5-triazine 10.0 g (26.0 mmol), Bis(pinacolato)diboron 13.0 g (52.0 mmol), Pd(dppf)Cl2·CH2Cl2 950 mg (0.647 mmol), potassium acetate (KOAc) 10.2 g (104 mmol), and dioxane 130 mL were input into a one-neck 250 mL flask to obtain a mixture. Then, the mixture was refluxed and stirred at 100° C. for 7 hours. After completion of the reaction, the reaction product was subjected to distillation under reduced pressure to remove the solvent from the reaction product. A thus-resulting solid was dissolved in dichloromethane, and filtered using Celite, and washed with dichloromethane. A thus-resulting product was crystallized using methanol (300 mL), to obtain a solid compound (intermediate 4) 10.5 g (yield: 93.1%).

Intermediate Synthesis Example 3: Intermediate 5 Synthesis

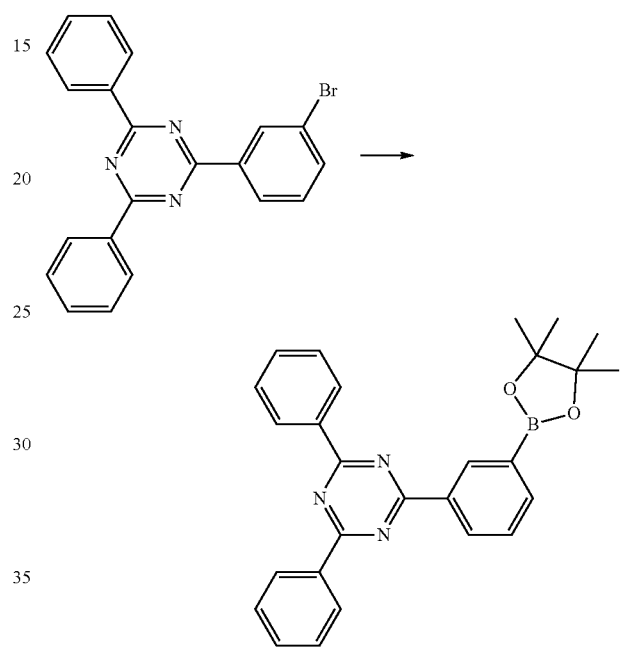

5

(Intermediate 5 Synthesis)

2-(3-bromophenyl)-4,6-diphenyl-1,3,5-triazine 15.0 g (32.4 mmol), Bis(pinacolato)diboron 12.3 g (48.6 mmol), Pd(dppf)Cl2·CH2Cl2 529 mg (0.647 mmol), potassium acetate (KOAc) 9.53 g (97.1 mmol), and dioxane 323 mL were input into a one-neck 500 mL flask to obtain a mixture. Then, the mixture was refluxed and stirred at 90° C. for 12 hours. After completion of the reaction, the reaction product was subjected to distillation under reduced pressure to remove the solvent from the reaction product. A thus-resulting solid was dissolved in dichloromethane, and filtered using Celite, and washed with dichloromethane. A thus-resulting product was crystallized using methanol, to obtain a solid compound (intermediate 5) 16.0 g (yield: 96.8%).

Intermediate Synthesis Example 4: Intermediate 8 Synthesis

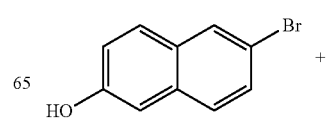

183
-continued

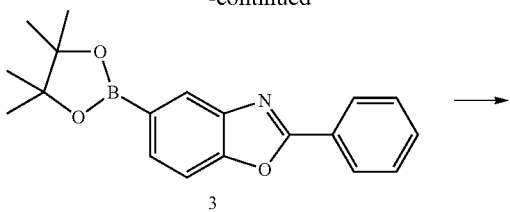
3

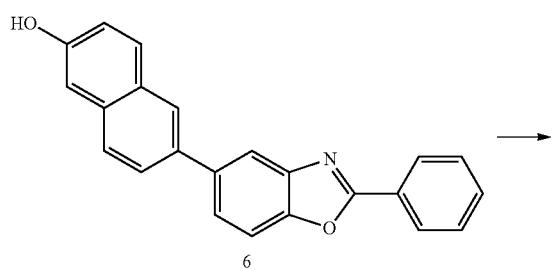
6

TfO
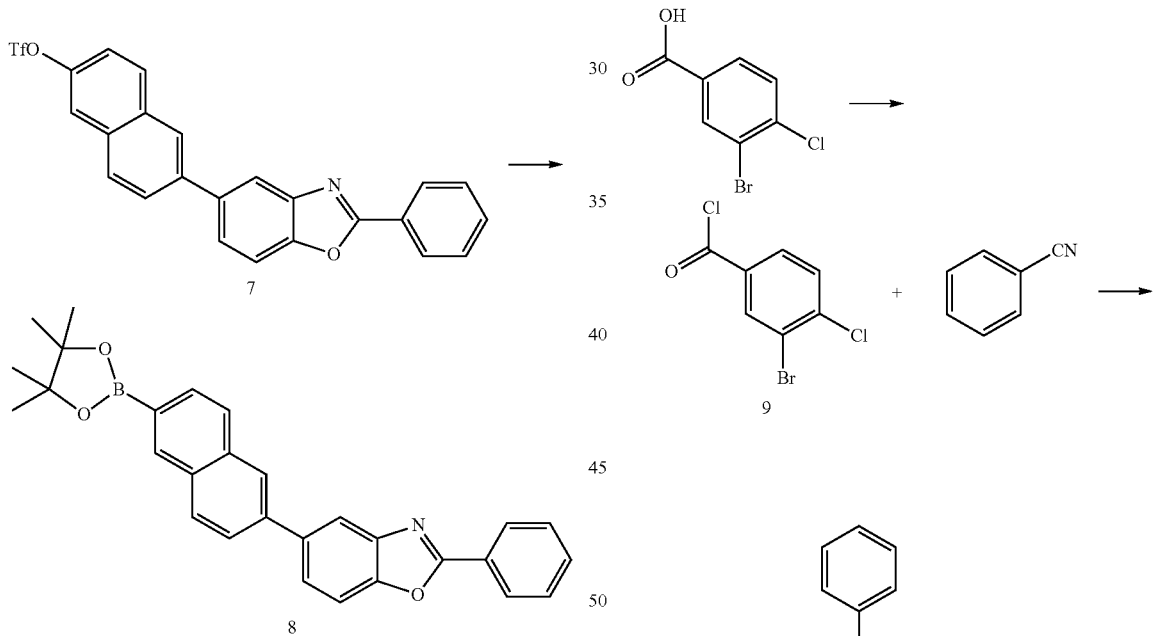
7

8

(Intermediate 6 Synthesis)

The intermediate 3 20.5 g (63.83 mmol), 6-bromonaphthalene-2-ol 14.3 g (63.83 mmol), Pd(PPh3)4 3.7 g 3.19 mmol), toluene 512 mL, ethanol 256 mL, and 2M K2CO3 128 mL (128.0 mmol) were input into a one-neck 2 L flask to obtain a mixture. Then, the mixture was refluxed and stirred. After completion of the reaction, the reaction production was cooled to room temperature to form a solid. The solid was washed with water and ethanol. The resulting solid was dissolved in chloroform, was filtered using silica gel, and then was concentrated, to produce a white solid compound (intermediate 6) 14.7 g (yield: 68.4%).

(Intermediate 7 Synthesis)

The intermediate 6 14.7 g (43.57 mmol), dichloromethane) 440 mL, and triethylamine 8.82 g (87.14 mmol) were

184 input into a one-neck 1 L flask to obtain a mixture. Then, the mixture was cooled to 0° C. in an ice bath, then, anhydrous trifluoroacetic acid was slowly added dropwise to the mixture, which, in turn, was reacted at room temperature for 12 hours. After completion of the reaction, 200 mL of water was added to the reaction product for extraction. Then, the extract was recrystallized using dichloromethane and methanol, to obtain a white solid compound (intermediate 7) 10.3 g (yield: 50.4%).

(Intermediate 8 Synthesis)

The intermediate 7 7.6 g (16.19 mmol), Bis(pinacolato) diboron 4.5 g (17.81 mmol), Pd(dppf)Cl2·CH2Cl2 0.7 g (0.81 mmol), potassium acetate (KOAc) 3.18 g 32.38 mmol), and dioxane 324 mL were input into a one-neck 500 mL flask to obtain a mixture. Then, the mixture was refluxed and stirred at 90° C. for 12 hours. The resulting product was purified using silica gel column chromatography, to prepare a white solid compound (intermediate 8) 5.2 g (yield: 53.0%).

Intermediate Synthesis Example 5: Intermediate 11 Synthesis

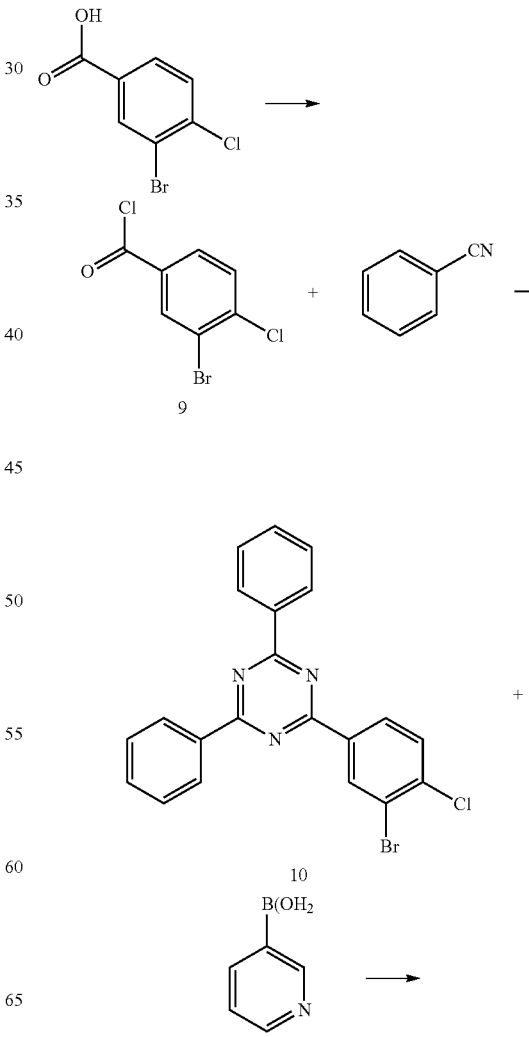
9

10

-continued

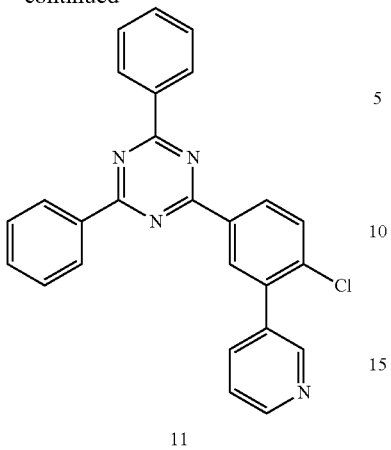

11

(Intermediate 9 Synthesis)
3-bromo-4-chlorobenzoic acid 15.0 g (63.7 mmol) and SOCl2 63.7 mL were input into a one-neck 500 mL flask to obtain a mixture. Then, the mixture was refluxed and stirred. After completion of the reaction, the reaction product was subjected to distillation under reduced pressure to remove the solvent from the reaction product. A thus-resulting product was crystallized, to obtain a brown solid compound (intermediate 9) 17.0 g (yield: quant.).

(Intermediate 10 Synthesis)
The intermediate 9 16.1 g (63.7 mmol), benzonitrile 13.4 mL (127 mmol), SbCl5 8.16 mL (63.7 mmol) and CHCl3 159 mL were input into a 2-neck 1 L flask and were mixed and refluxed. After the reaction therebetween was completed, the reaction product was cooled to room temperature to form a yellow solid compound, which in turn was filtered. Then, 28% NH4OH 1 L was input into a one-neck 2 L flask, and, then, the thus obtained yellow solid compound was added slowly thereto. Then, the one-neck 2 L flask was raised up to room temperature. After the reaction was completed, the reaction product was filtered and was washed several times with distilled water and methanol (MeOH) and was dried, to obtain a white solid compound (intermediate 10 17.5 g (yield: 65.0%).

(Intermediate 11 Synthesis)
The intermediate 10 9.00 g (21.3 mmol), pyridin-3-ylboronic acid 3.14 g (25.5 mmol), Pd(PPh3)4 1.23 g (1.06 mmol), 2 M aqueous solution K2CO3 32 mL (63.9 mmol), and a mixed solvent 105 mL (toluene:EtOH=2:1) were input into a one-neck 500 mL flask to form a mixture. The mixture was refluxed and stirred. After completion of the reaction, the reaction product was cooled to room temperature. Then, methanol (MeOH) was added thereto, followed by a stirring operation for 30 minutes. The resulting white solid was filtered and then purified using silica gel column chromatography (CHCl3 only to CHCl3:EtOAc=10:1), to obtain a white solid compound (intermediate 11) 3.66 g (yield: 41.0%).

Intermediate Synthesis Example 6: Intermediate 13 Synthesis

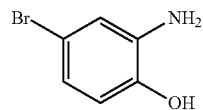 

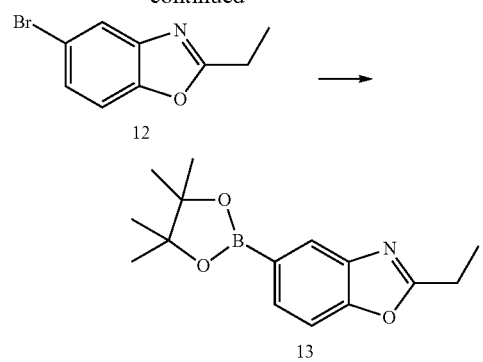

(Intermediate 12 Synthesis)
2-Amino-4-bromophenol 50.0 g (0.266 mol), triethyl orthopropionate 64 mL (0.319 mol), p-TsOH 2.53 g (0.0117 mol) and toluene 250 mL were input into a one-neck 500 mL flask to obtain a mixture. Then, the mixture was refluxed and stirred at 110 to 120° C. for 12 hours. After completion of the reaction, the reaction product was cooled to room temperature and then subjected to distillation under reduced pressure to remove the solvent from the reaction product. A thus-resulting solid was purified using silica gel column chromatography (hexane:EA=8:1), to obtain a solid compound (intermediate 12) 33.3 g (yield: 55.4%).

(Intermediate 13 Synthesis)
The intermediate 12 22.0 g (97.3 mmol), Bis(pinacolato)diboron 49.4 g (194.6 mmol), Pd(dppf)Cl2·CH2Cl2 3.97 g (4.87 mmol), potassium acetate (KOAc) 19.0 g (291.9 mmol), and dioxane 486 mL were input into a one-neck 500 mL flask to obtain a mixture. Then, the mixture was refluxed and stirred at 100° C. for 12 hours. After completion of the reaction, the reaction product was subjected to distillation under reduced pressure to remove the solvent from the reaction product. A thus-resulting solid was dissolved in dichloromethane, and filtered using Celite, and washed with dichloromethane. A thus-resulting product was crystallized using hexane, to obtain a solid compound (intermediate 13) 18.0 g (yield: 67.7%).

Intermediate Synthesis Example 7: Intermediate 16 Synthesis

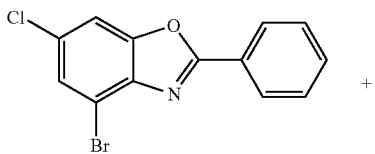

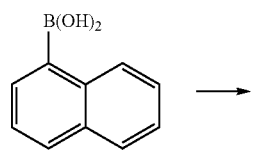

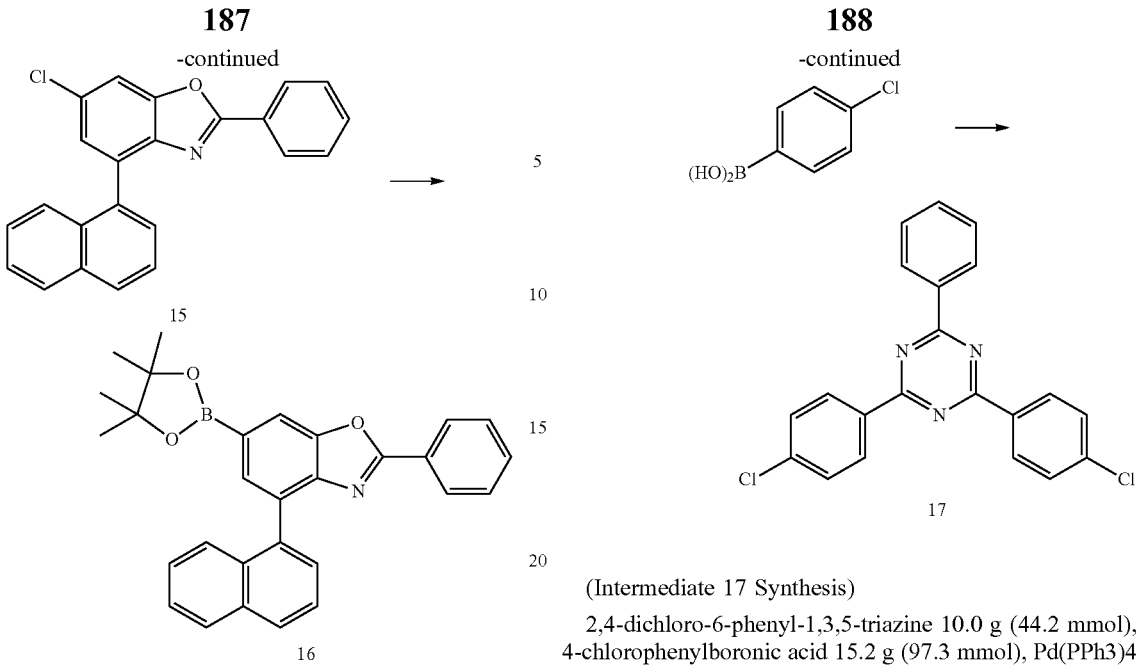

(Intermediate 15 Synthesis)

The thus-obtained intermediate 14 10.0 g (62.4 mmol), 1-naphthylboronic acid 5.6 g 32.4 mmol), Pd(PPh3)4 1.9 g (1.6 mmol), K2CO3 13.0 g (97.2 mmol), toluene 200 mL, ethanol 40 mL, and water 40 mL were input into a one-neck 500 mL flask to obtain a mixture. Then, the mixture was refluxed and stirred at 90° C. for 2 hours. After the reaction was terminated, the reaction product was cooled to room temperature and an organic layer was separated therefrom. The organic layer was concentrated under reduced pressure to obtain a solid. The solid was purified using silica gel column chromatography, to obtain 11.5 g (yield: 100%) of a white solid compound (intermediate 15).

(Intermediate 16 Synthesis)

The intermediate 15 11.5 g (40.8 mmol), Bis(pinacolato) diboron 15.5 g (61.1 mmol), Pd(dba)2 4.7 g (8.2 mmol), potassium acetate (KOAc) 20.0 g (204.0 mmol), and dioxane 300 mL were input into a one-neck 500 mL flask to obtain a mixture. Then, the mixture was refluxed and stirred at 120° C. for 24 hours. After the reaction was terminated, the reaction product was cooled to room temperature and was concentrated under reduced pressure to obtain a solid. The solid thus obtained was dissolved in dichloromethane and was filtered using silica gel. The filtrate was concentrated under reduced pressure, to obtain a gray solid compound (intermediate 16) 18.0 g (yield: 100%).

Intermediate Synthesis Example 8: Intermediate 17 Synthesis

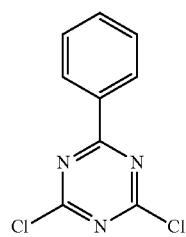

(Intermediate 17 Synthesis)

2,4-dichloro-6-phenyl-1,3,5-triazine 10.0 g (44.2 mmol), 4-chlorophenylboronic acid 15.2 g (97.3 mmol), Pd(PPh3)4 2.5 g (2.2 mmol), K2CO3 18.3 g (132.6 mmol), toluene 200 mL, ethanol (EtOH) 50 mL, and H2O 50 mL were input into a one-neck 500 mL flask to obtain a mixture. Then, the mixture was refluxed and stirred at 90° C. for 2 hours. After completion of the reaction, the reaction product was cooled to room temperature and an organic layer was separated therefrom. The organic layer was concentrated under reduced pressure, and was dissolved in CHCl3, and was filtered using silica gel. Then, the filtered organic layer was concentrated under reduced pressure, to obtain a gray solid compound (intermediate 17) 11.4 g (yield: 68.2%).

Intermediate Synthesis Example 9: Intermediate 20 Synthesis

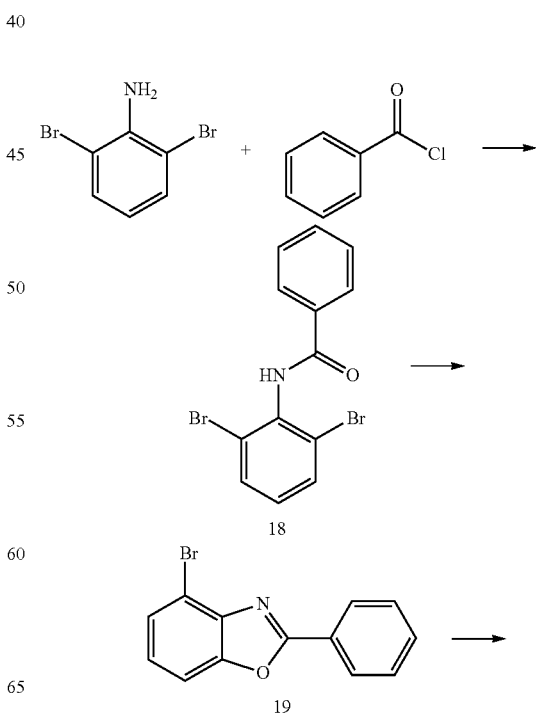

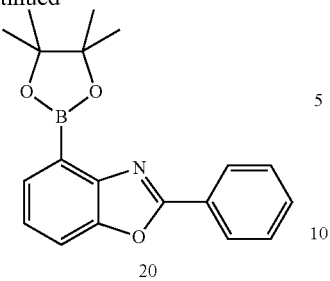

20

(Intermediate 18 Synthesis)

2,6-dibromoaniline 40.0 g (175.34 mmol), 4-bromobenzoyl chloride 38.4 g (175.34 mmol) and tetrahydrofuran (THF) 360 mL were input into a flask to obtain a mixture. Then, the mixture was refluxed and stirred at room temperature for 3 hours. After completion of the reaction, the reaction product was subjected to distillation under reduced pressure to remove the solvent from the reaction product. Then, the reaction product was solidified using diisopropyl ether, to obtain a light-yellow solid compound (intermediate 18) 55.8 g (yield: 87.8%).

(Intermediate 19 Synthesis)

The thus-obtained intermediate 18 55.8 g (154.03 mmol), CuI 1.47 g (7.70 mmol), 1,10-phenanthroline 2.7 g (15.40 mmol), Cs2CO3 100.3 g (308.07 mmol), and 1,2-dimethoxyethane 500 mL were input into a one-neck 1 L flask to obtain a mixture. Then, the mixture was refluxed and stirred at 90° C. for 24 hours. After the reaction was completed, the reaction product was dissolved in dichloromethane which in turn passed through a Celite pad. After removing the solvent therefrom, a resulting solid was dissolved in chloroform and purified using column chromatography. Then, the purified product was solidified using methanol, to obtain a light-yellow solid compound (intermediate 19) 46.8 g (yield: 92.0%).

(Intermediate 20 Synthesis)

The intermediate 19 10.0 g (36.48 mmol), bis(pinacolato)diboron 13.9 g (54.72 mmol), Pd(dppf)Cl2·CH2Cl2 1.5 g (1.82 mmol), potassium acetate (KOAc) 7.2 g (72.96 mmol), and dioxane 270 mL were input into a one-neck 500 mL flask to obtain a mixture. Then, the mixture was refluxed and stirred at 90° C. for 12 hours. After the reaction was completed, the reaction product was purified using silica gel column chromatography, to obtain a white solid compound (intermediate 20) 9.0 g (yield: 85.3%).

Intermediate Synthesis Example 10: Intermediate 21 Synthesis

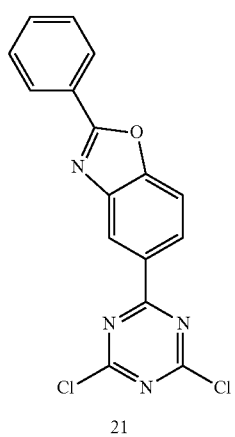

21

(Intermediate 21 Synthesis)

Mg 0.97 g (40.1 mmol), I2 0.184 g (0.73 mmol), and anhydrous tetrahydrofuran (THF) 10 mL were input into a 3-neck 250 mL flask to obtain a mixture. The mixture was stirred and refluxed for 1 hour. Then, a solution in which the intermediate 2 10 g (36.5 mmol) was dissolved in 10 mL of tetrahydrofuran (THF) was slowly added dropwise to the mixture, followed by refluxing and stirring for 2 hours. Then, the reaction product was cooled to 0° C. Then, a solution in which a compound 2,4,6-trichloro-1,3,5-triazine (6.7 g, 36.5 mmol) was dissolved in 16 mL of tetrahydrofuran (THF) was slowly added dropwise to the cooled reaction product to form a mixed solution. Then, the temperature was slowly raised to room temperature. The mixed solution was then stirred for 12 hours. Then, the reaction product was cooled to 0° C., and then distilled water was slowly added dropwise to the cooled reaction product, which, in turn, was subjected to extraction with dichloromethane. Then, a thus-obtained organic layer was dried over anhydrous Na2SO4 and then the solvent was removed under reduced pressure therefrom. The thus obtained solid was purified using silica gel column chromatography (CHCl3:Hexane=1:1), to obtain a white solid compound (intermediate 21) 1.96 g (yield: 15.9%).

Using the synthesized intermediate compounds, various benzazole derivatives having heteroaryl groups were synthesized as follows.

Synthesis Example 1 of Benzazole Derivative Having Heteroaryl Group: Compound (LT18-30-129) Synthesis

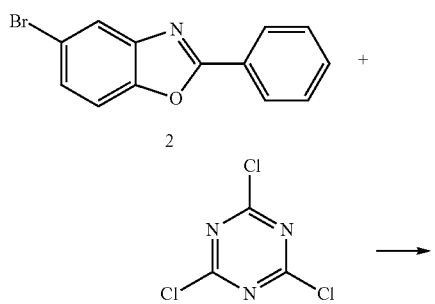

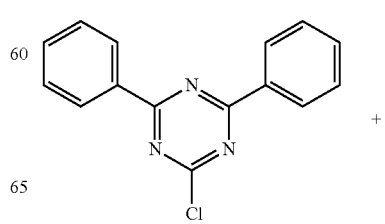

-continued

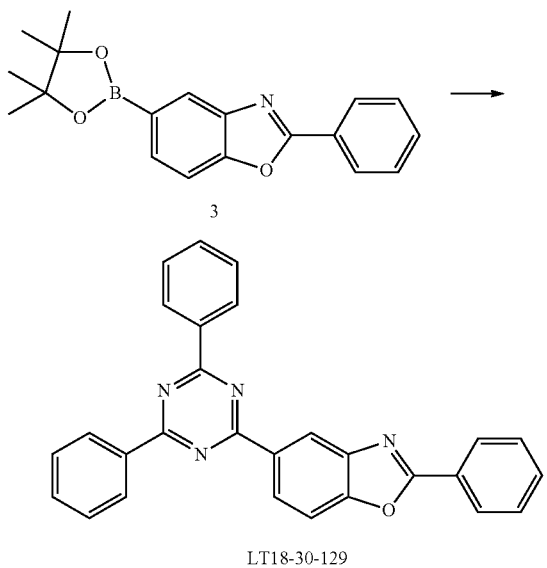

LT18-30-129

The intermediate 3 5 g (15.5 mmol), 2-chloro-4,6-diphenyl-1,3,5-triazine 4.5 g (17.0 mmol), Pd(PPh3)4 0.89 g (0.77 mmol), K2CO3 4.2 g 31 mmol), toluene 150 mL, ethanol (EtOH) 75 mL, and water 75 mL were input into a one-neck 500 mL flask to form a mixture which was reacted at 80☐. After the reaction was completed, the reaction product was cooled to room temperature, water was added to the cooled product, which in turn was subjected to extraction with dichloromethane. A thus obtained organic layer was dried using anhydrous MgSO4, and was subjected to purification by silica gel column chromatography, to obtain a yellow solid compound (LT18-30-129) 4.4 g (yield: 67.4%).

Synthesis Example 2 of Benzazole Derivative Having Heteroaryl Group: Compound (LT18-30-033) Synthesis

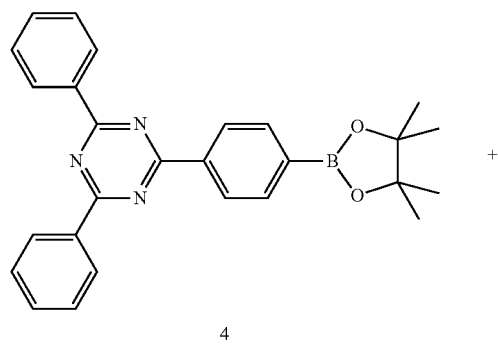

4

-continued

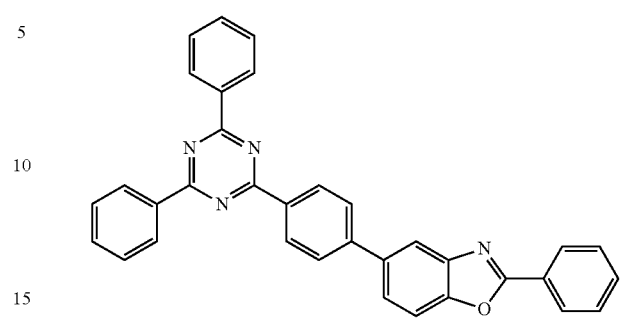

LT18-30-033

The intermediate 4 4.76 g (10.9 mmol), the intermediate 2 3.0 g (10.9 mmol), Pd(PPh3)4 0.38 g (0.545 mmol), toluene 36 mL, ethanol (EtOH) 18 mL, and 2M K2CO3 11 mL (10.9 mmol) were input into a one-neck 100 mL flask to form a mixture. The mixture was refluxed and stirred. After completion of the reaction, the reaction product was cooled at room temperature and a resulting solid was filtered and washed with toluene, water, and acetone. The solid was dissolved in chlorobenzene, was filtered using Celite, and washed with chlorobenzene. Then, the solvent was removed under reduced pressure from the washed product, followed by crystallization with methanol (MeOH) and by filtration, to obtain a white solid compound (LT18-30-033) 3.6 g (yield: 66.1%).

Synthesis Example 3 of Benzazole Derivative Having Heteroaryl Group: Compound (LT18-30-022) Synthesis

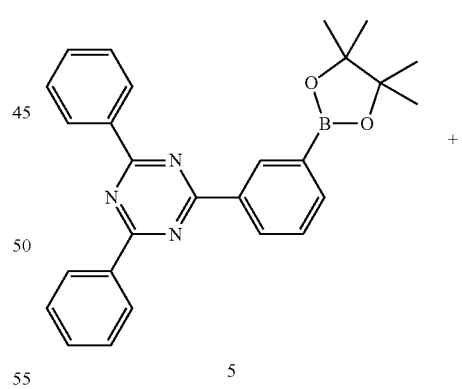

5

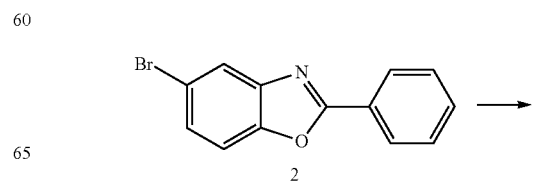

2

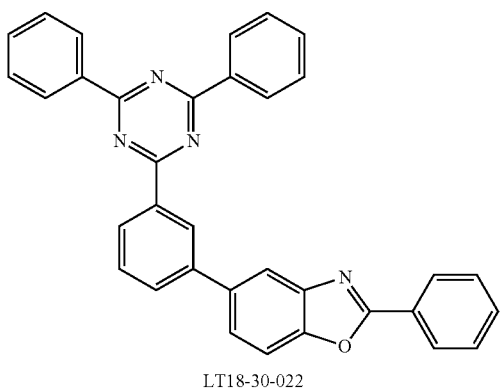

LT18-30-022

The intermediate 5 3.2 g (7.30 mmol), the intermediate 2 2 g (7.30 mmol), Pd(PPh3)4 0.42 g (0.365 mol), toluene 24 mL, ethanol (EtOH) 1 mL, and 2M K2CO3 7.3 mL (7.30 mmol) were input into a one-neck 100 mL flask to form a mixture. The mixture was refluxed and stirred. After completion of the reaction, the reaction product was cooled at room temperature and then a resulting solid was filtered using ethanol (EtOH). The solid was dissolved in chloroform and was purified by silica gel column chromatography. The purified product was subjected to crystallization with methanol (MeOH) and to filtration, to obtain a white solid compound (LT18-30-022) 1.9 g (yield: 52.1%).

Synthesis Example 4 of Benzazole Derivative Having Heteroaryl Group: Compound (LT18-30-141) Synthesis

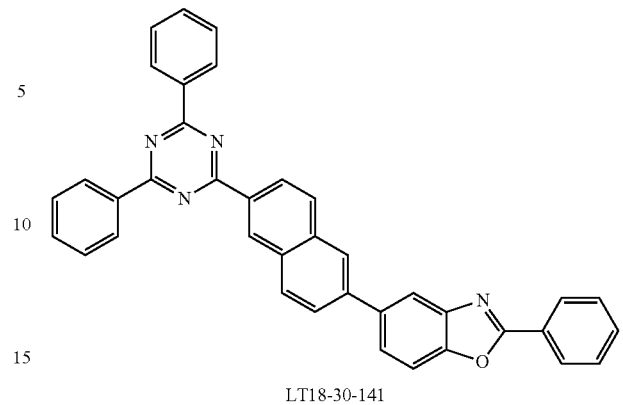

LT18-30-141

The intermediate 8 2.5 g (5.59 mmol), 2-chloro-4,6-diphenyl-1,3,5-triazine 1.5 g (5.59 mmol), Pd(PPh3)4 0.3 g (0.28 mmol), toluene 48 mL, ethanol (EtOH) 24 mL, and 2M K2CO3 12 mL (12 mmol) were input into a one-neck 250 mL flask to form a mixture. The mixture was refluxed and stirred. After completion of the reaction, the reaction product was cooled at room temperature and then a resulting solid was filtered and was washed using water and ethanol (EtOH). Then, 150 mL of xylene was added to the obtained solid, heated the same, filtered the same through a short silica gel, cooled the same to room temperature, and stirred the same for 3 hours. The resulting solid was filtered, to obtain a white solid compound (LT18-30-141) 1.8 g (yield: 56.6%).

Synthesis Example 5 of Benzazole Derivative Having Heteroaryl Group: Compound (LT18-30-201) Synthesis

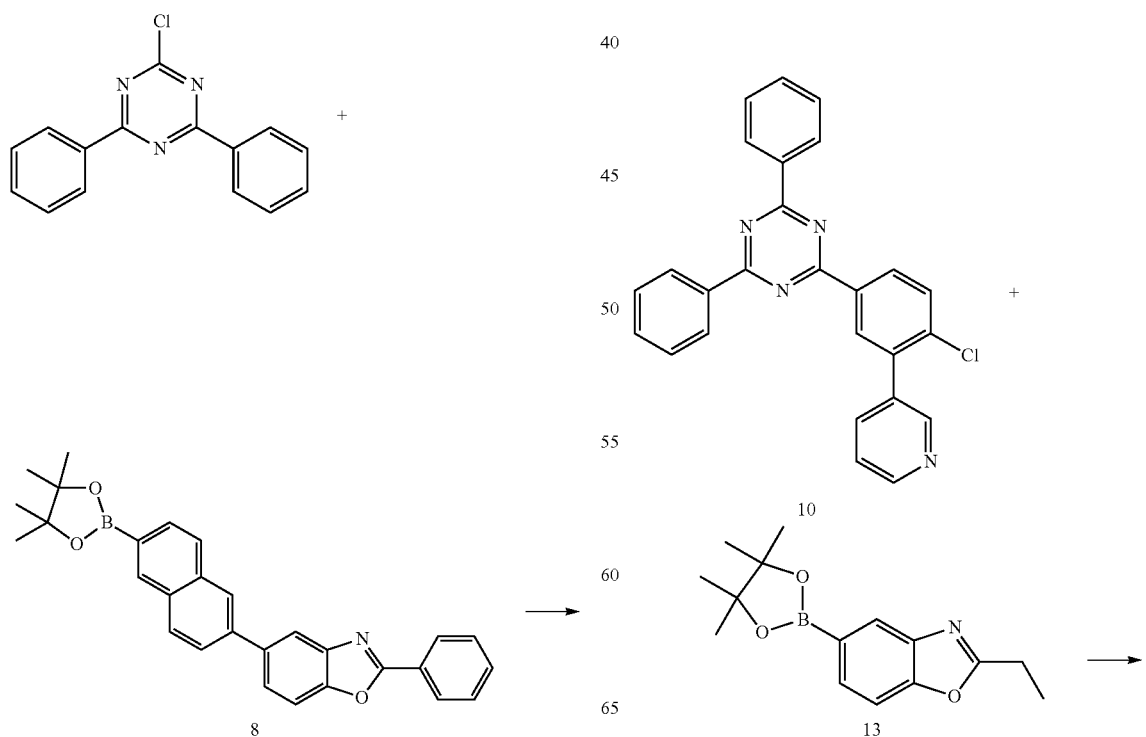

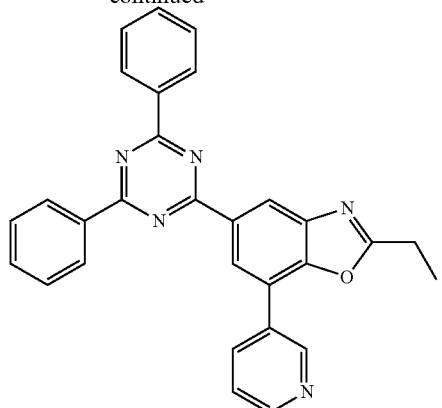

LT18-30-201

The thus-obtained intermediate 10 3.66 g (8.71 mmol), the intermediate 13 3.09 g (11.3 mmol), Pd(dba)2 250 mg (0.430 mmol), S-Phos 357 mg (0.871 mmol), K3PO4 5.53 g (26.1 mmol), toluene 40 mL, and water 40 mL were input into a one-neck 500 mL flask to form a mixture. The mixture was refluxed and stirred. After completion of the reaction, distilled water and dichloromethane were added to the reaction product at room temperature which in turn was subjected to an extraction process. An organic layer thus extracted was dried using anhydrous Na2SO4 and then the solvent was removed under reduced pressure therefrom. The thus-obtained concentrate was purified using silica gel column chromatography (CH3Cl:EtOAc=30:1 to 9:1), and then, xylene was added to the purified concentrate, which in turn was refluxed, and recrystallized, to obtain a light-yellow solid compound (LT18-30-201) 1.63 g (yield: 35.2%).

Synthesis Example 6 of Benzazole Derivative Having Heteroaryl Group: Compound (LT18-30-065) Synthesis

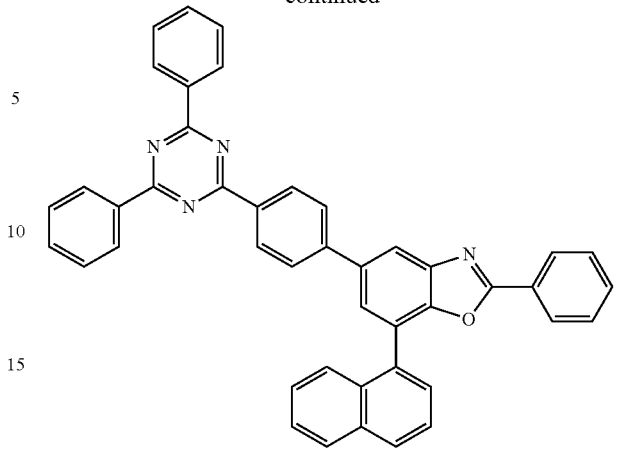

LT18-30-065

The intermediate 16 4.7 g (10.4 mmol), 2-(4-bromophenyl)-4,6-diphenyl-1,3,5-triazine 4.0 g (10.4 mmol), Pd(PPh3)4 0.6 g (0.5 mmol), K2CO3 4.3 g 31.2 mmol), toluene 100 mL, ethanol (EtOH) 20 mL, and water 20 mL were input into a one-neck 250 mL flask to obtain a mixture. Then, the mixture was refluxed and stirred at 110° C. for three days. After completion of the reaction, the reaction product was cooled to room temperature, and then the reaction product was filtered to obtain a solid. Then, 1,2-dichlorobenzene was added to the obtained solid which in turn was heated, and was dissolved and was filtered through silica gel. The filtrate was stirred at room temperature for 12 hours and the resulting solid was filtered, to obtain a light-yellow solid compound (LT18-30-065) 1.9 g (yield: 28.3%).

Synthesis Example 7 of Benzazole Derivative Having Heteroaryl Group: Compound (LT18-30-023) Synthesis

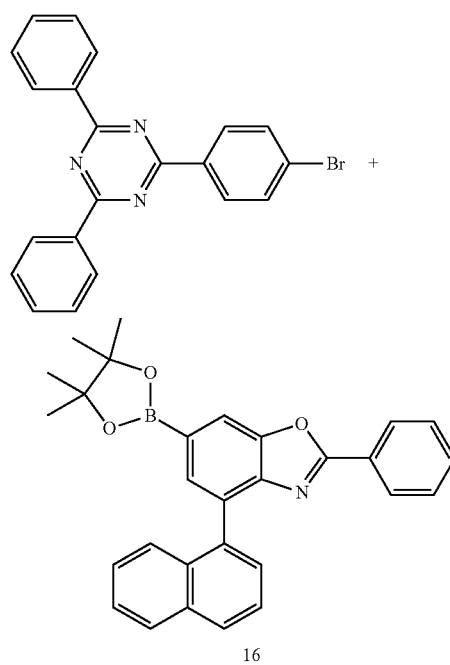

16

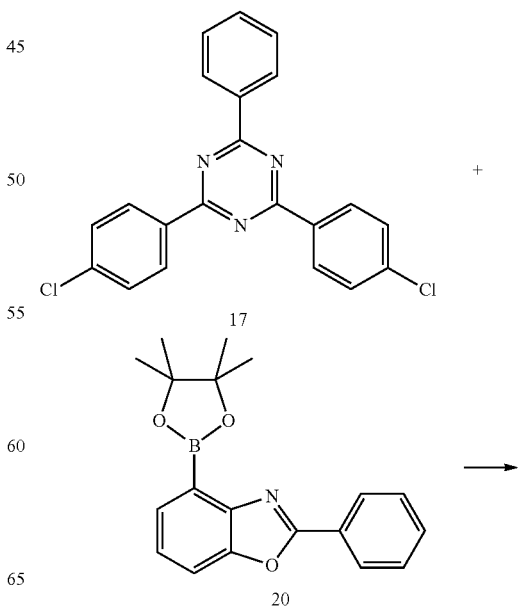

20

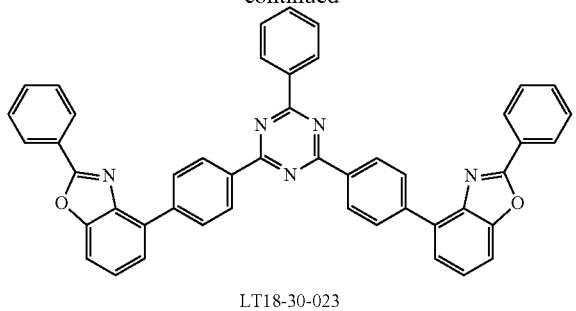

LT18-30-023

The intermediate 17 2.5 g (6.6 mmol), the intermediate 20 5.6 g (17.5 mmol), Pd(dba)2 0.4 g (0.7 mmol), S-Phos 0.5 g (1.3 mmol), K3PO4 5.6 g (26.4 mmol), toluene 50 mL, and water 50 mL were input into a one-neck 250 mL flask to obtain a mixture. Then, the mixture was refluxed and stirred at 110° C. for 15 hours. After completion of the reaction, the reaction product was cooled to room temperature, and then the reaction product was filtered to obtain a solid. Then, 1,2-dichlorobenzene was added to the obtained solid which in turn was heated, and was dissolved and was filtered through silica gel. The filtrate was stirred at room temperature for 12 hours and the resulting solid was filtered, to obtain a light-yellow solid compound (LT18-30-023) 1.4 g (yield: 30.5%).

Synthesis Example 8 of Benzazole Derivative Having Heteroaryl Group: Compound (LT18-30-054) Synthesis

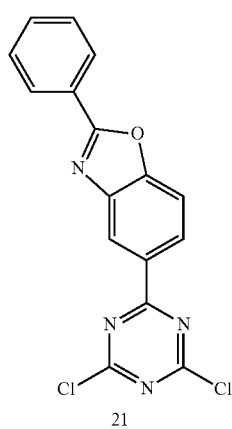

21

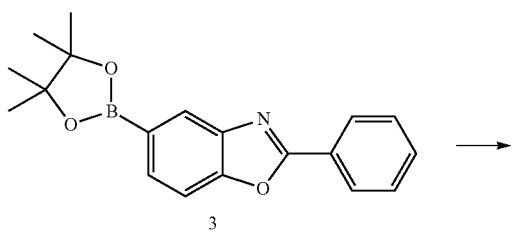

3

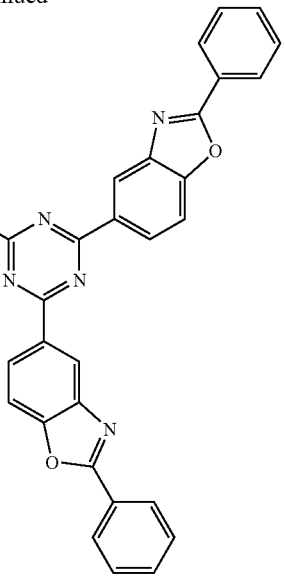

LT18-30-054

The intermediate 21 1.96 g (5.73 mmol), the intermediate 3 4.6 g (14.3 mmol), Pd(PPh3)4 0.33 g (0.29 mmol), toluene 20 mL, ethanol (EtOH) 10 mL and 2M K2CO3 6 mL (11.5 mmol) were input into a one-neck 100 mL flask to obtain a mixture. Then, the mixture was refluxed and stirred at 110° C. for 15 hours. After completion of the reaction, the reaction product was cooled to room temperature, and then the resulting solid was filtered and washed with toluene, water, and acetone. Then, the solid was dissolved and refluxed in chlorobenzene, followed by Celite based filtration and washing with chlorobenzene. Then, the solvent was removed under reduced pressure from the washed product which then was crystallized with methanol (MeOH), to acquire a white solid compound (LT18-30-054) 0.48 g (yield: 12.7%).

Another implementation of the present disclosure provides an organic electroluminescence device containing the benzazole derivative having the heteroaryl group as defined above.

The organic electroluminescence device includes an anode, a cathode, and an organic layer disposed between the anode and the cathode. The organic layer includes a light-emission layer and an electron transport layer. In this connection, the light-emission layer may be disposed between the anode and the electron transport layer. The electron transport layer may be disposed between the light-emission layer and the cathode.

The organic layer may further include, in addition to the light-emission layer and the electron transport layer, at least one selected from a group consisting of a hole injection layer, a hole transport layer, and a first functional layer having both a hole injection function and a hole transport function, a buffer layer, an electron blocking layer, a hole blocking layer, an electron injection layer, and a second functional layer having both an electron injection function and an electron transport function.

In one example, when the organic layer includes all of the hole injection layer, the hole transport layer, the first functional layer, the buffer layer, the electron blocking layer, the light-emission layer, the hole blocking layer, the electron transport layer, the electron injection layer and the second functional layer, spatial relationships therebetween may be as follows. When one of the hole injection layer, the hole transport layer, the first functional layer, the buffer layer, the electron blocking layer, the hole blocking layer, the electron injection layer and the second functional layer is not included in the organic layer, spatial relationships therebetween may be modified by the skilled person to the art with reference to following spatial relationships.

The hole injection layer may be disposed between the anode and the hole transport layer. The hole transport layer may be disposed between the hole injection layer and the first functional layer. The first functional layer may be disposed between the hole transport layer and the buffer layer. The buffer layer may be disposed between the first functional layer and the electron blocking layer. The electron blocking layer may be disposed between the buffer layer and the light-emission layer. The light-emission layer may be disposed between the electron blocking layer and the hole blocking layer. The hole blocking layer may be disposed between the light-emission layer and the electron transport layer. The electron transport layer may be disposed between the hole blocking layer and the electron injection layer. The electron injection layer may be disposed between the electron transport layer and the second functional layer. The second functional layer may be disposed between the electron injection layer and the cathode.

The electron transport layer contains the benzazole derivative having the heteroaryl group as defined above.

The benzazole derivative having the heteroaryl group may be contained in the light-emission layer.

When the organic layer further includes at least one of the hole injection layer, the hole transport layer, the first functional layer, the buffer layer, the electron blocking layer, the hole blocking layer, the electron injection layer or the second functional layer, the at least one of the hole injection layer, the hole transport layer, the first functional layer, the buffer layer, the electron blocking layer, the hole blocking layer, the electron injection layer, or the second functional layer may contain the benzazole derivative having the heteroaryl group as defined above.

When the organic layer further includes at least one of the hole injection layer, the hole transport layer, the first functional layer, the buffer layer, the electron blocking layer, the hole blocking layer, the electron injection layer, or the second functional layer, the benzazole derivative having the heteroaryl group may be contained in at least one selected from a group consisting of the electron blocking layer, the electron injection layer and the second functional layer.

The benzazole derivative having the heteroaryl group includes a compound represented by Chemical Formula 1. The heteroaryl group is bonded to the 6-membered aromatic ring of the benzazole derivative. Since the benzazole derivative with the heteroaryl group has high triplet energy, the benzazole derivative with the heteroaryl group may improve performance of an organic electroluminescence device containing the benzazole derivative with the heteroaryl group.

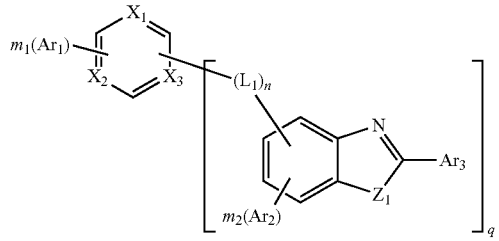

<Chemical Formula 1>

In Chemical Formula 1, each of Z1, X1, X2, X3, Ar1, Ar2, Ar3, m1, m2 and q is defined as follows.

Z1 represents O or S.

L1 represents either a substituted or unsubstituted C6 to C15 arylene or a substituted or unsubstituted C2 to C15 heteroarylene.

In (L1)n, n is 0 or 1.

Each of X1, X2 and X3 independently represents N or CH, and at least one of X1, X2 and X3 is N.

Each of Ar1, Ar2 and Ar3 independently represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

Each of m1 and m2 denotes an integer of 1 or 2.

The q denotes an integer of 1, 2 or 3.

In Chemical Formula 1, the benzazole derivative refers to a condensed ring compound in which a hetero five-membered ring containing two different heteroatoms is coupled to a six-membered aromatic ring. One of the two different heteroatoms is N, while the other thereof is S or O.

In Chemical Formula 1, the heteroaryl group is bonded to the 6-membered aromatic ring of the benzazole derivative. The heteroaryl group may include pyridine, pyrimidine or triazine. In Chemical Formula 1, when one of X1, X2 and X3 is N, the heteroaryl group includes pyridine. In Chemical Formula 1, when two of X1, X2 and X3 are N, the heteroaryl group includes pyrimidine. In Chemical Formula 1, when all of X1, X2 and X3 are N, the heteroaryl group include triazine.

In Chemical Formula 1, the heteroaryl group may be bonded directly to the 6-membered aromatic ring of the benzazole derivative. In Chemical Formula 1, when n is 0, the heteroaryl group may be bonded directly to the 6-membered aromatic ring of the benzazole derivative.

In Chemical Formula 1, the heteroaryl group may be coupled via a linker to the 6-membered aromatic ring of the benzazole derivative. In Chemical Formula 1, when n is 1, the heteroaryl group may be bonded via L1 to the 6-membered aromatic ring of the benzazole derivative.

The present inventors have confirmed that an organic electroluminescence device containing the compound of Chemical Formula 1 where Z1 is O or S could be driven at a lower driving voltage, and has improved light-emission efficiency, external quantum efficiency and life-span, compared to an organic electroluminescence device containing the compound of Chemical Formula 1 where Z1 is N. This will be demonstrated by the comparison experimental results as described below and FIG. 1 to FIG. 4.

In Chemical Formula 1, each of Ar1, Ar2, and Ar3 independently represents one selected from a group consisting of hydrogen, a methyl group, an ethyl group, an isopropyl group, an isobutyl group, a t-butyl group, a trimethylsilyl group, a triphenylsilyl group, a trifluoromethyl group, a substituted or unsubstituted phenyl group, a substituted or unsubstituted biphenyl group, a substituted or unsubstituted naphthyl group, a substituted or unsubstituted phenanthrene group, a substituted or unsubstituted pyridine, a substituted or unsubstituted quinoline group, a substituted or unsubstituted benzoquinoline group, a substituted or unsubstituted phenanthridine group, a substituted or unsubstituted dibenzothiophene group, and a substituted or unsubstituted dibenzofuran group.

In one example, the benzazole derivative having the heteroaryl group may include at least one of a compound represented by Chemical Formula 2-1, a compound represented by Chemical Formula 2-2, or a compound represented by Chemical Formula 2-3:

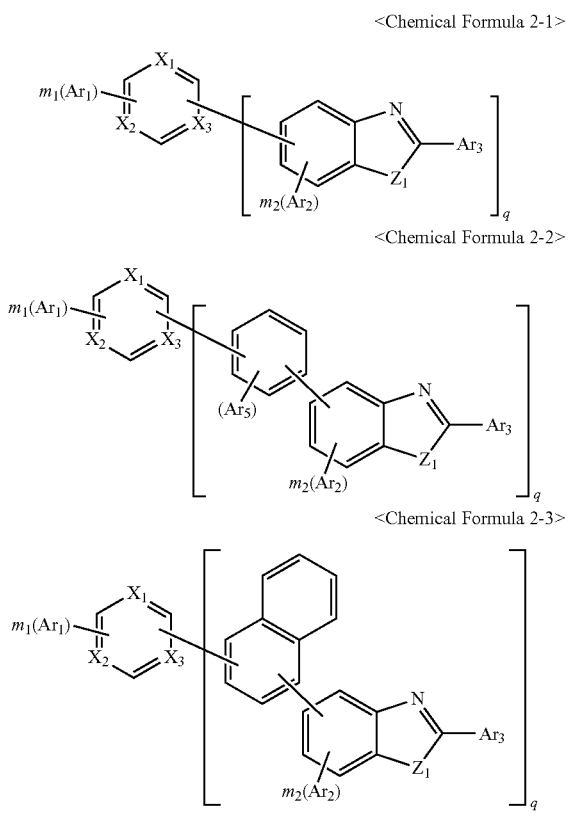

In each of Chemical Formula 2-1, Chemical Formula 2-2, and Chemical Formula 2-3, each of Z1, X1, X2, X3, Ar1, Ar2, Ar3, m1, m2 and q is the same as defined above with reference to Chemical Formula 1.

The compound represented by Chemical Formula 2-1 may refer to the compound of Chemical Formula 1 where n is 0, and the heteroaryl group is directly bonded to the 6-membered aromatic ring of the benzazole derivative.

The compound represented by Chemical Formula 2-2 may refer to the compound of Chemical Formula 1 where n is 1, and L1 is phenylene, and, thus, the heteroaryl group is bonded via phenylene as a linker to the six-membered aromatic ring of the benzazole derivative.

The compound represented by Chemical Formula 2-3 may refer to the compound of Chemical Formula 1 where n is 1, and L1 is naphthalenediyl, and, thus, the heteroaryl group is bonded via naphthalenediyl as a linker to the six-membered aromatic ring of the benzazole derivative.

In each of Chemical Formula 2-1, Chemical Formula 2-2 and Chemical Formula 2-3, Ar5 represents one selected from a group consisting of hydrogen, a substituted or unsubstituted C1 to C6 alkyl group, a substituted or unsubstituted silyl group, a substituted or unsubstituted C6 to C30 aryl group, and a substituted or unsubstituted C2 to C30 heteroaryl group.

In each of Chemical Formula 2-1, Chemical Formula 2-2, and Chemical Formula 2-3, Ar5 represents one selected from a group consisting of hydrogen, a methyl group, an ethyl group, an isopropyl group, an isobutyl group, a t-butyl group, a trimethylsilyl group, a triphenylsilyl group, a trifluoromethyl group, a substituted or unsubstituted phenyl group, a substituted or unsubstituted biphenyl group, a substituted or unsubstituted naphthyl group, a substituted or unsubstituted phenanthrene group, a substituted or unsubstituted pyridine, a substituted or unsubstituted quinoline group, a substituted or unsubstituted benzoquinoline group, a substituted or unsubstituted phenanthridine group, a substituted or unsubstituted dibenzothiophene group, and a substituted or unsubstituted dibenzofuran group.

In each of Chemical Formula 2-1, Chemical Formula 2-2 and Chemical Formula 2-3, r denotes an integer of 1 or 2.

In one example, the benzazole derivative having the heteroaryl group may include at least one of compounds represented by following structural formulas:

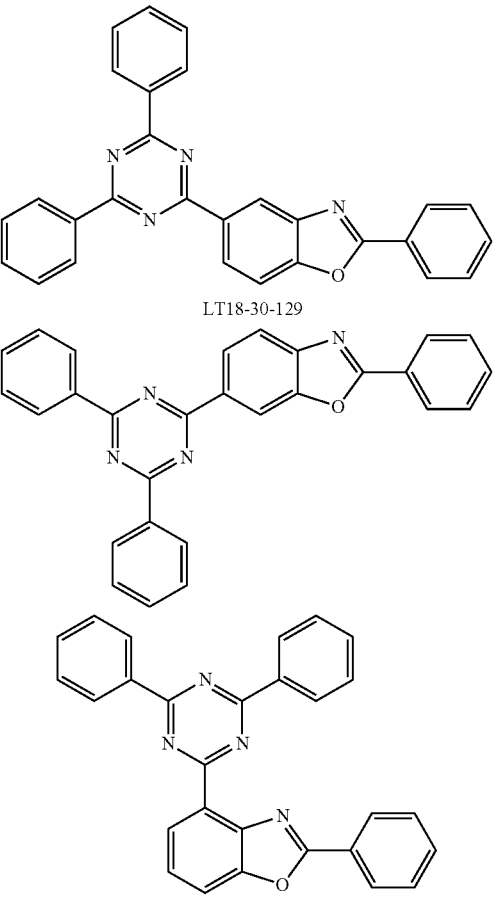

LT18-30-129

-continued
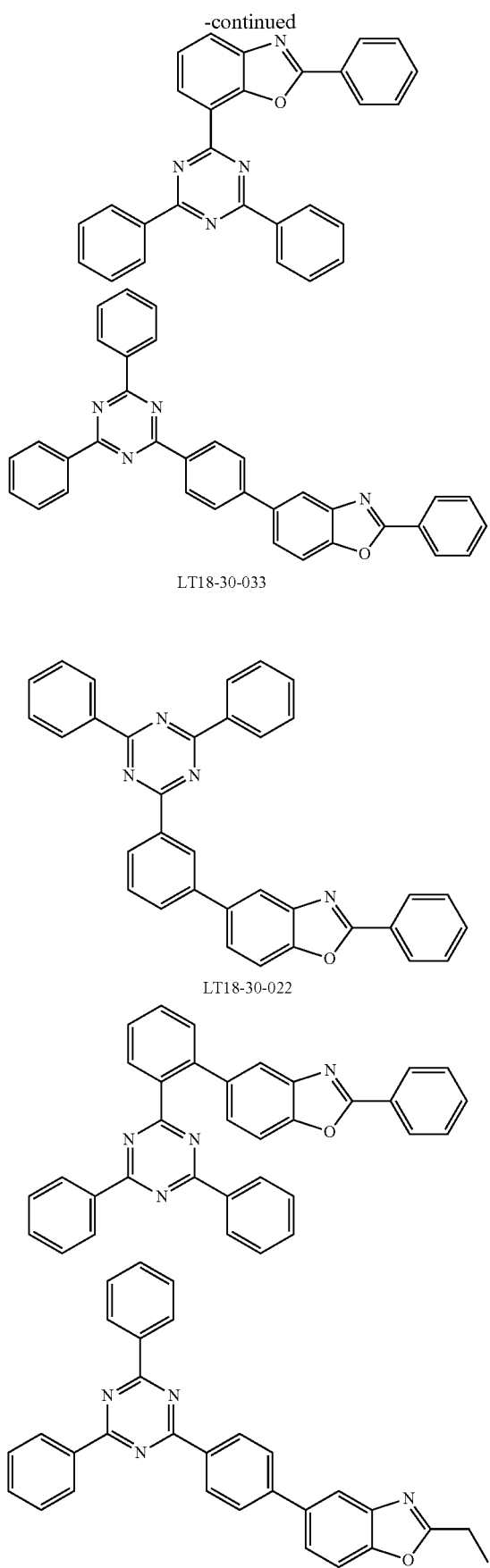
LT18-30-033
LT18-30-022
-continued
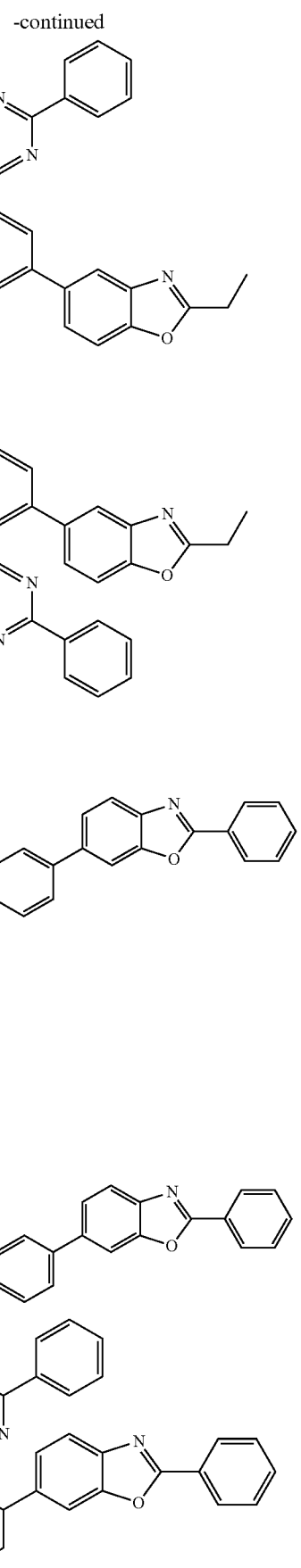

205
-continued
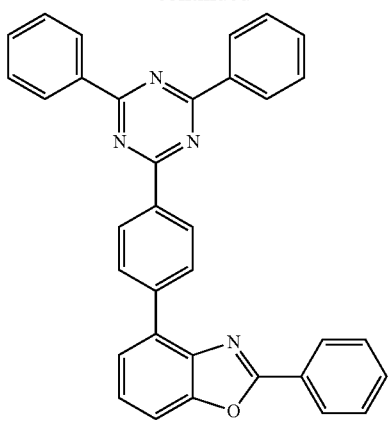
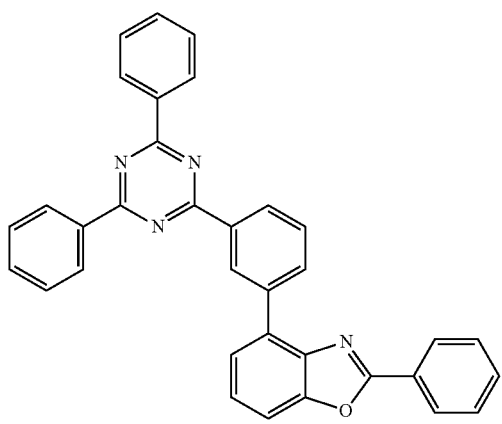
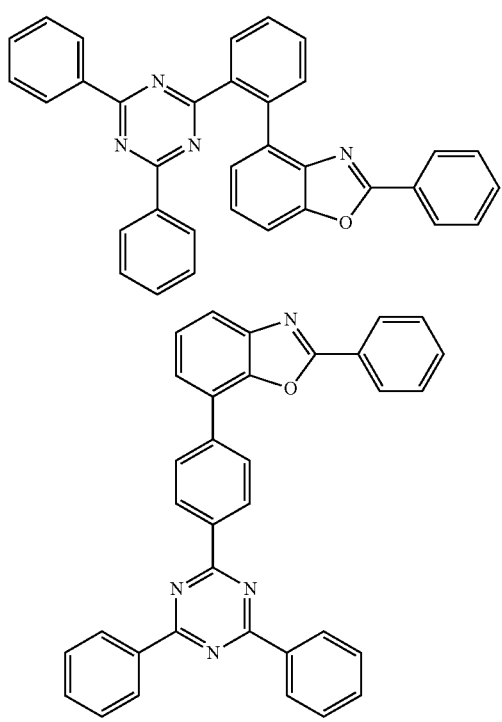
206
-continued
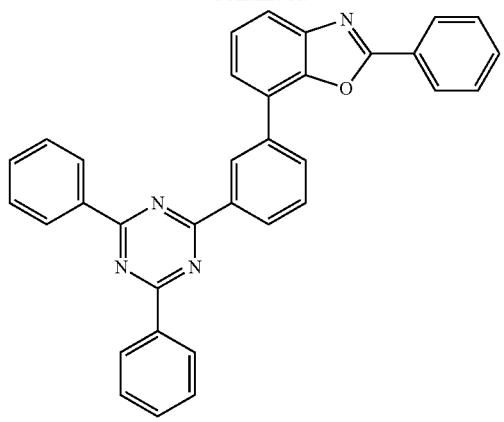
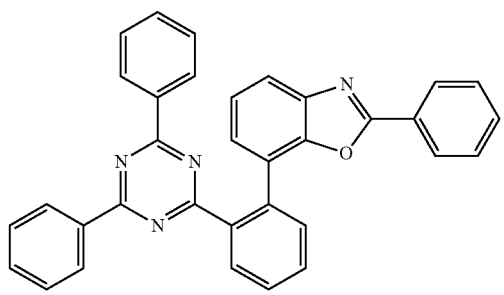
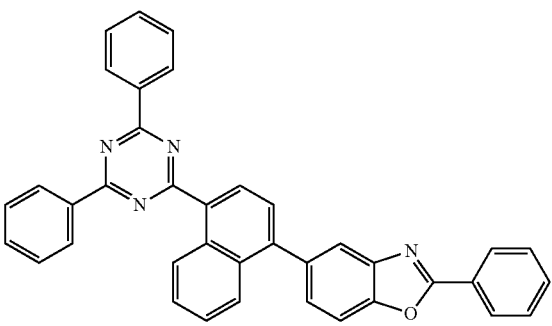
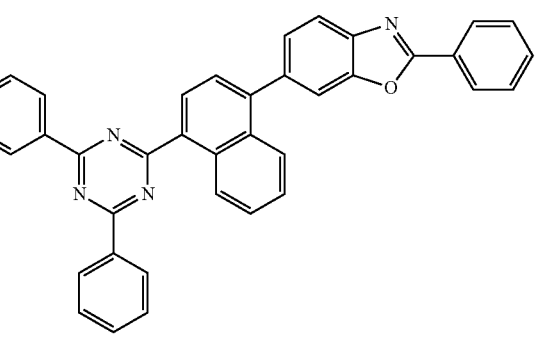

-continued
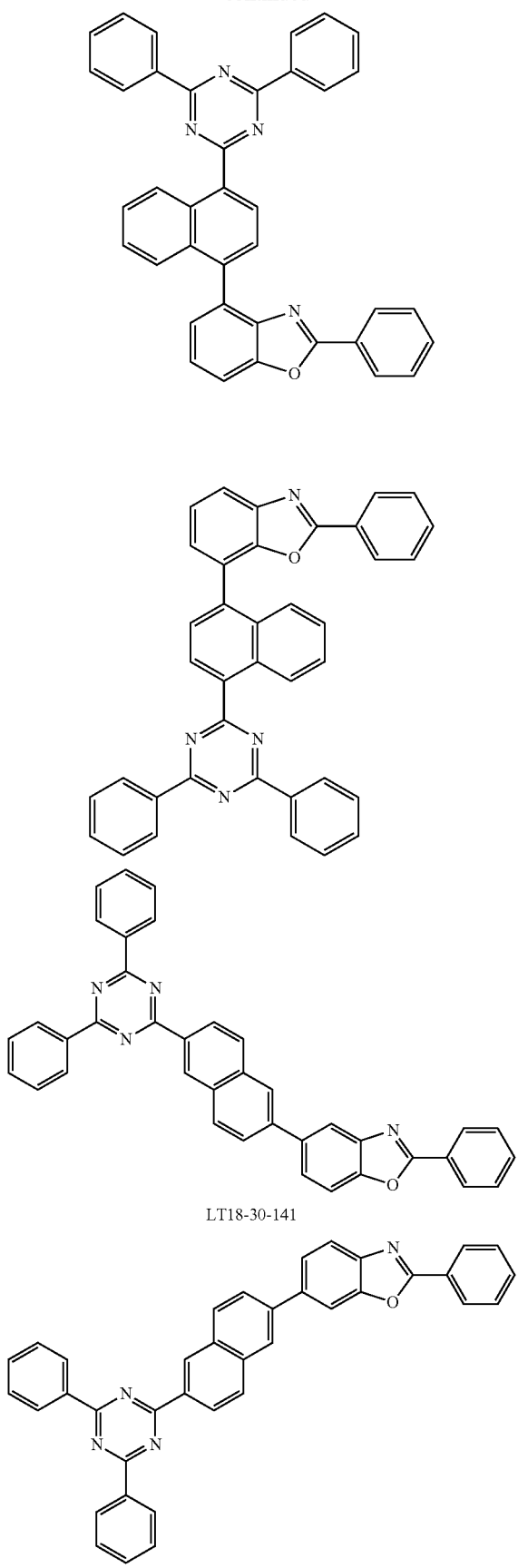
-continued
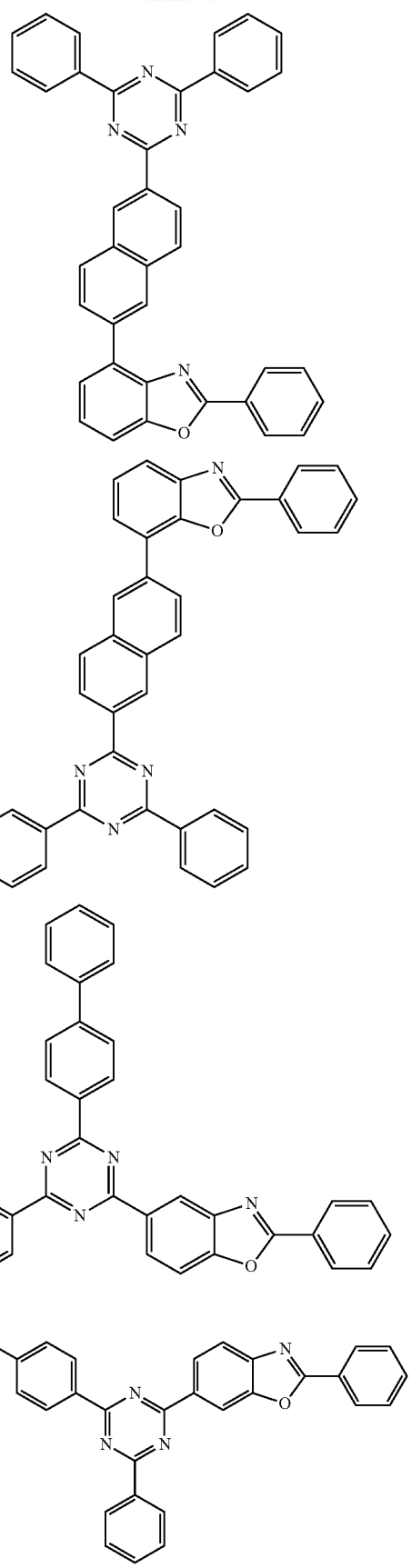

209
-continued
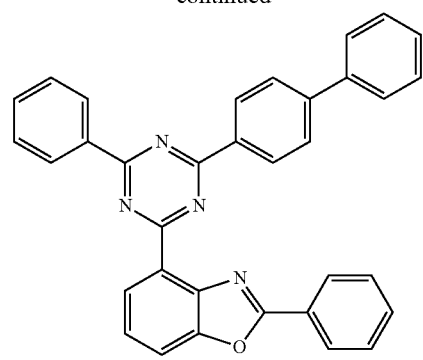
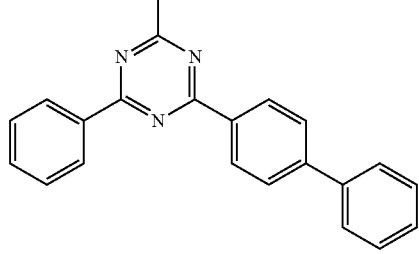
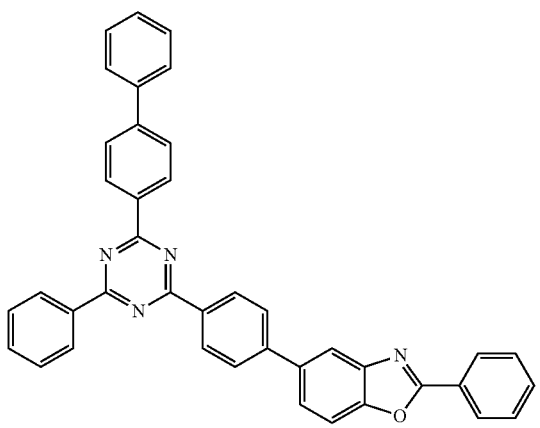
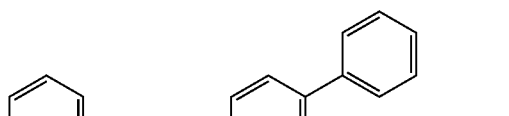
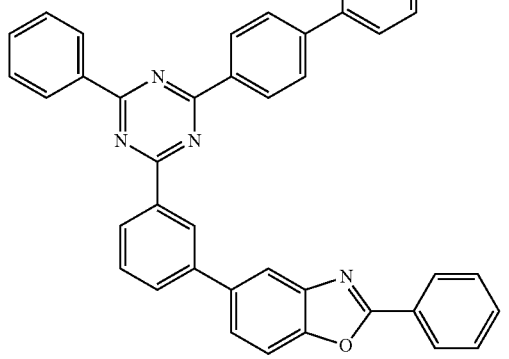
210
-continued
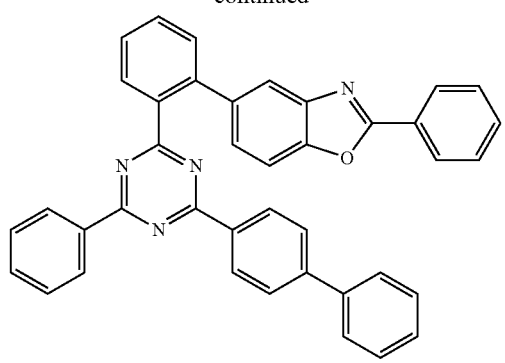
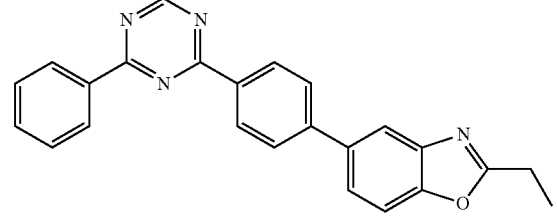
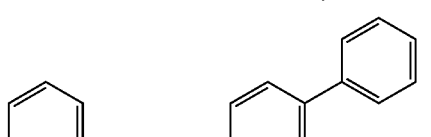
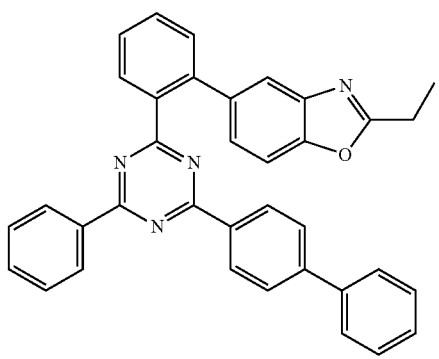

211
-continued
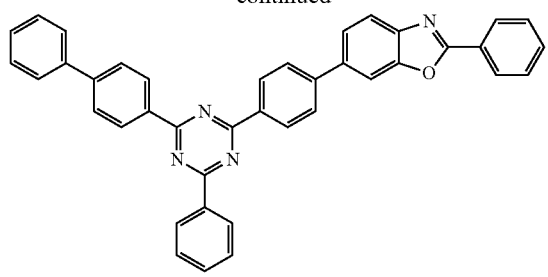
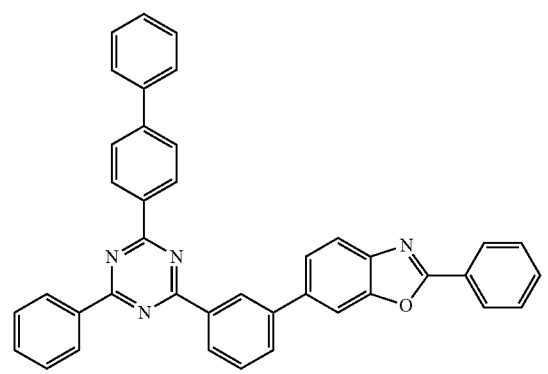
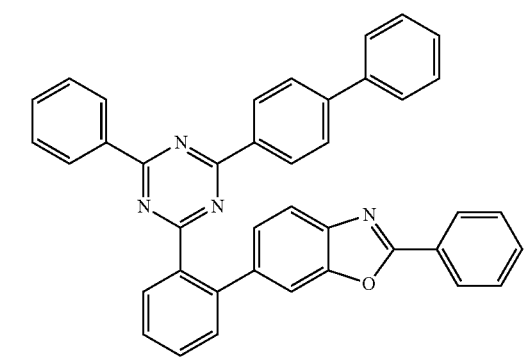
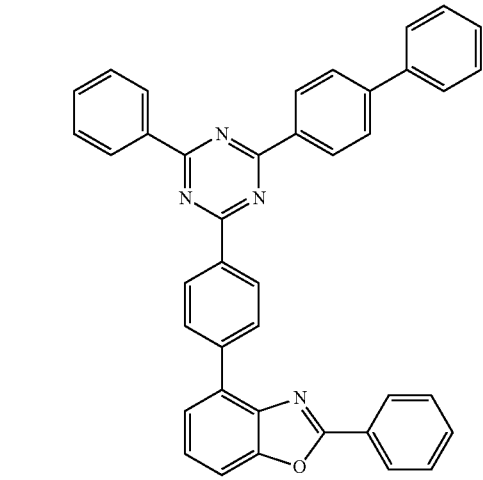
212
-continued
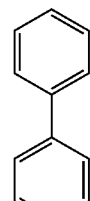
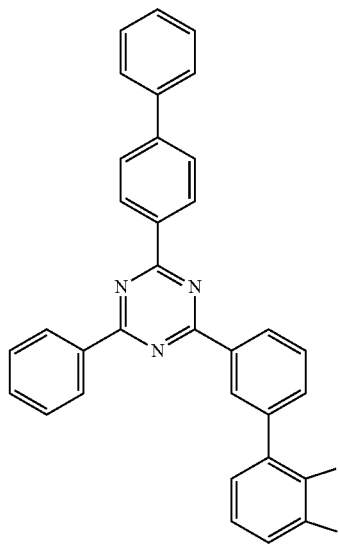
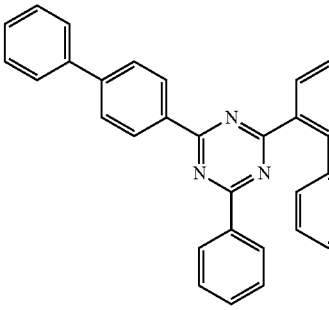
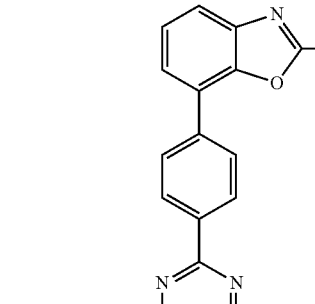
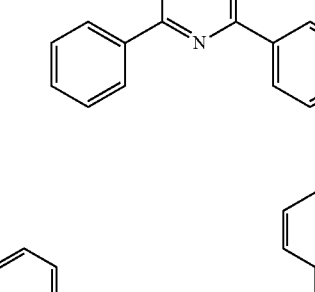
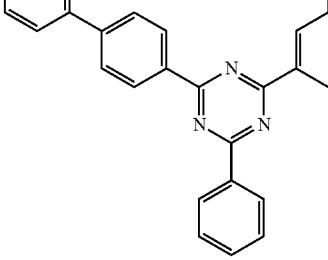

213
-continued
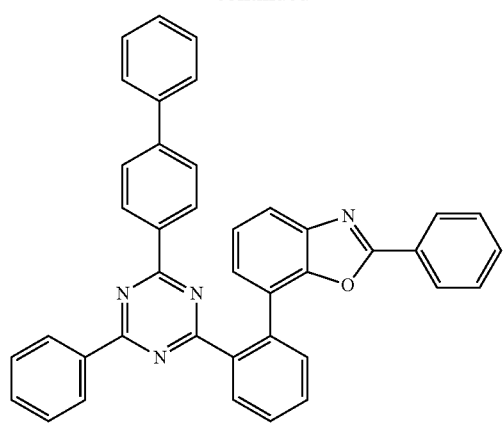
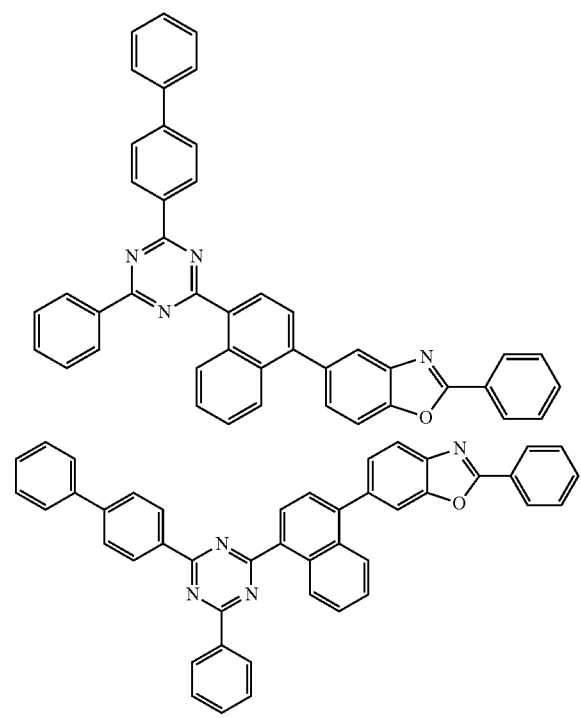
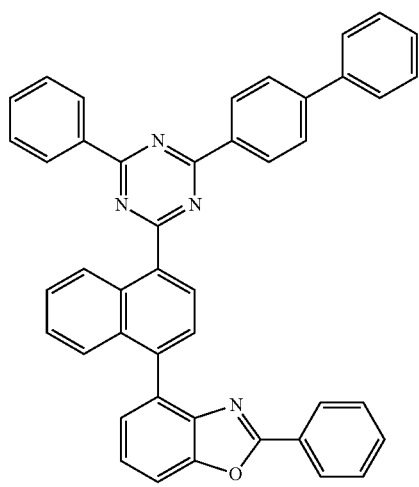
214
-continued
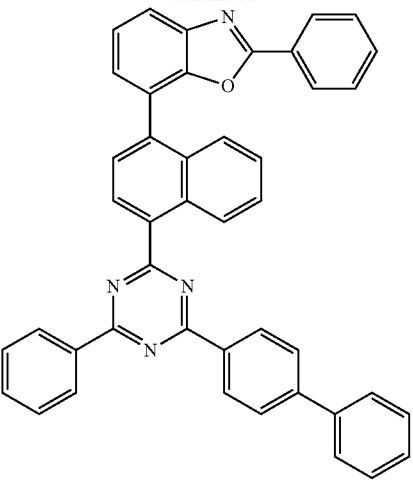
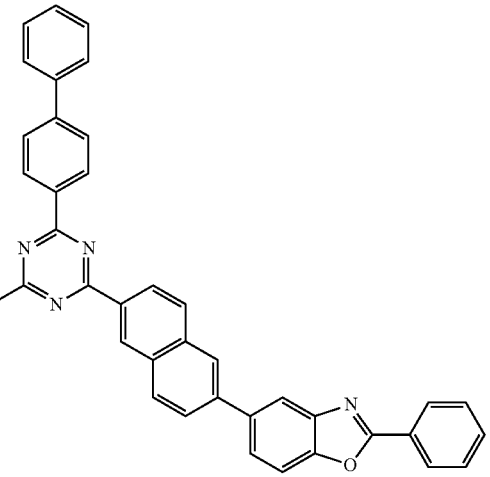
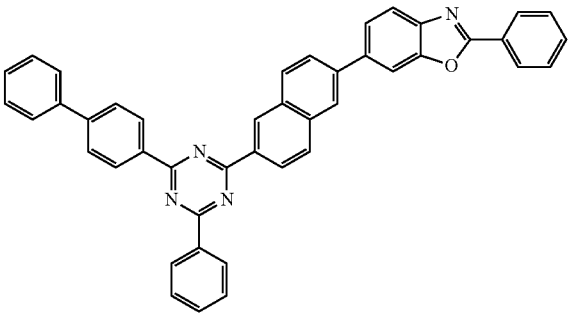

215
-continued
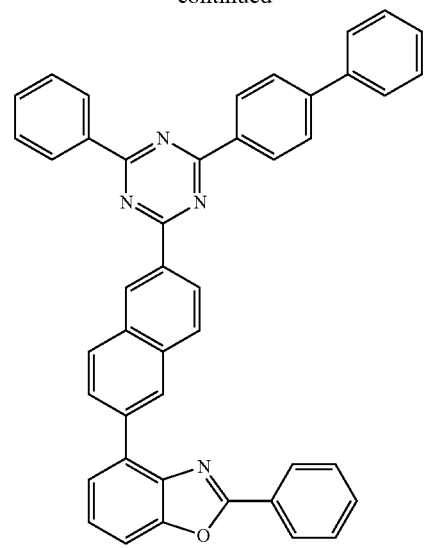
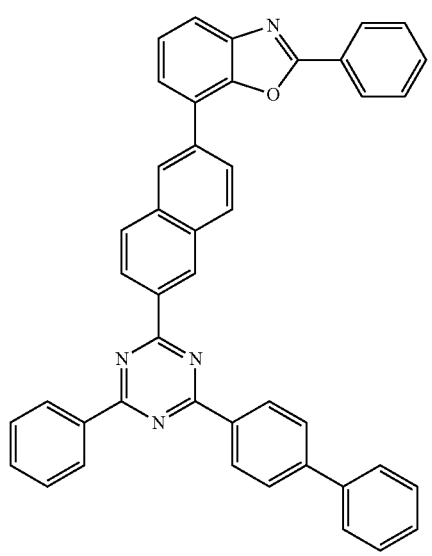
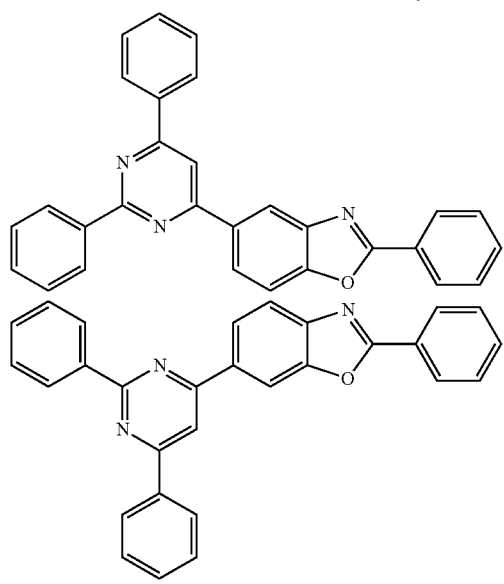
216
-continued
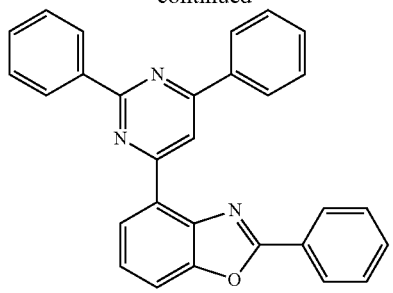
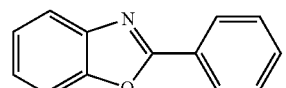
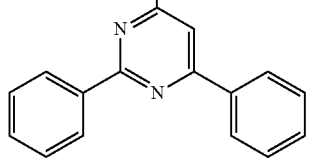
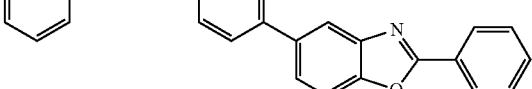

217
-continued
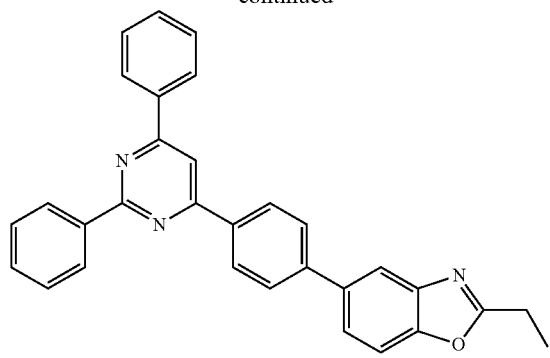
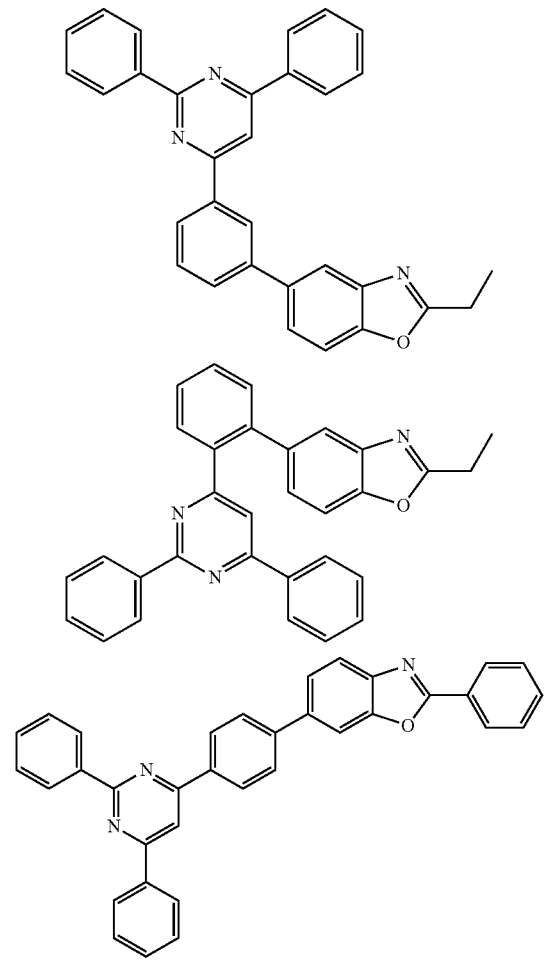
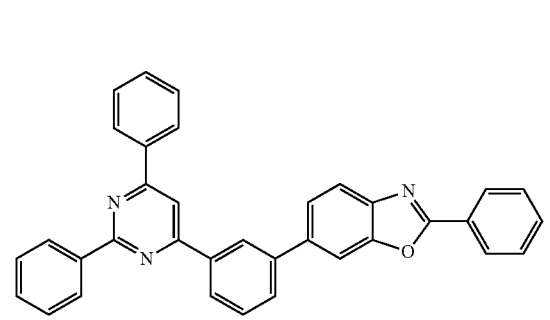
218
-continued
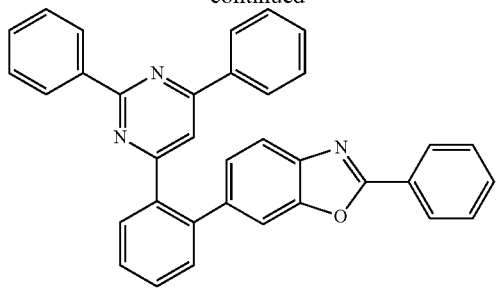
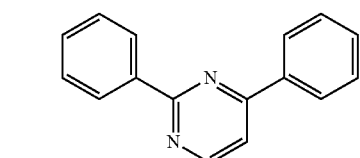
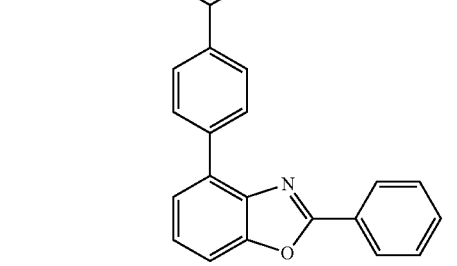
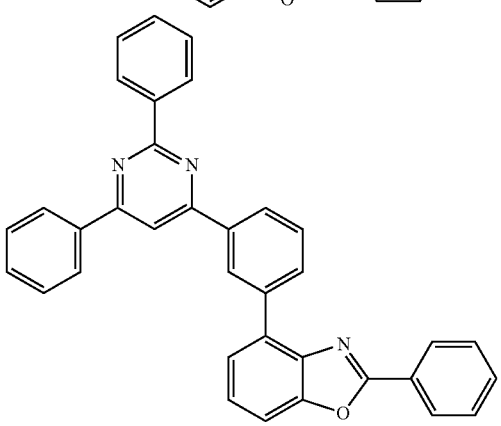
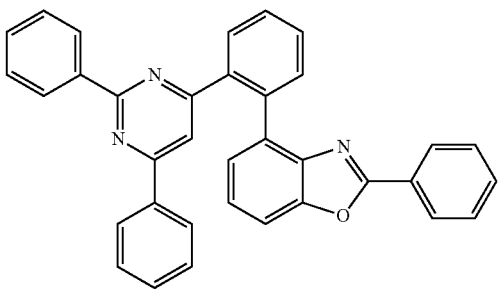

219
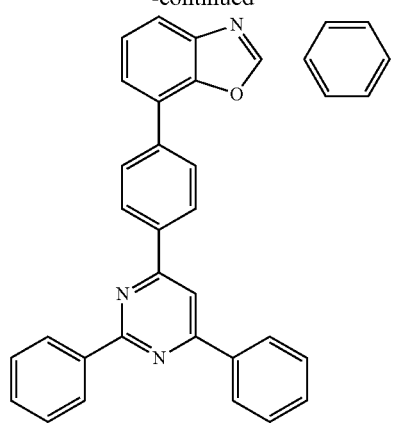
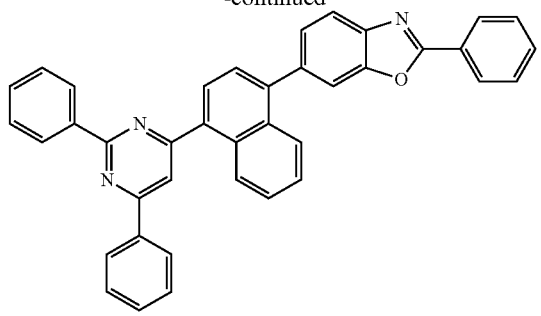
220
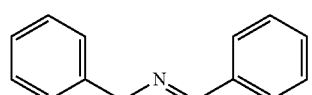
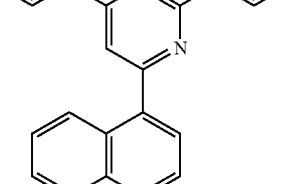
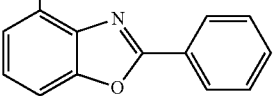
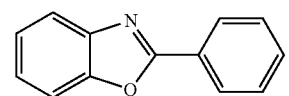
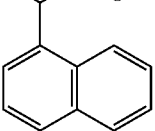
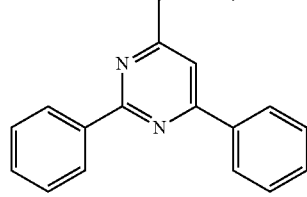
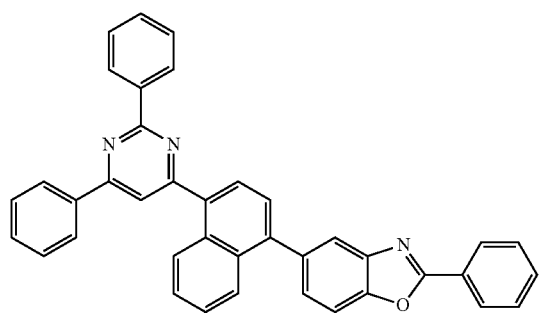
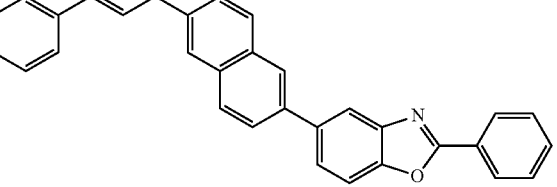

-continued

223
-continued
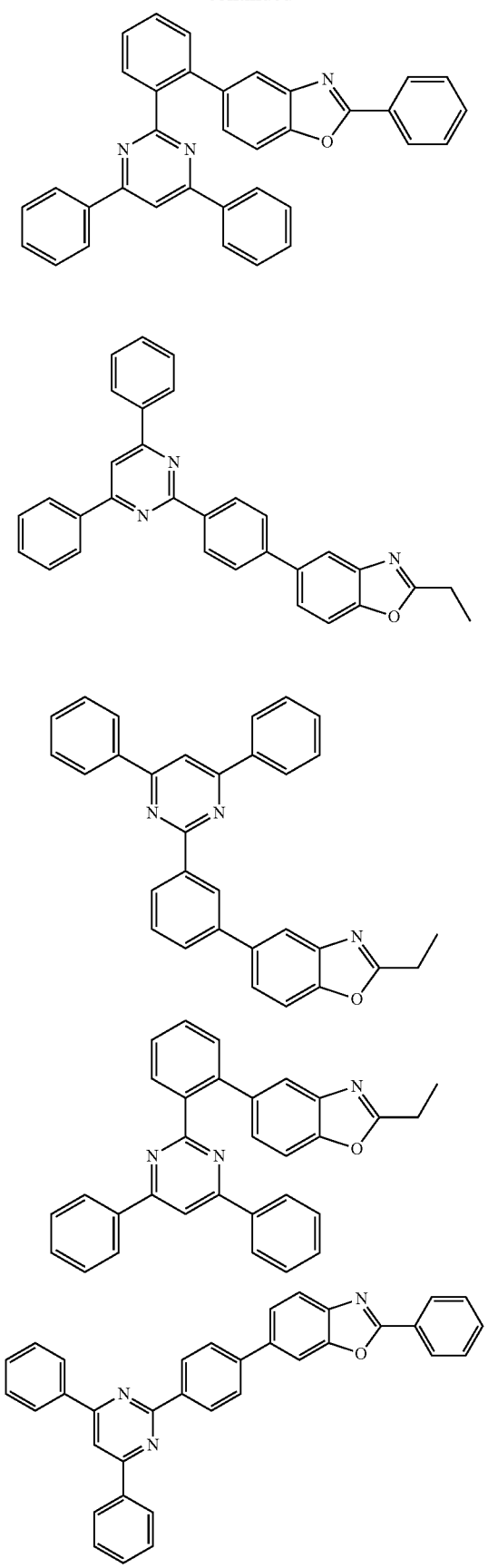
224
-continued
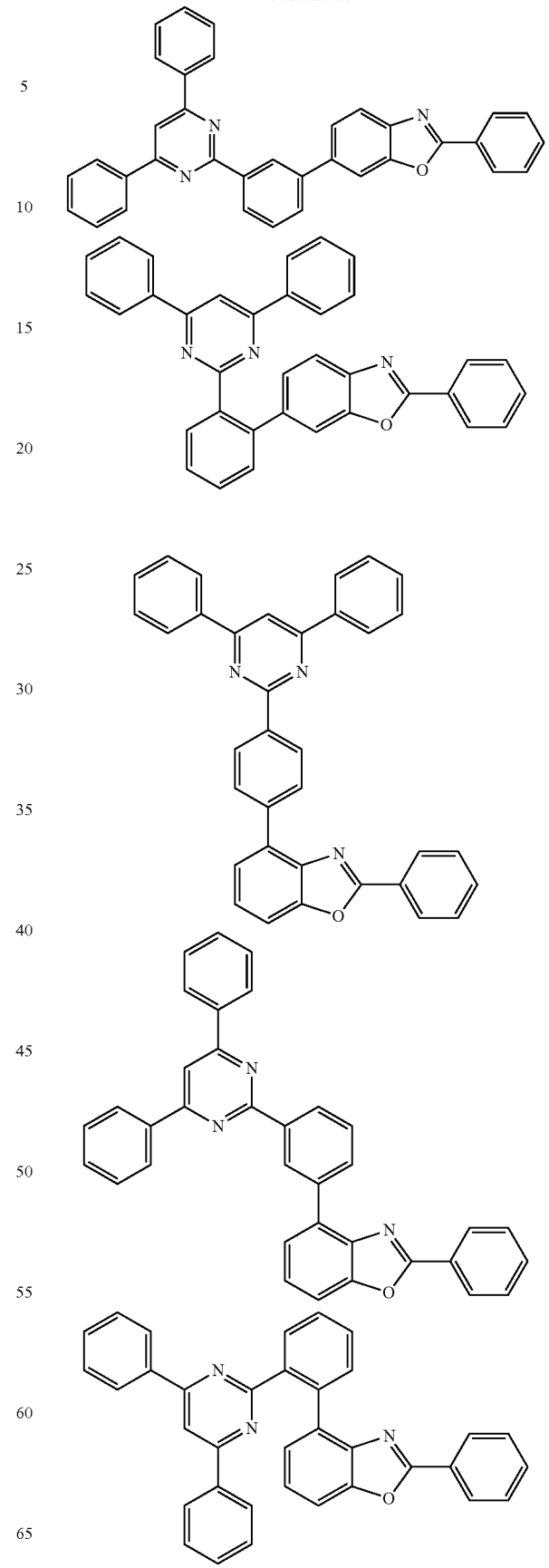

225
-continued
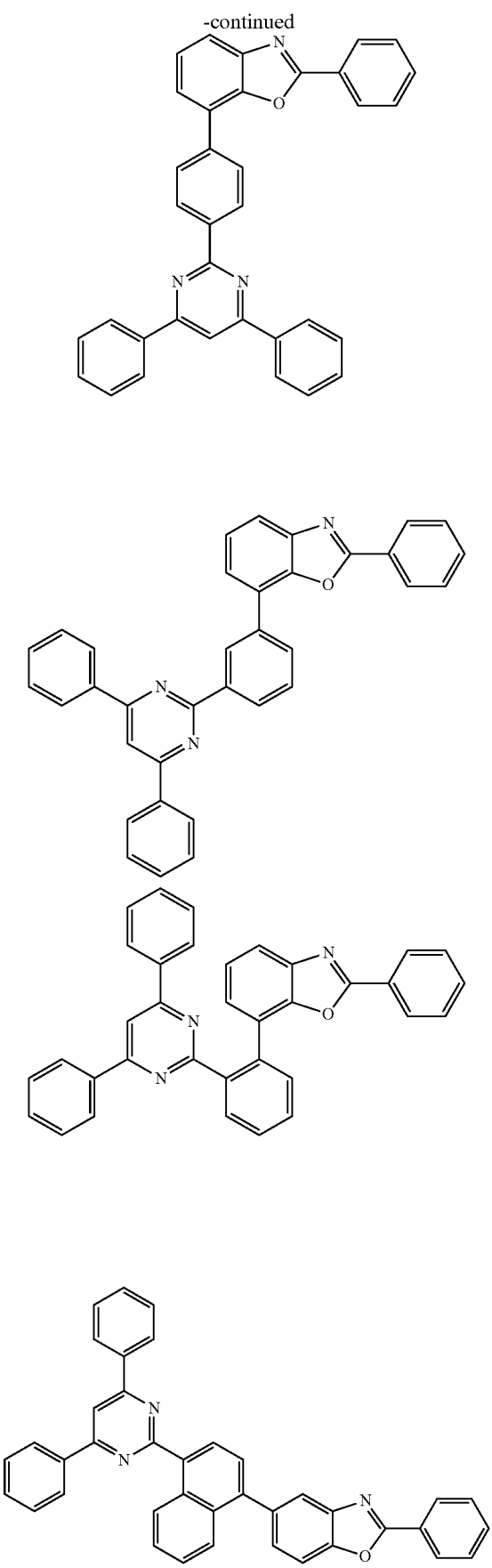
226
-continued
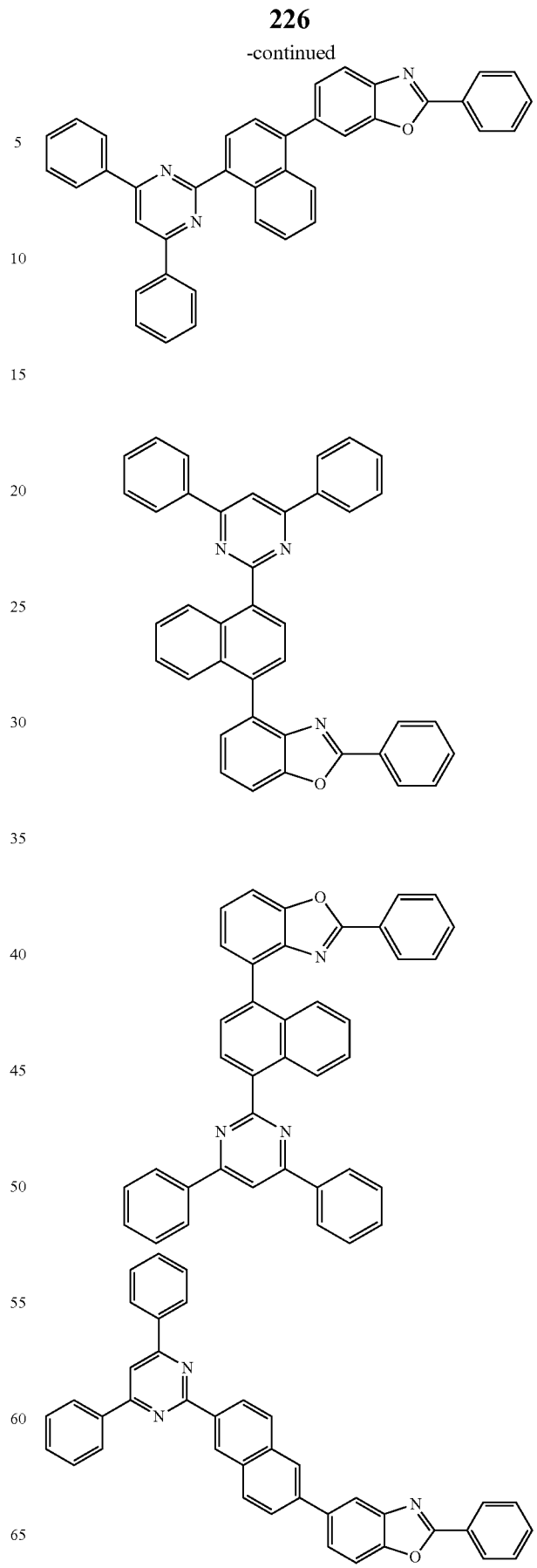

227
-continued
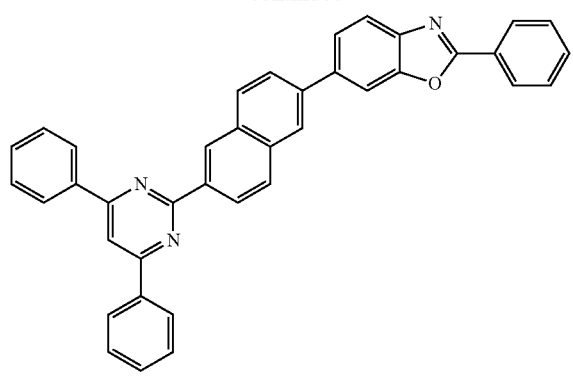
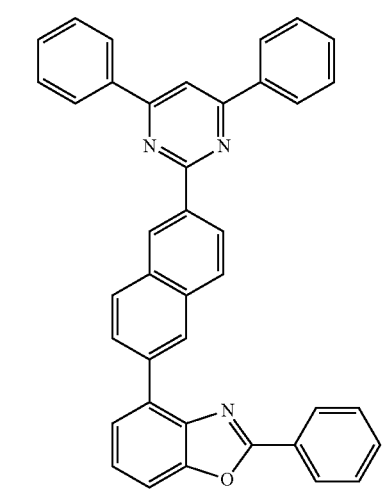
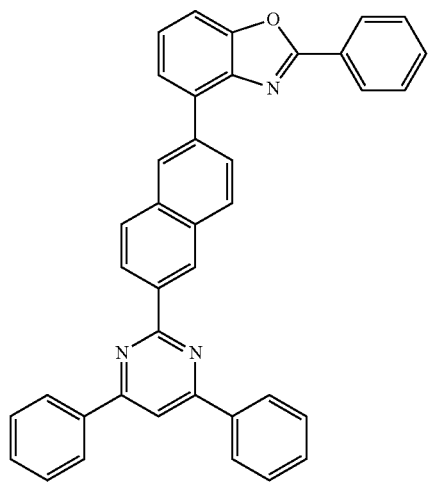
228
-continued
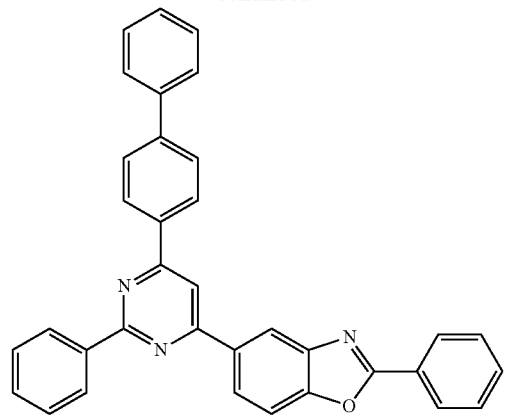
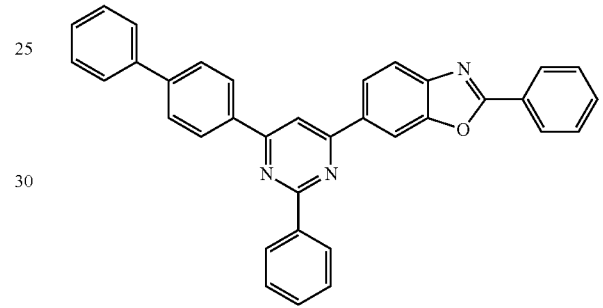
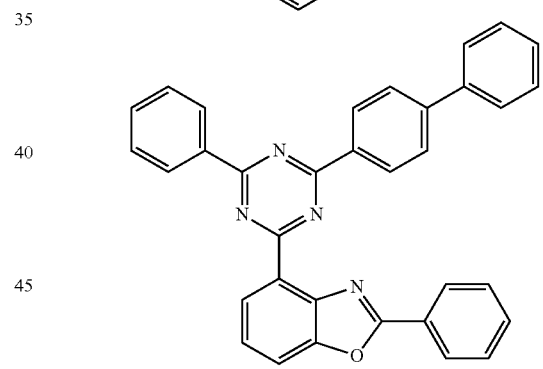
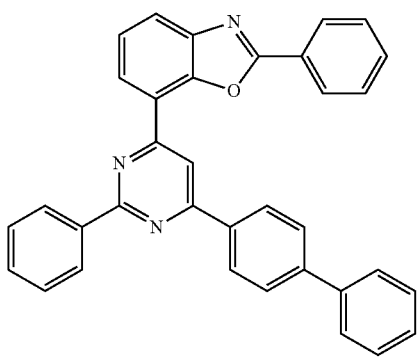 [SMILES: c1ccc(-c2ccc(-c3nc(-c4ccccc4)cc(-c4cccc5nc(-c6ccccc6)oc45)n3)cc2)cc1]

-continued
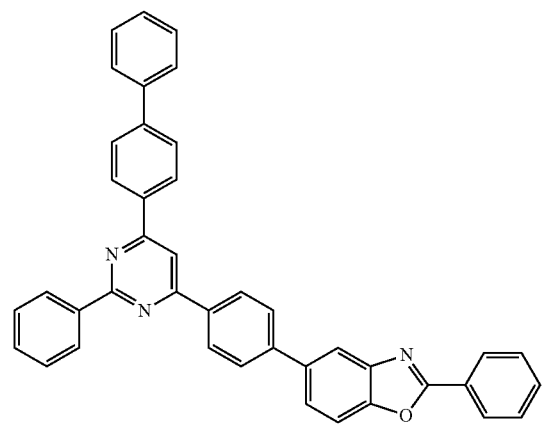
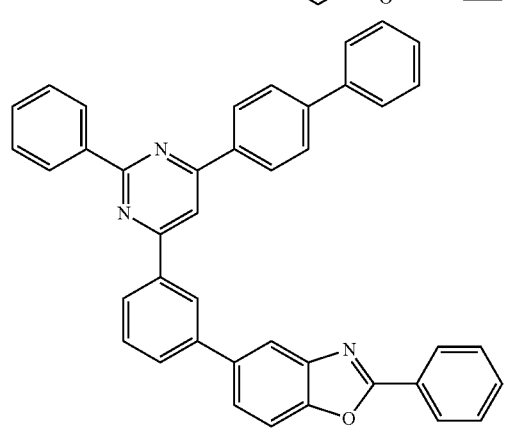
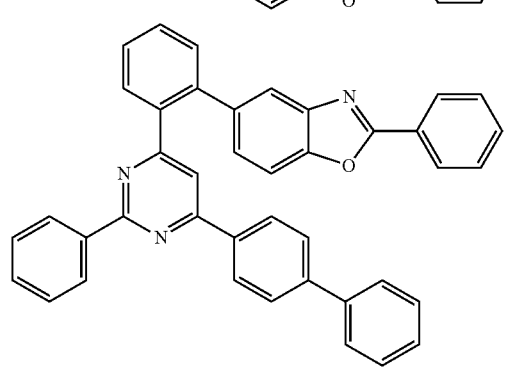
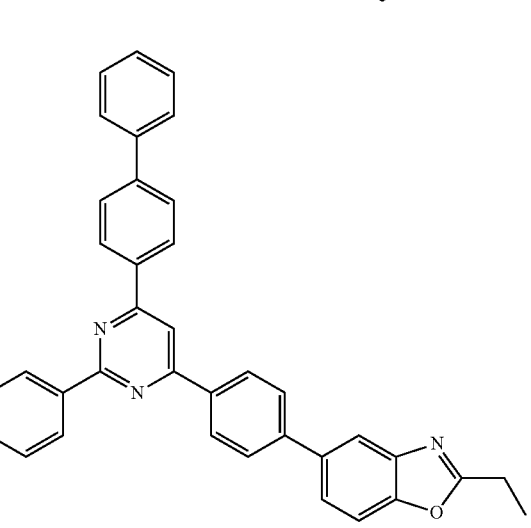
-continued
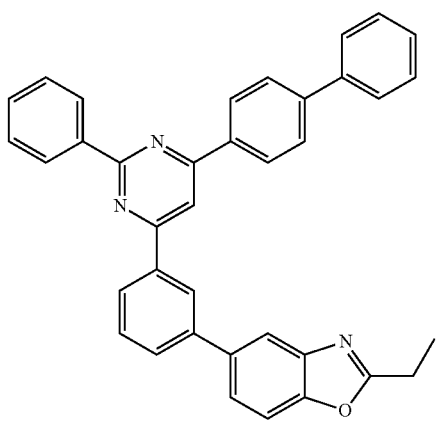
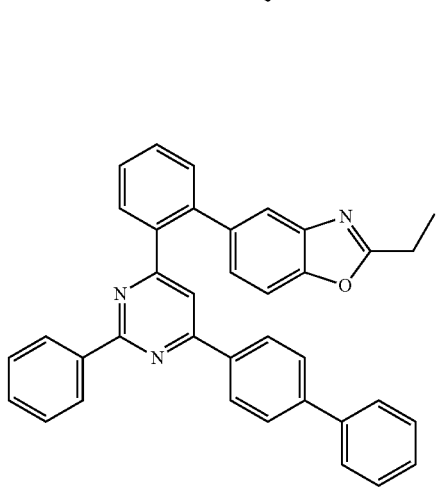
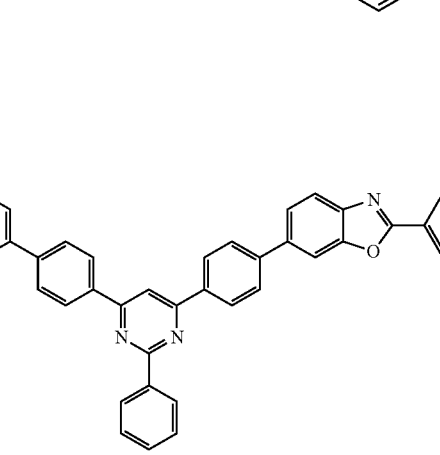

231
-continued
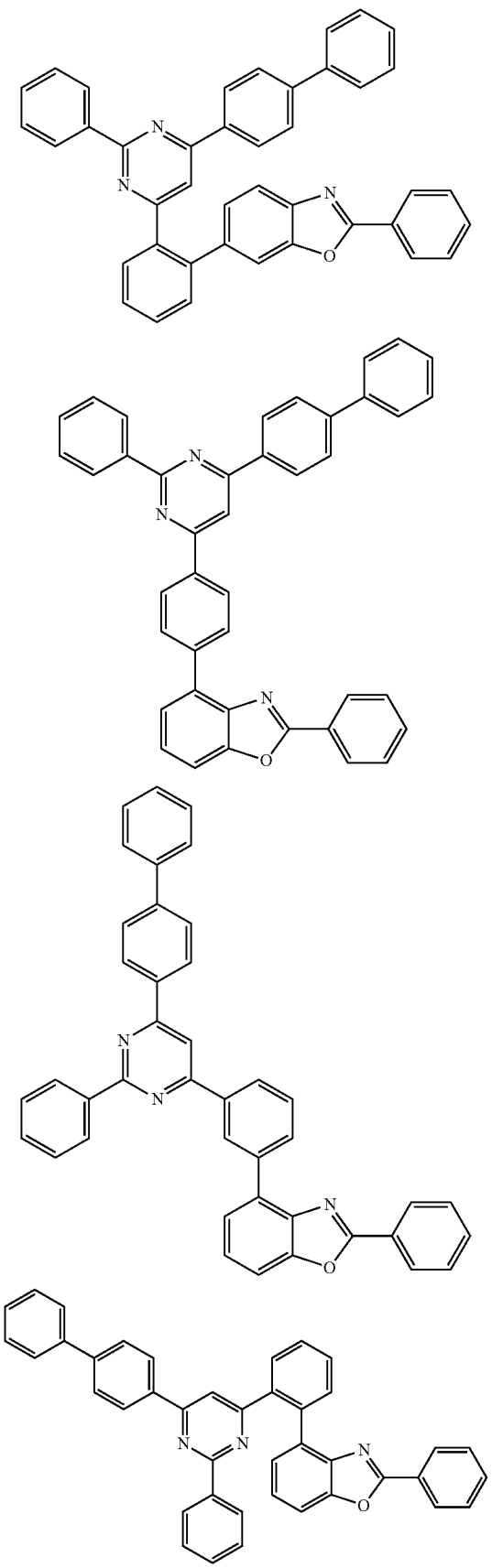
232
-continued
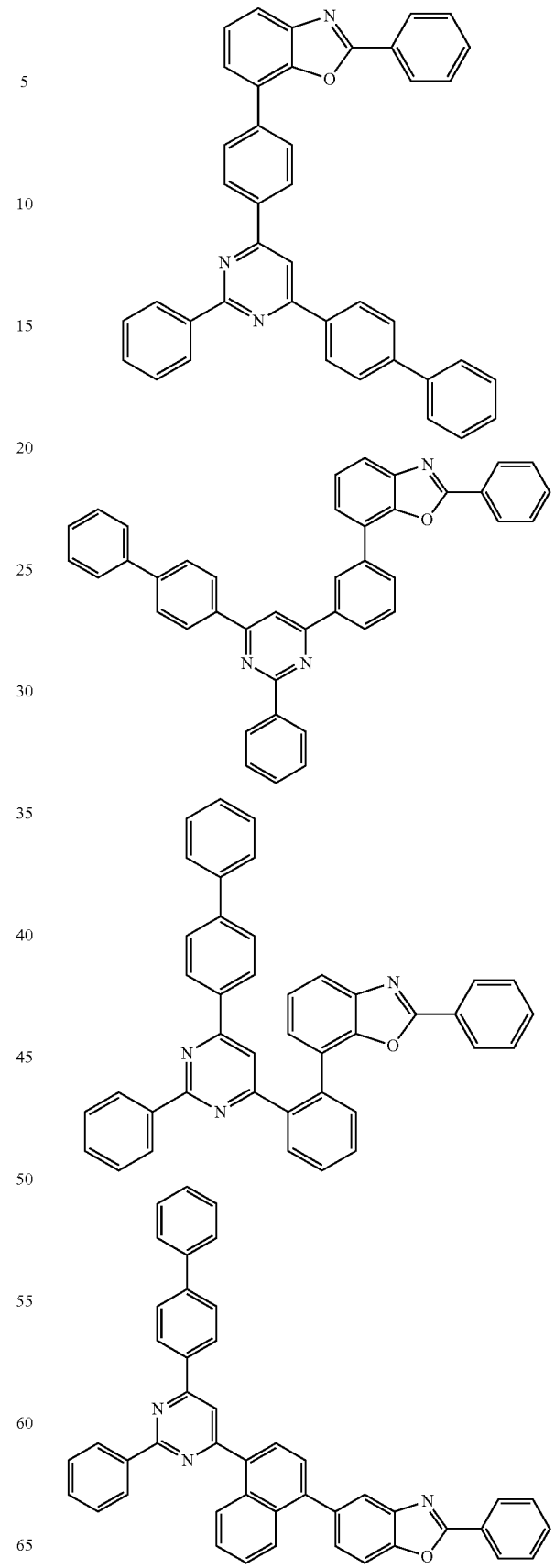

233
-continued
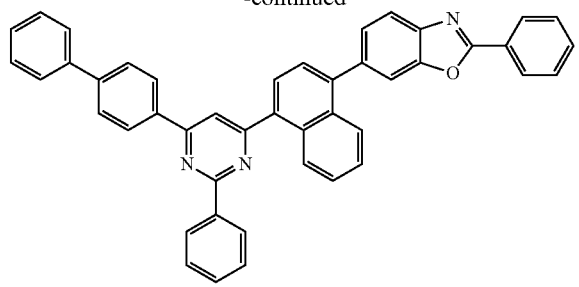
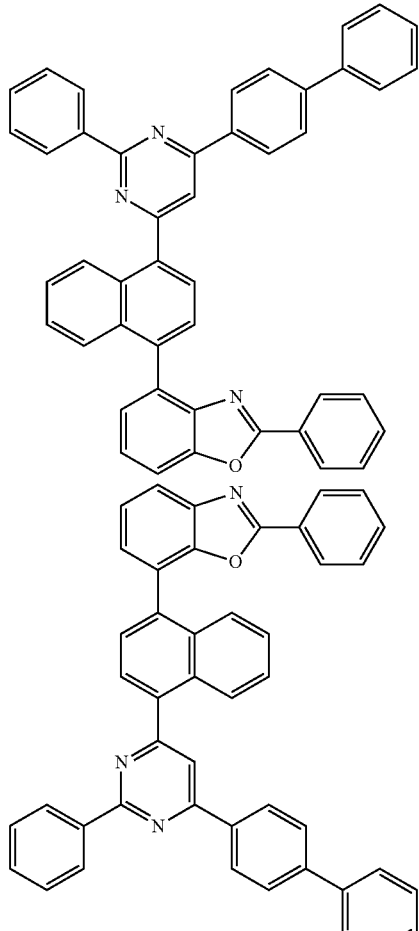
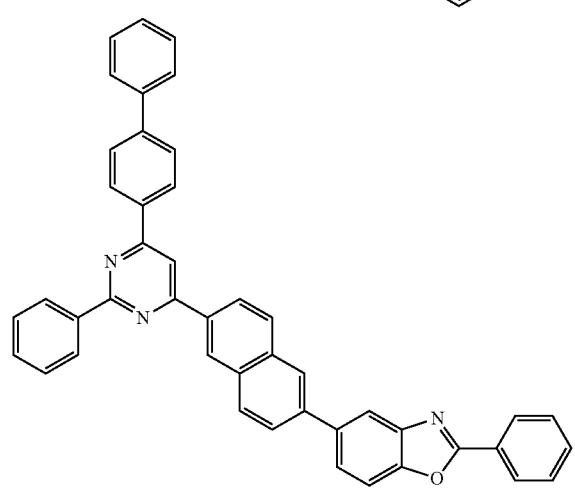
234
-continued
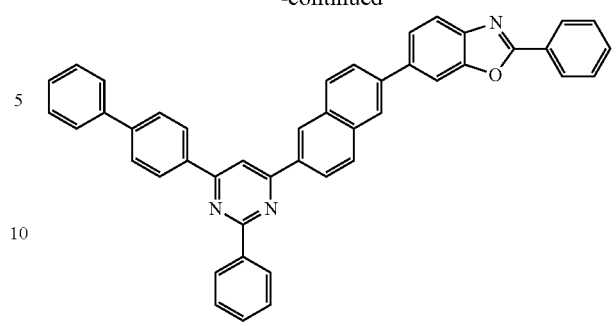
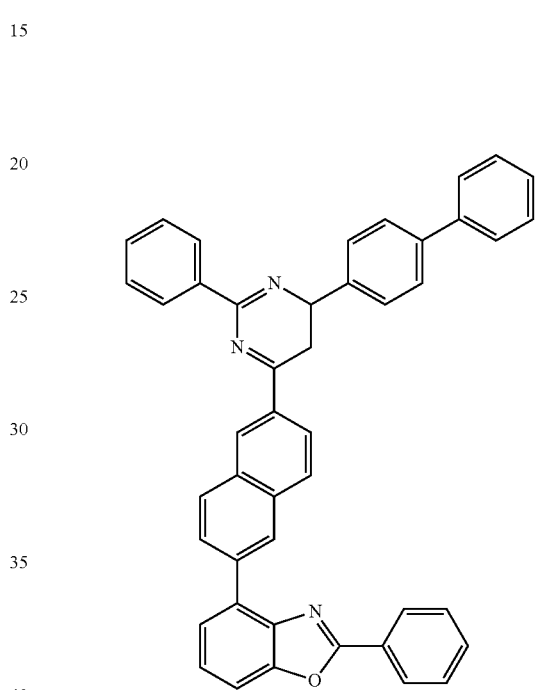
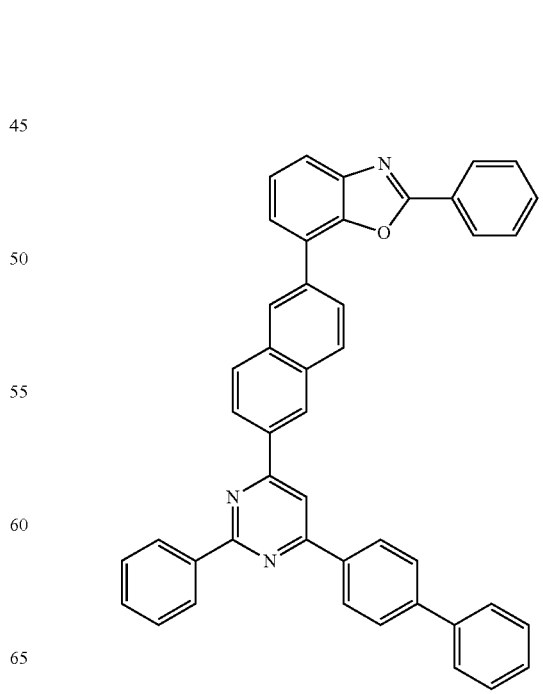

235
236
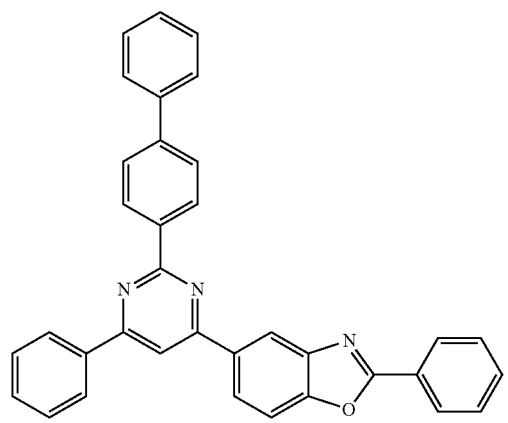
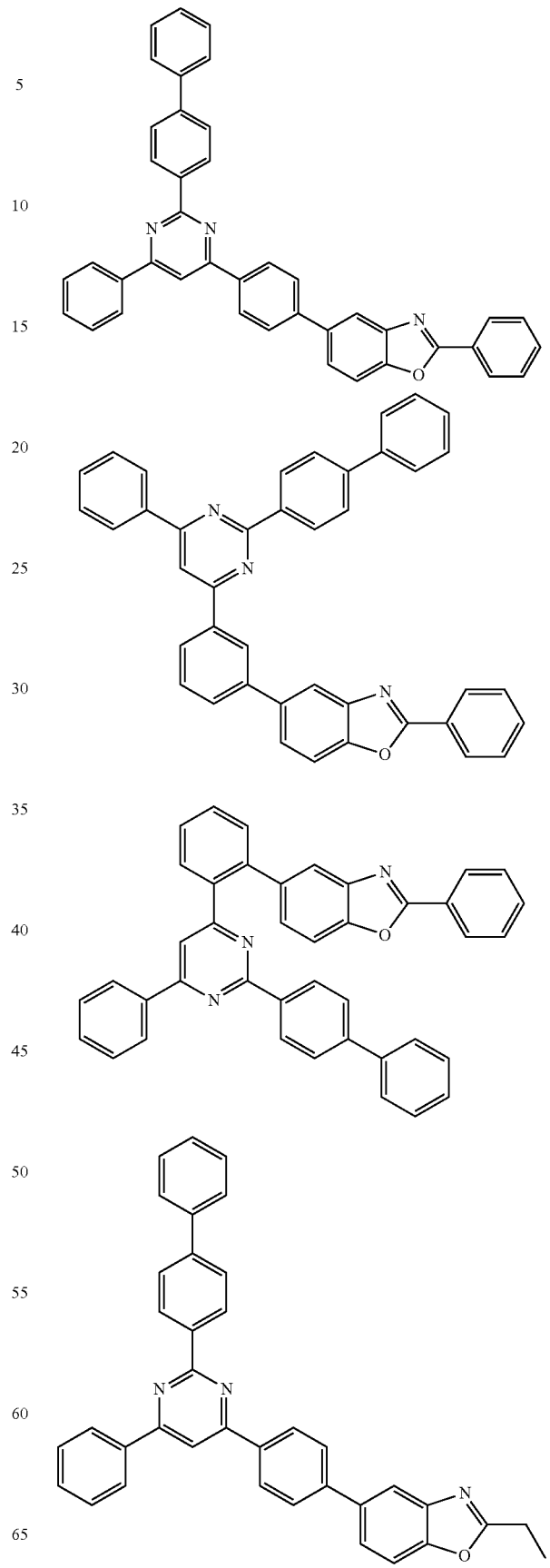

237
-continued
238
-continued
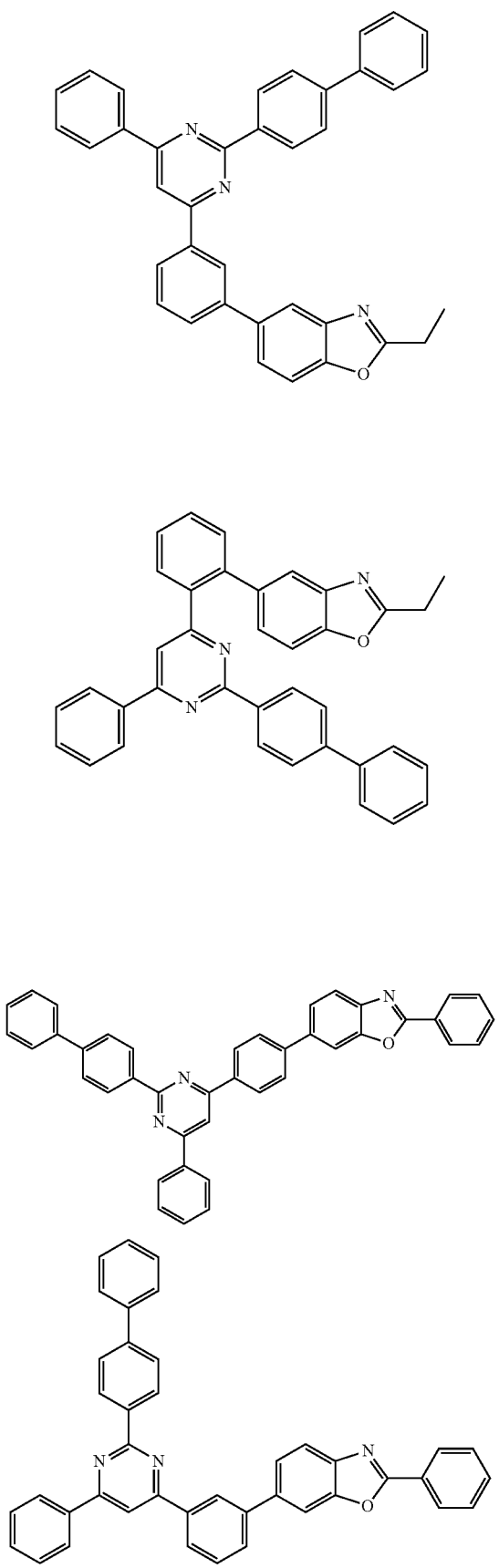
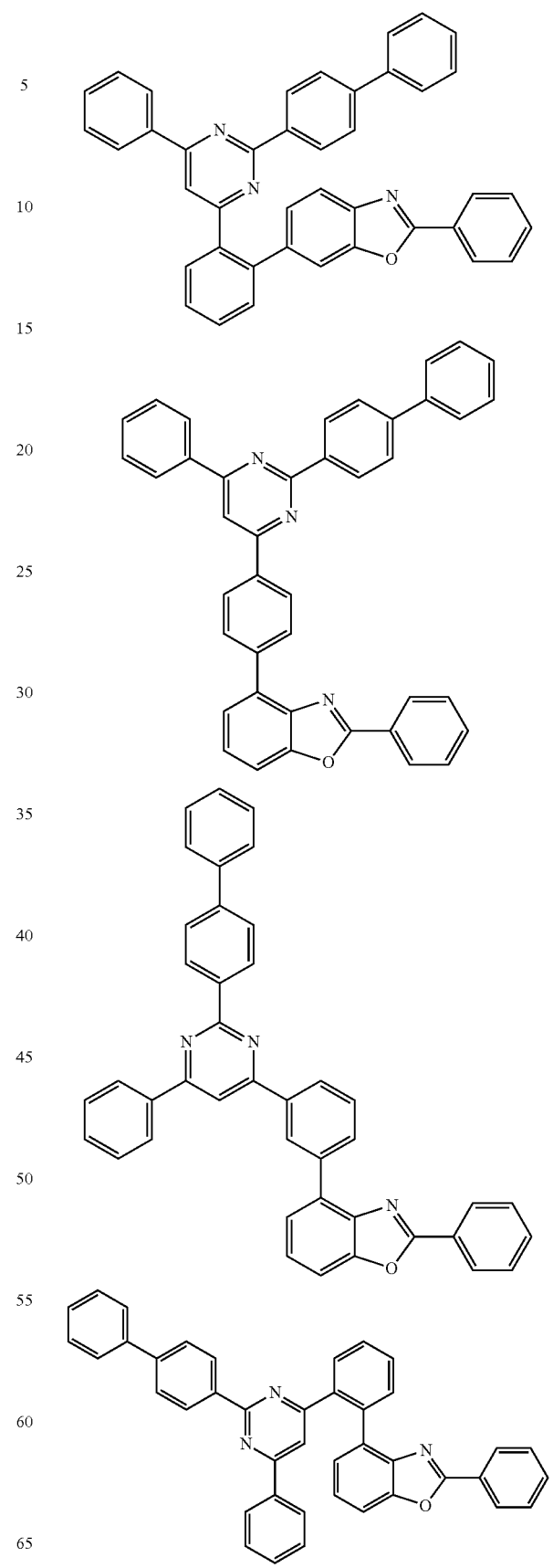

239
-continued
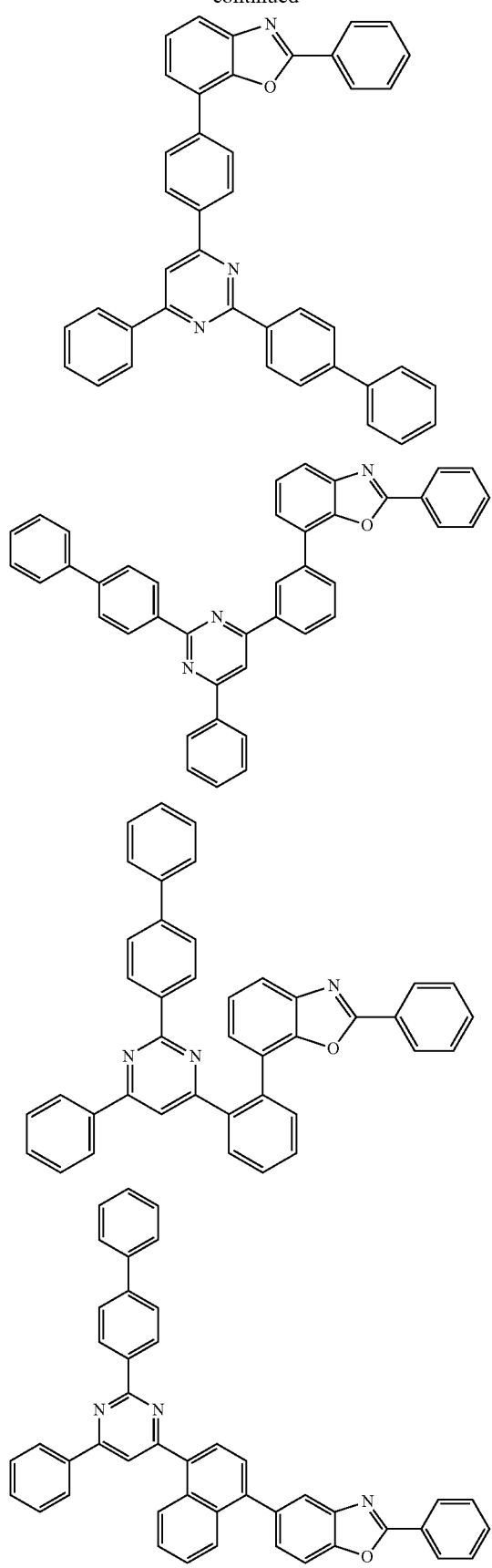
240
-continued
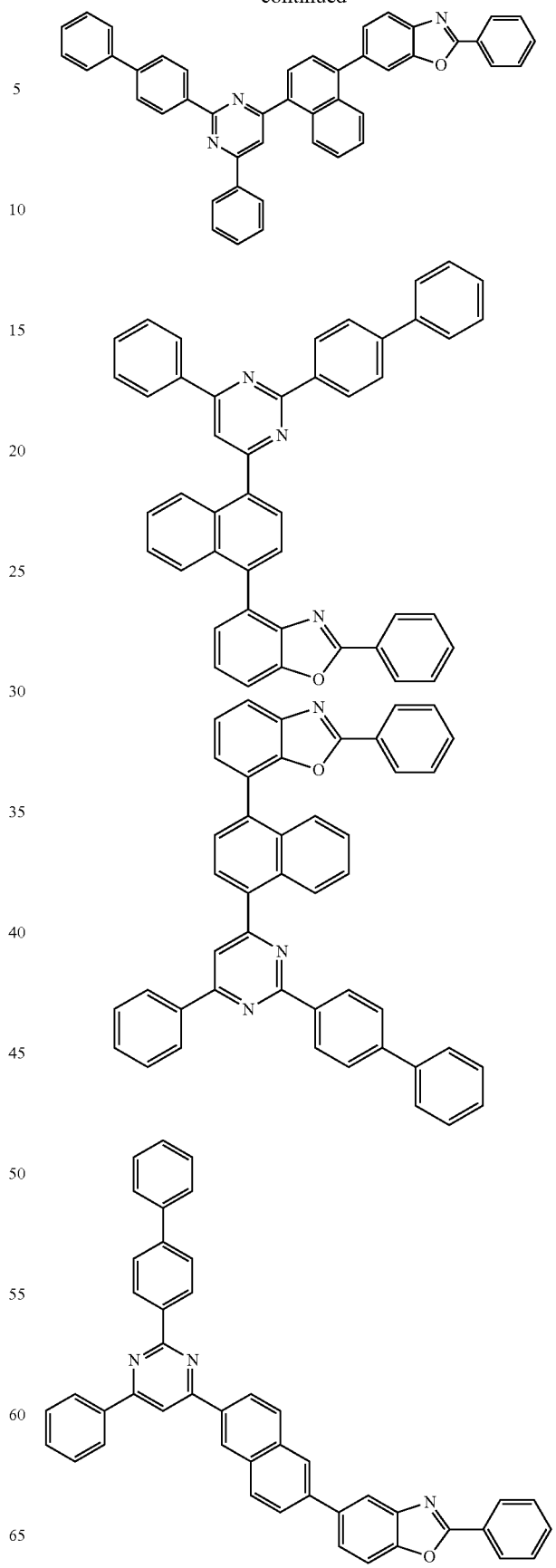

241
-continued
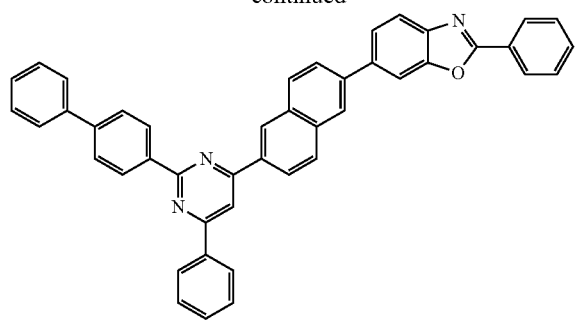
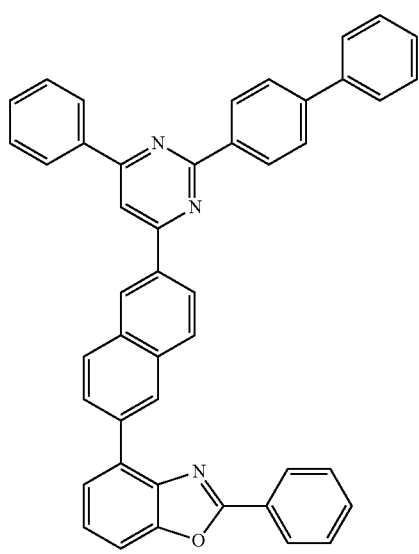
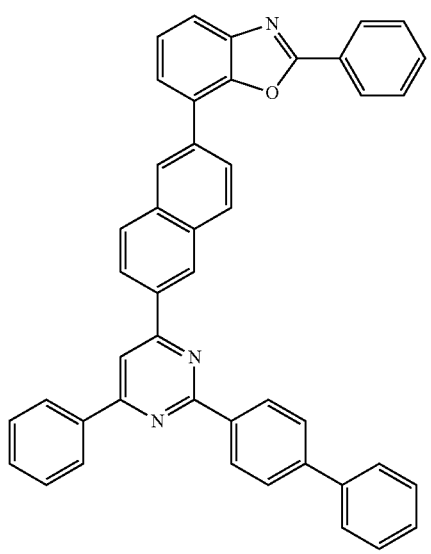
242
-continued
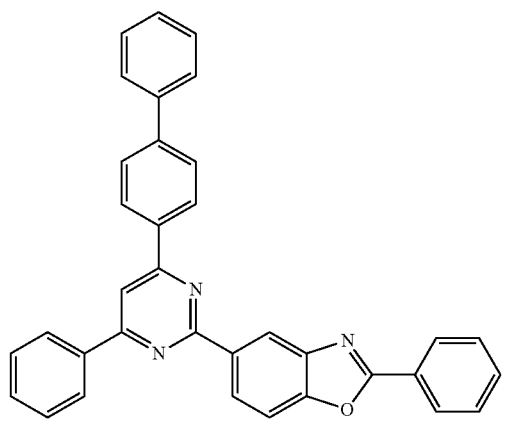
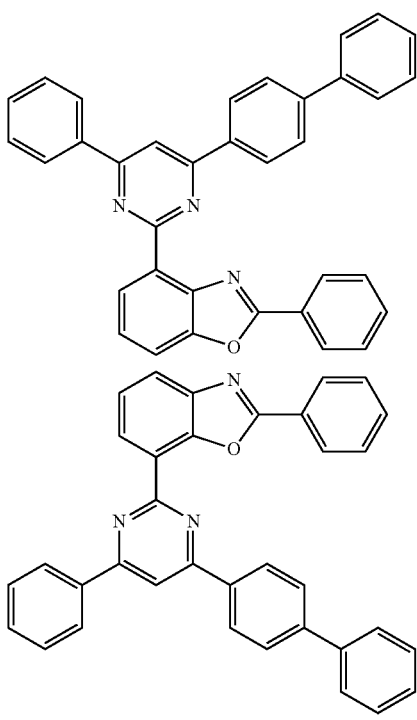

243
-continued
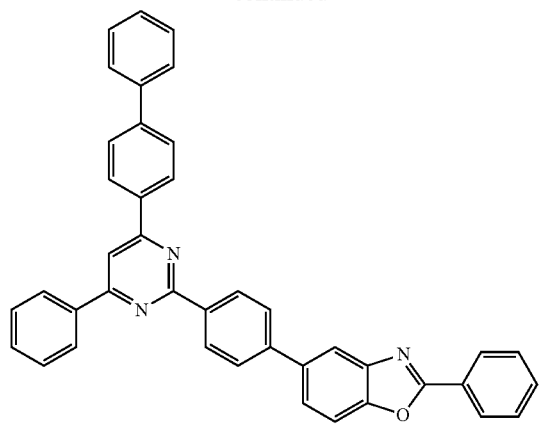
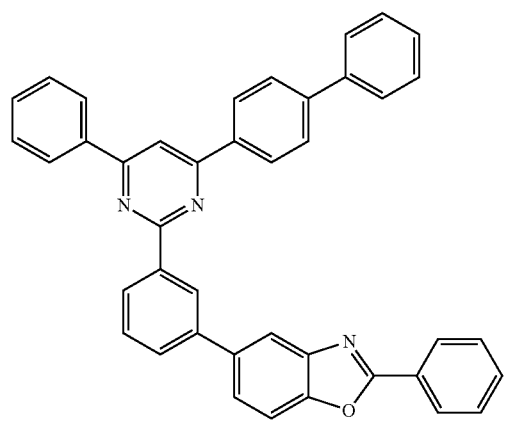
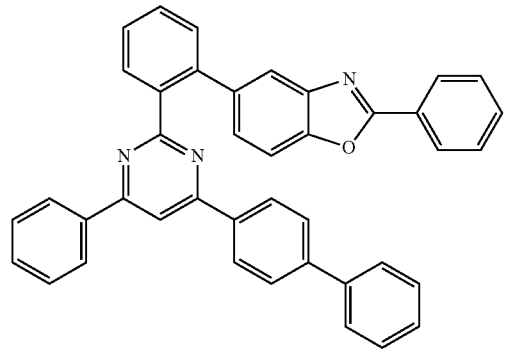
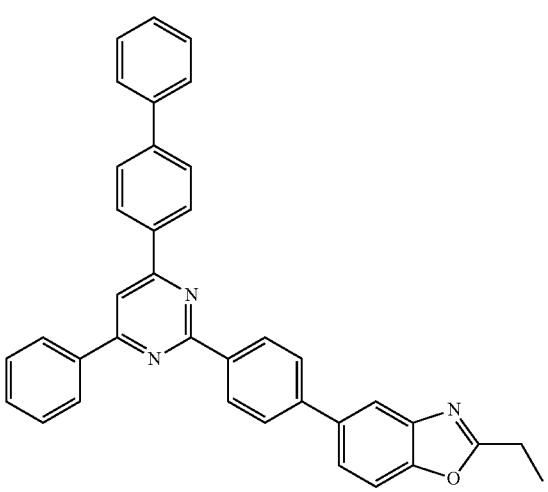
244
-continued
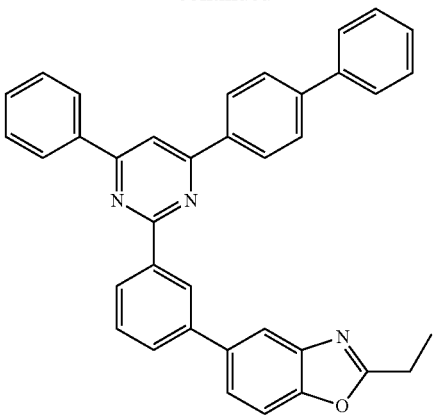
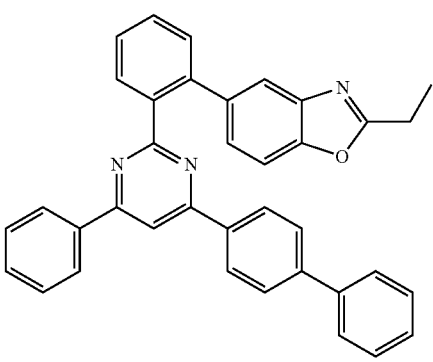
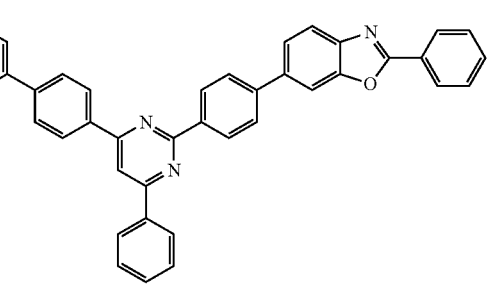
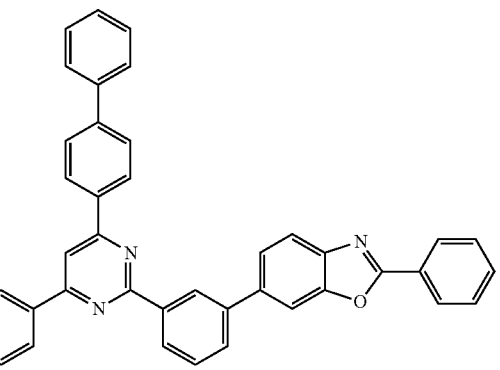

245
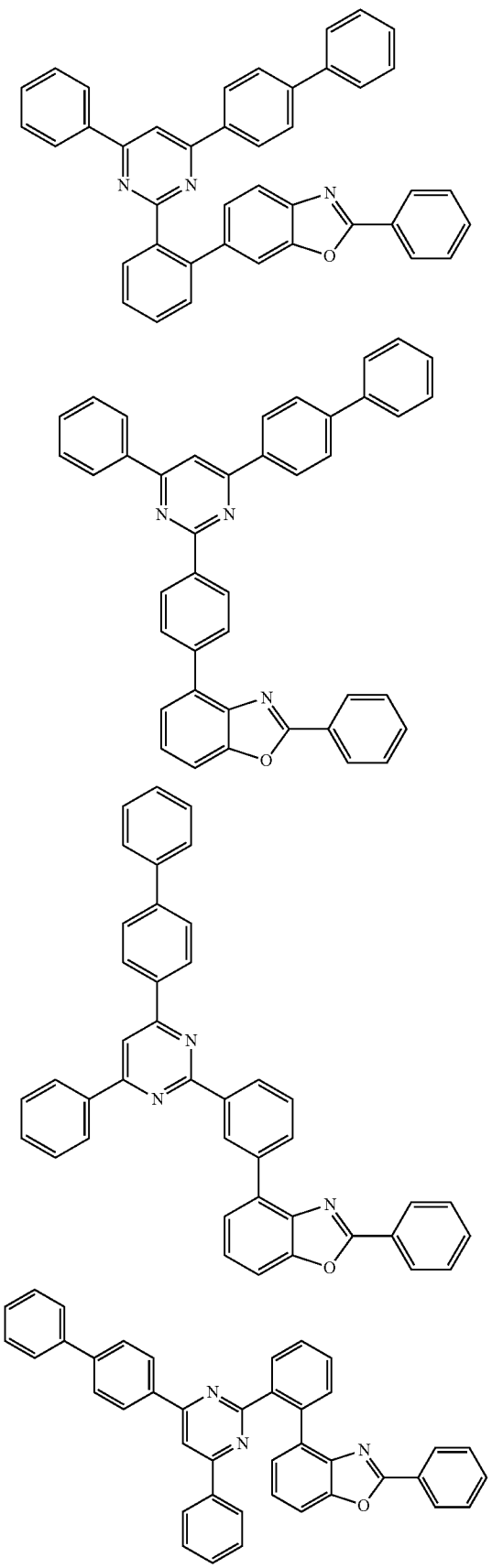
246
-continued
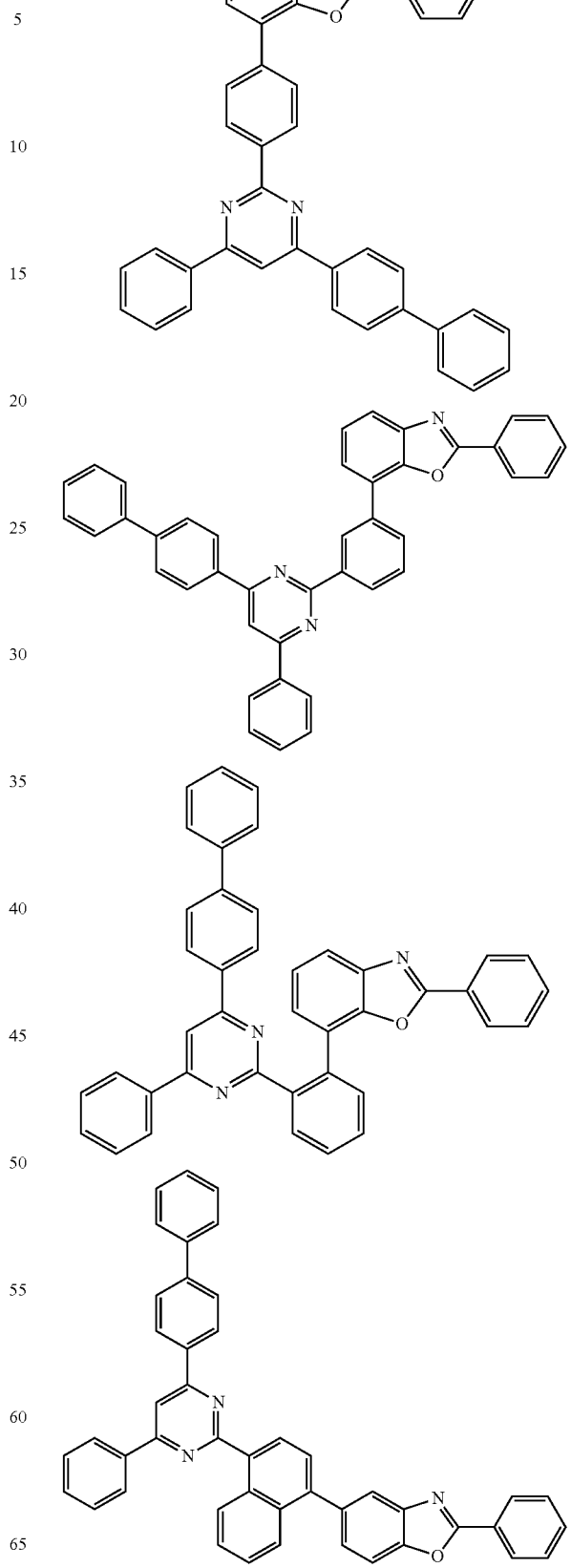

247
-continued
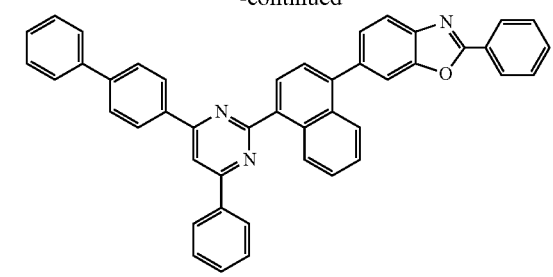
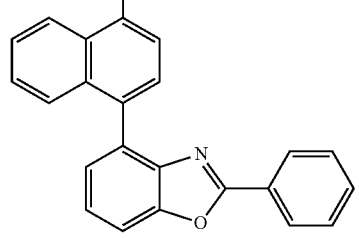
248
-continued
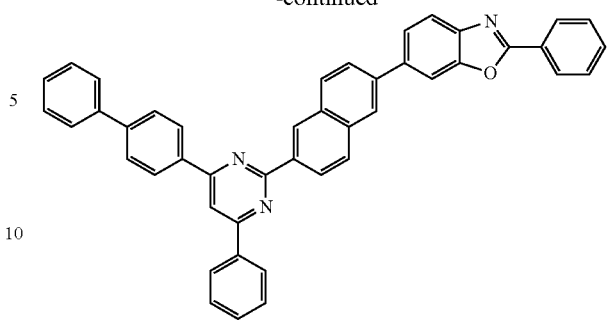
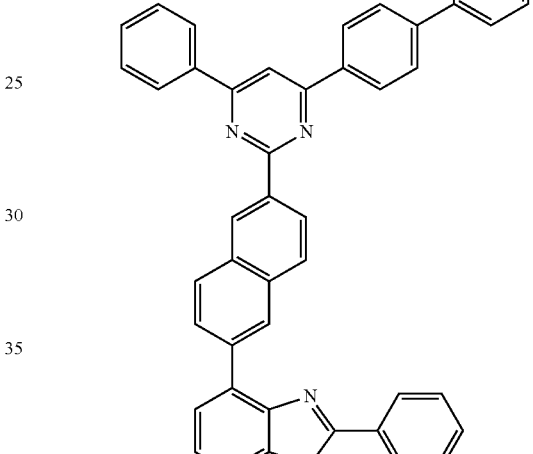
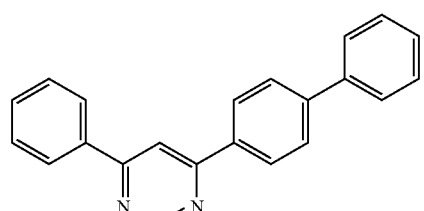

249
-continued
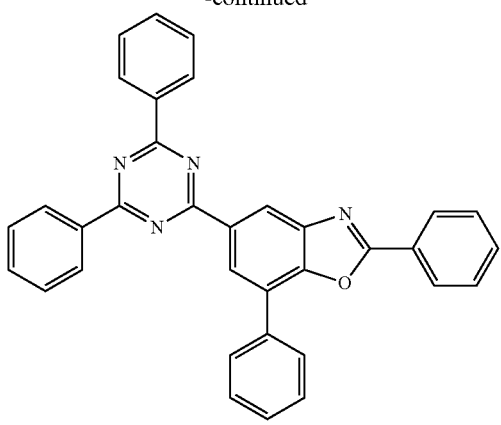
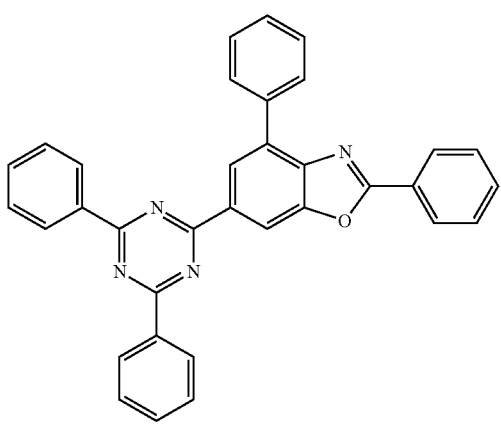
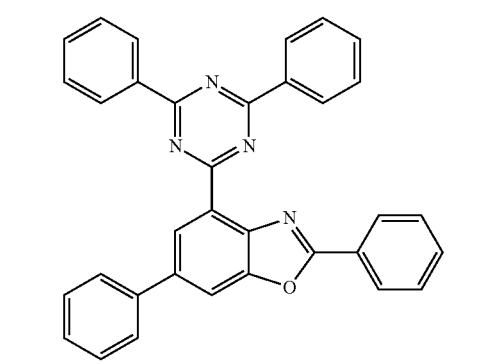
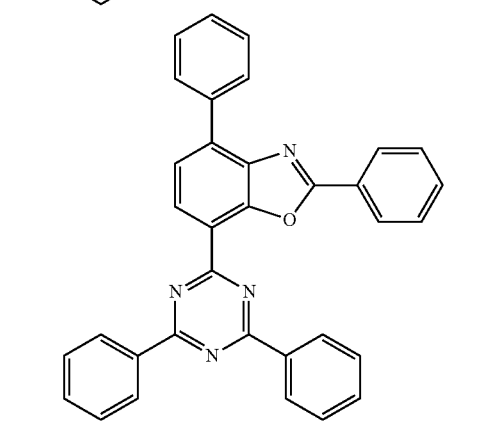
250
-continued
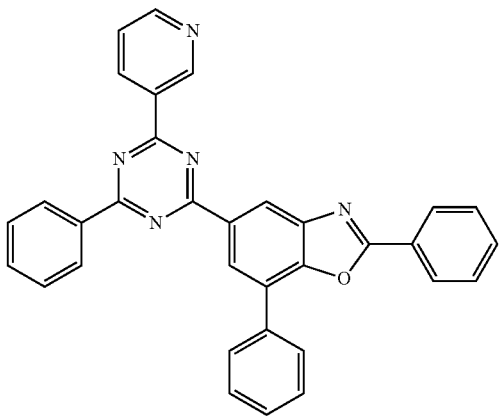
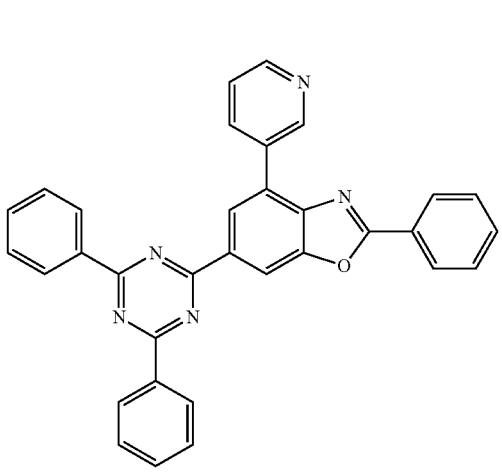
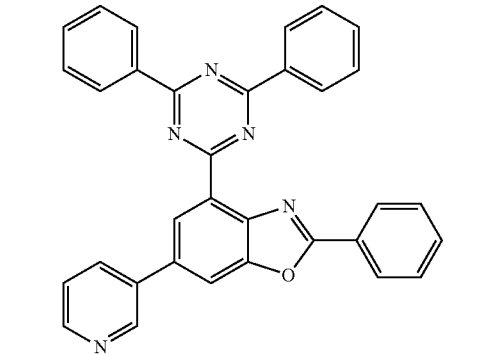
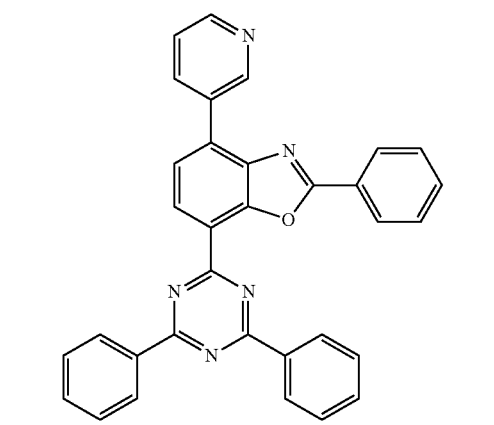

251
-continued
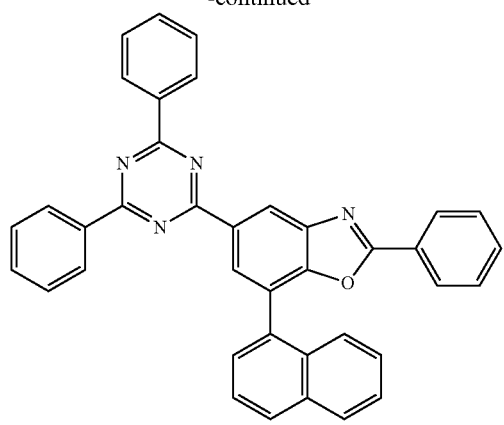
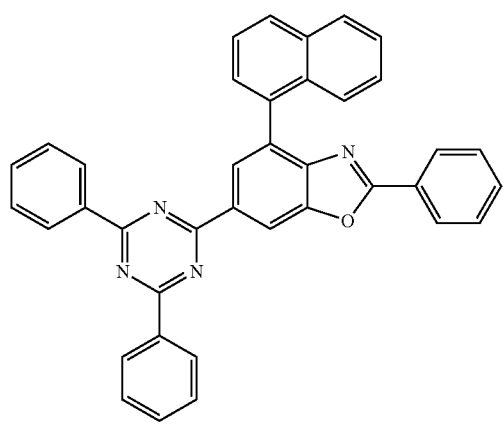
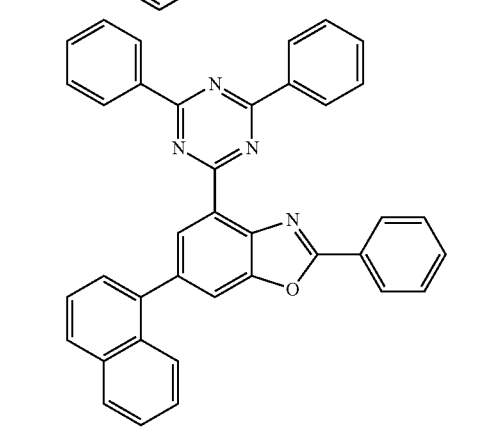
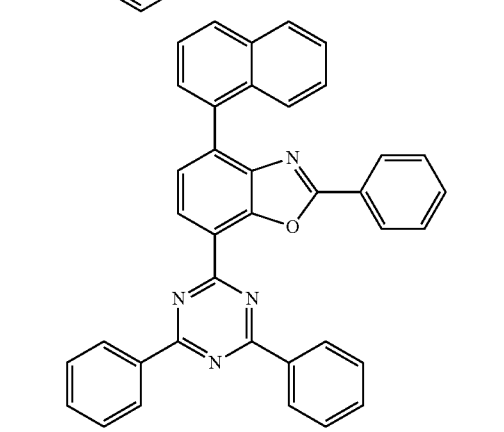
252
-continued
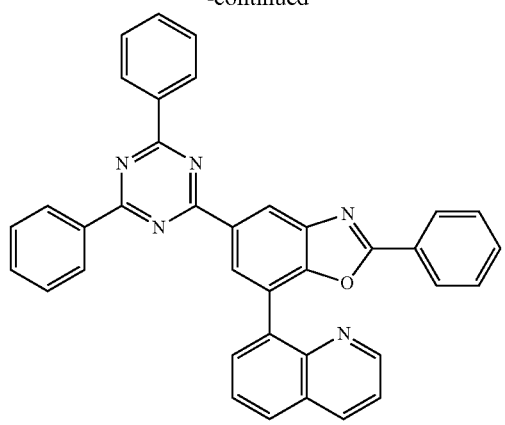
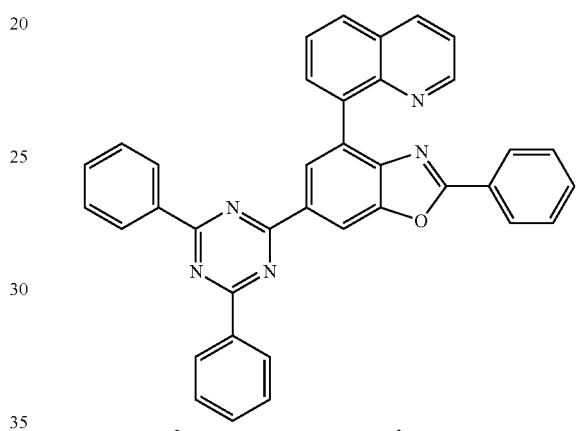
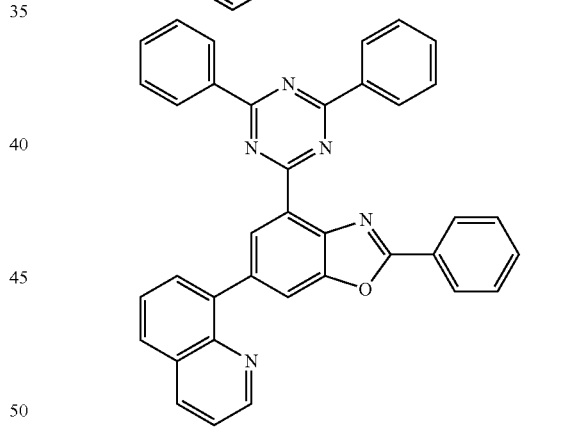
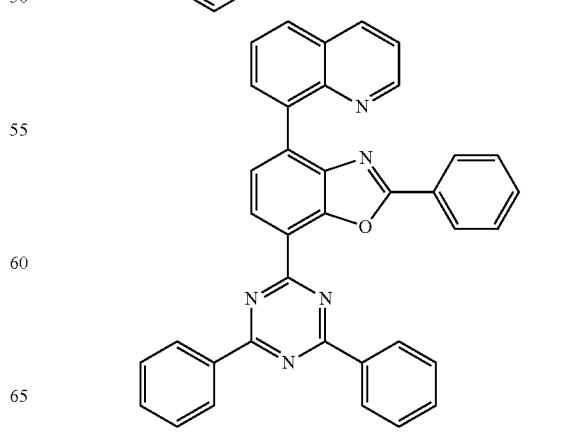

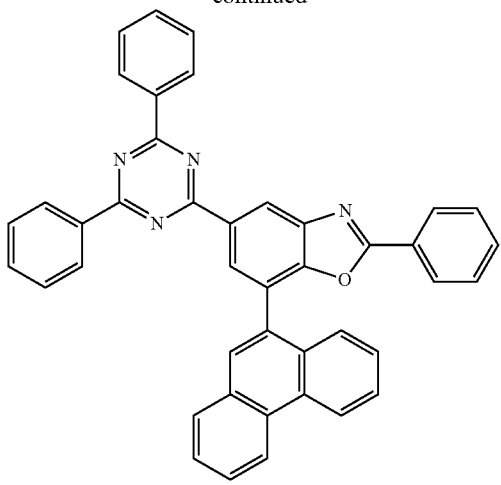
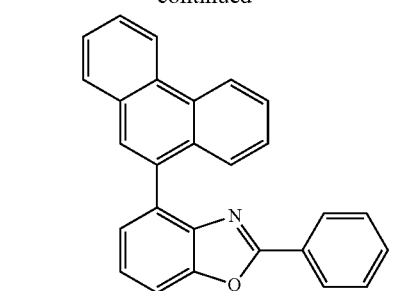
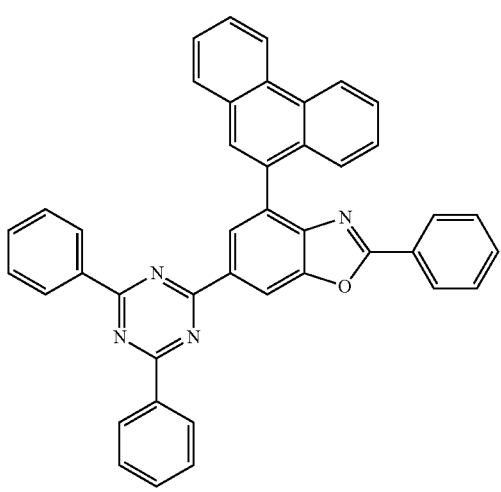
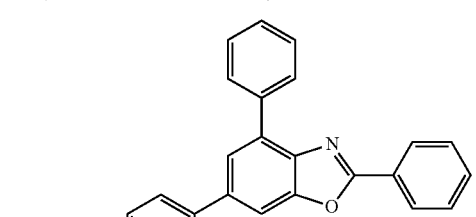
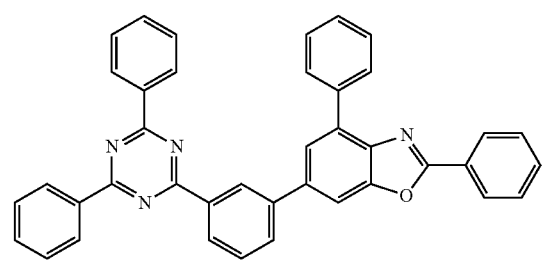
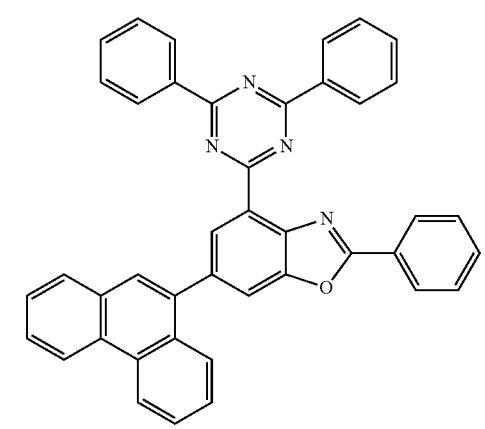
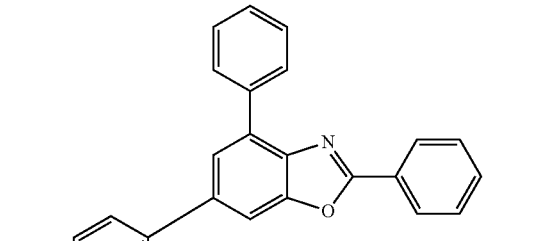
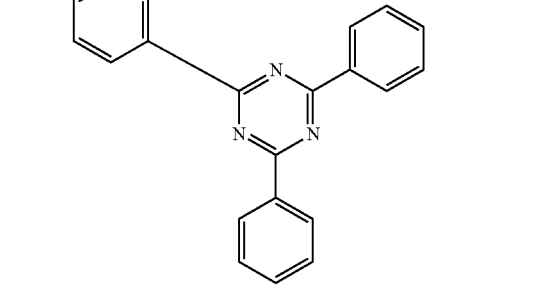

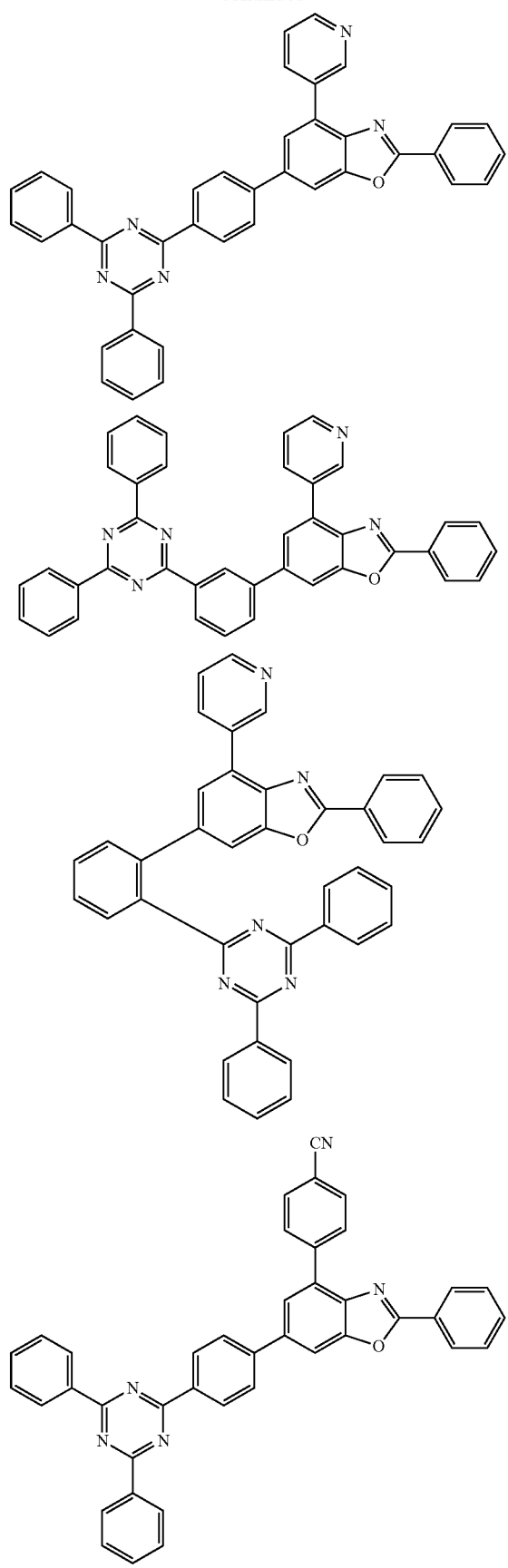
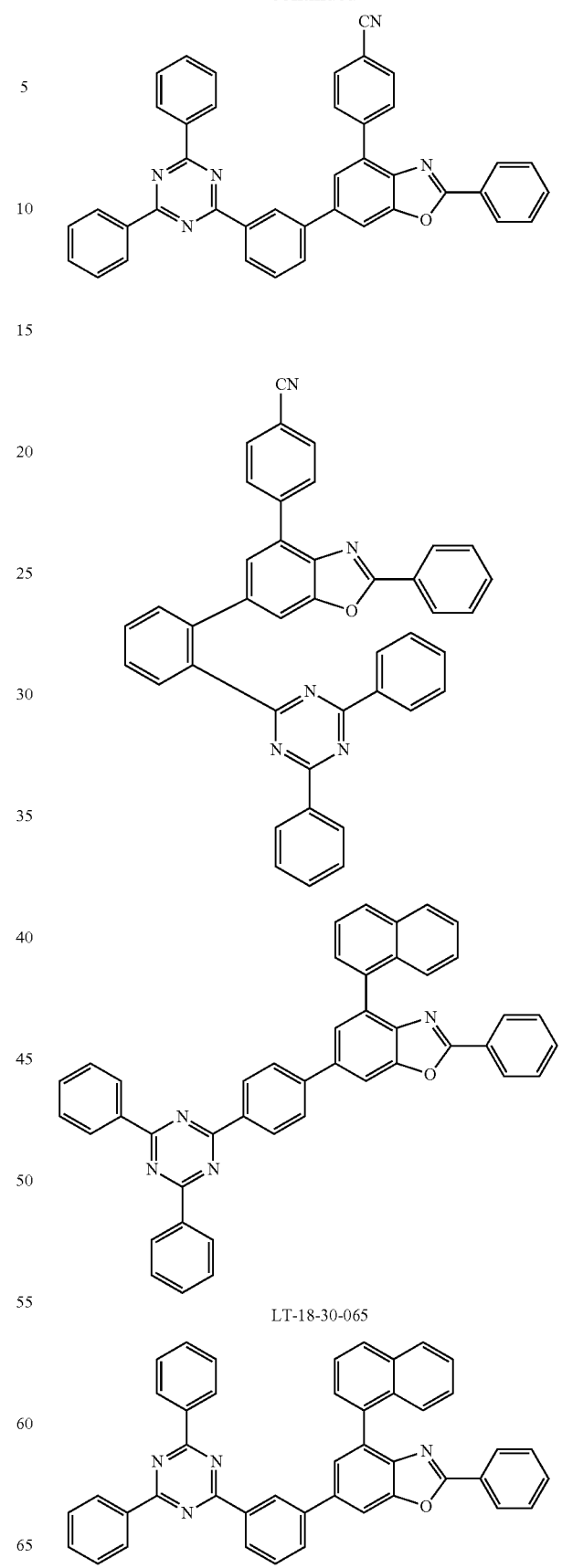
LT-18-30-065

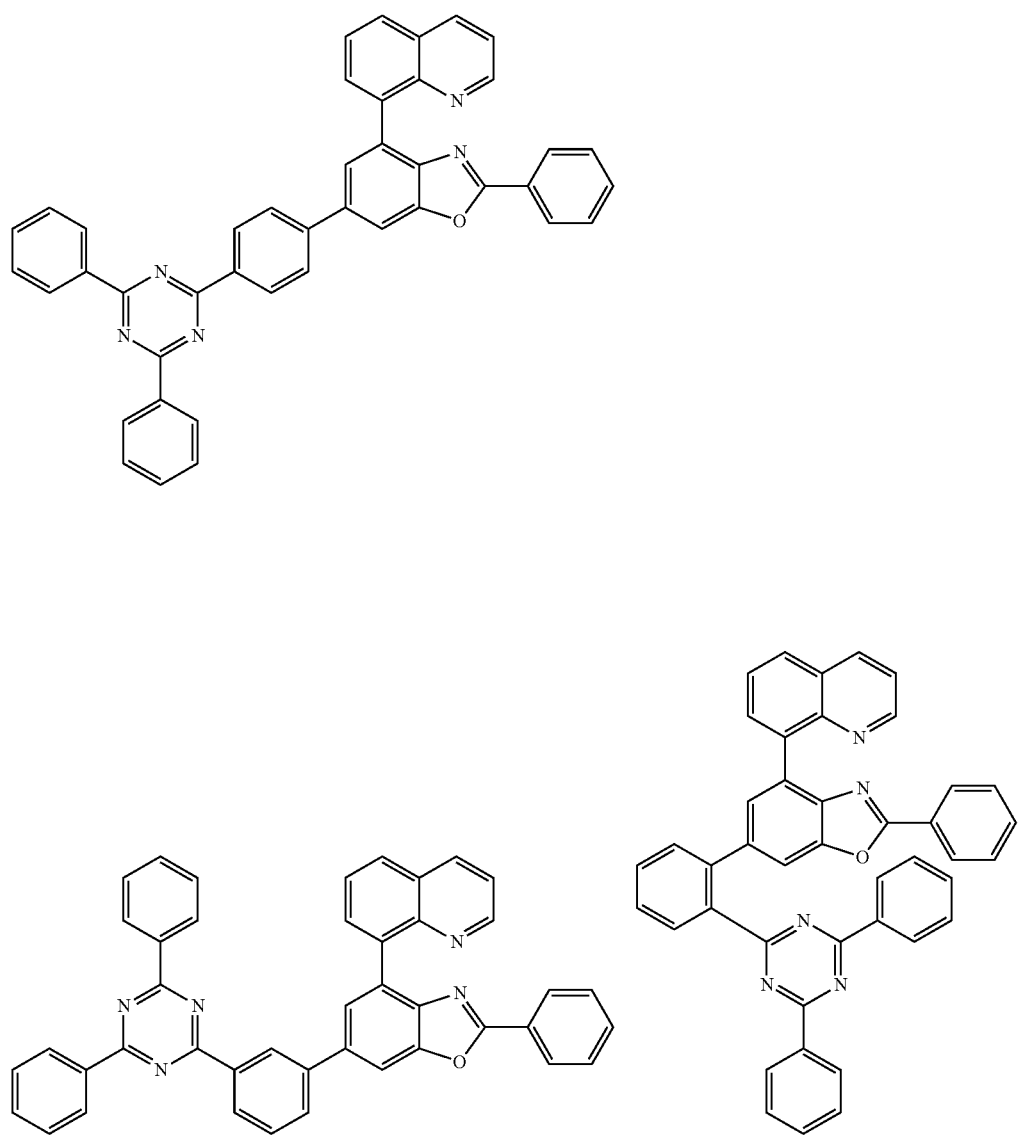

-continued
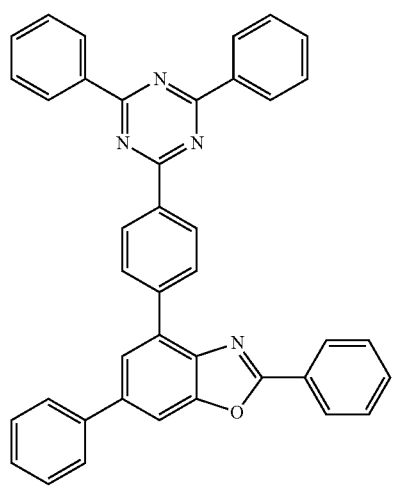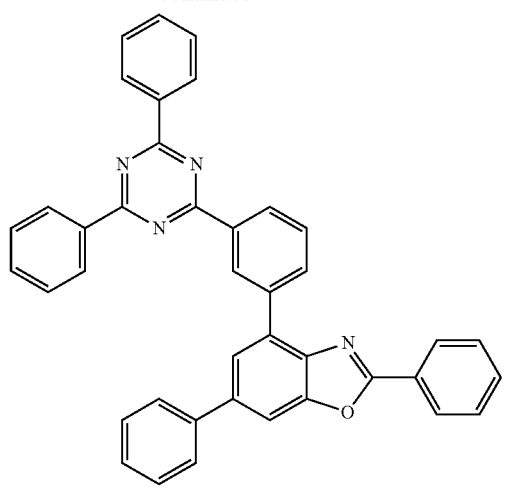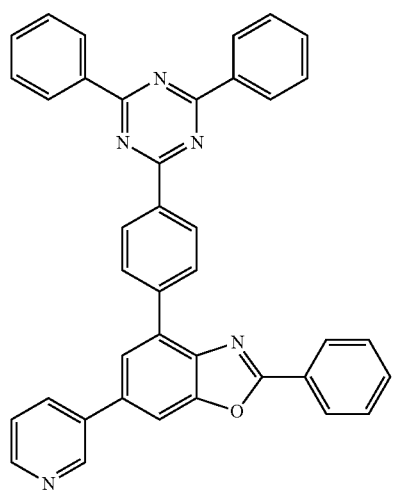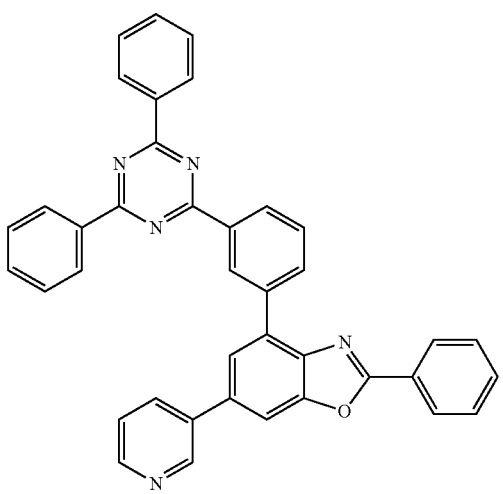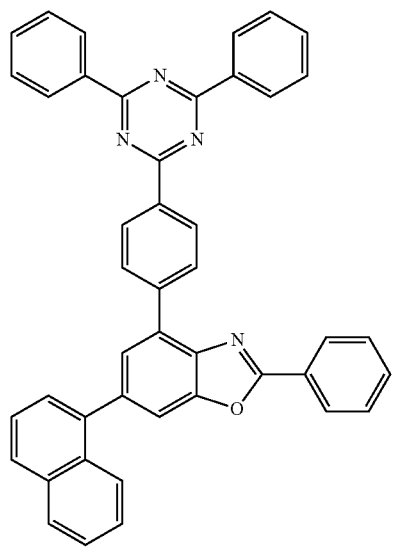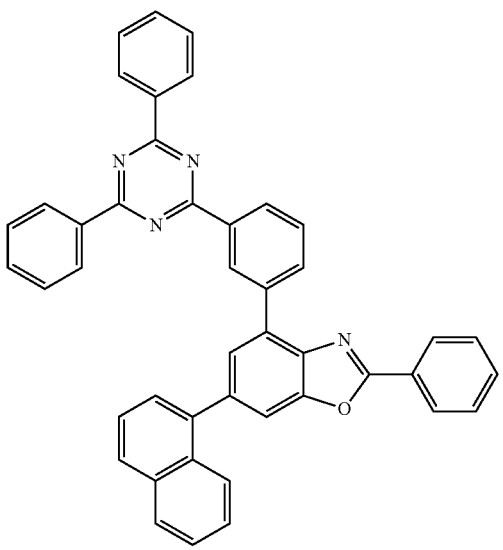

261
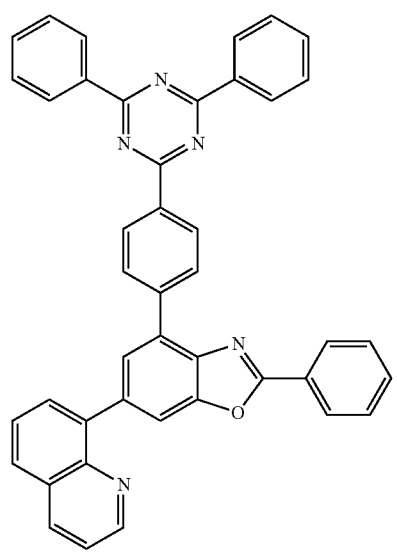
262
-continued
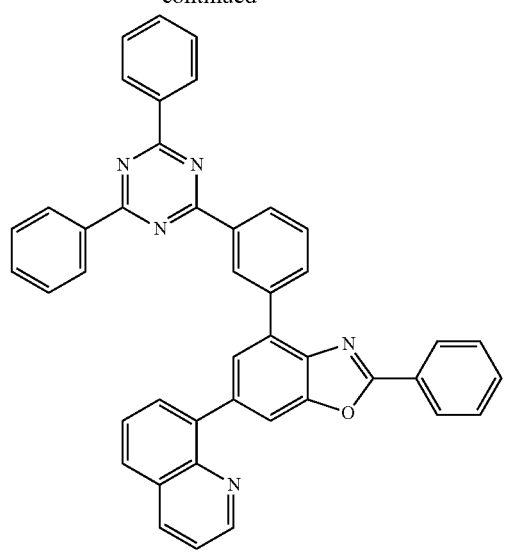
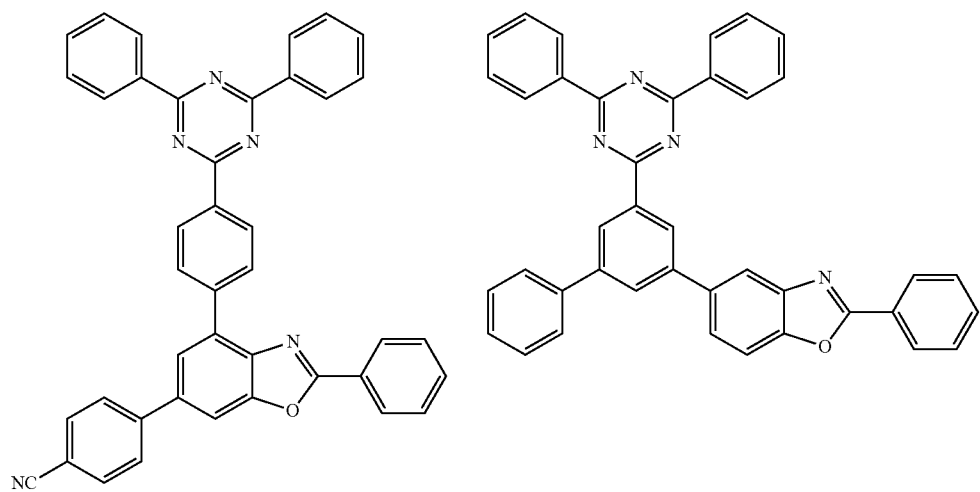
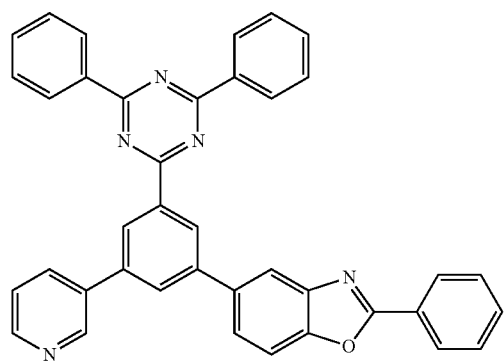
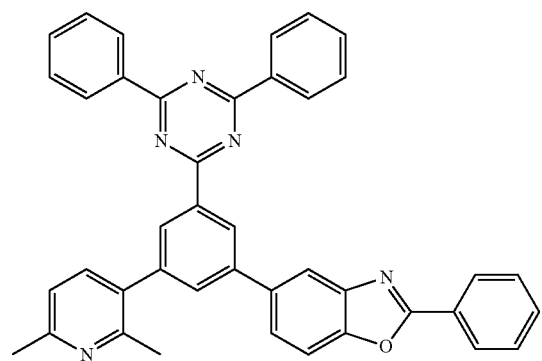

263
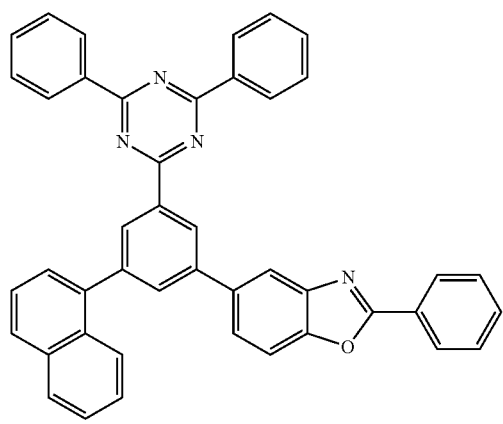
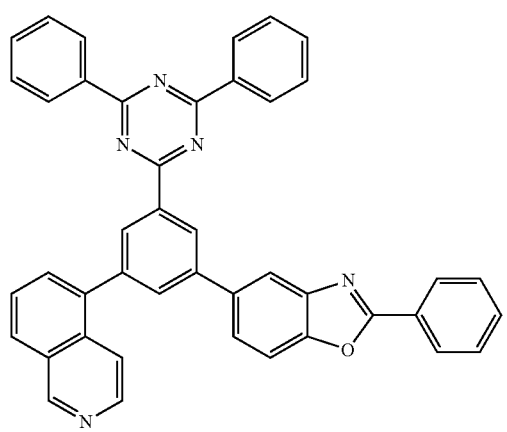
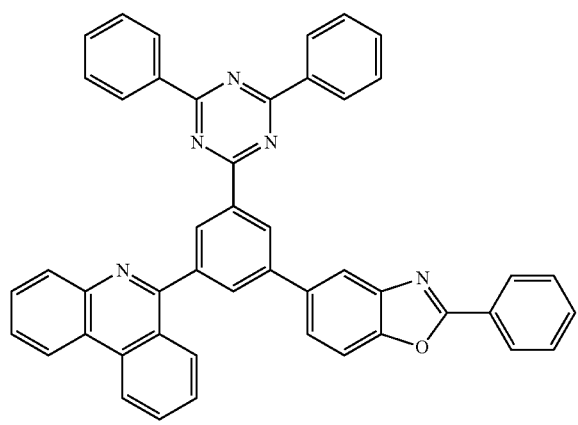
264
-continued
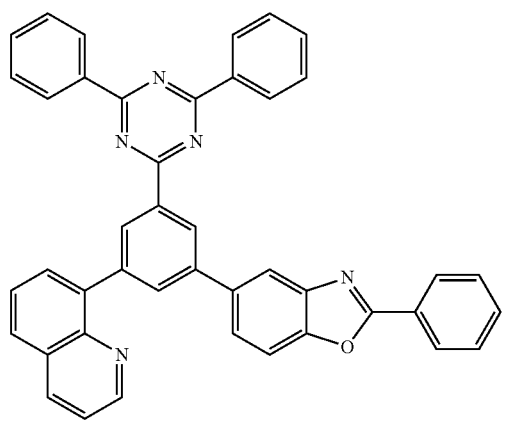
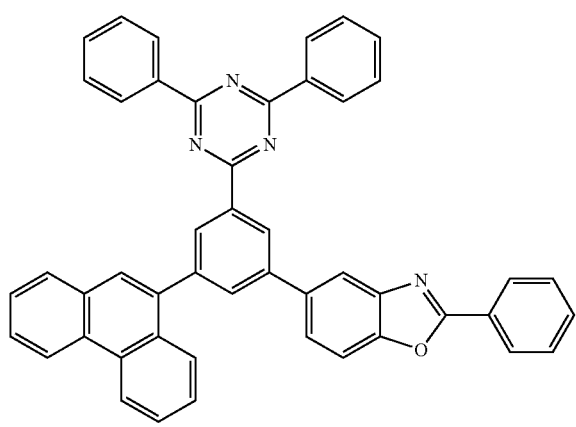
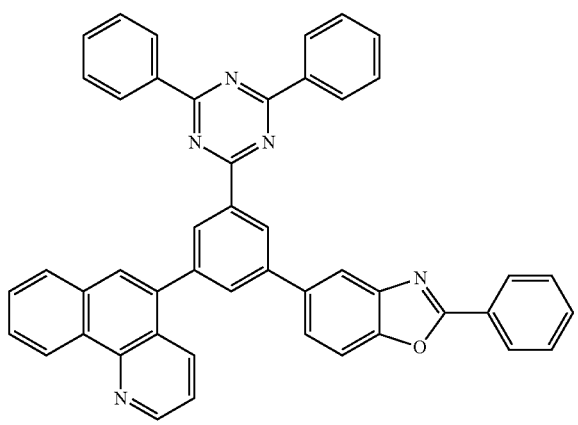

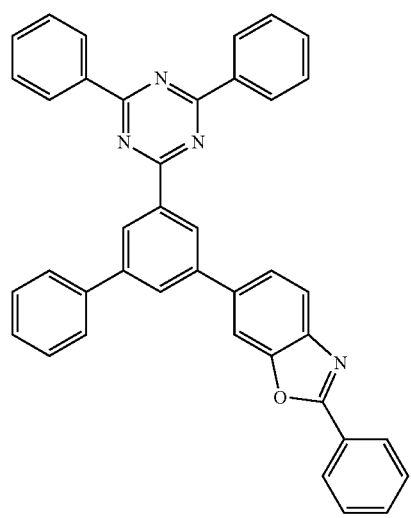
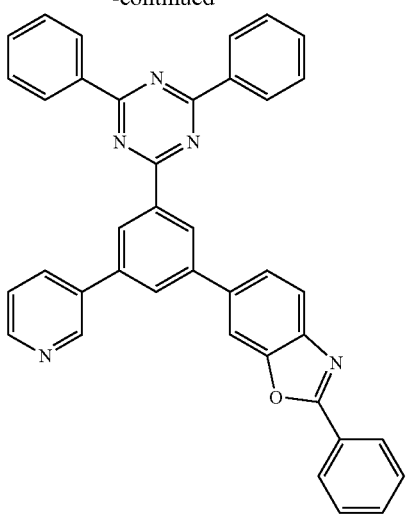
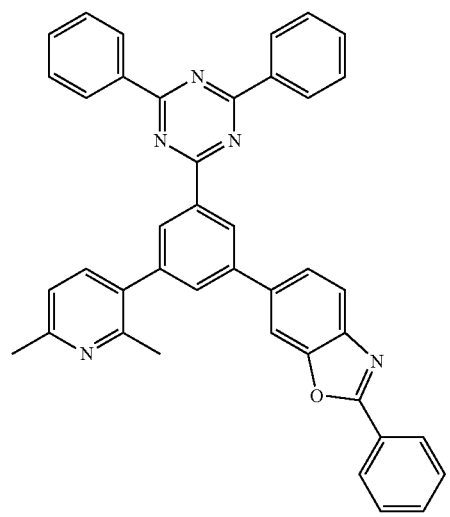
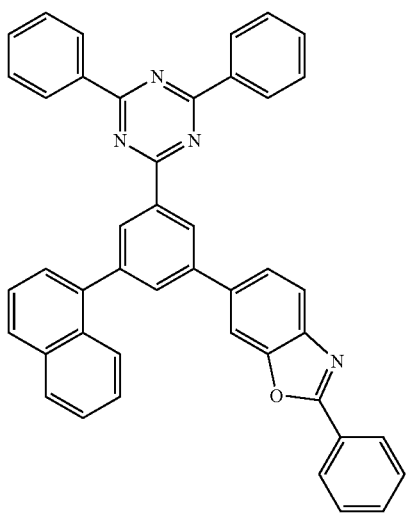
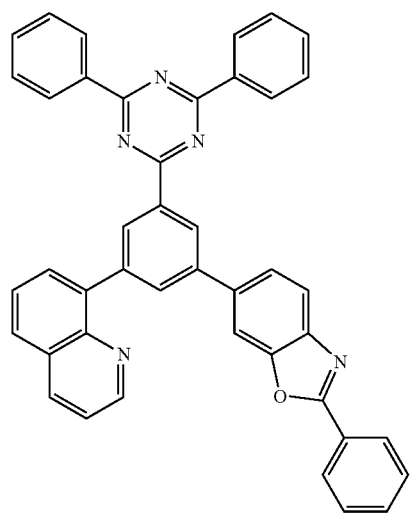
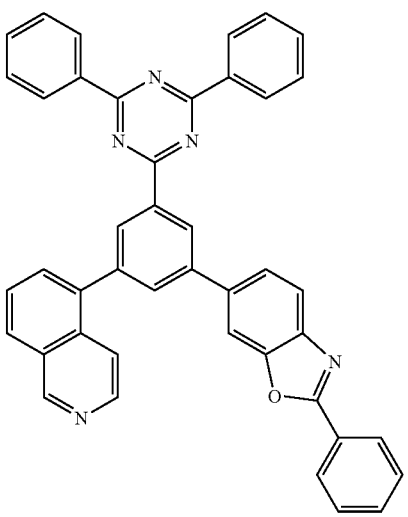

267
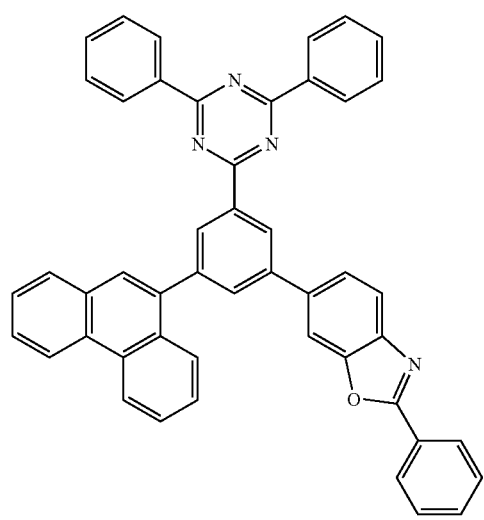
268
-continued
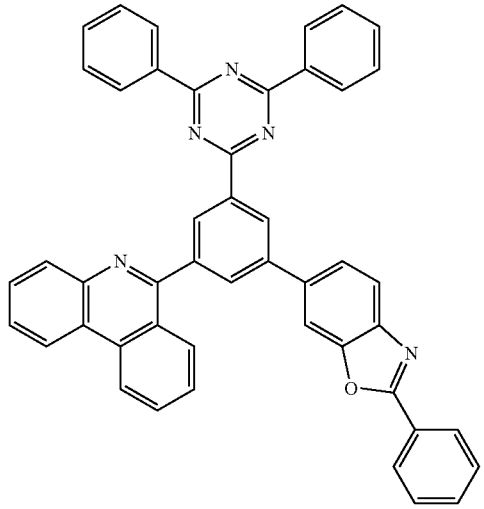
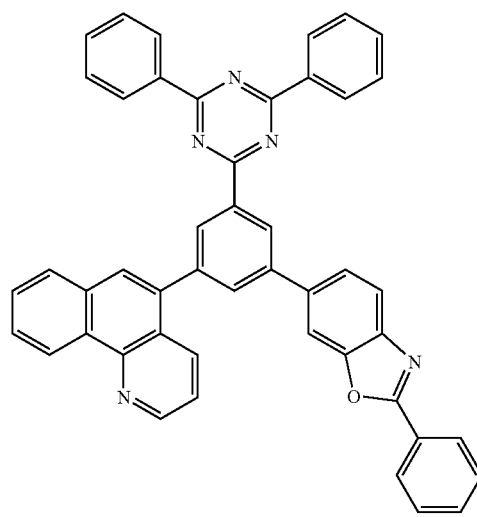
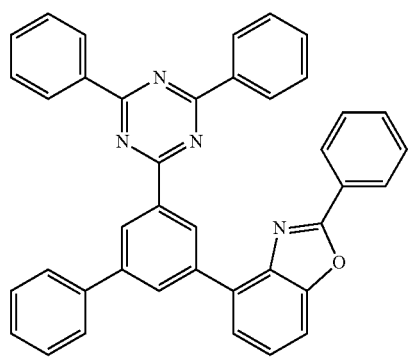
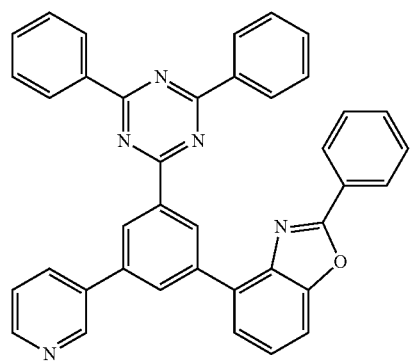
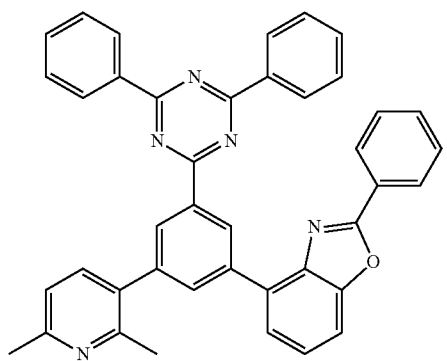

-continued
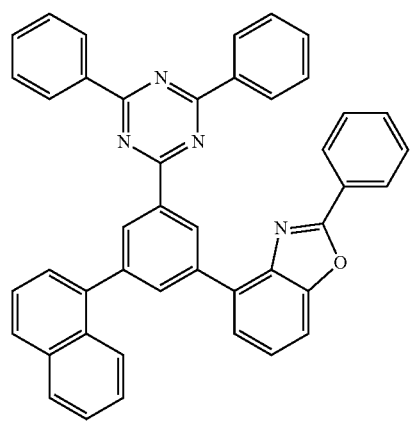
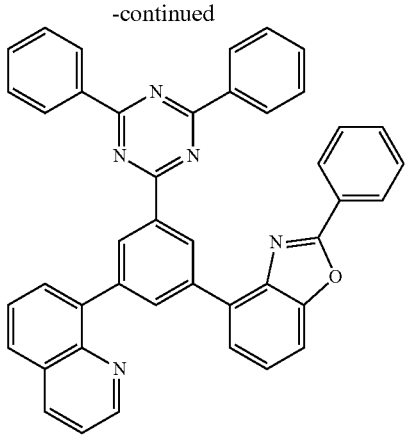
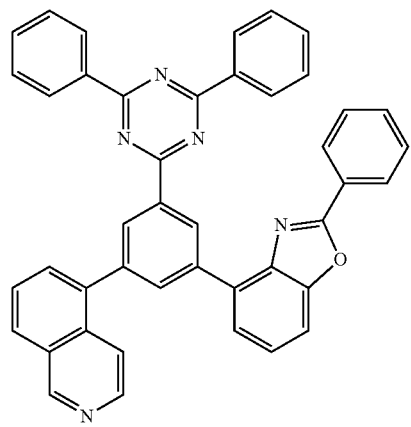
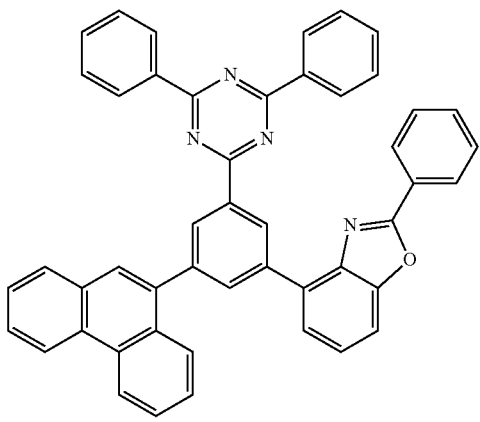
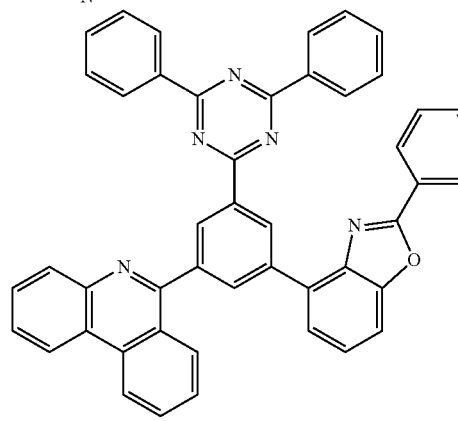
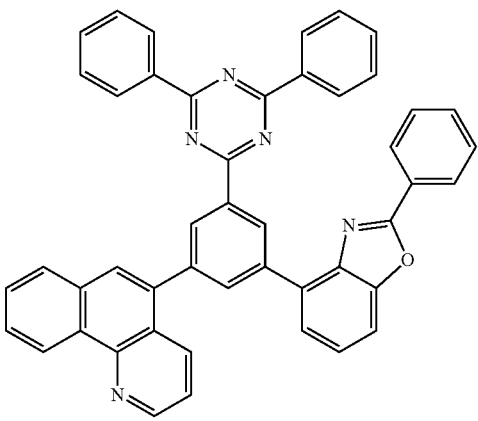
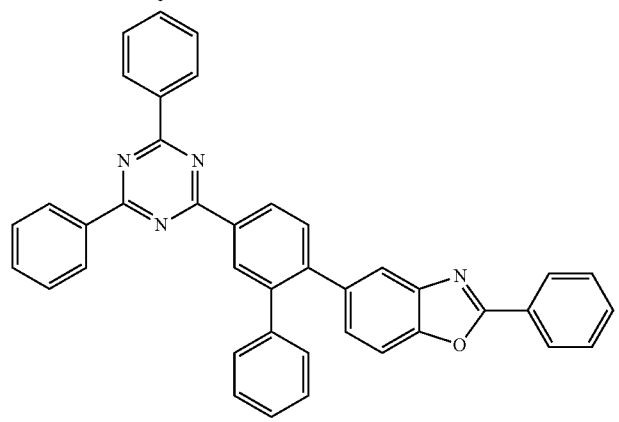

271
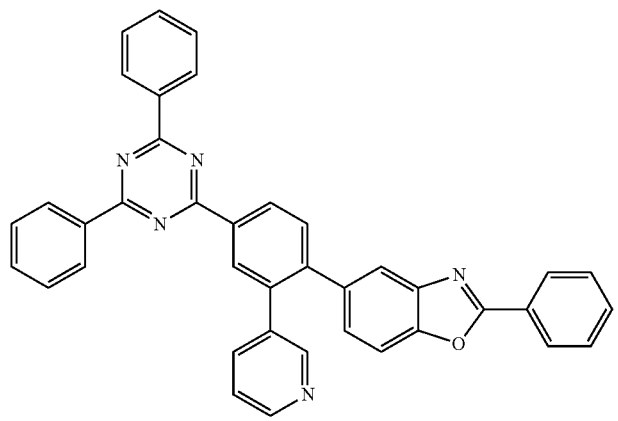
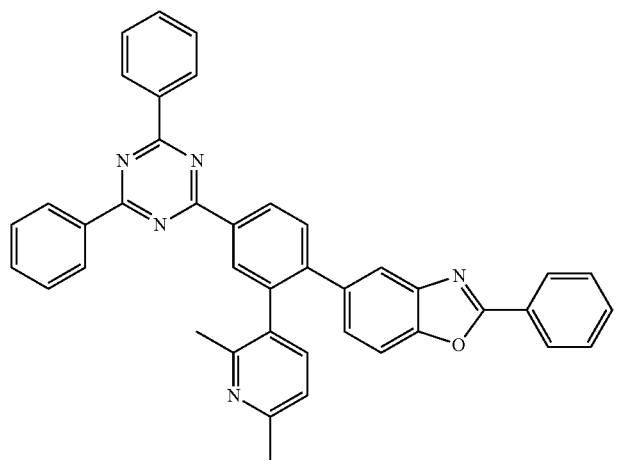
272
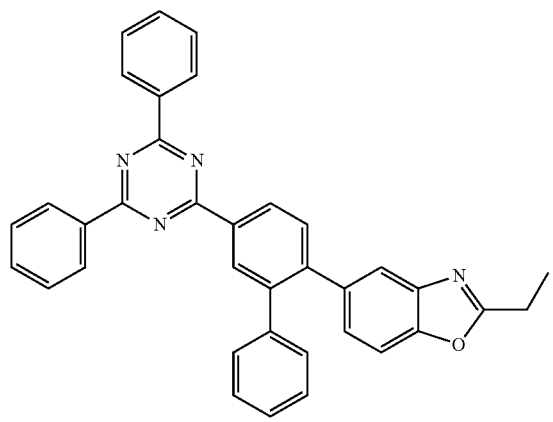
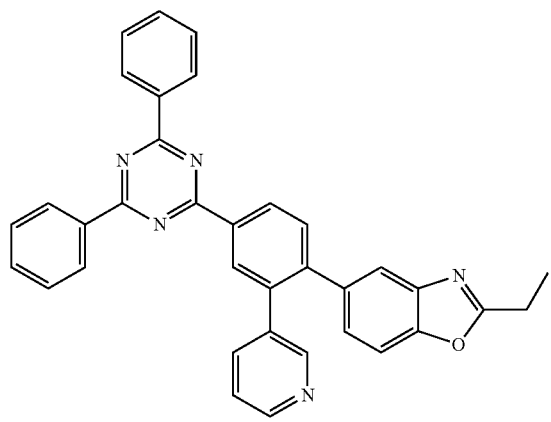

-continued
273
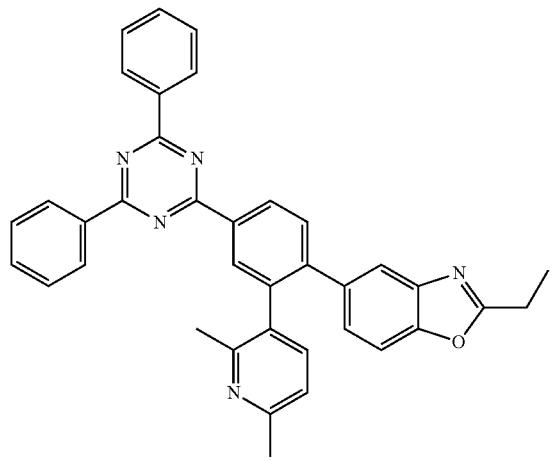
274
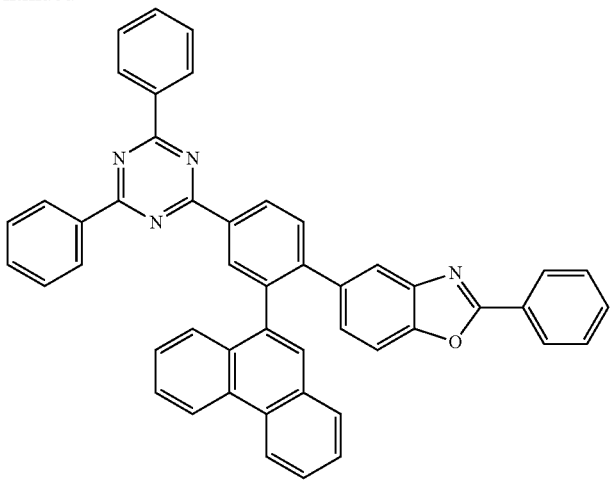
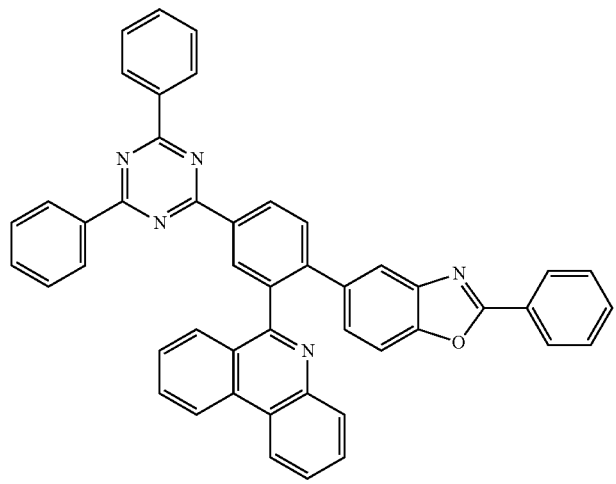
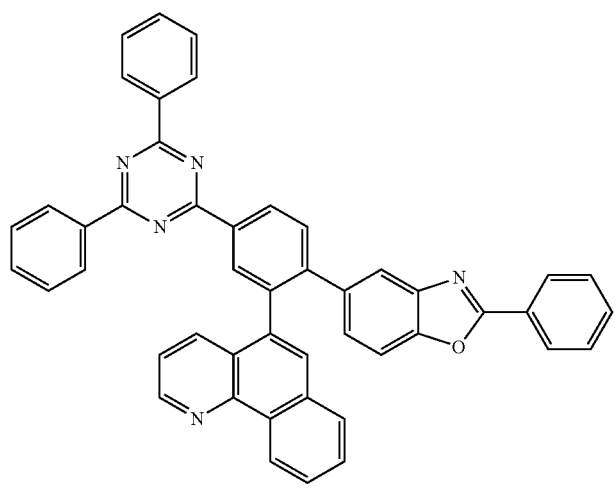

-continued
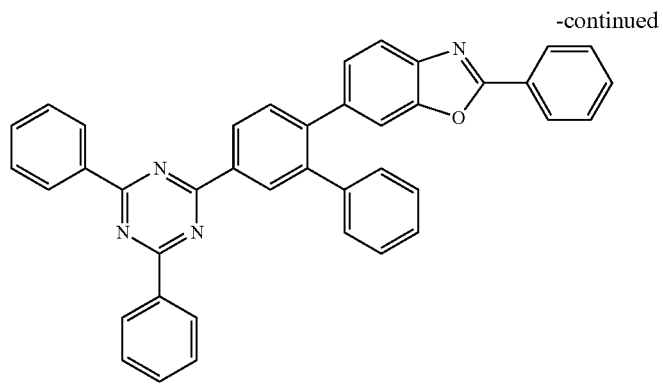
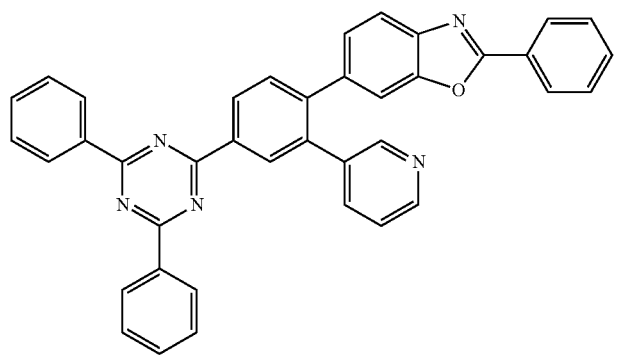
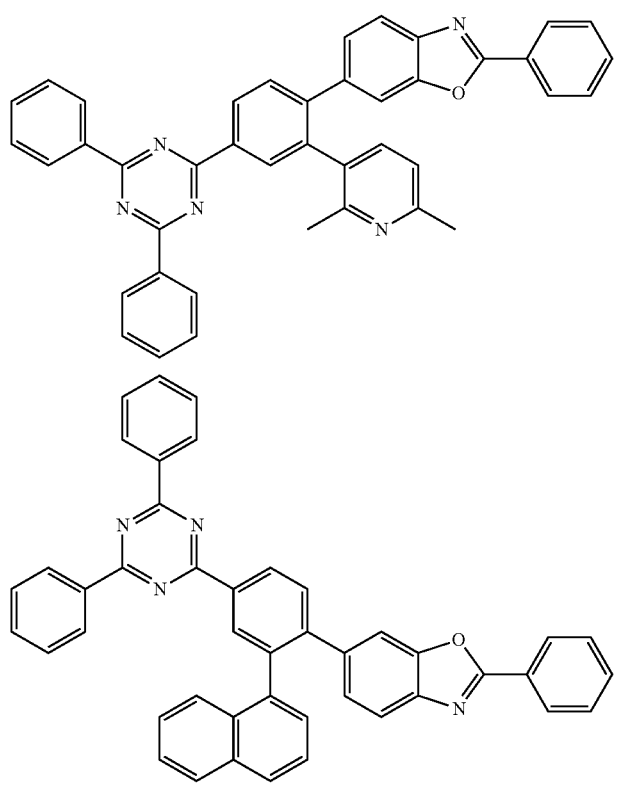

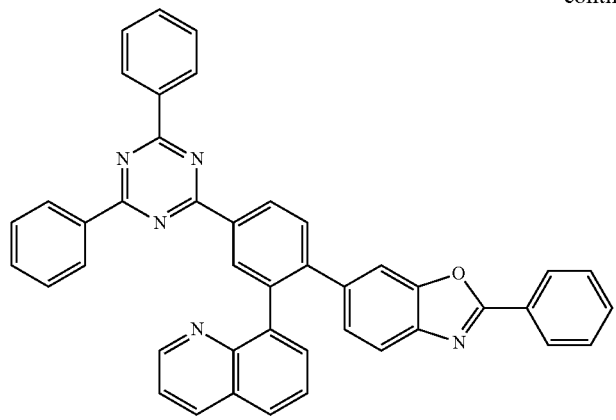
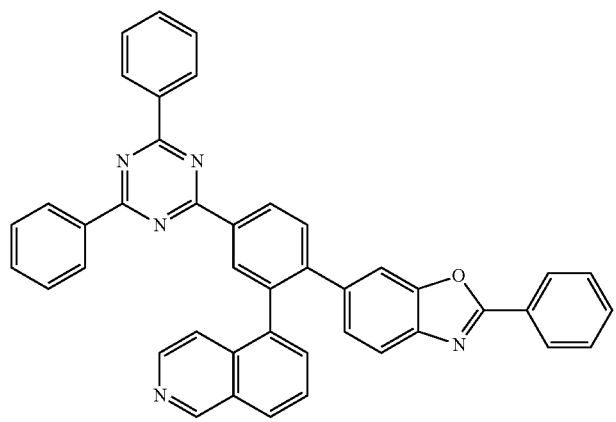
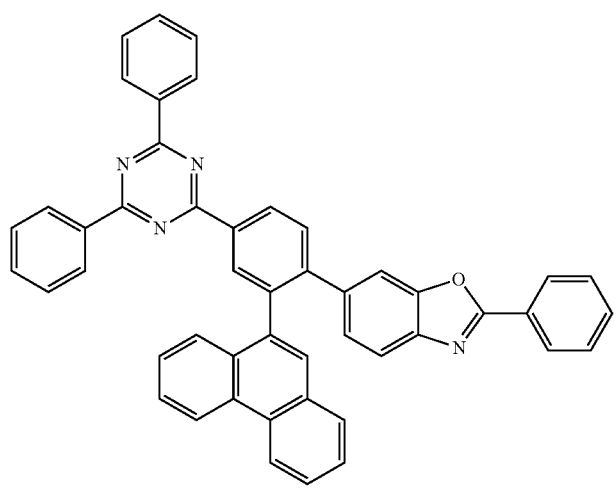

-continued
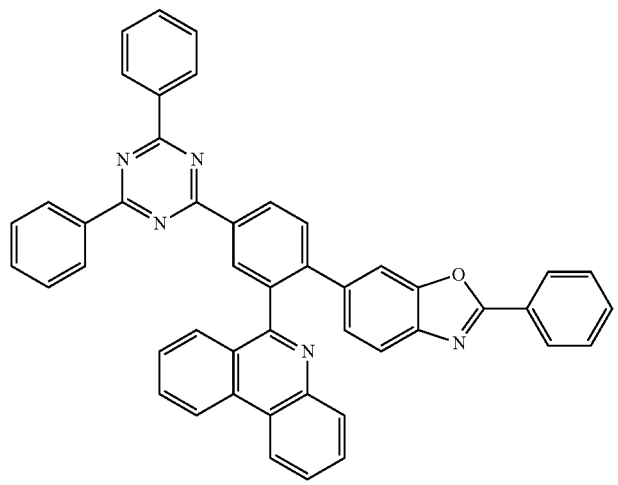
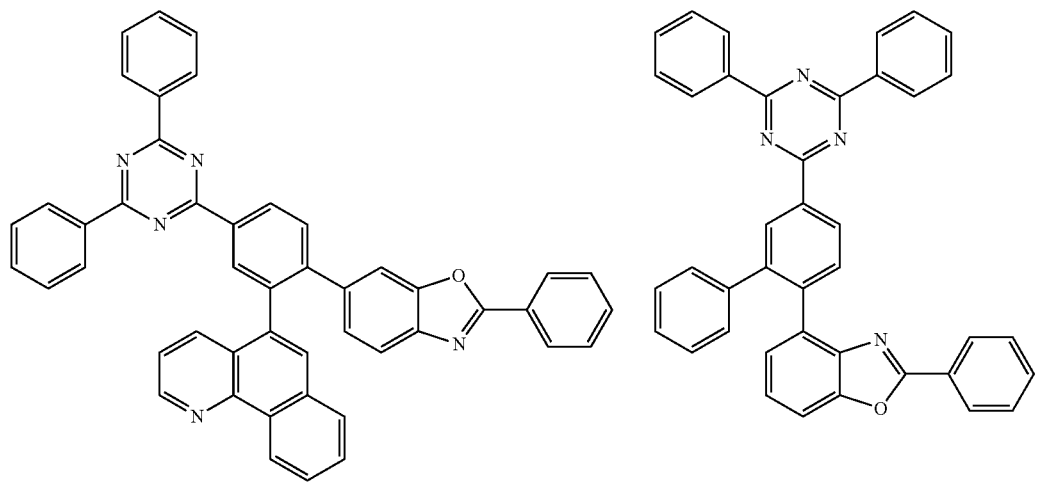
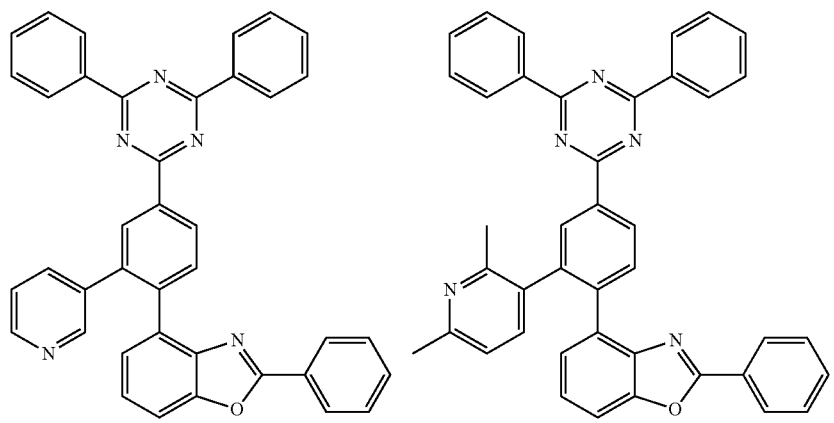

-continued
281
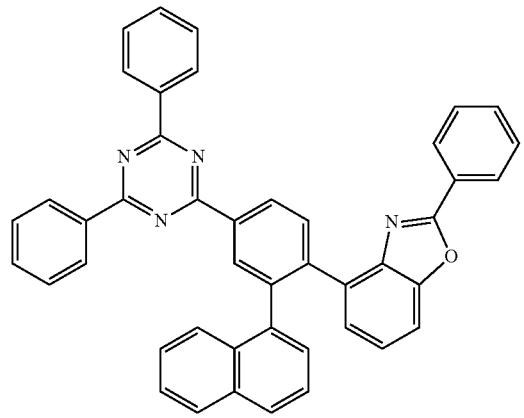
282
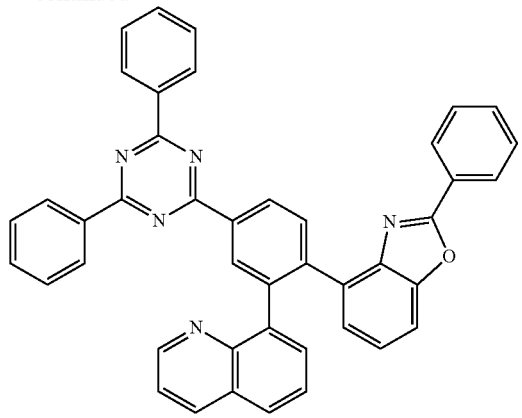
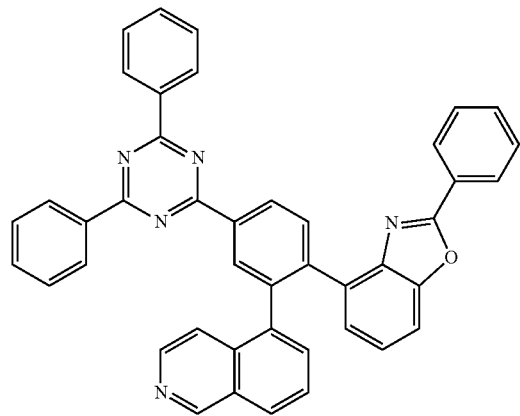
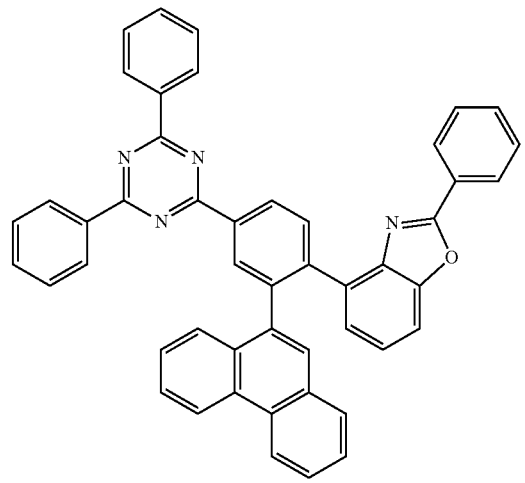
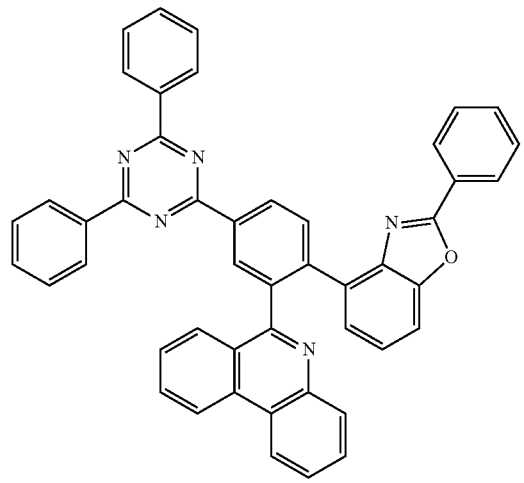
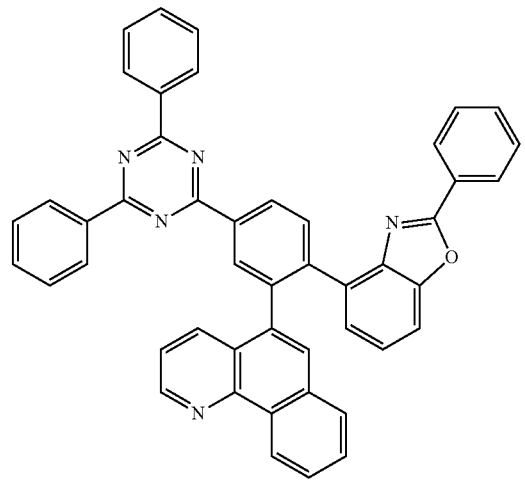
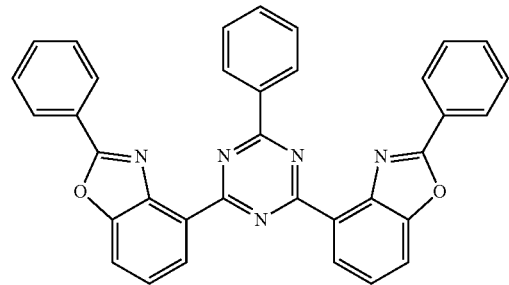

-continued
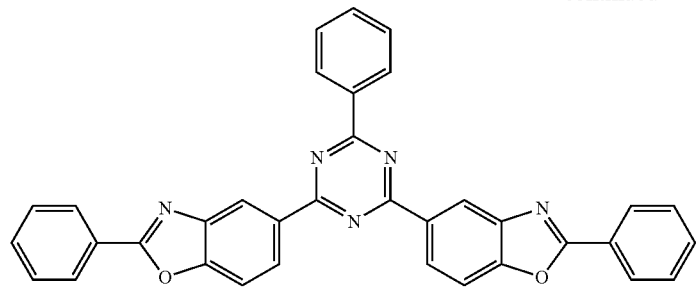
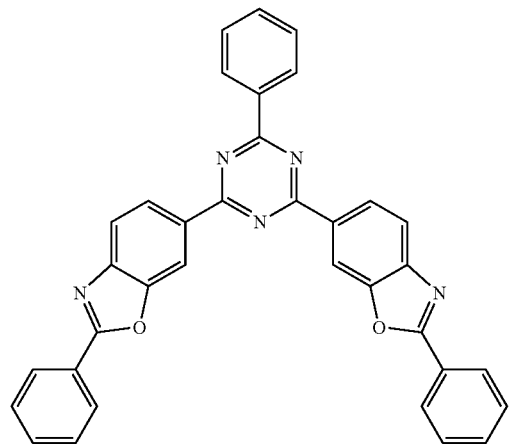
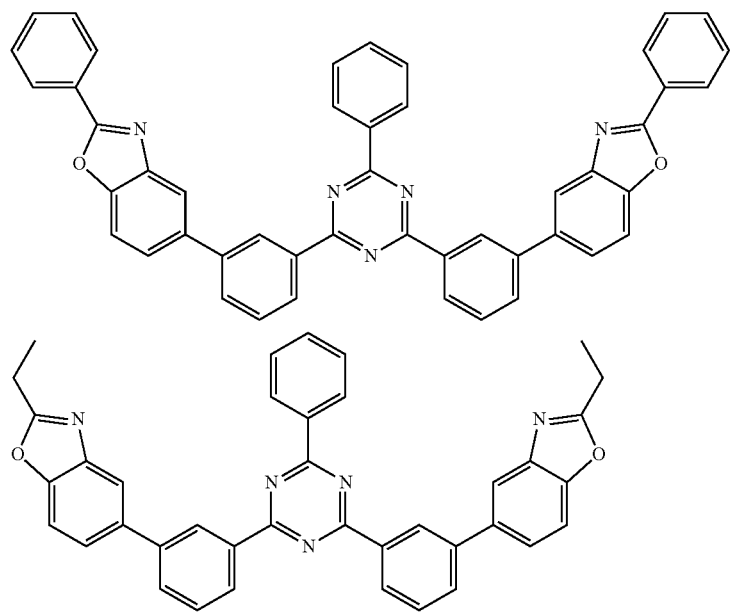

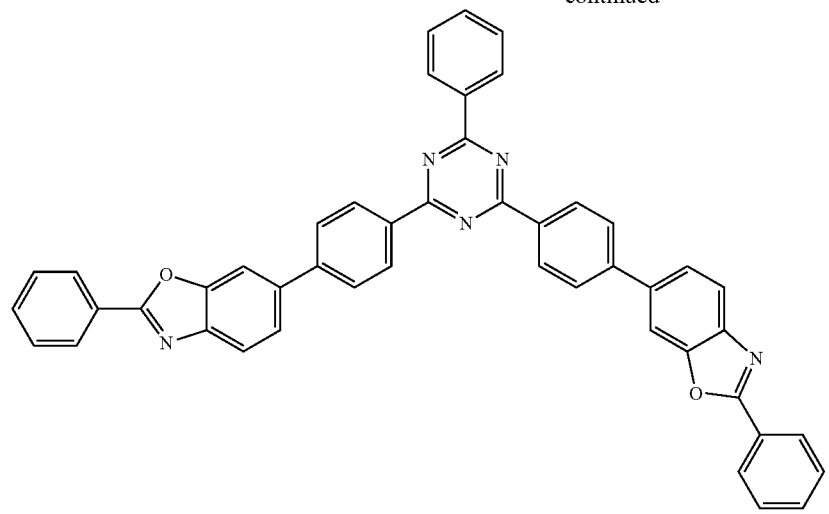
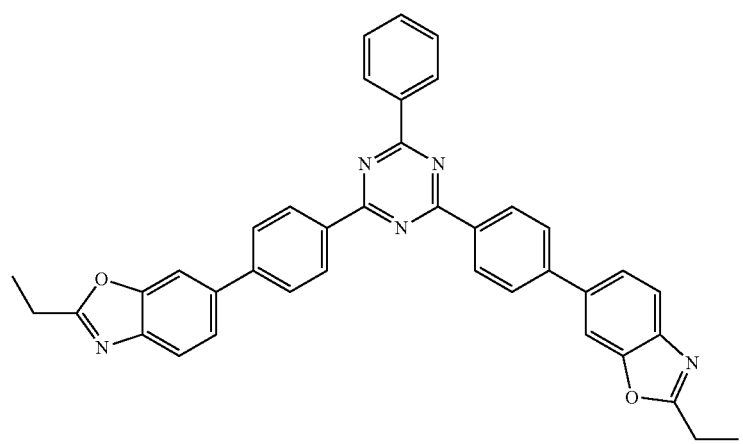
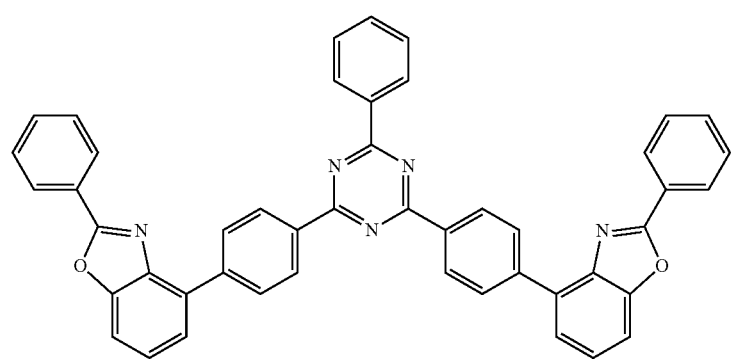
LT18-30-023
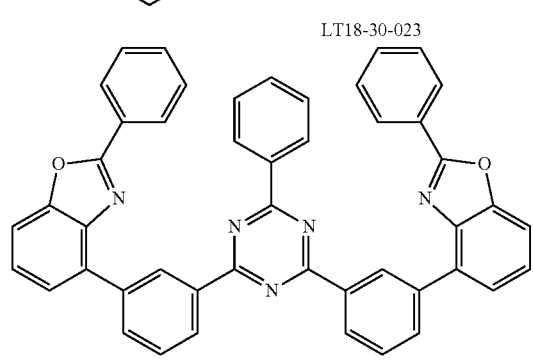

287
288
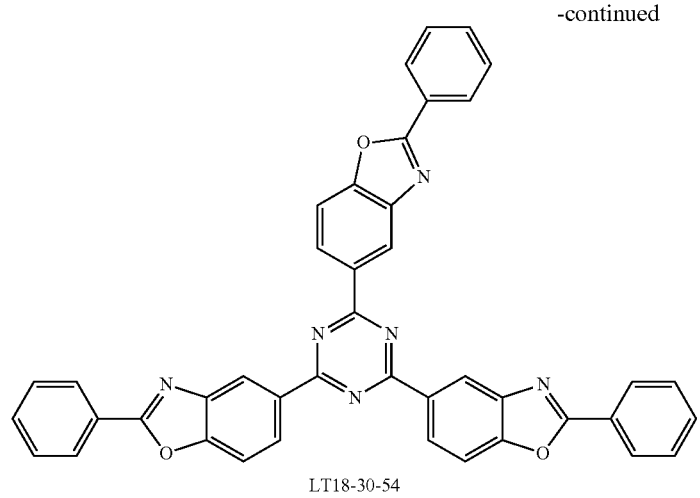
LT18-30-54
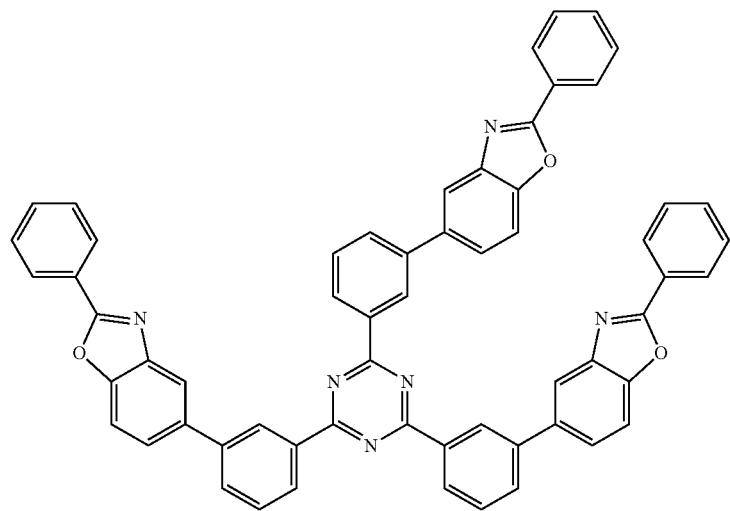
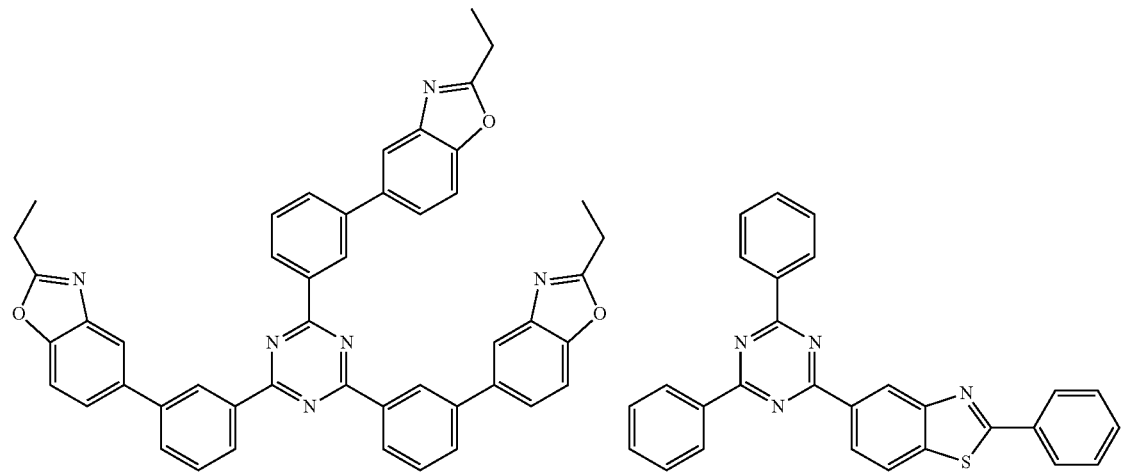

-continued
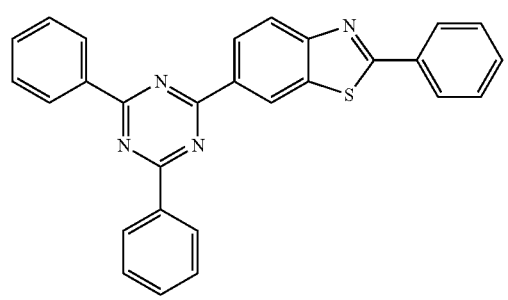
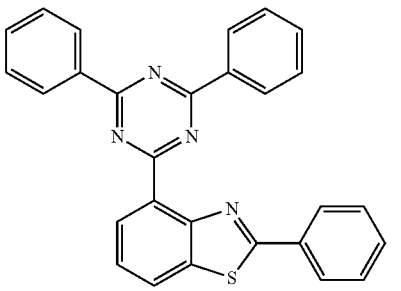
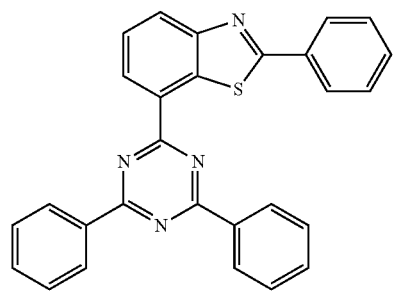
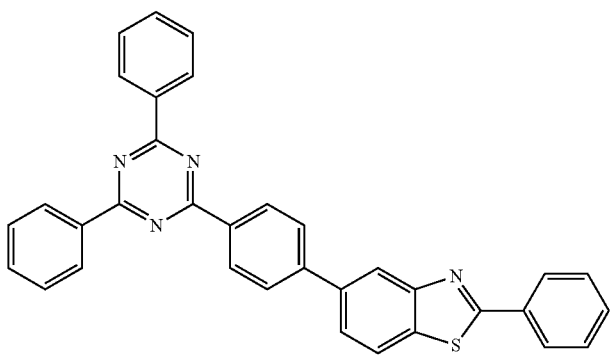
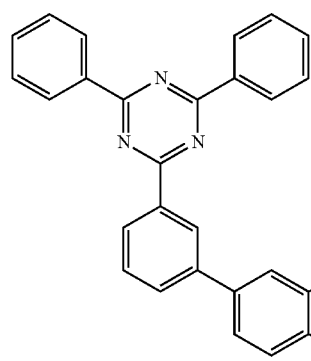
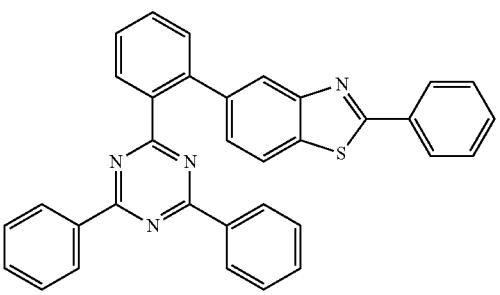
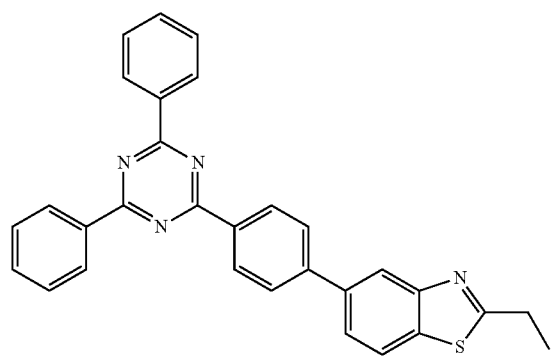
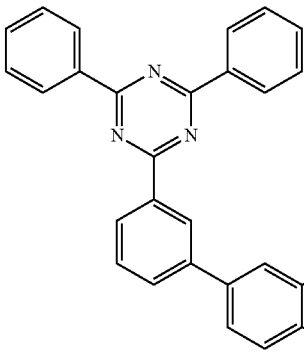
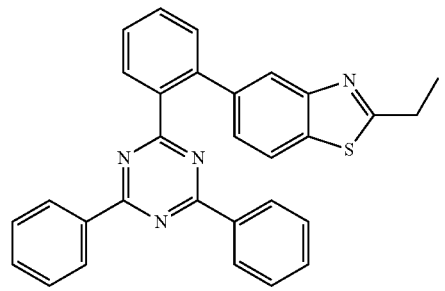
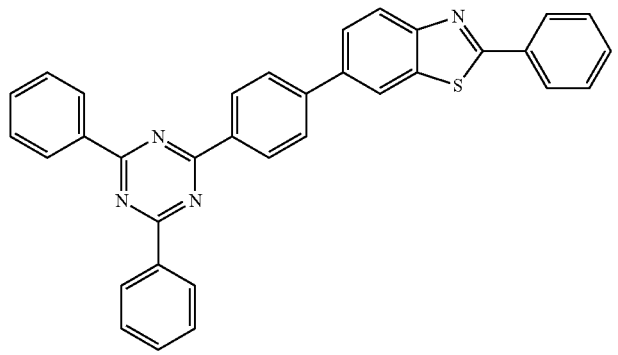

291 292
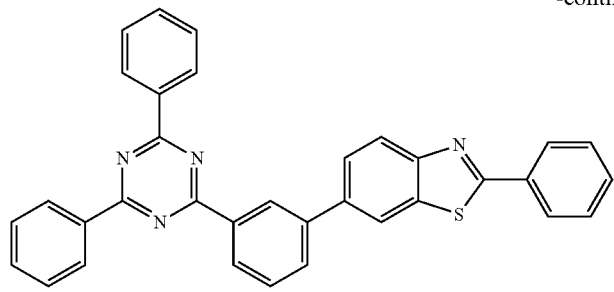
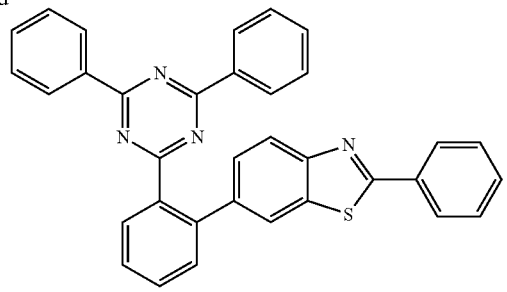
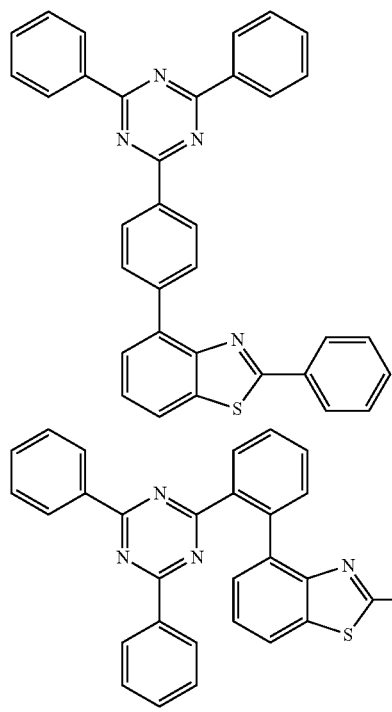
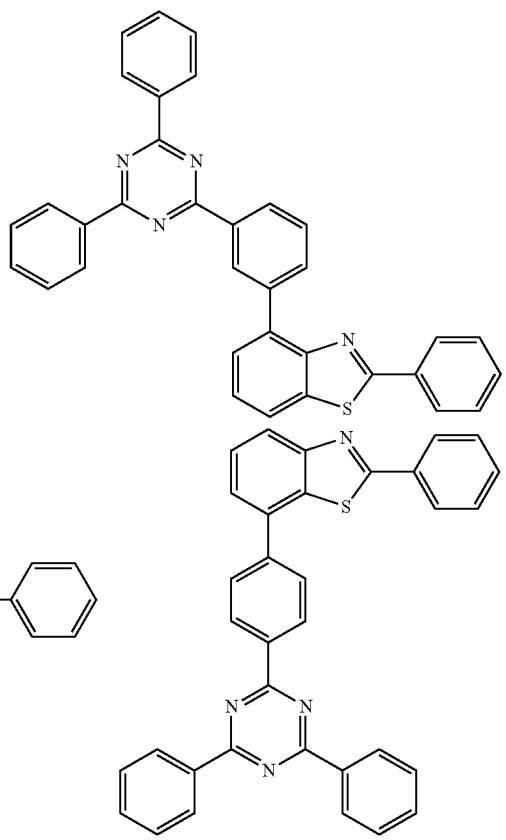
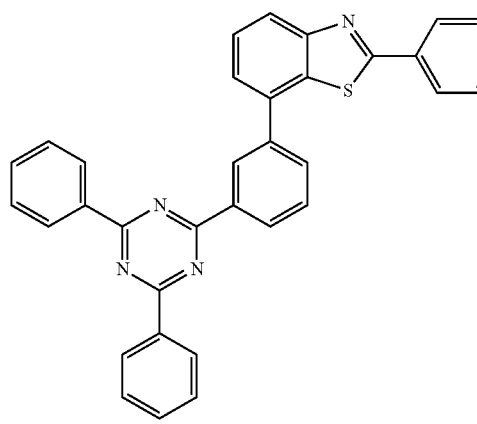
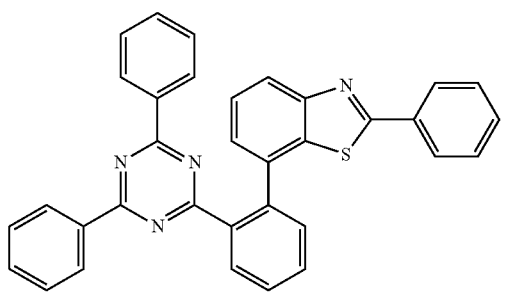

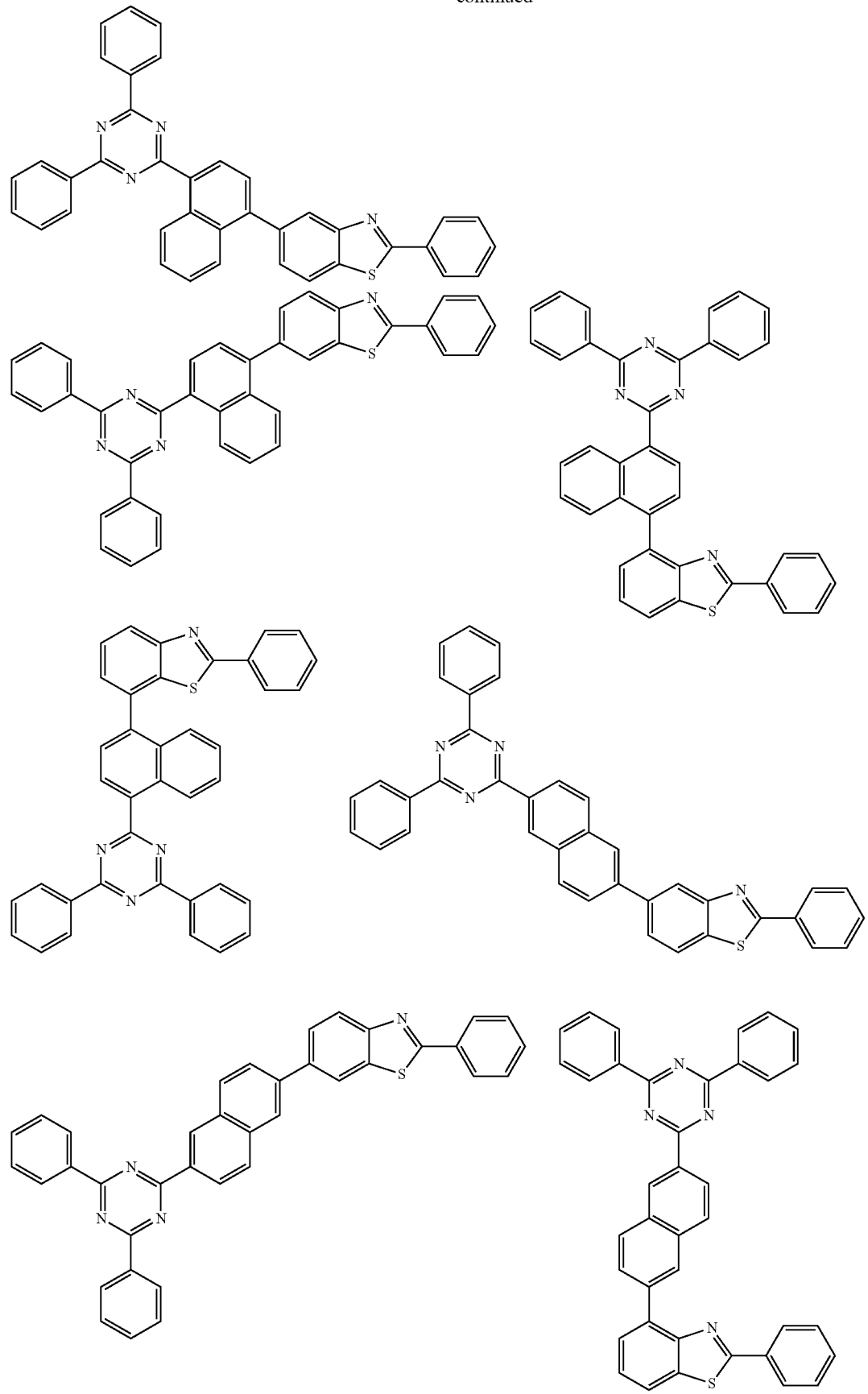

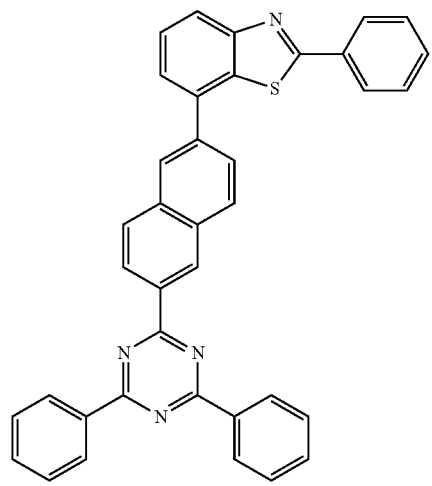
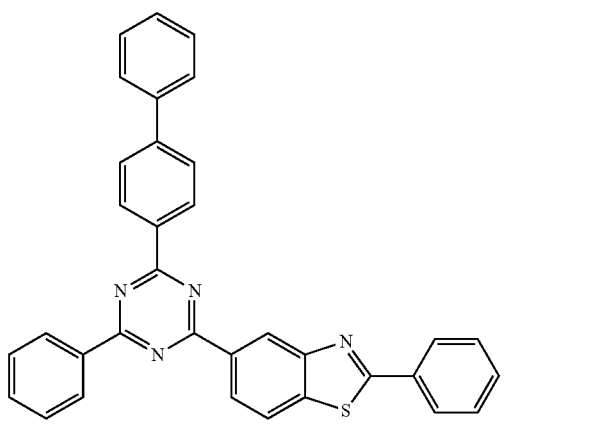
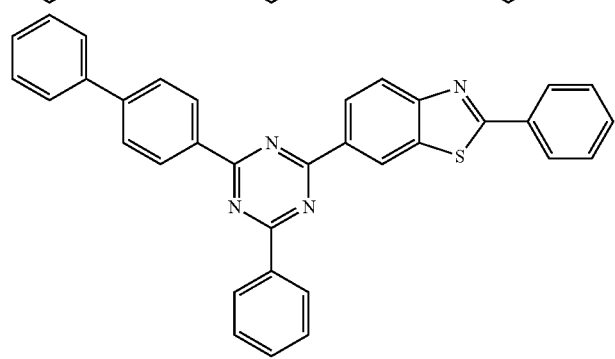
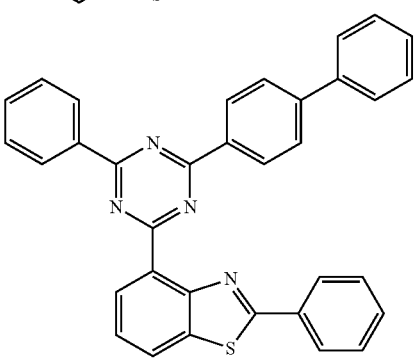
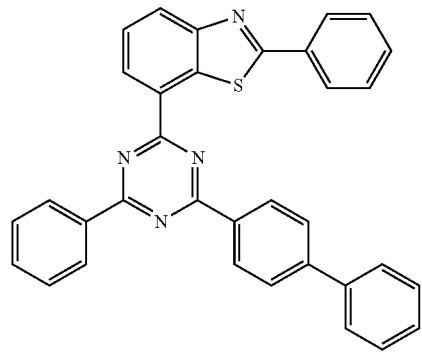
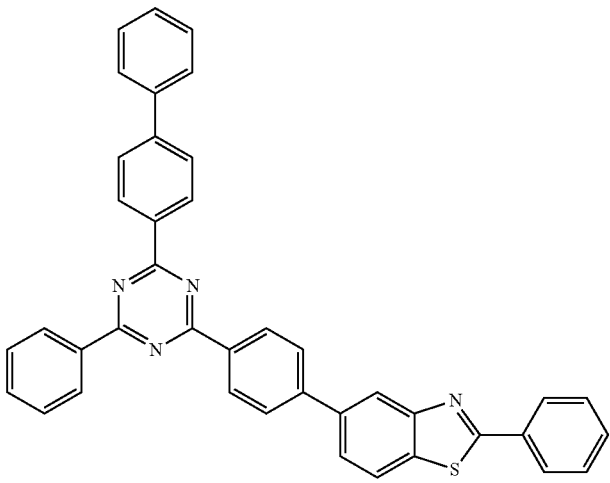
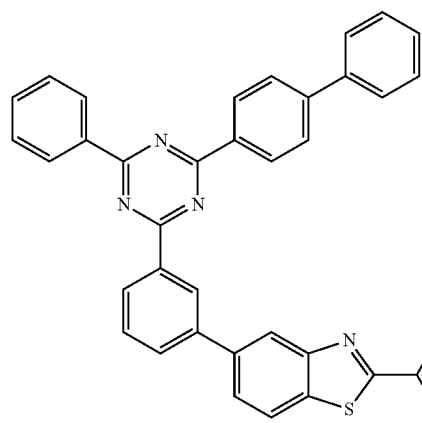
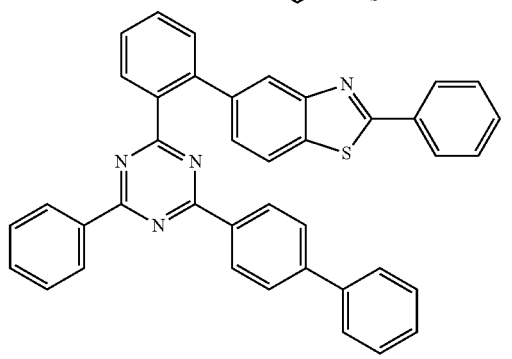

297
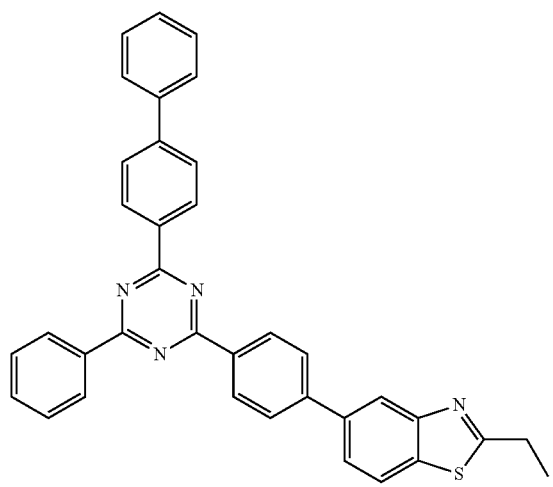
298
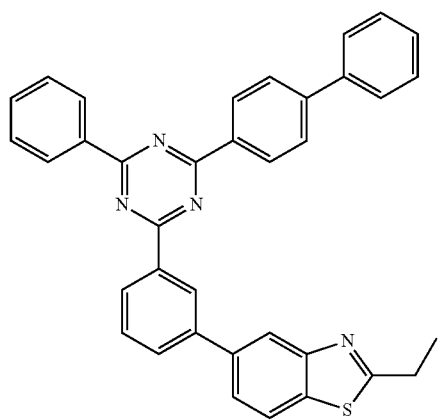
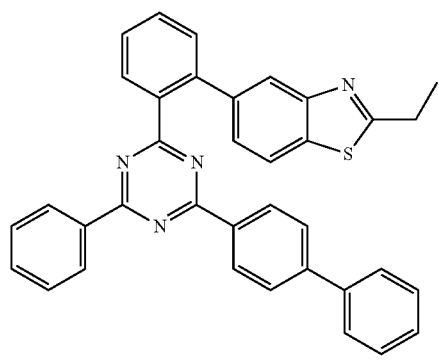
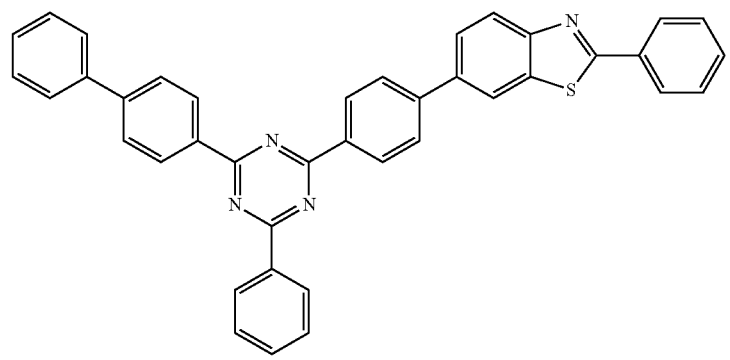
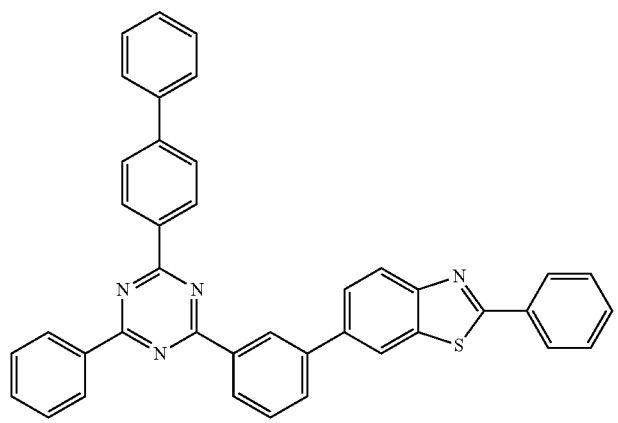
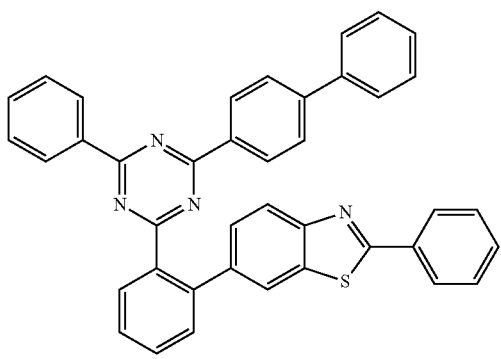

-continued
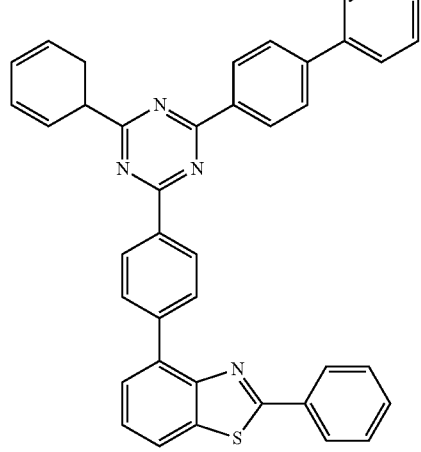
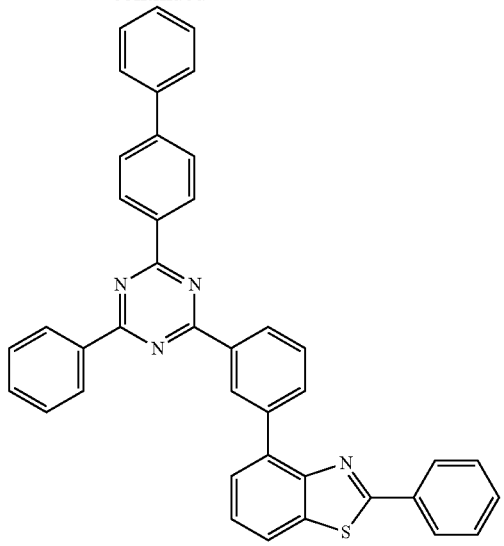
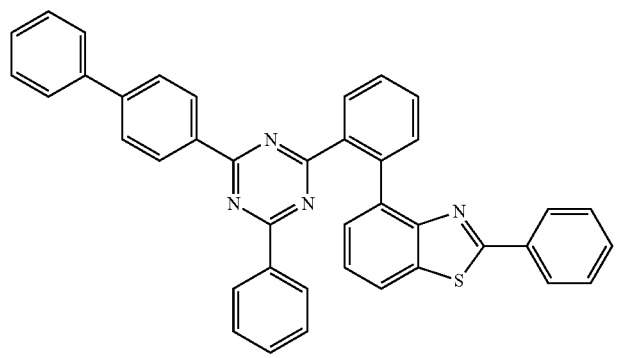
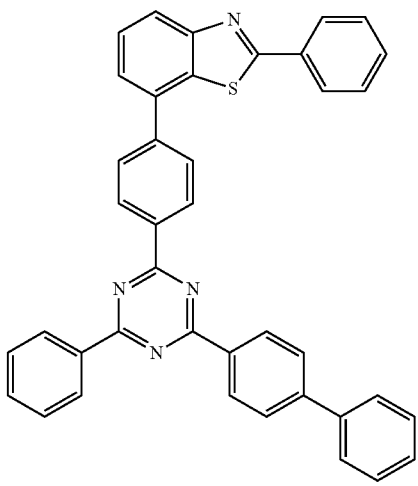
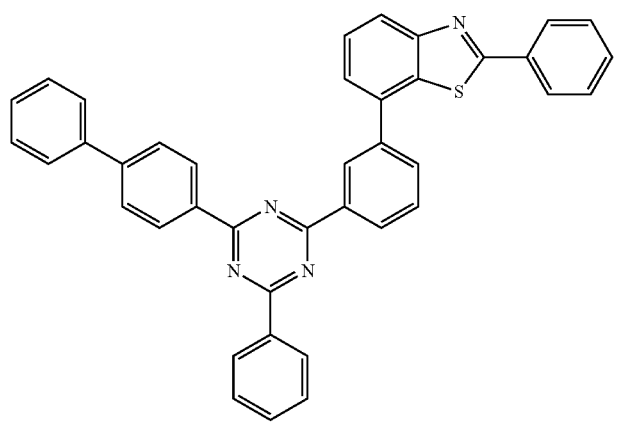
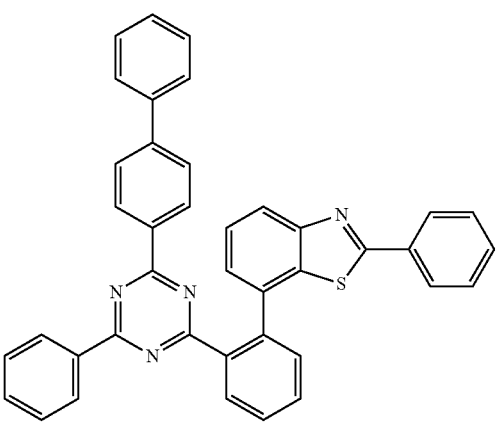

-continued
301
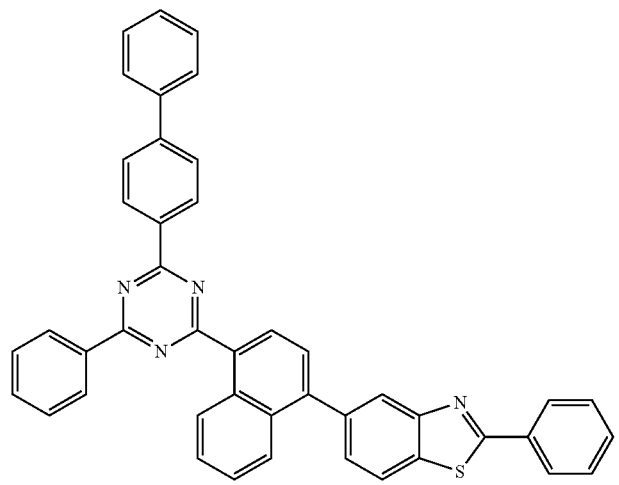
302
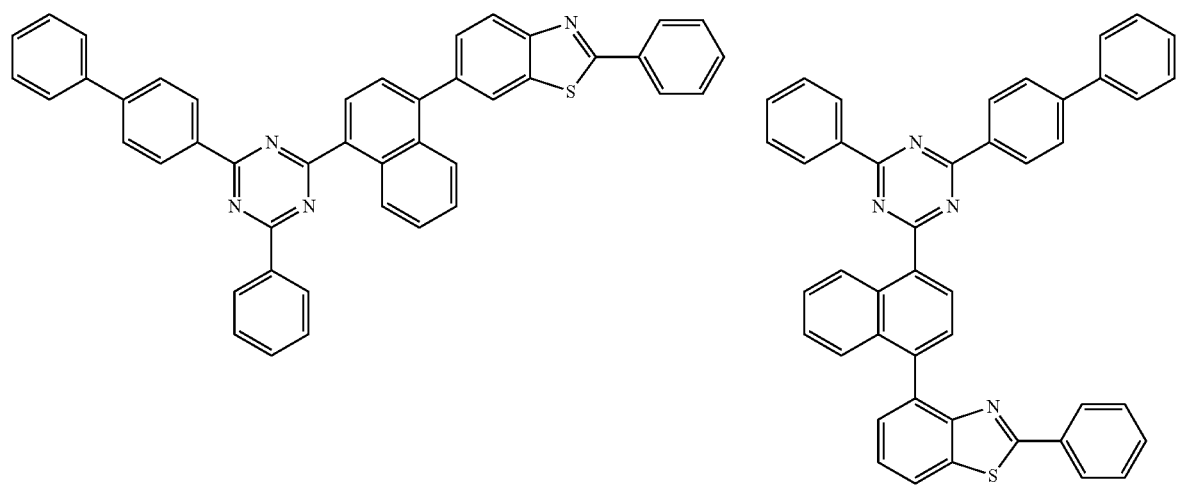
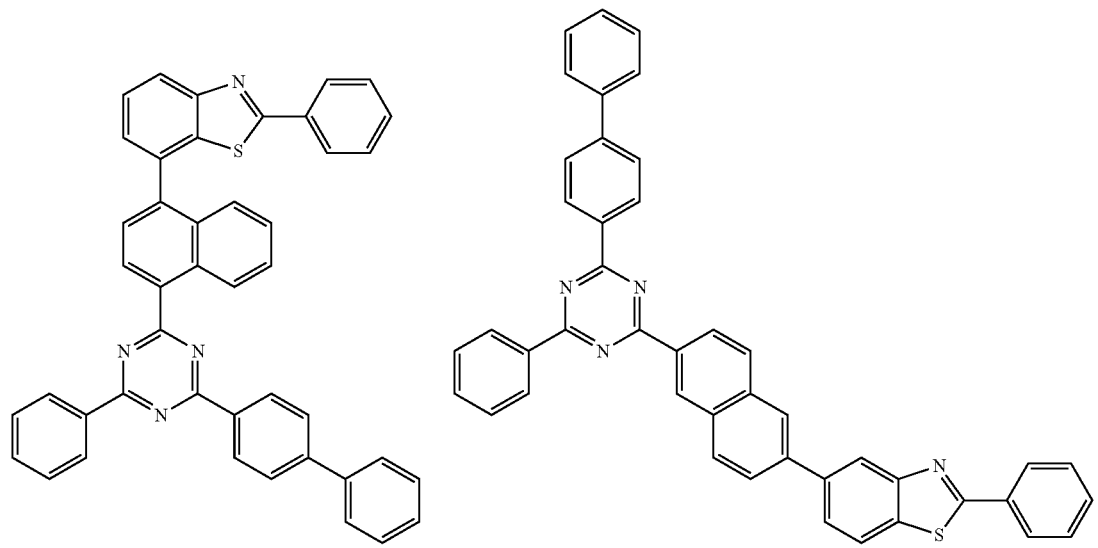

303 304
-continued
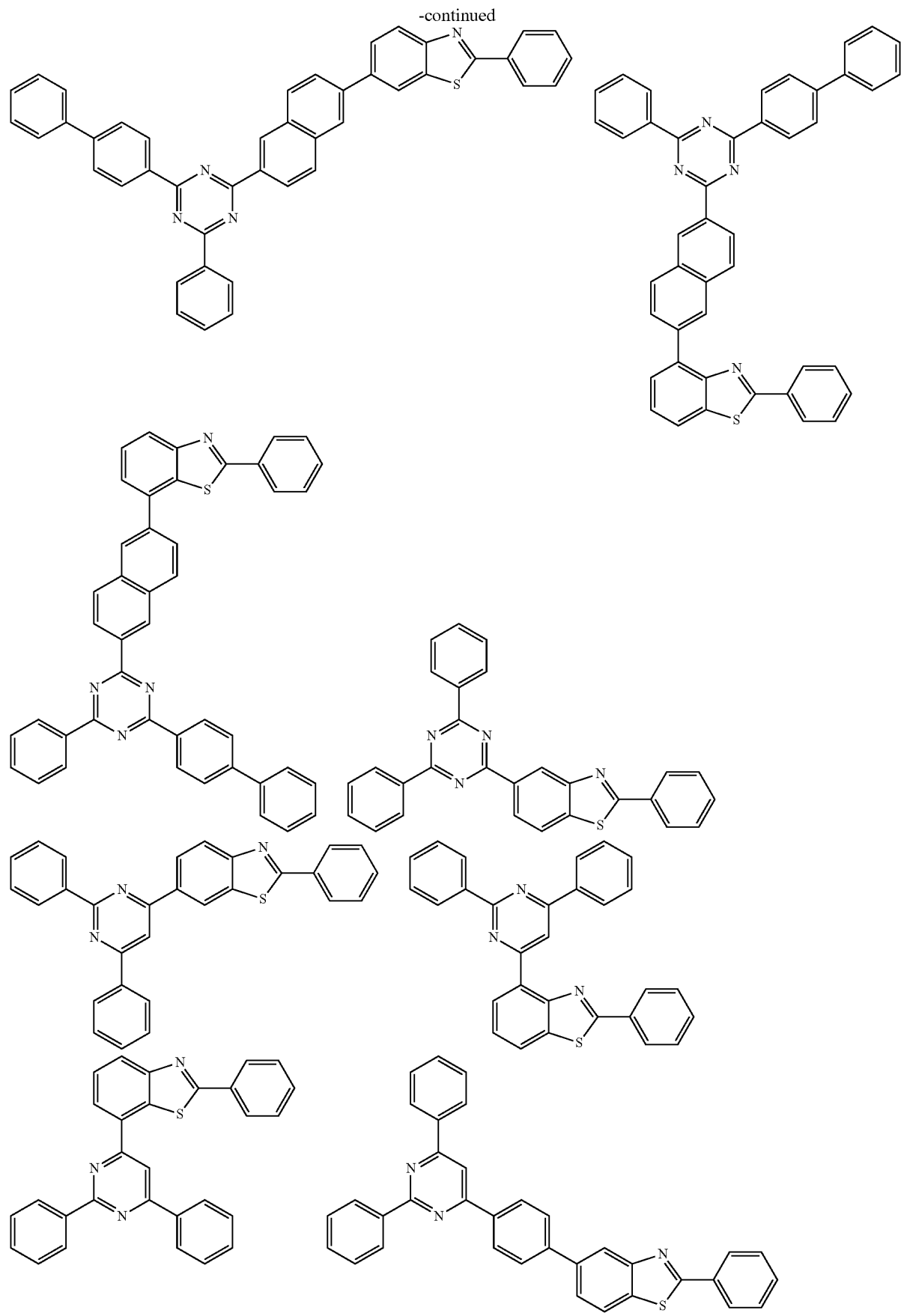

-continued
| 305 | 306 |
|---|---|
| 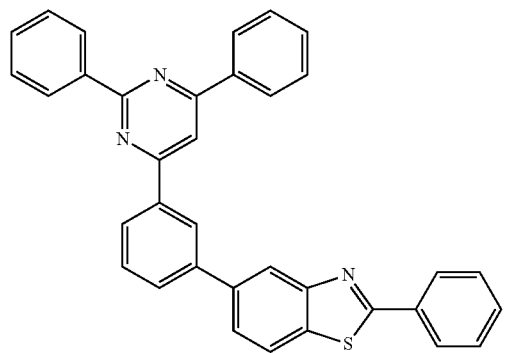 | 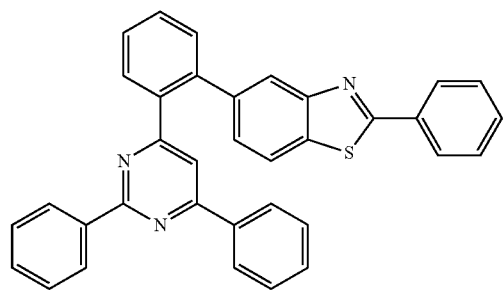 |
| 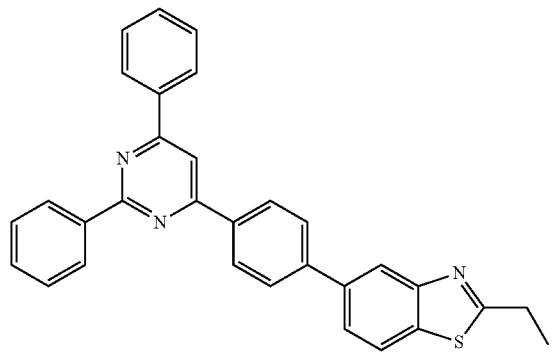 | 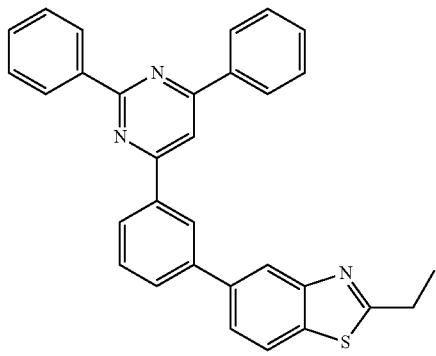 |
| 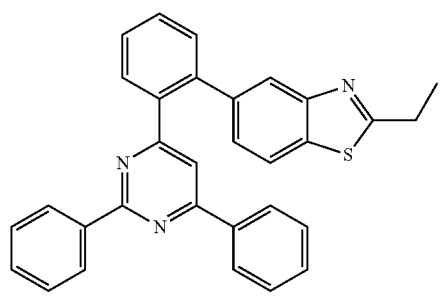 | 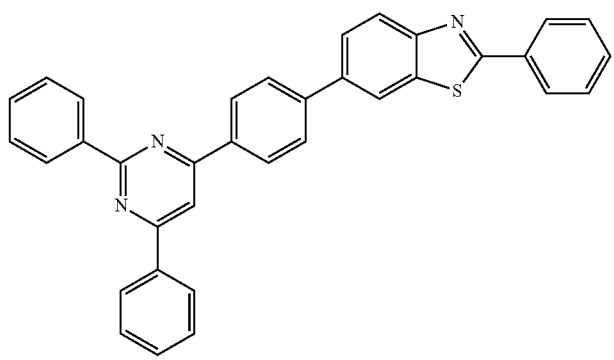 |
| 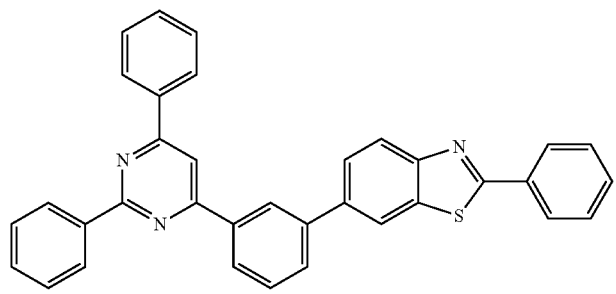 | 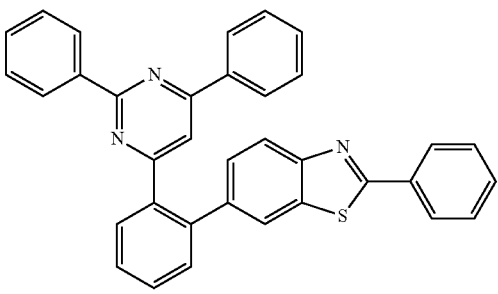 |

-continued
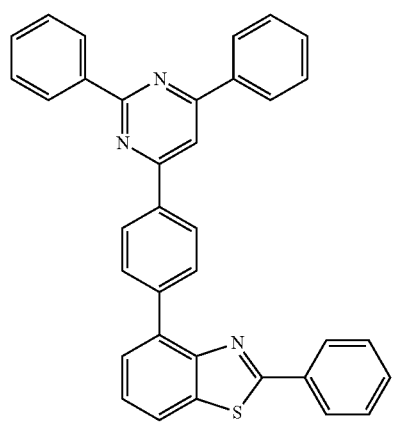
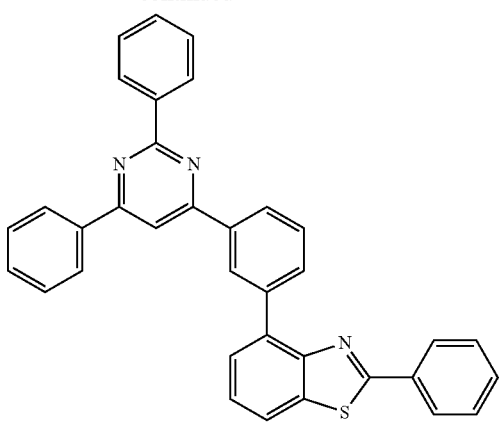
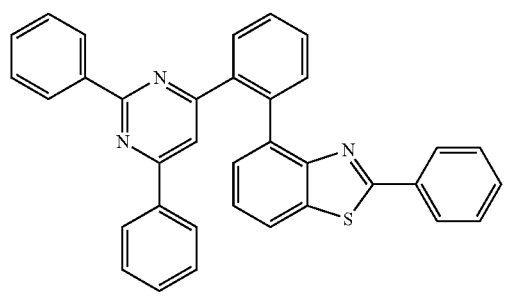
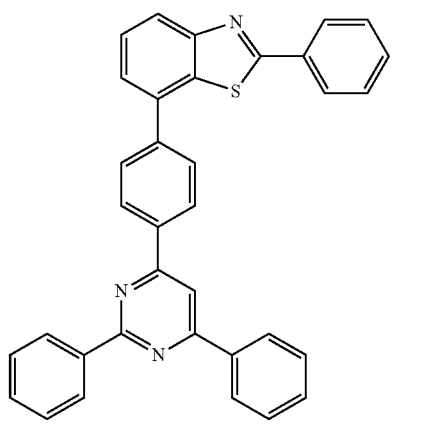
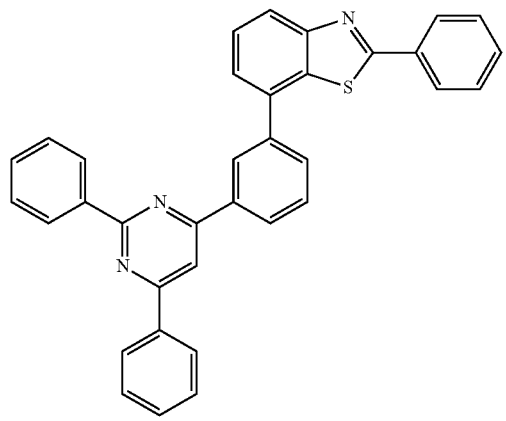
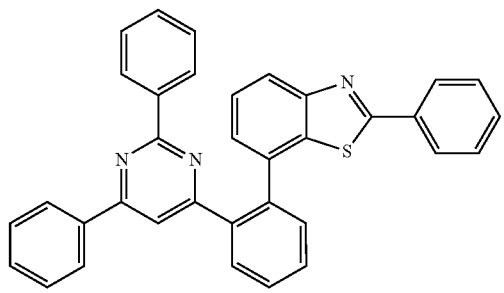
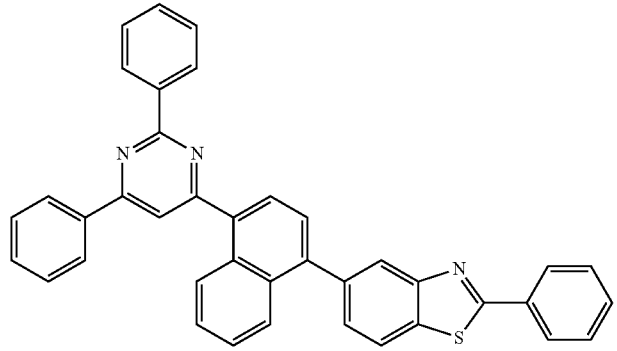

309
310
-continued
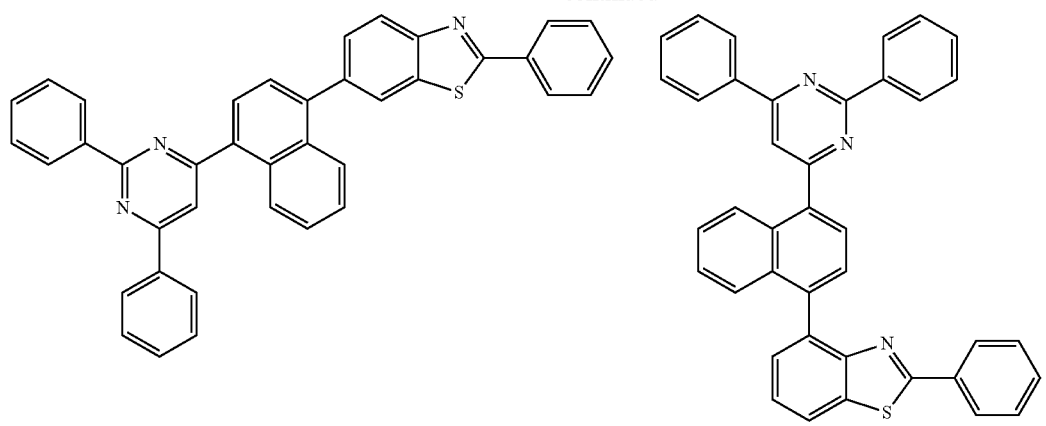
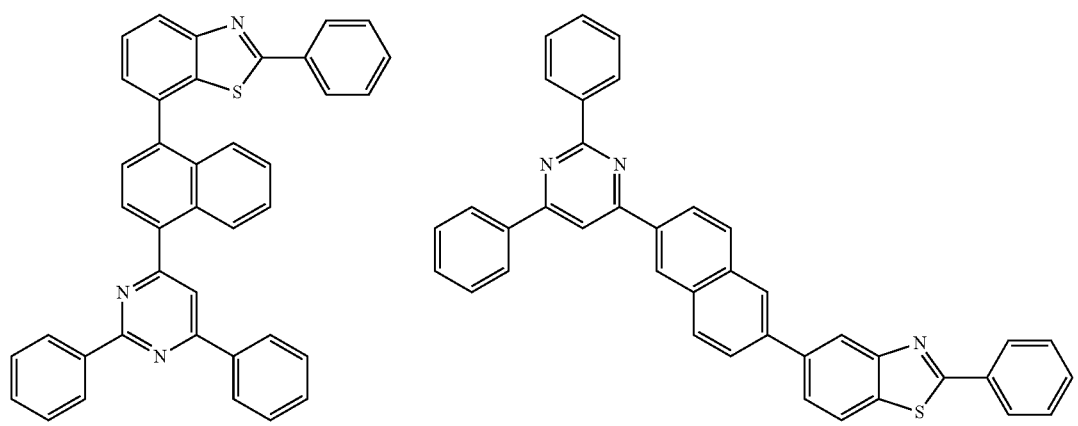
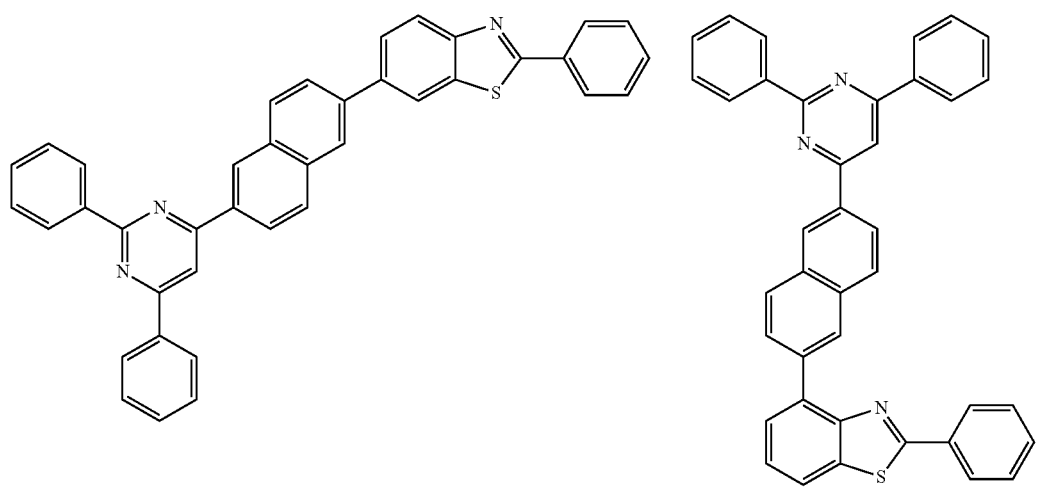

-continued
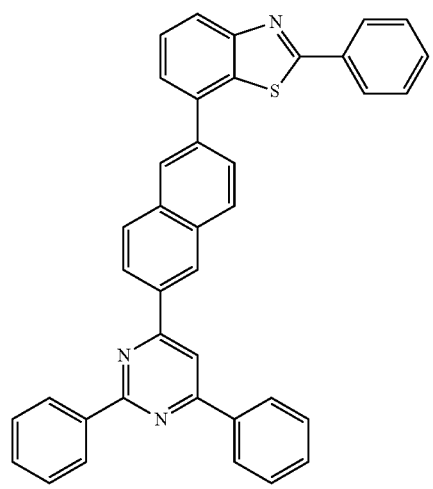
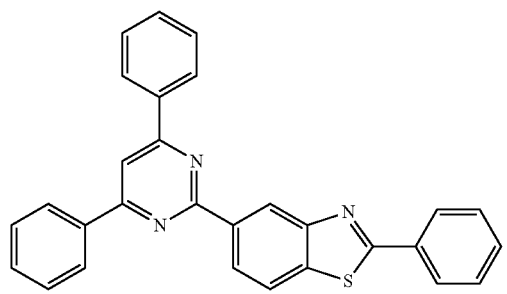
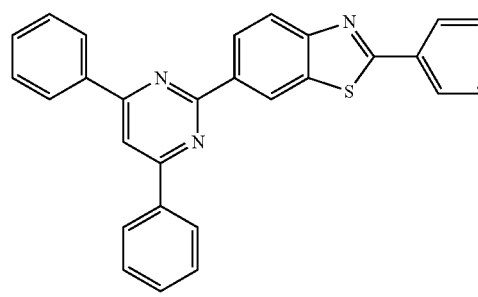
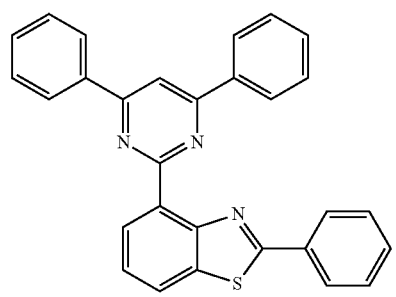
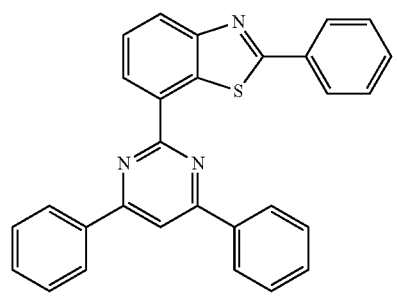
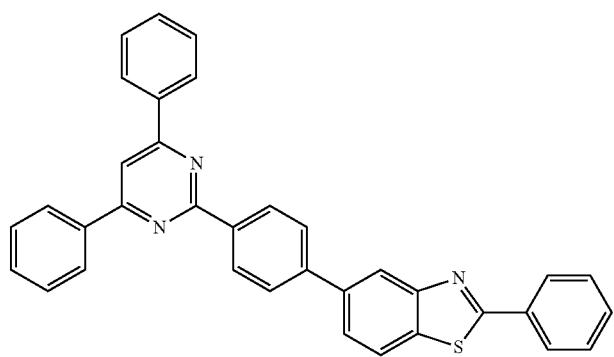
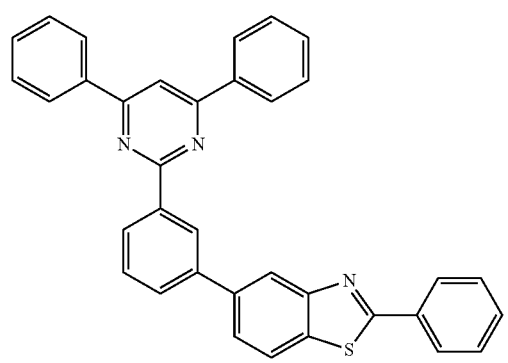
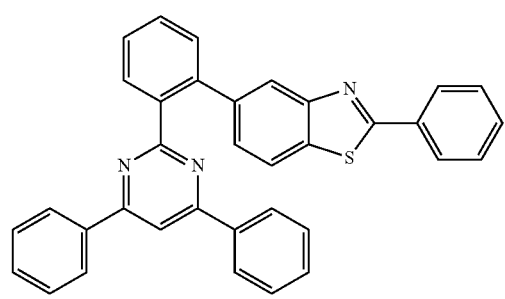

313
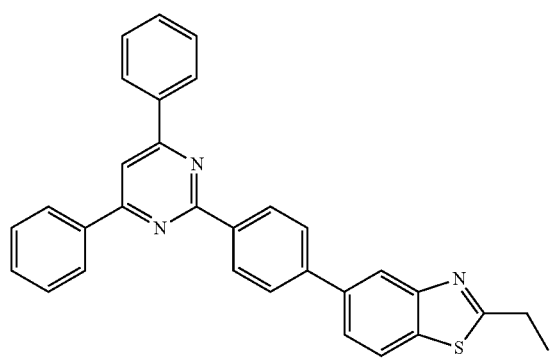
314
-continued
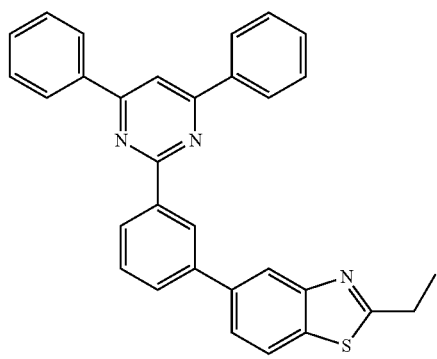
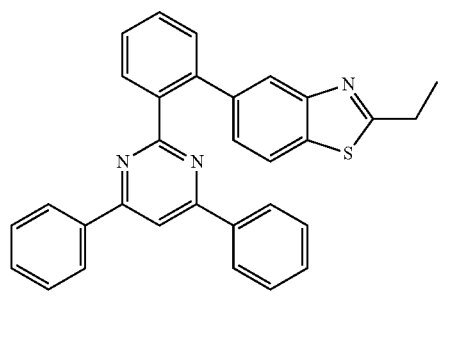
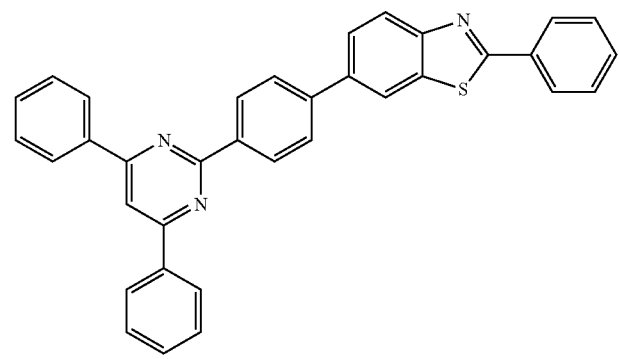
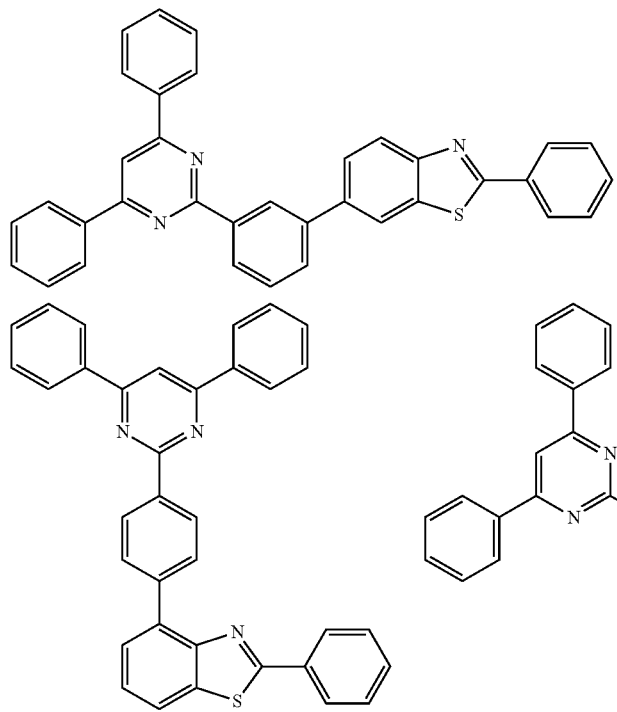
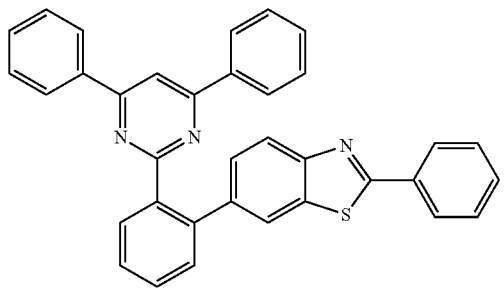
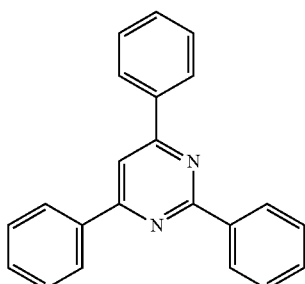
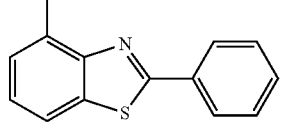

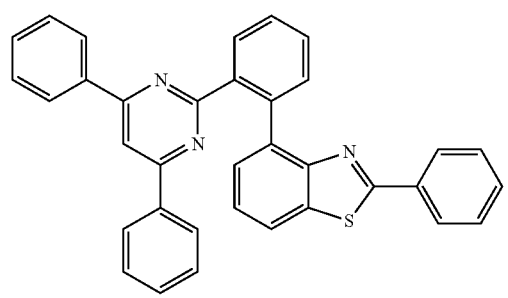
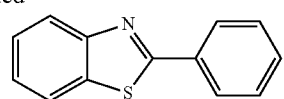
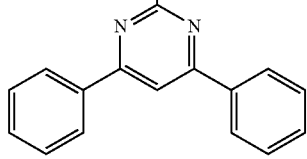
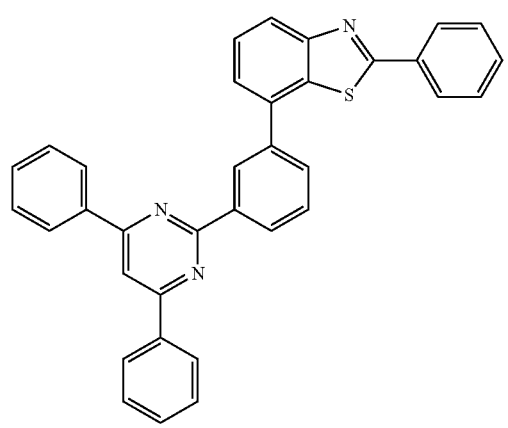
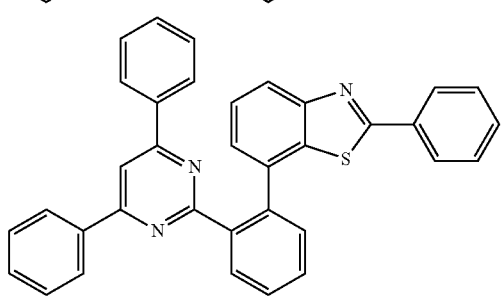
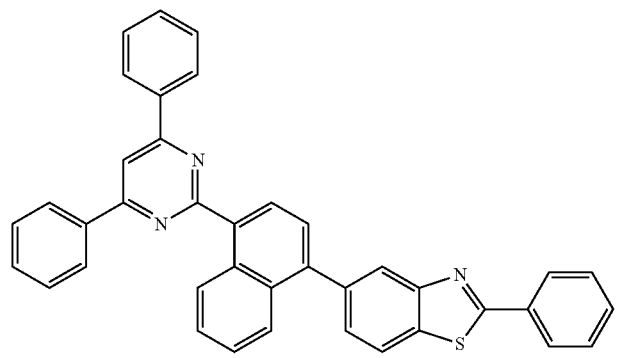
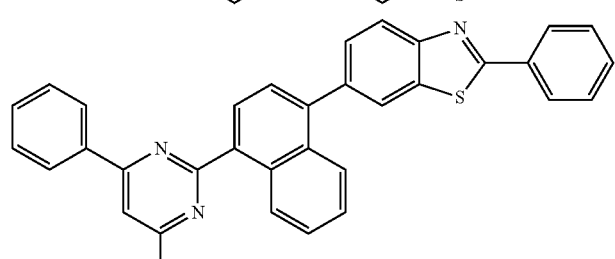
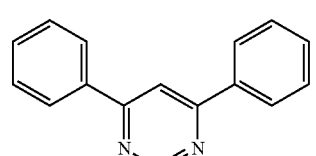
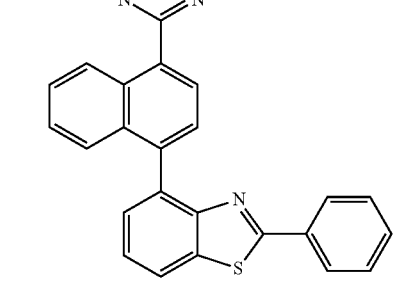

317
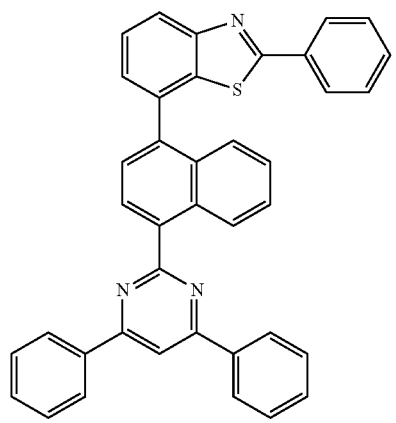
318
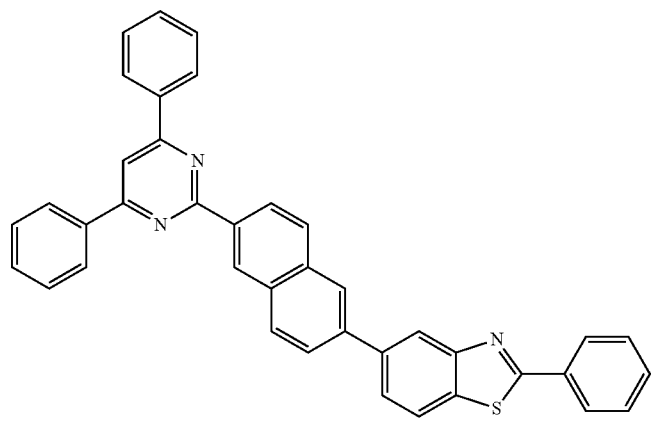
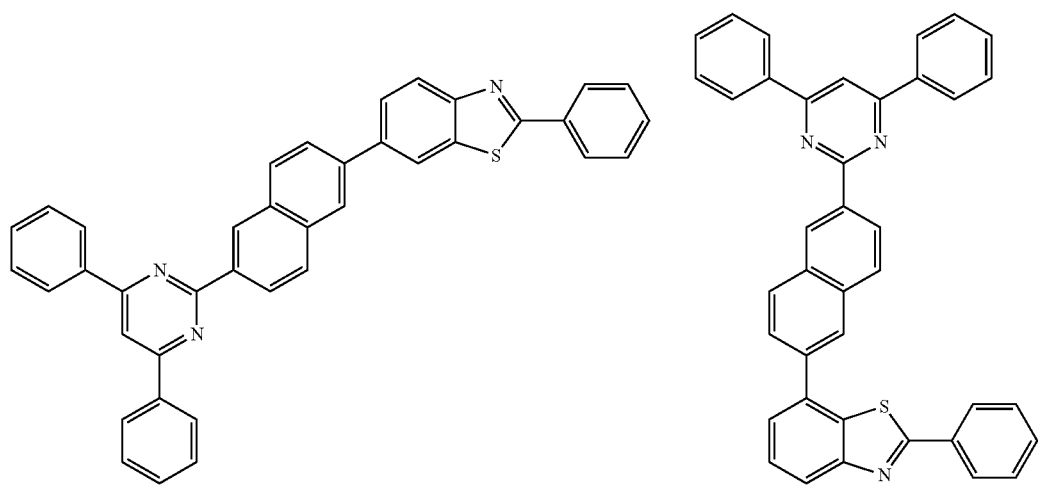
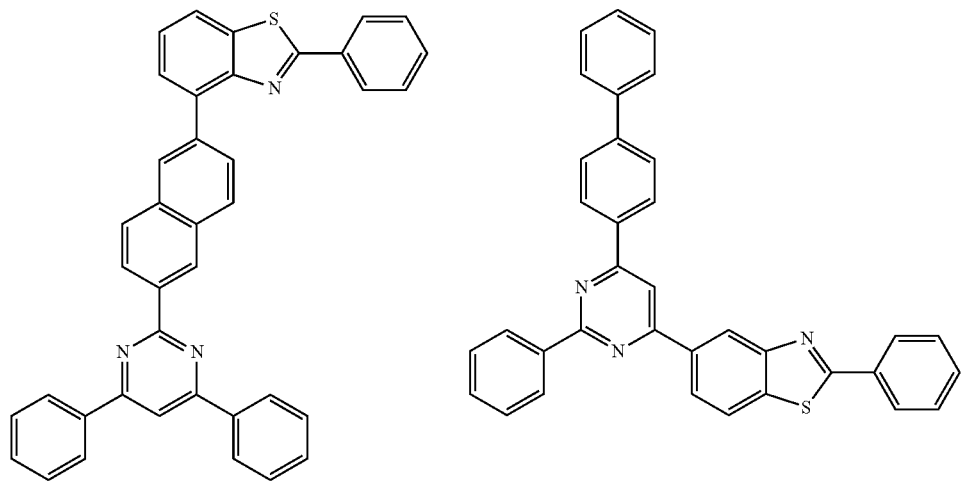

319 320
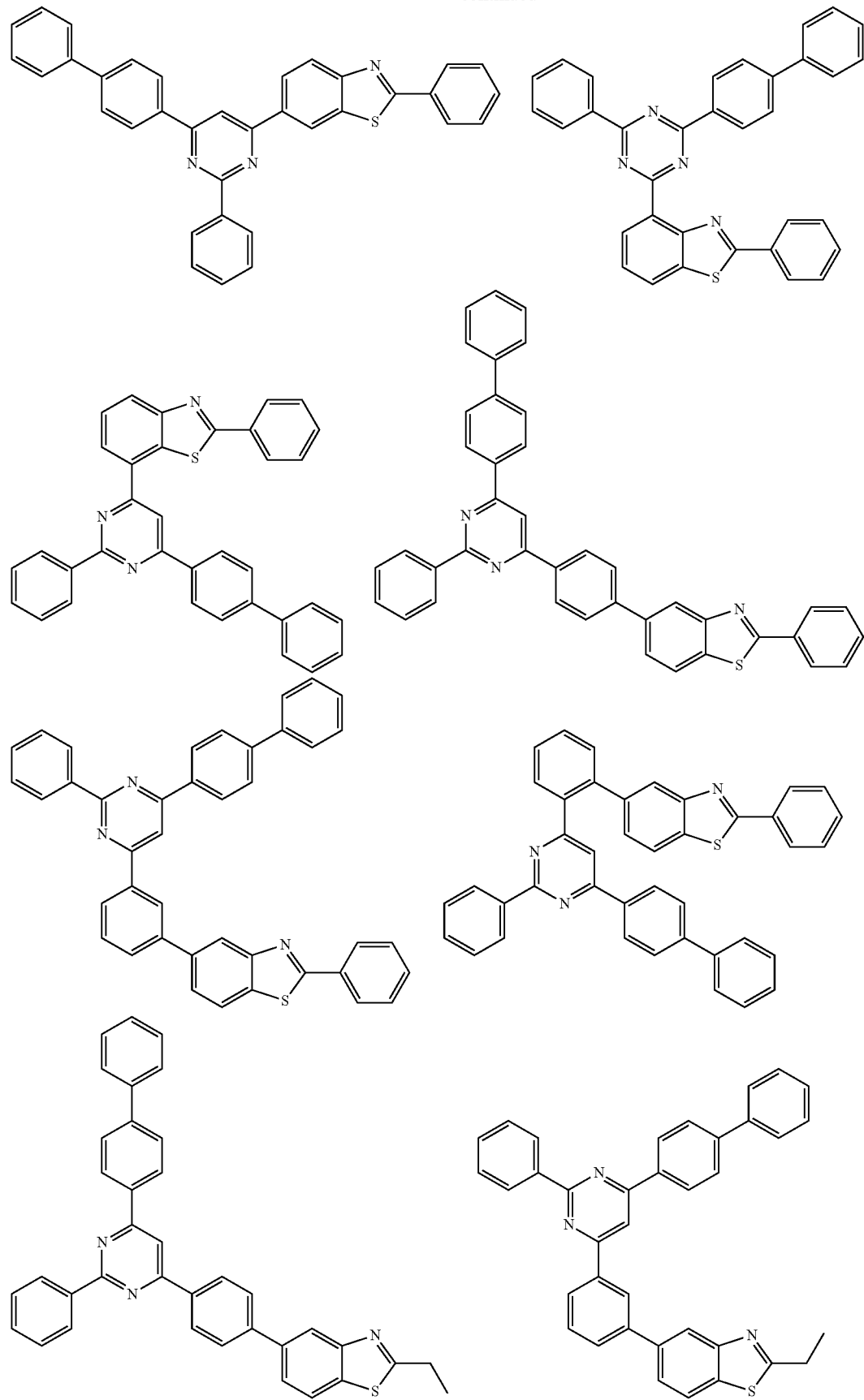
-continued

-continued
| 321 | 322 |
|---|---|
| 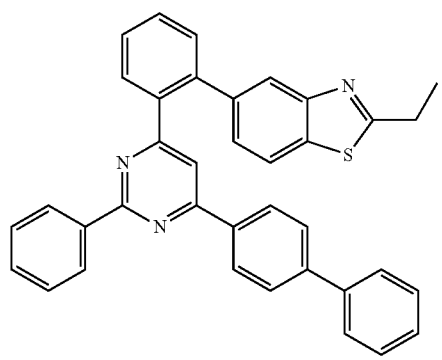 | 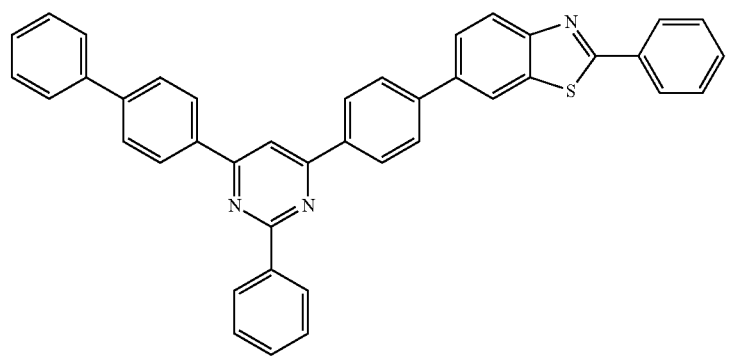 |
| 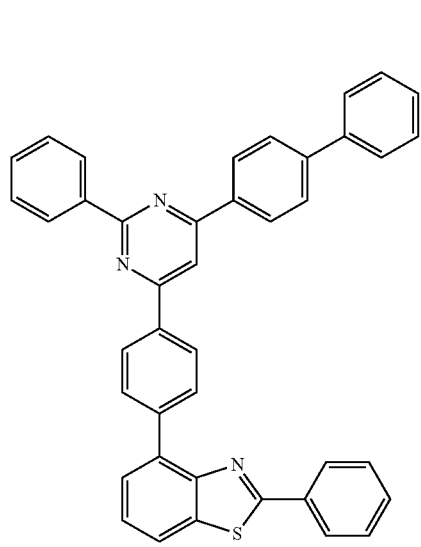 | 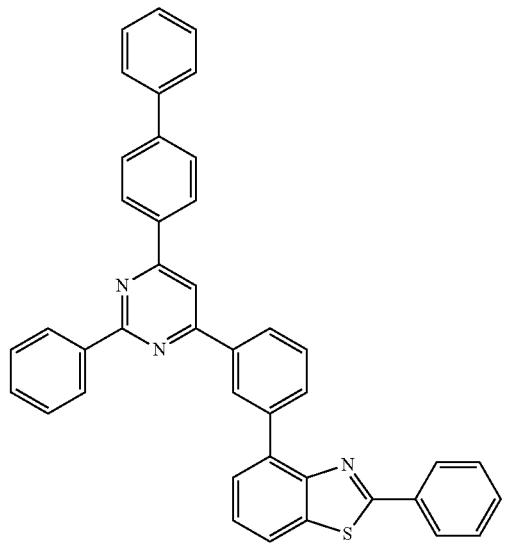 |
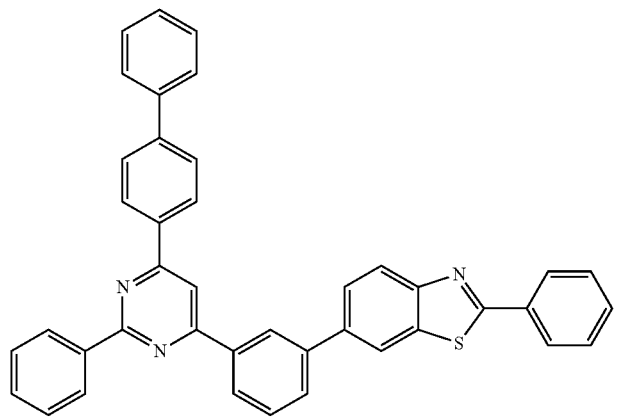
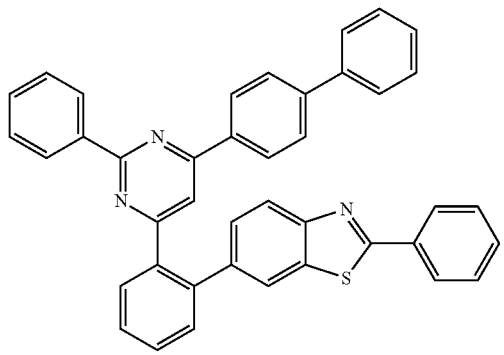

323
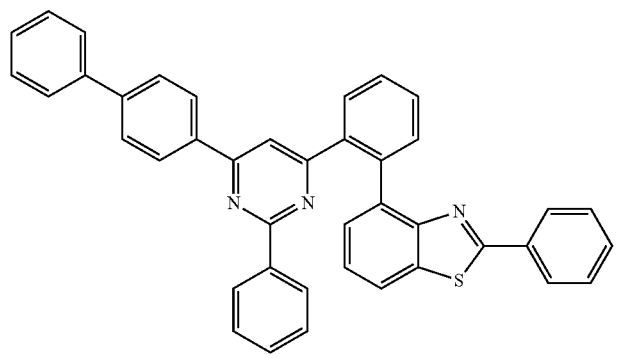
324
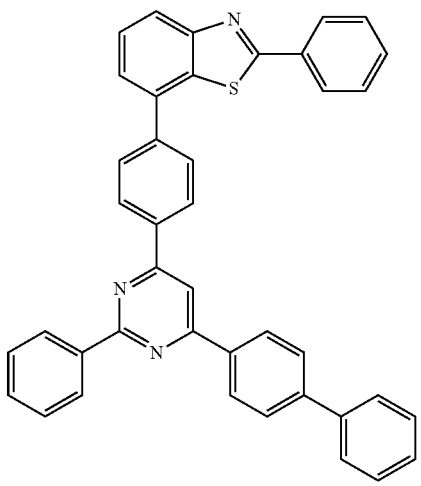
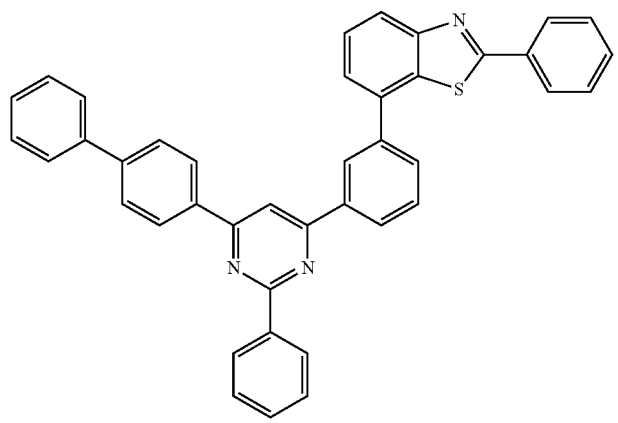
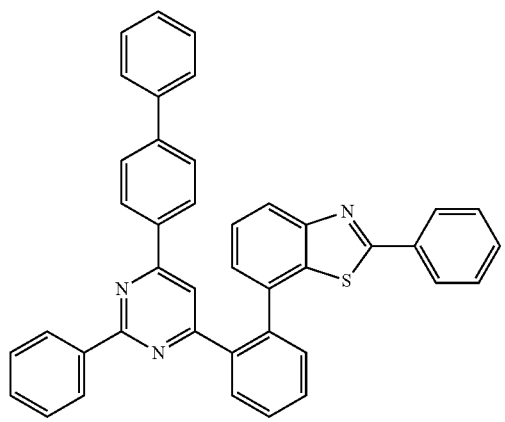
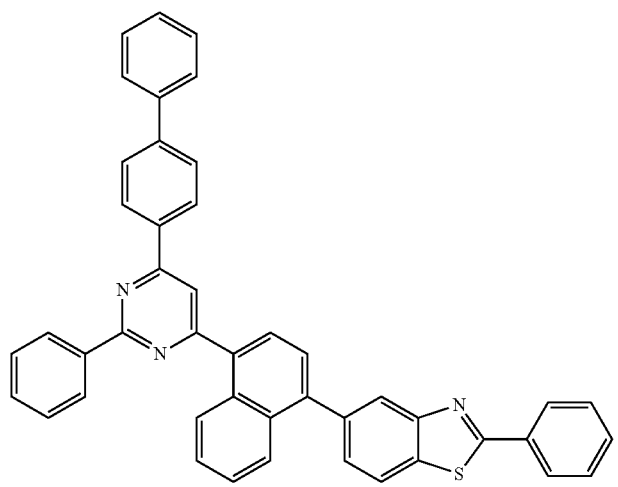

-continued
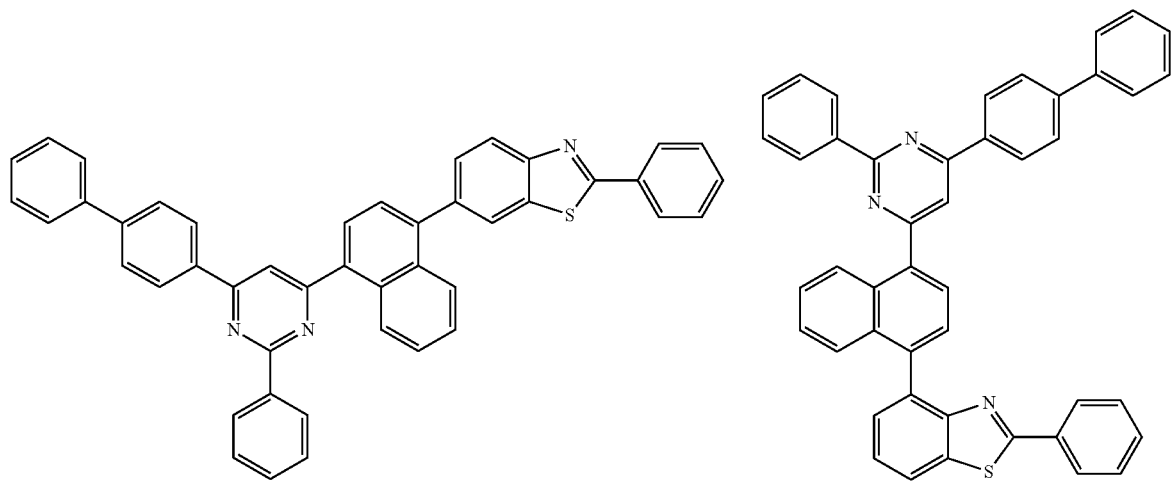
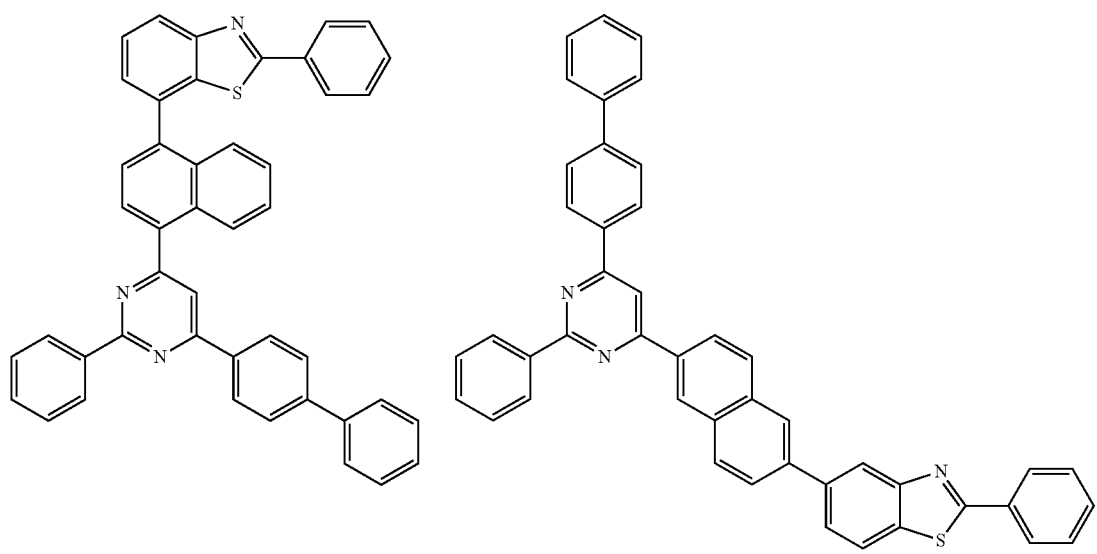
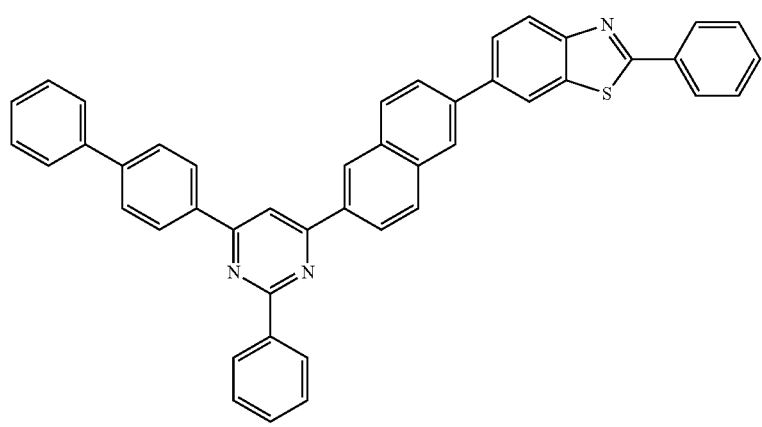

327
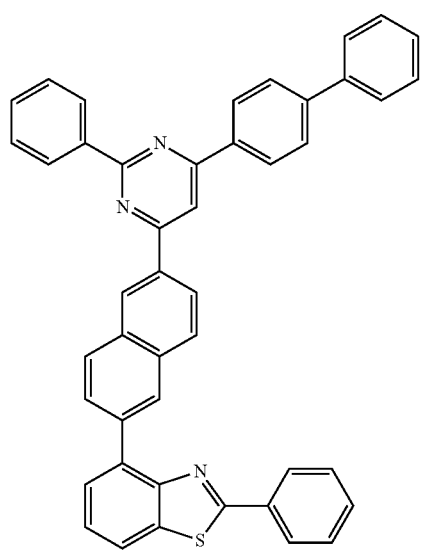
328
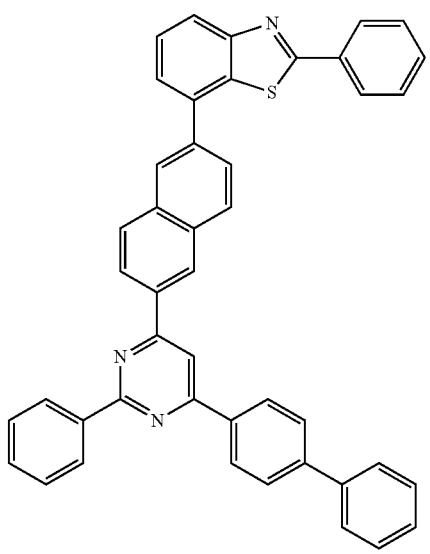
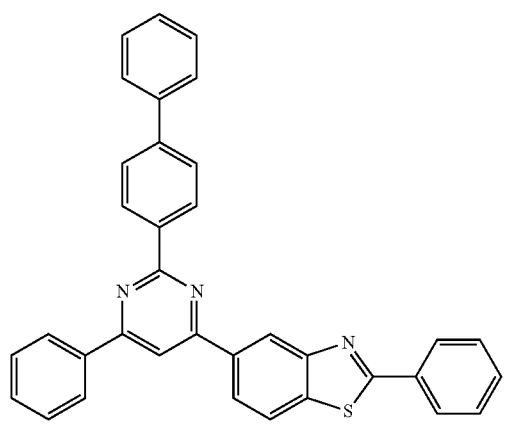
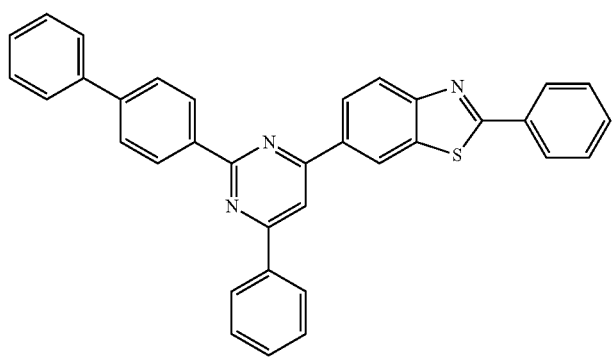
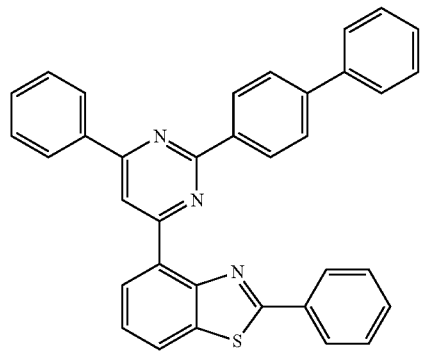
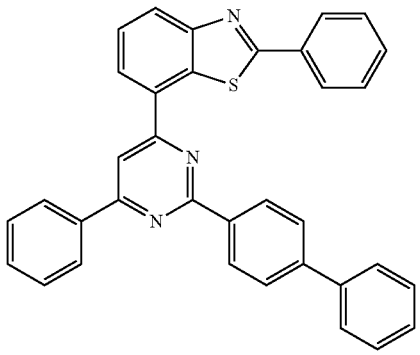

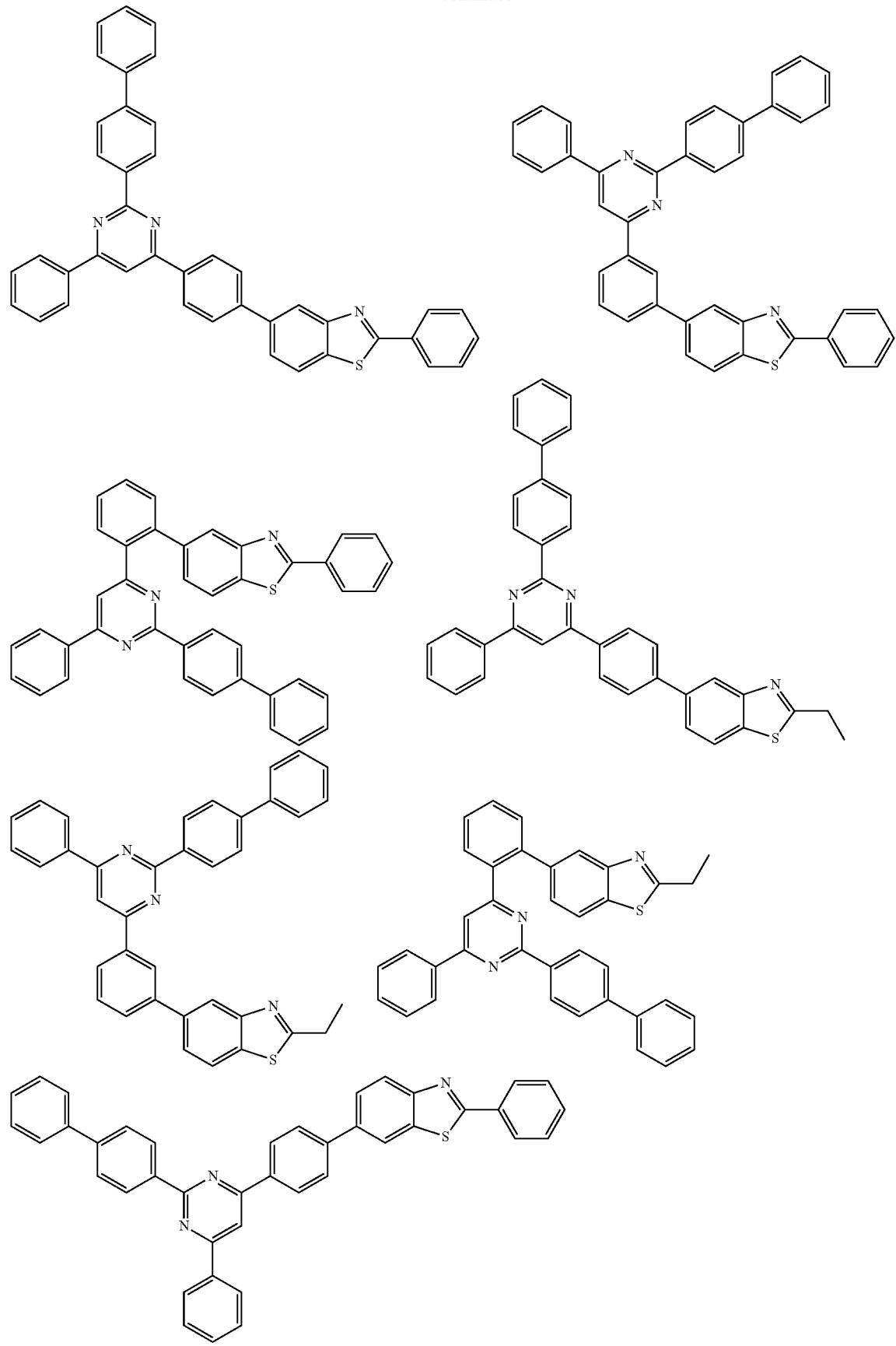

331
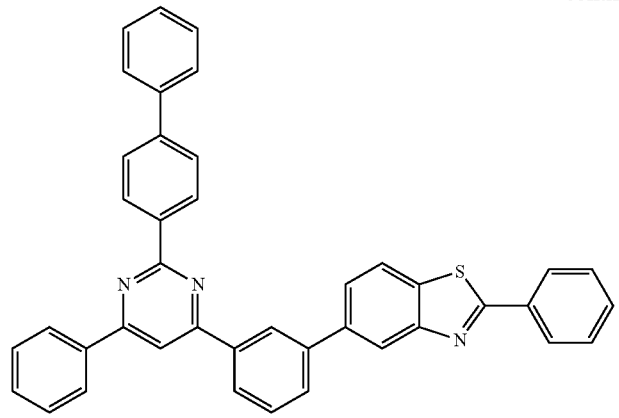
332
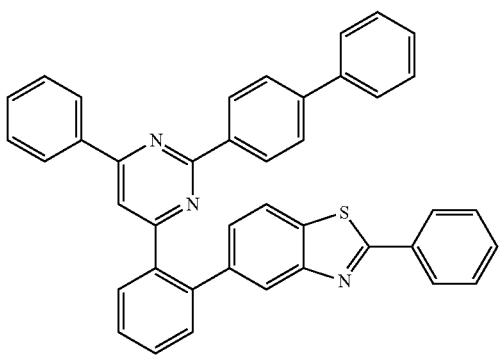
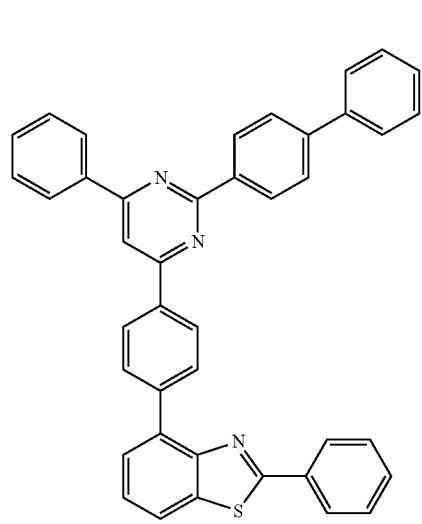
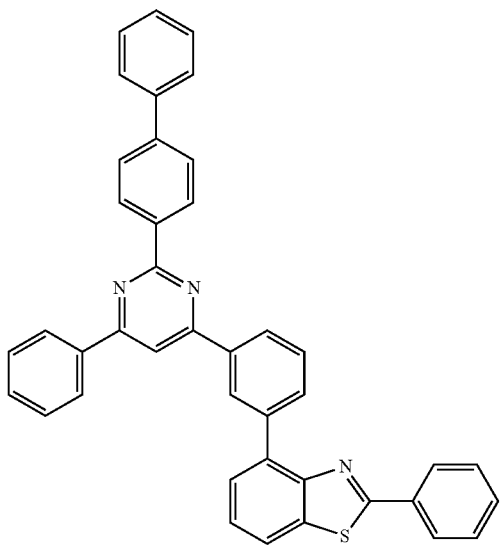
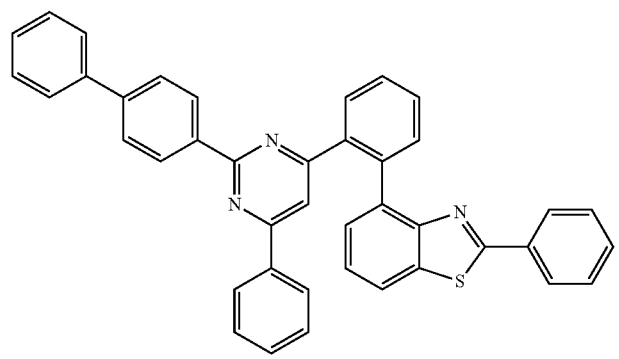
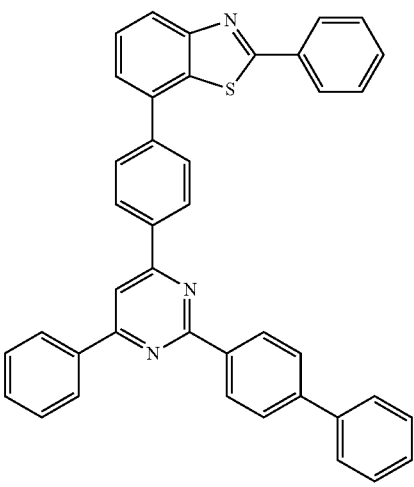

-continued
333
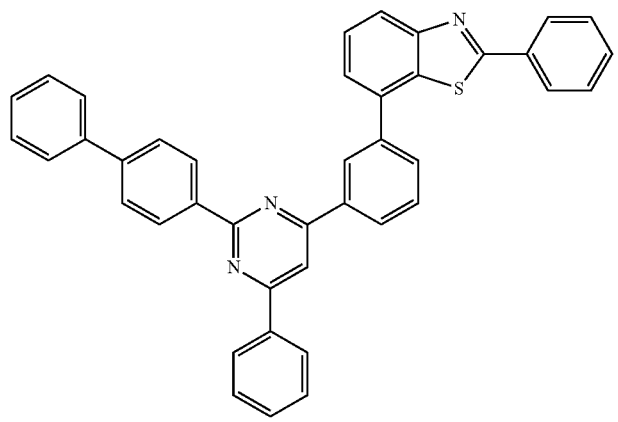
334
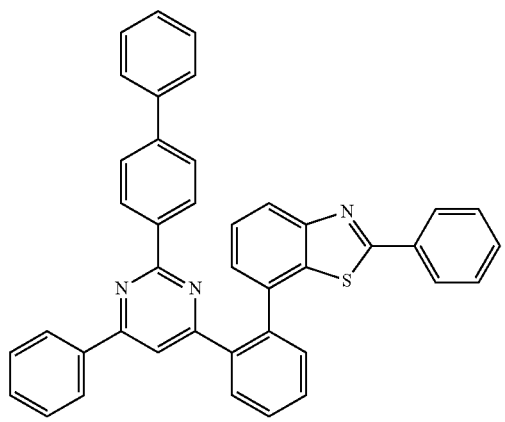
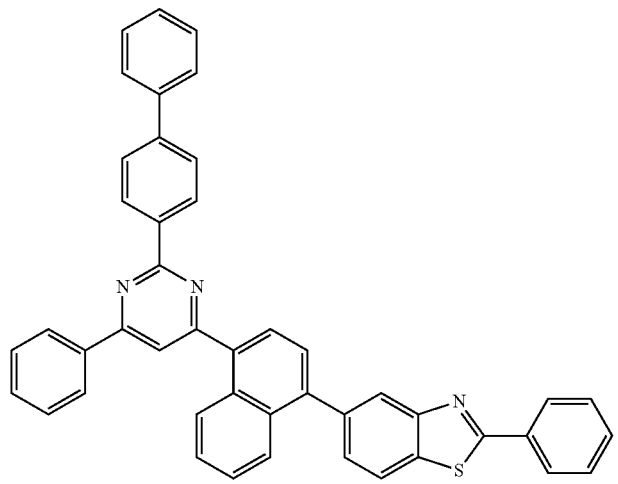
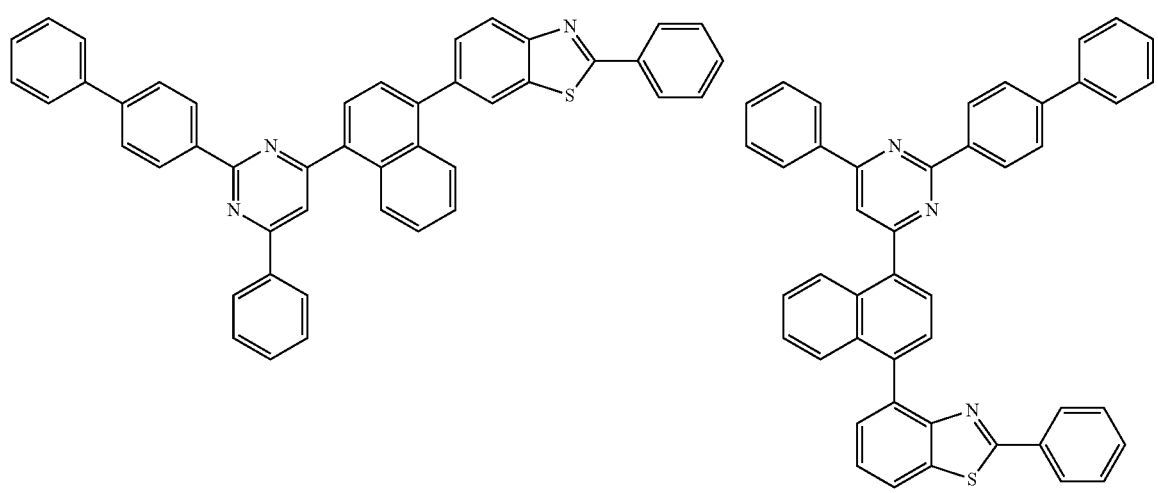

335
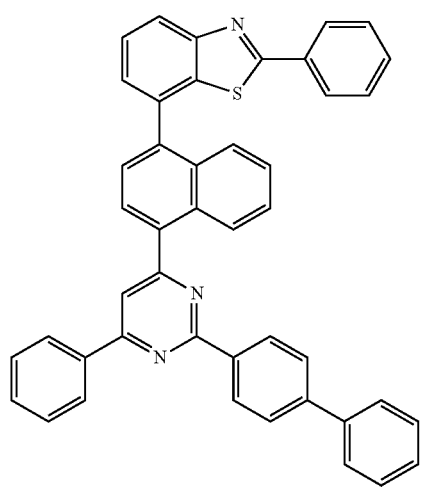
-continued
336
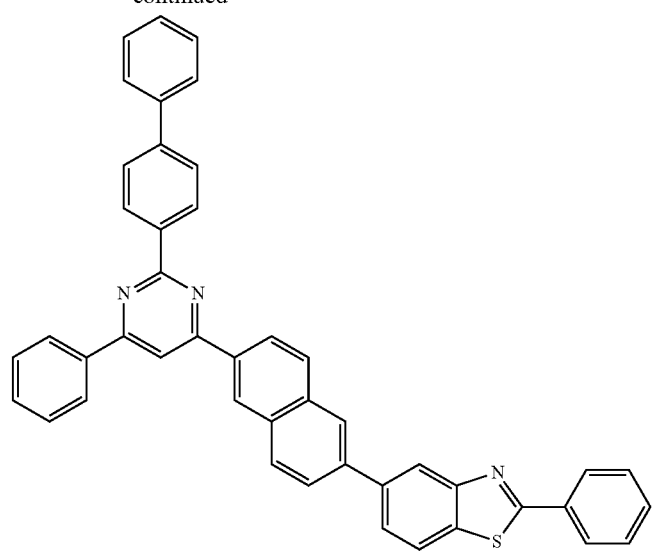
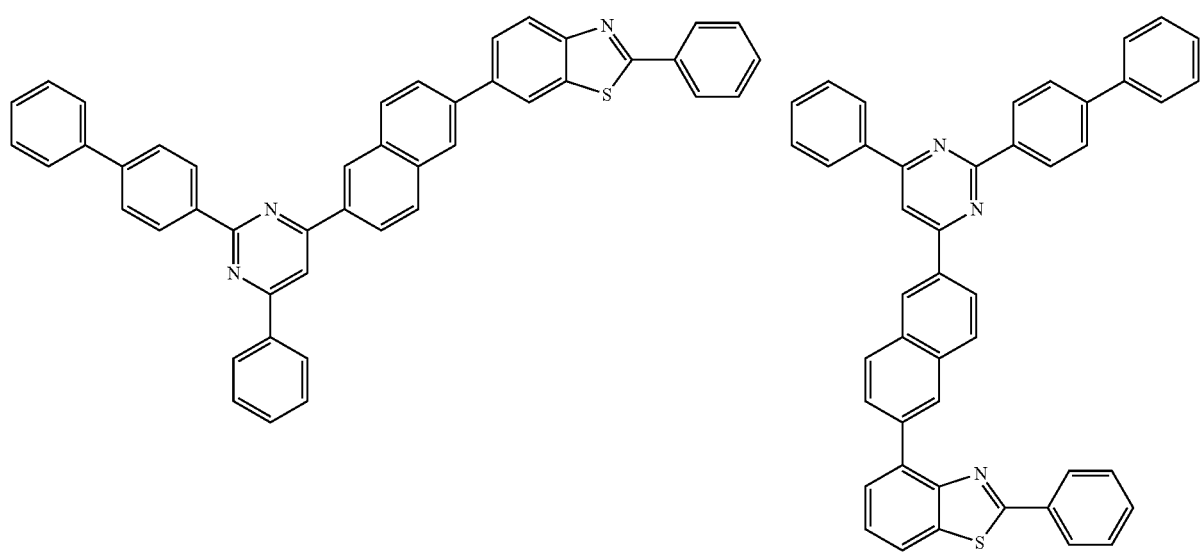
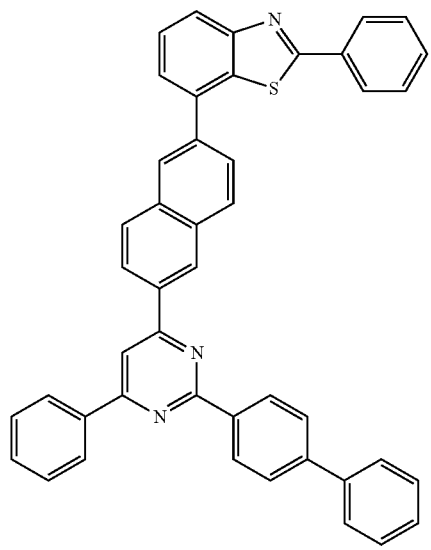
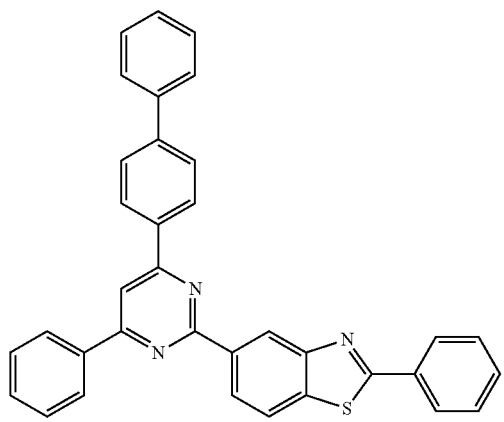

337 338
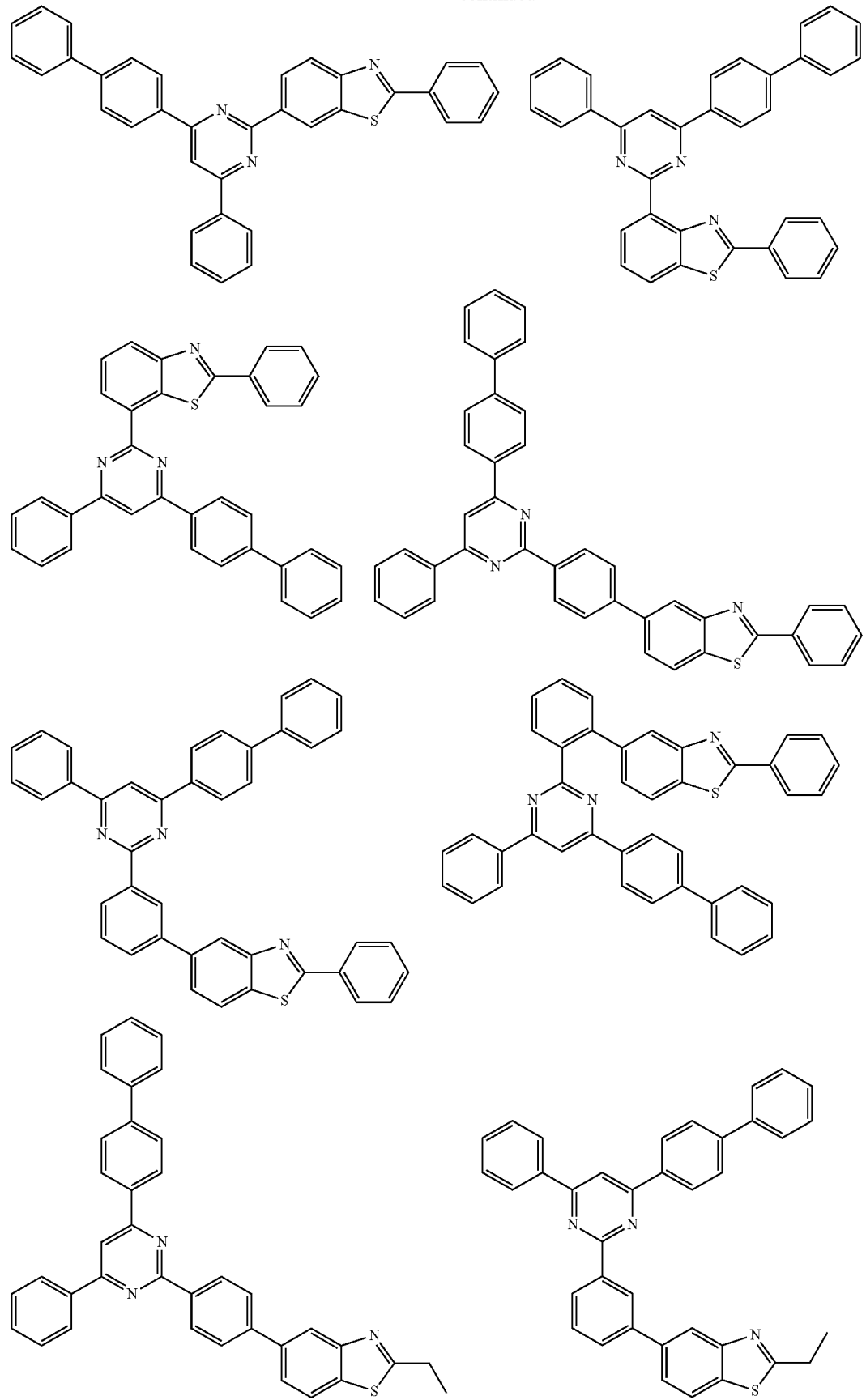
-continued

-continued
339
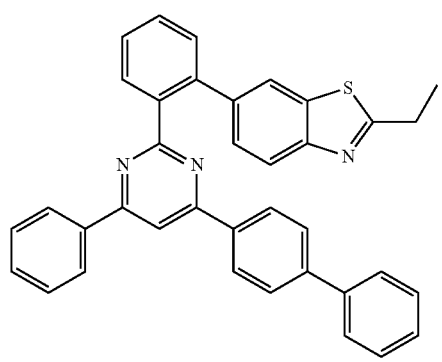
340
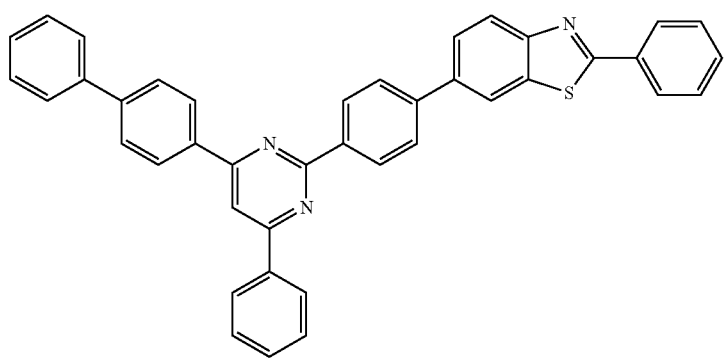
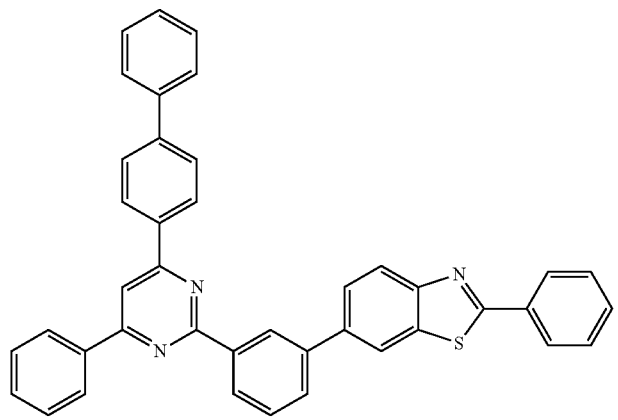
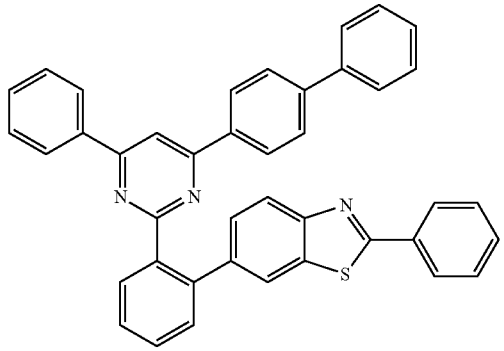
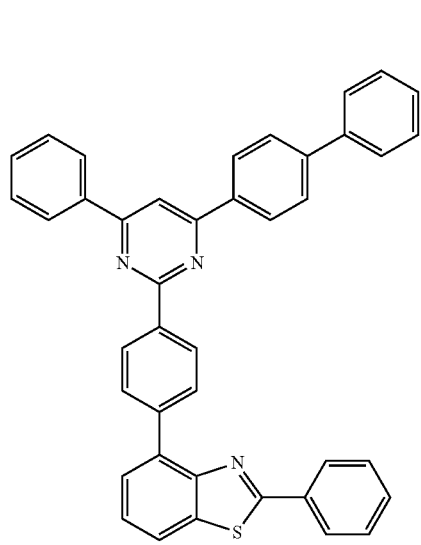
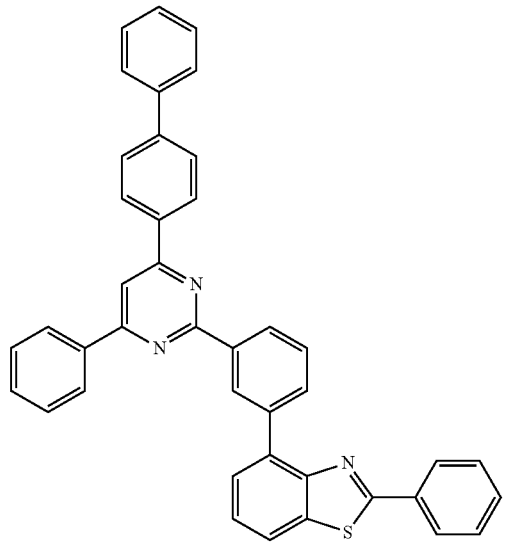

341
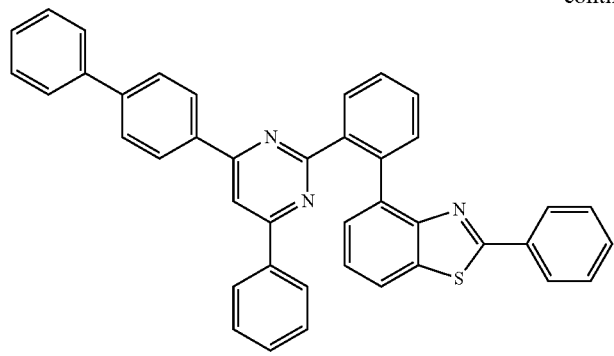
342
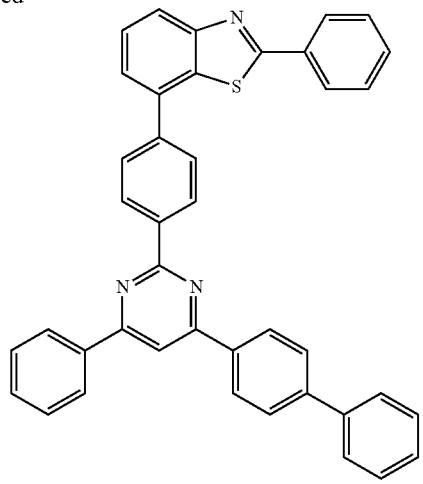
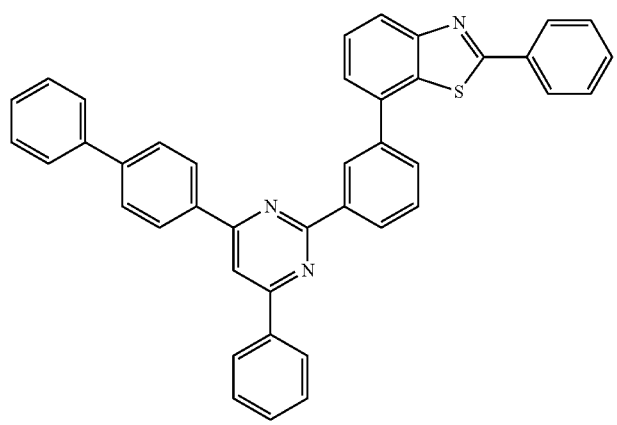
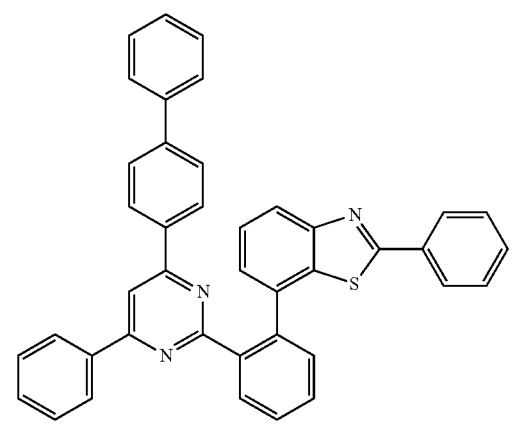
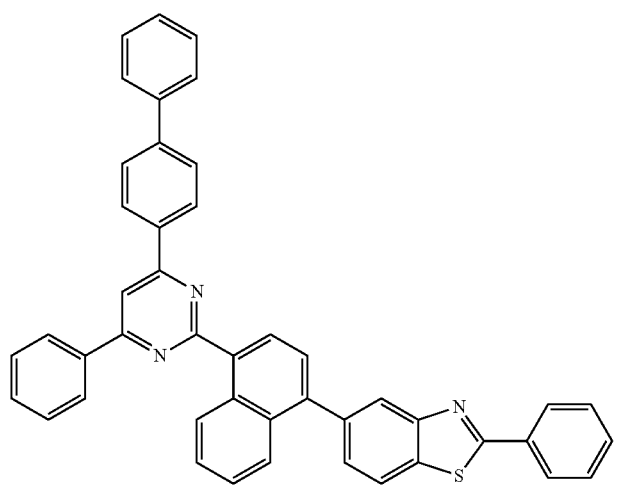

-continued
343
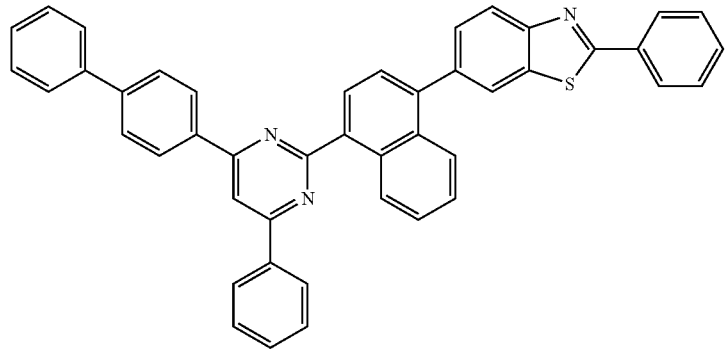
344
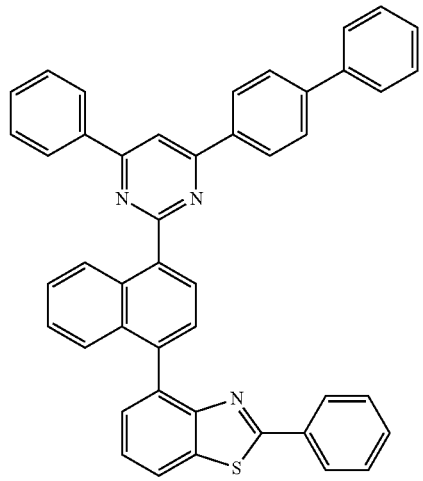
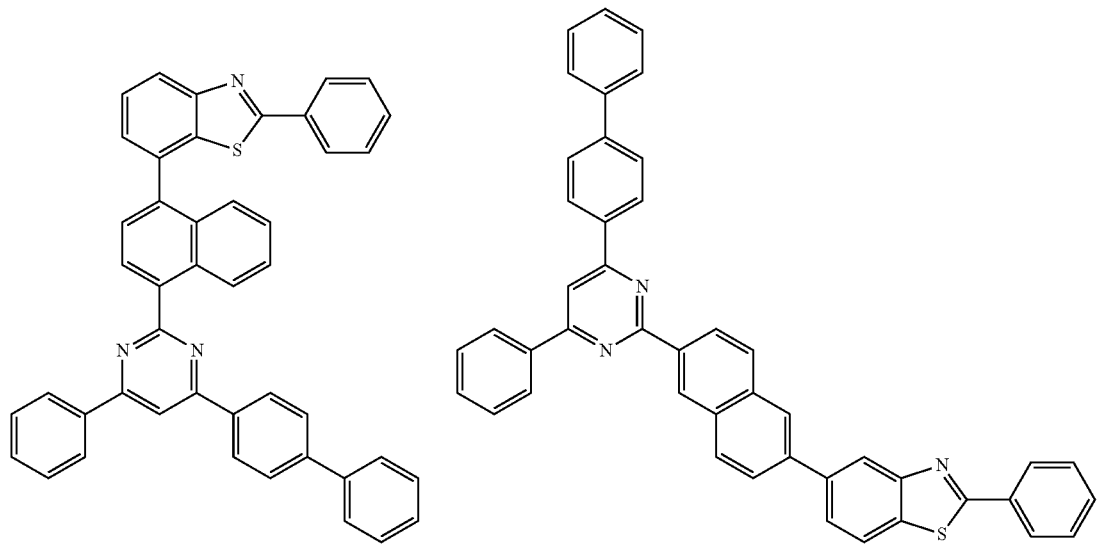
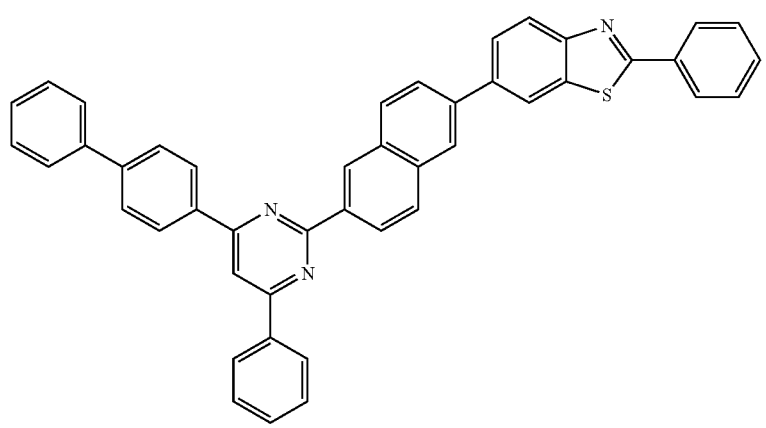

345
346
-continued
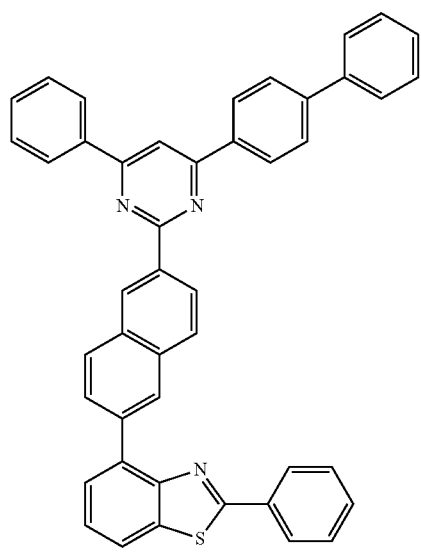
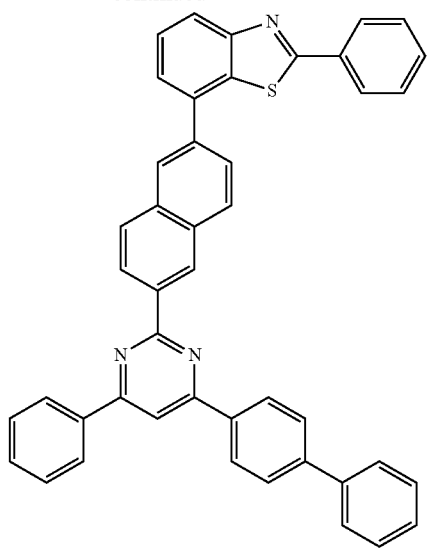
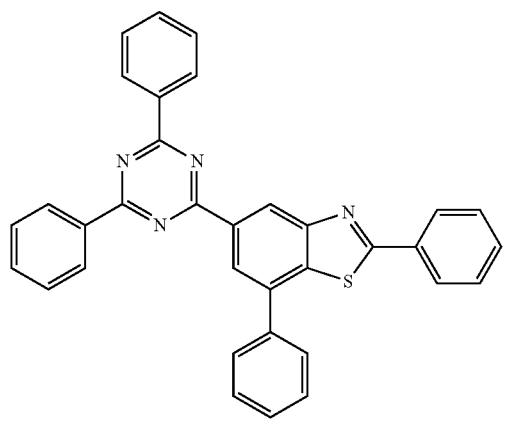
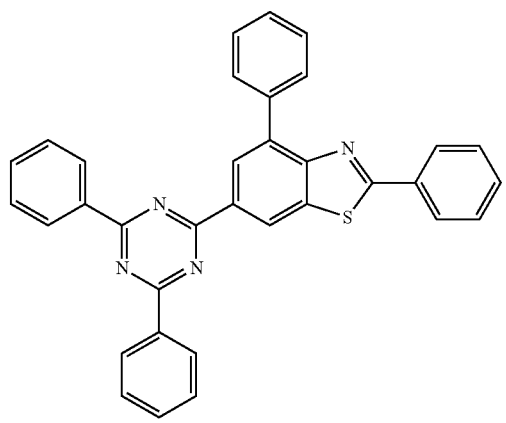
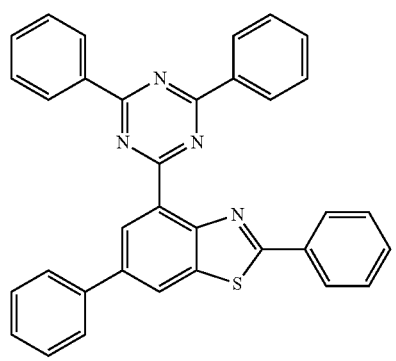
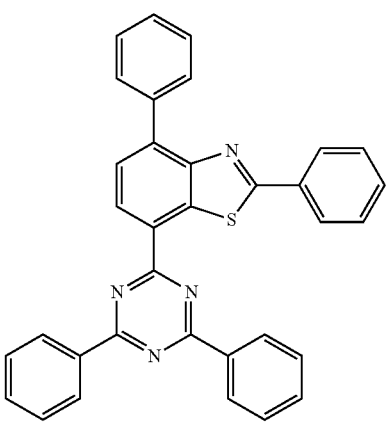

-continued
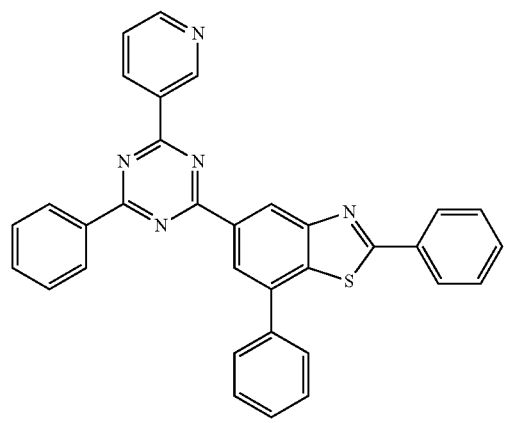
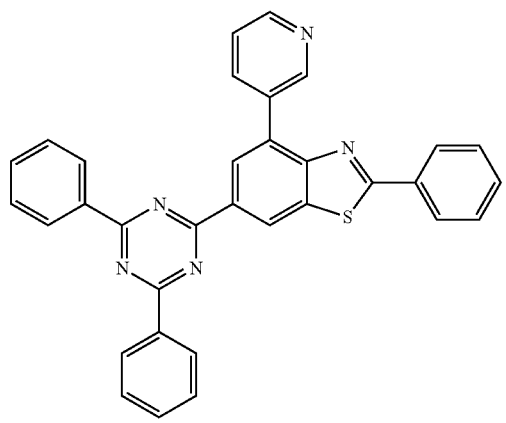
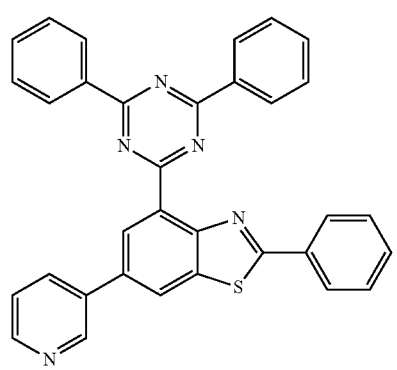
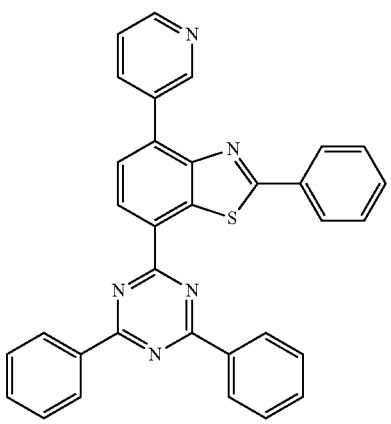
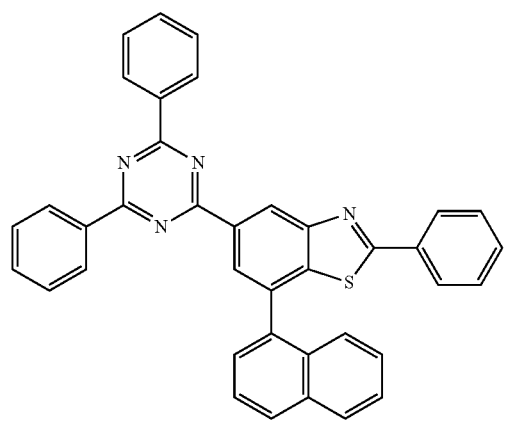
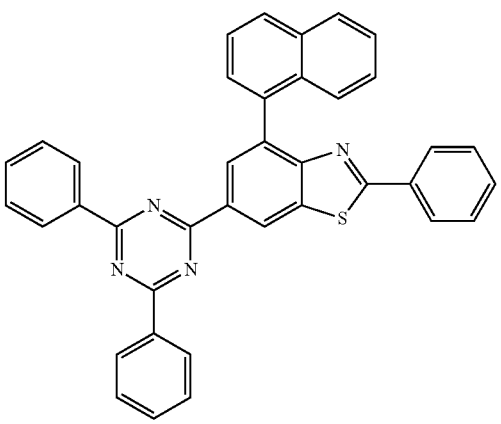
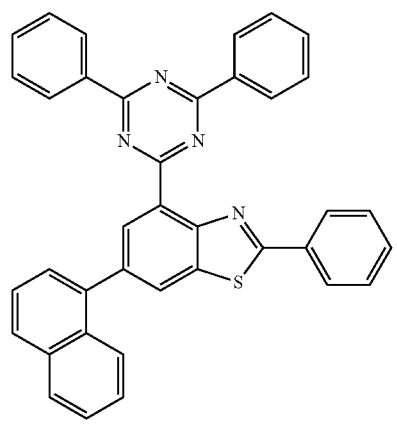
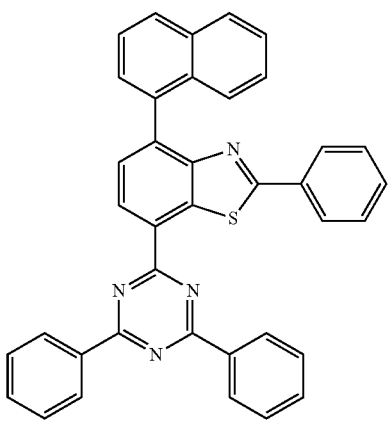

349
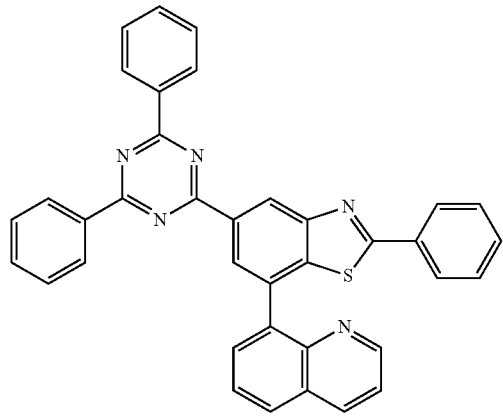
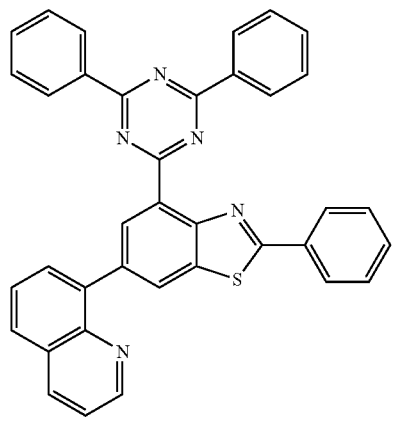
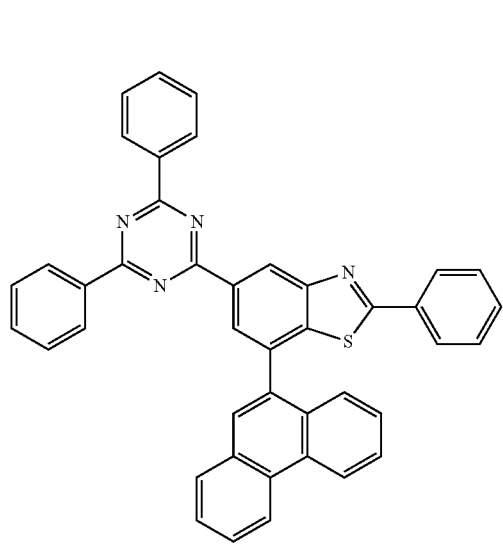
350
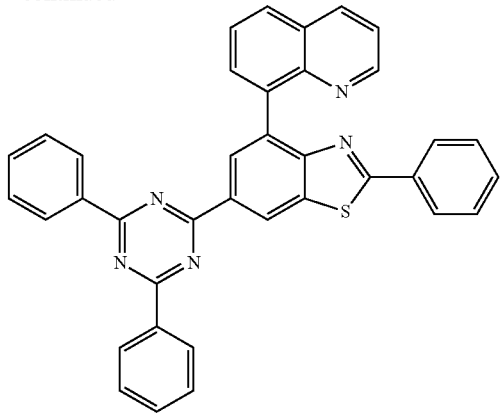
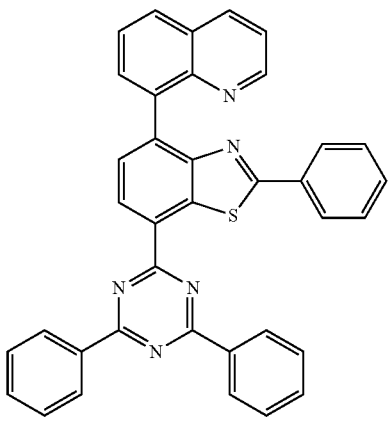
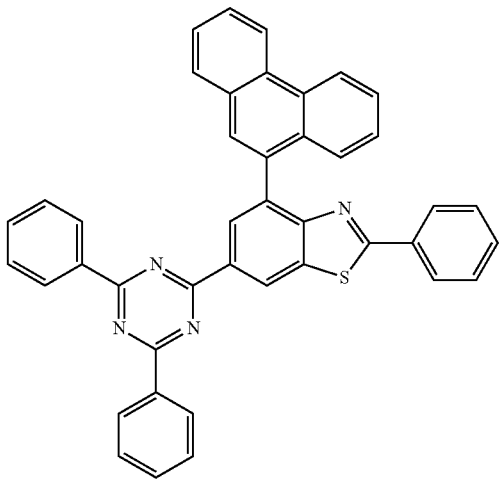

-continued
351
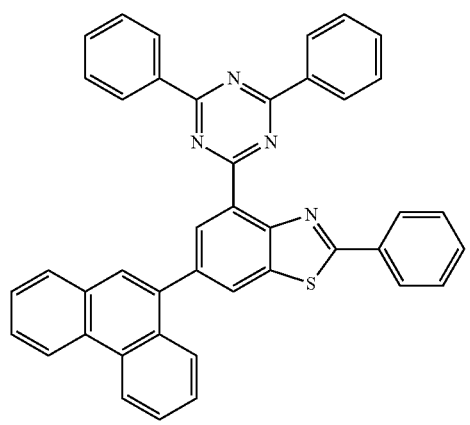
352
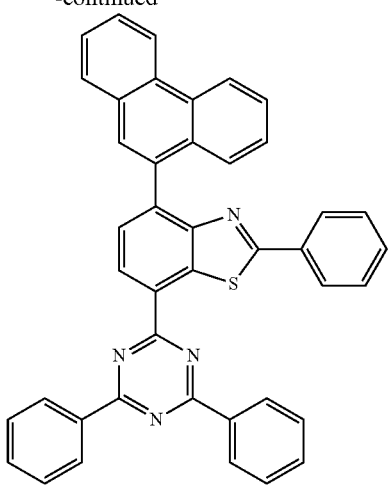
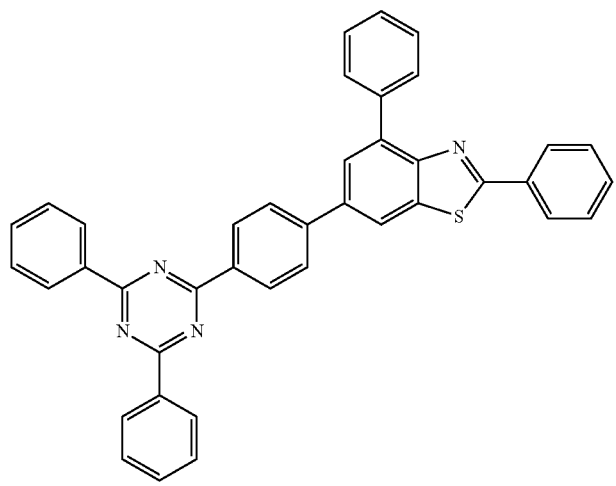
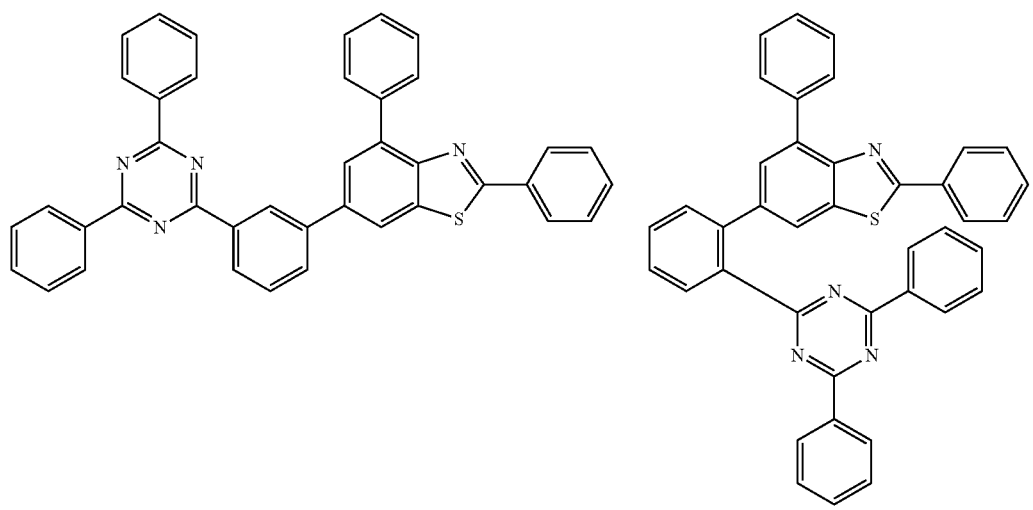

-continued
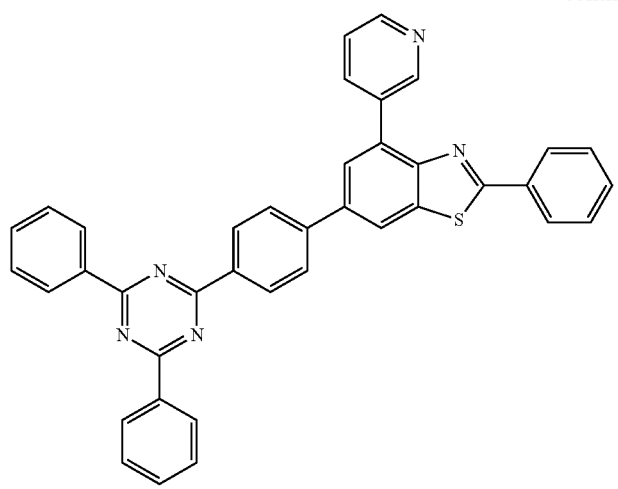
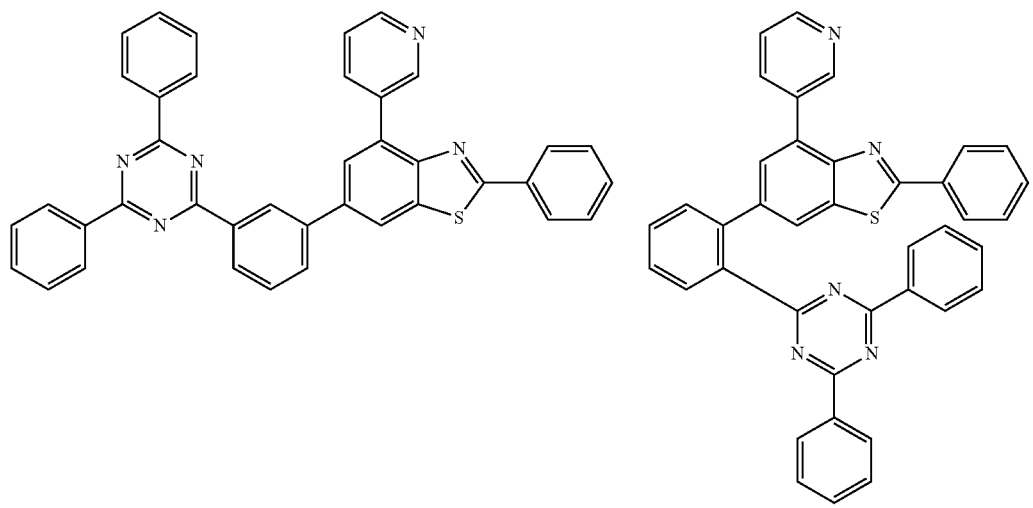
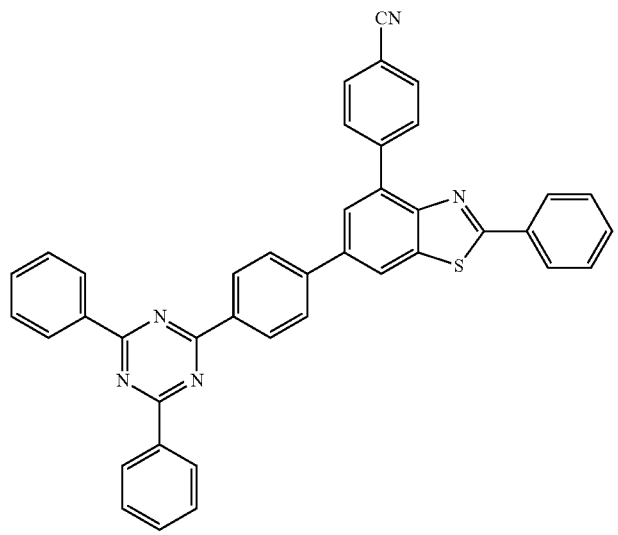

355
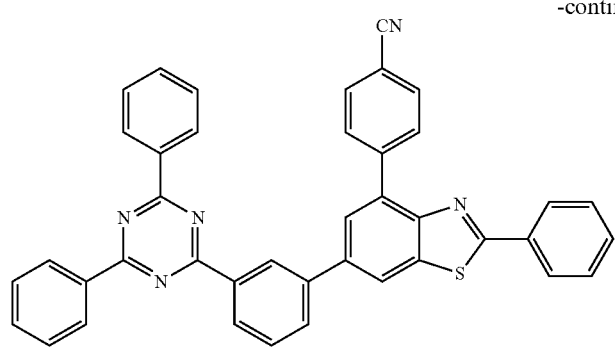
356
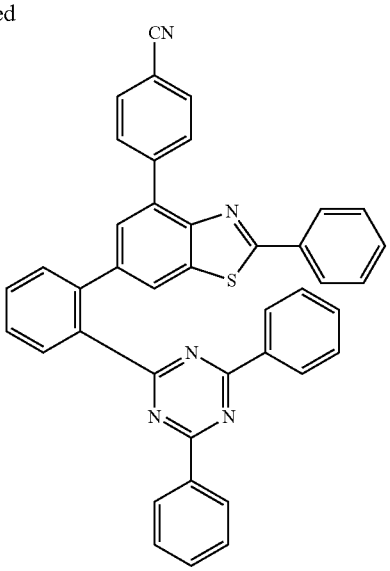
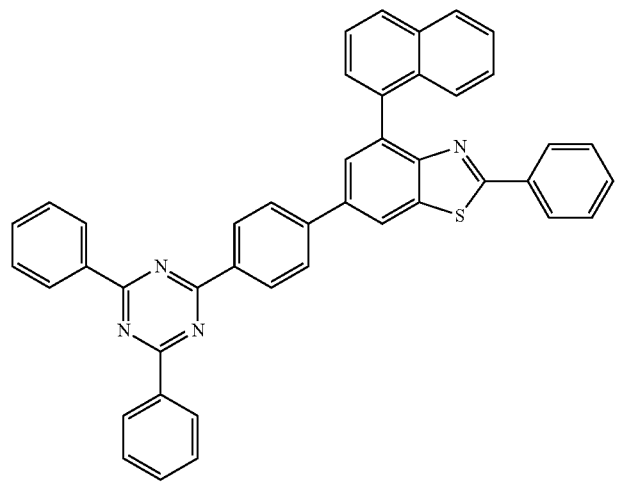
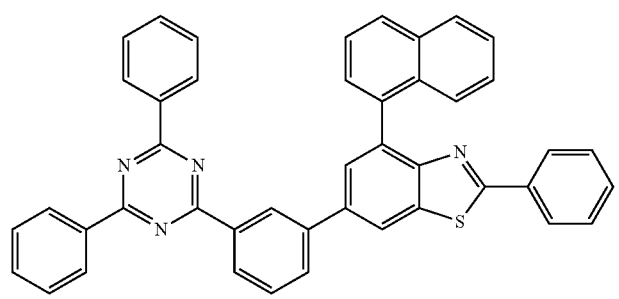
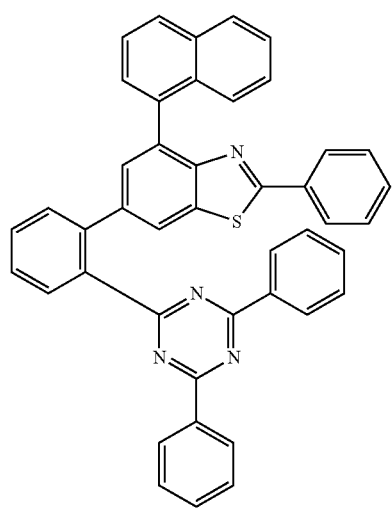

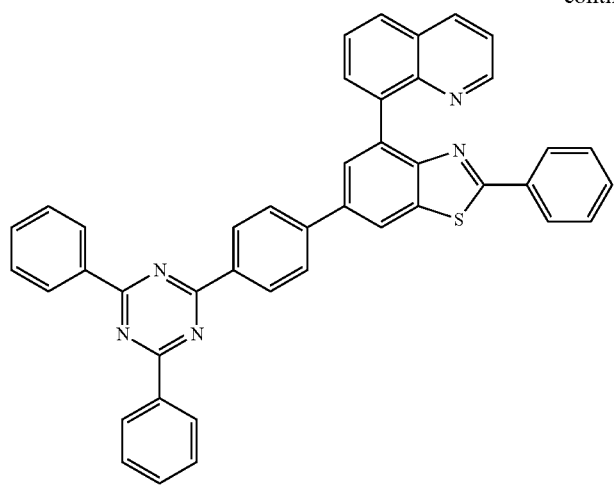
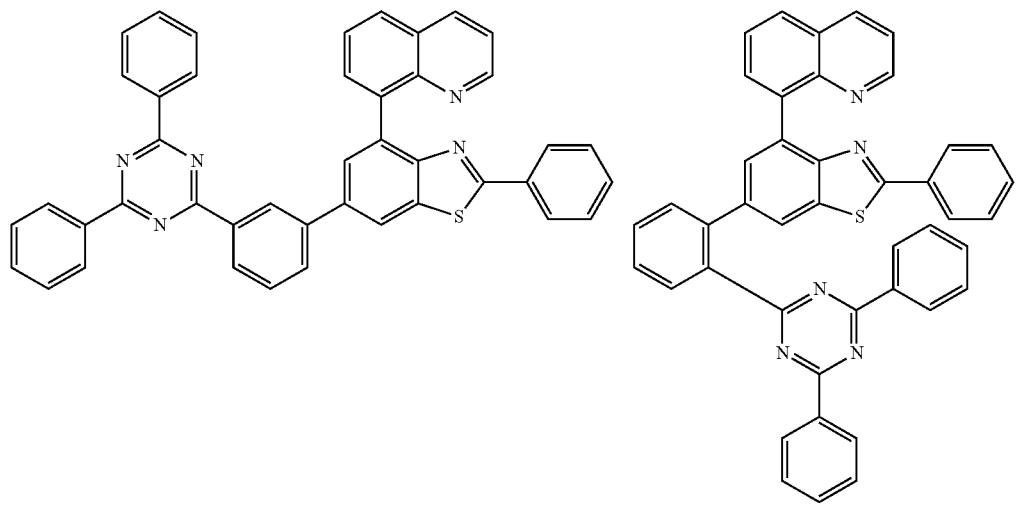
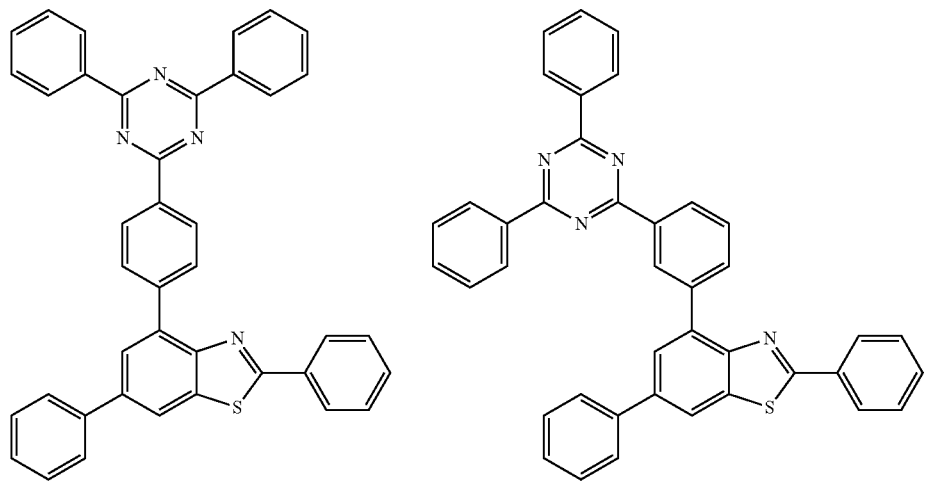

-continued
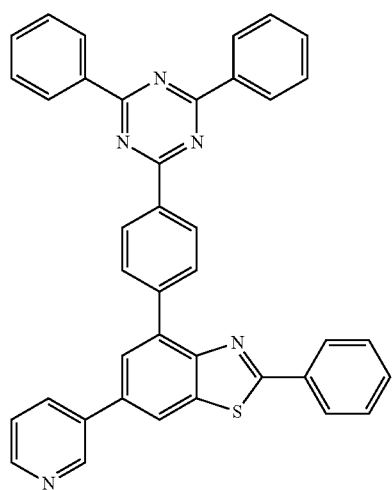
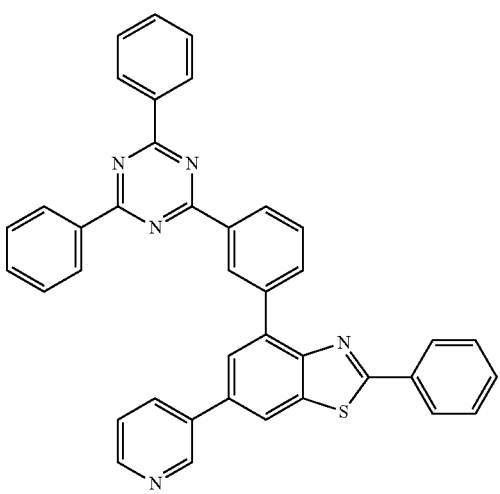
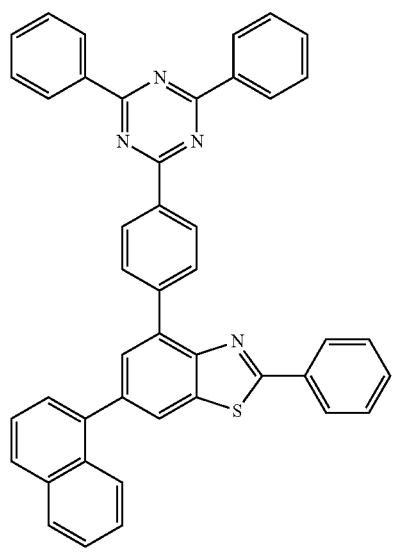
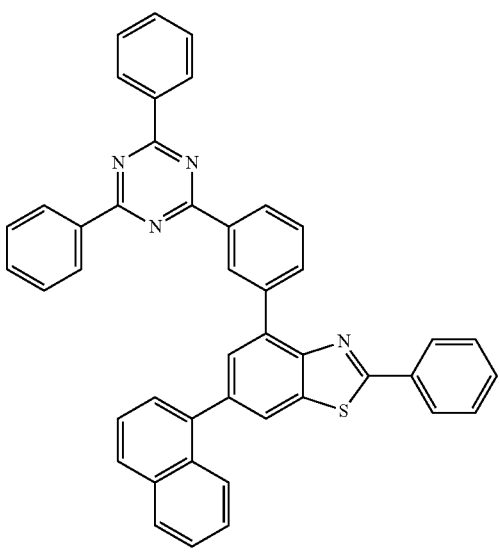
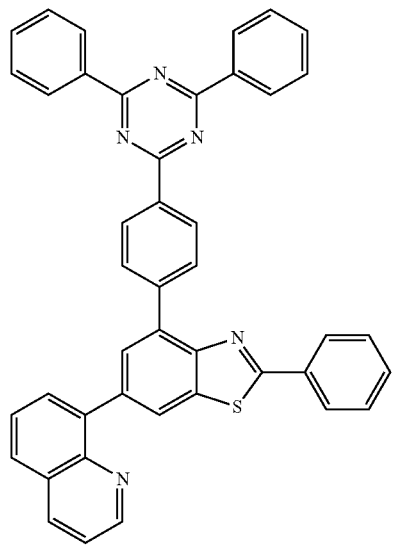
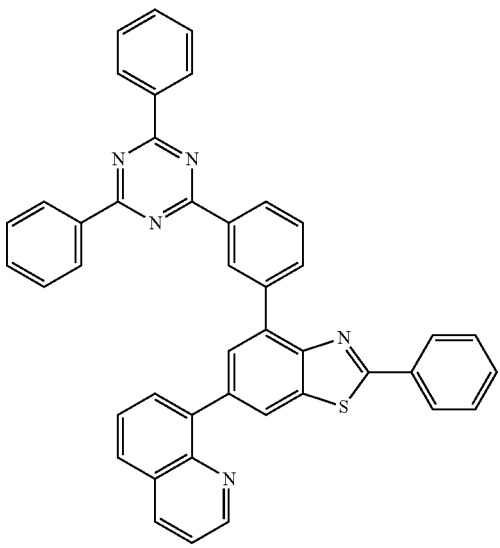

-continued
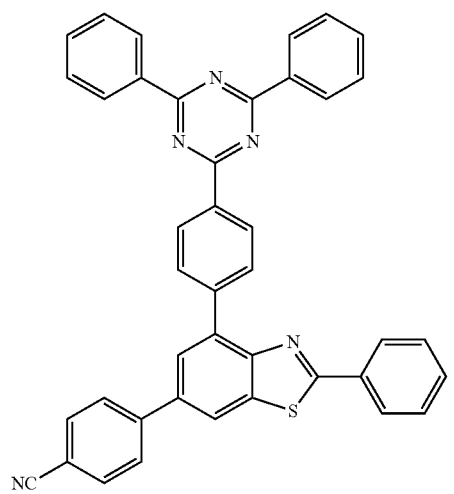
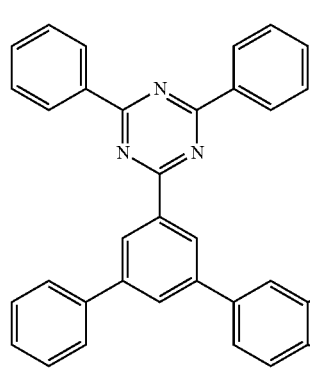
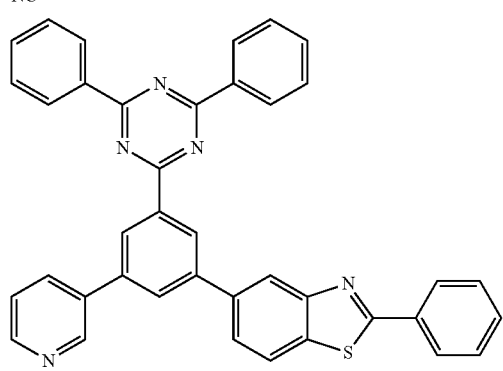
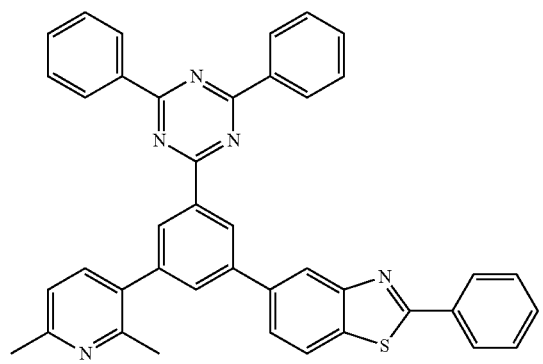
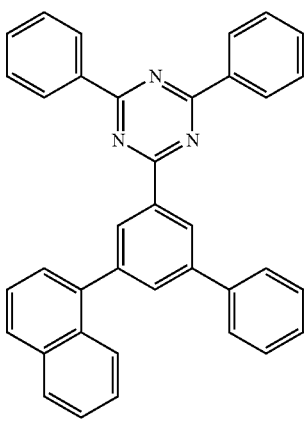
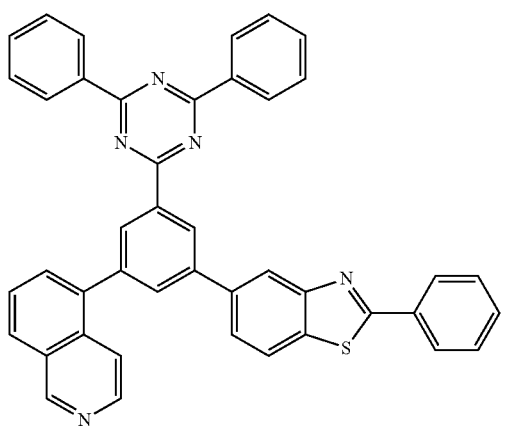

-continued
363
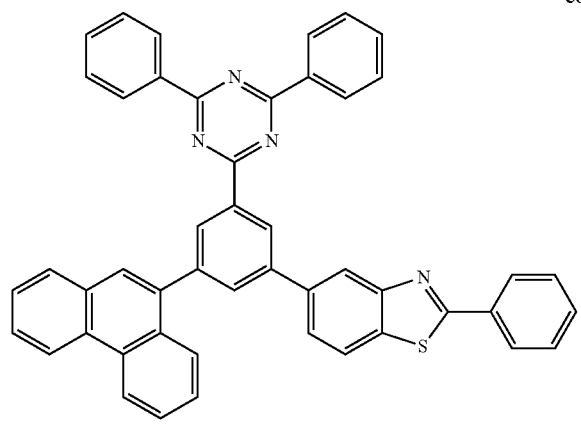
364
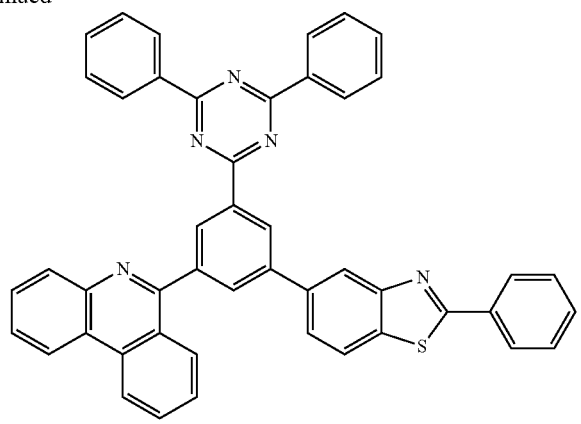
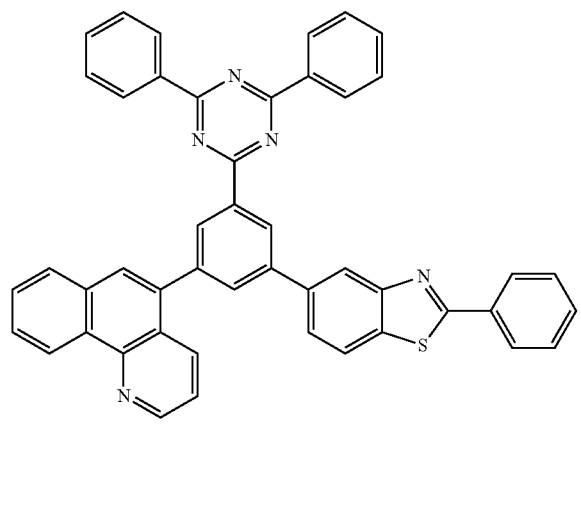
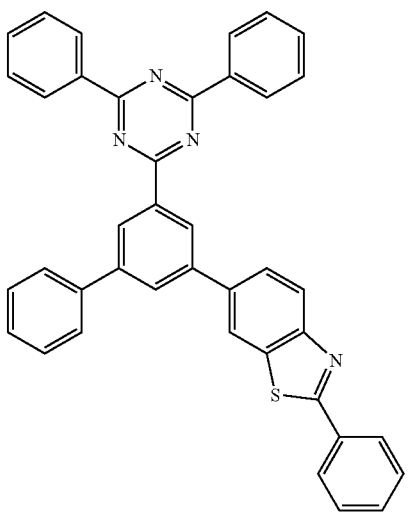
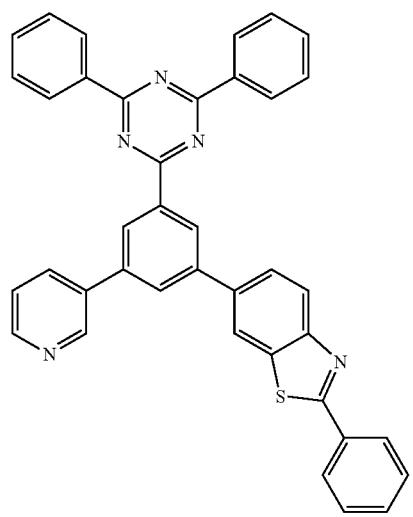
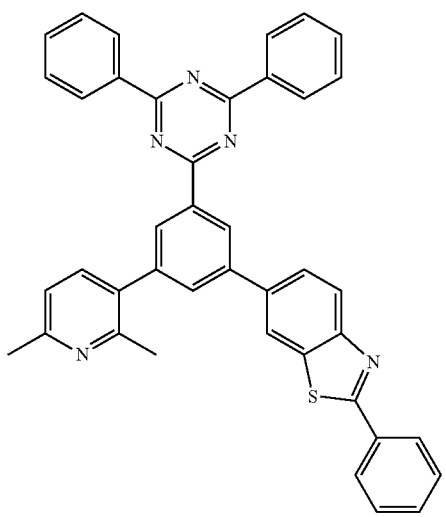

-continued
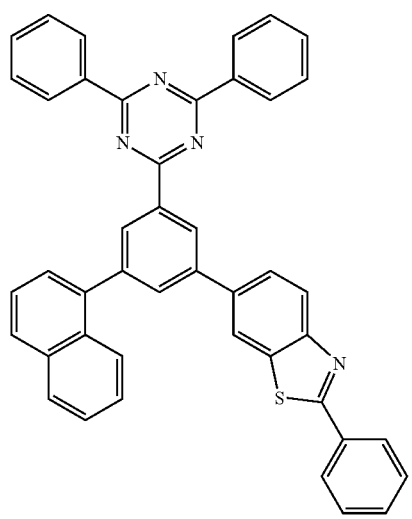
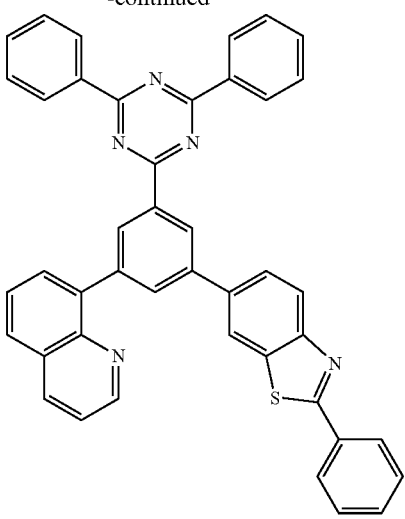
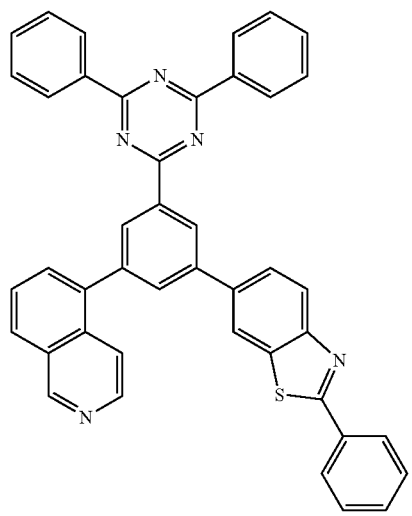
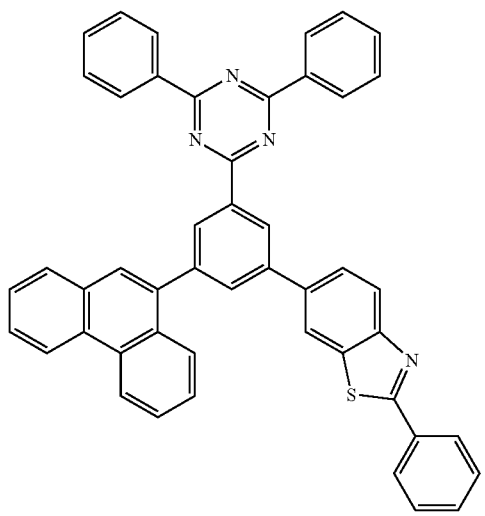
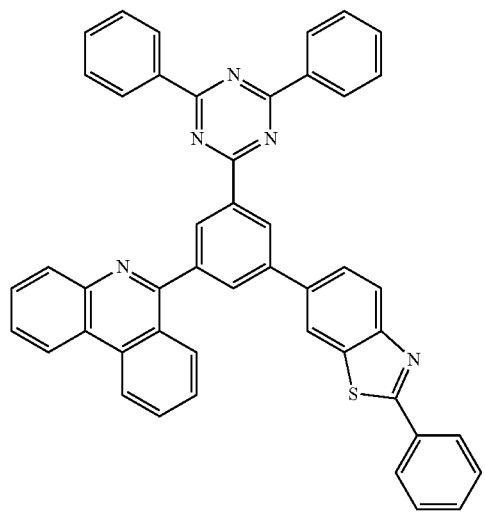
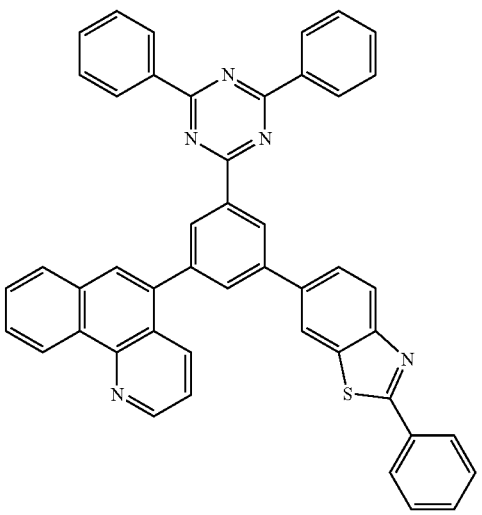

-continued
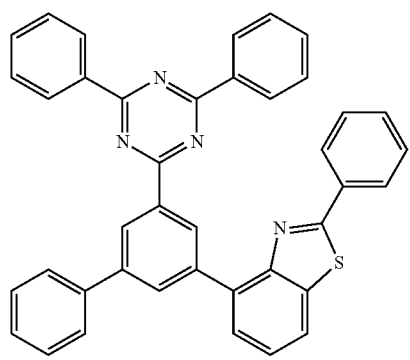
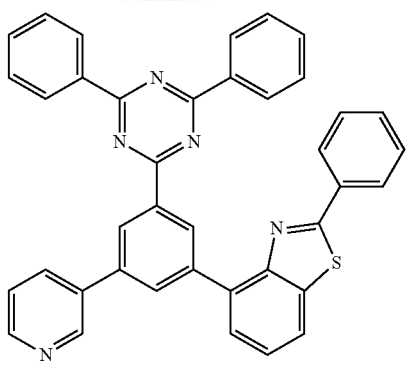
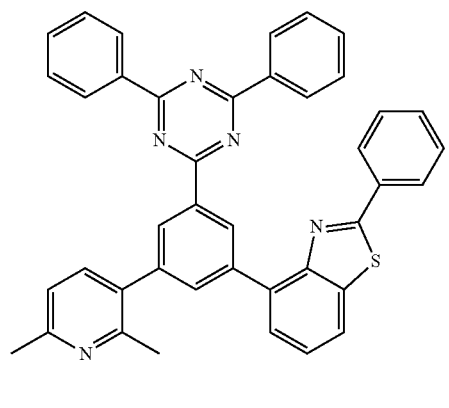
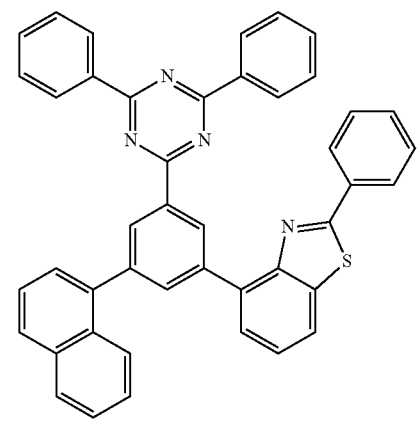
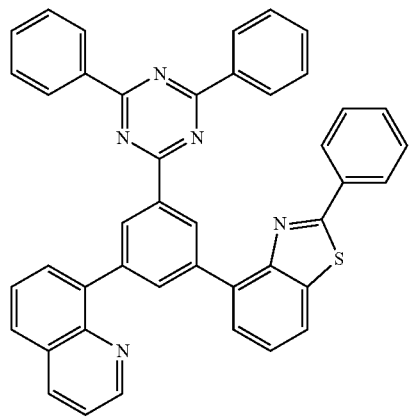
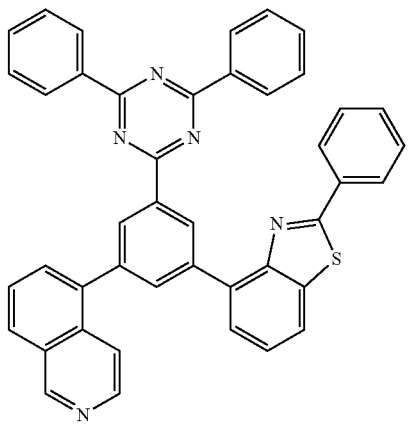
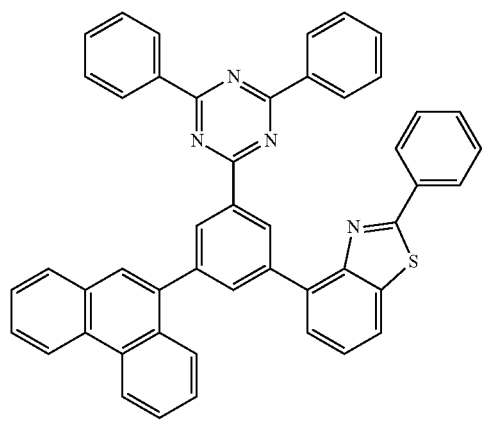
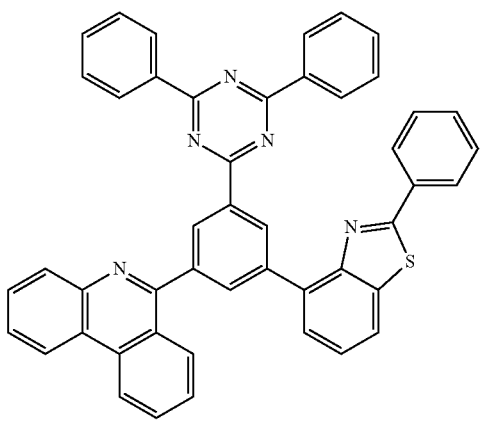

369
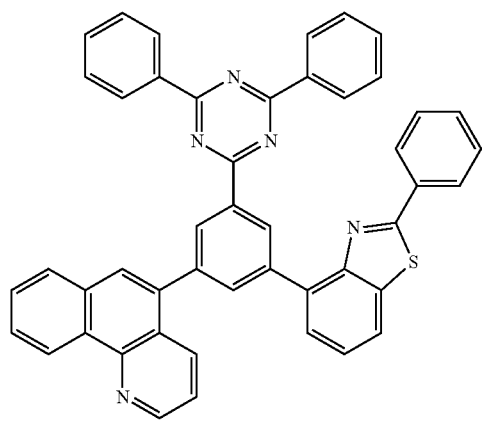
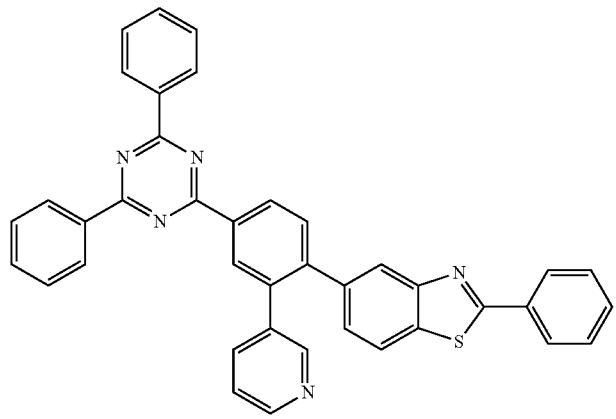
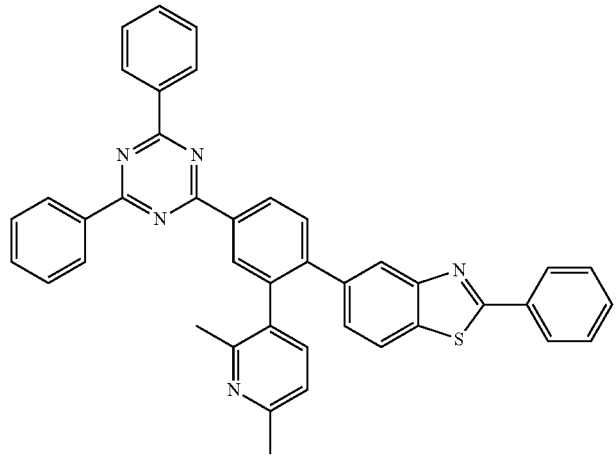
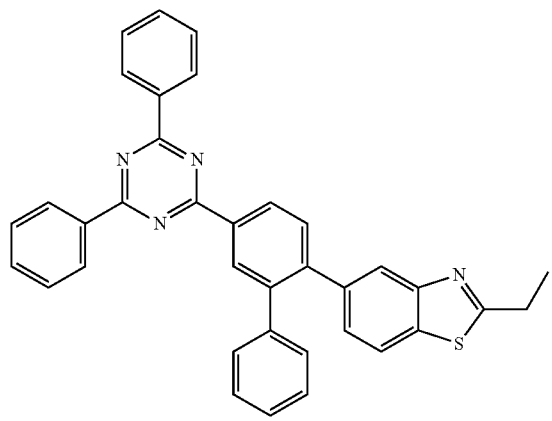
-continued
370
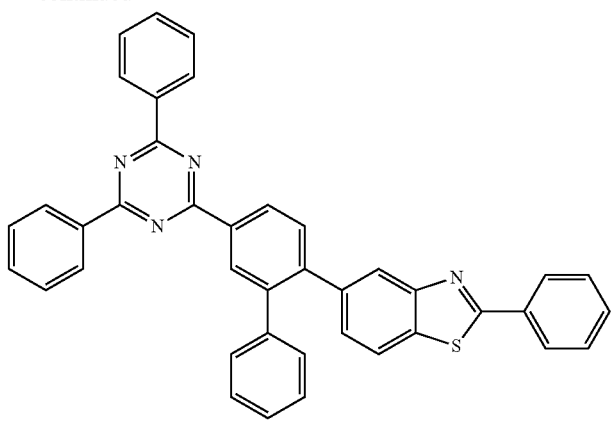
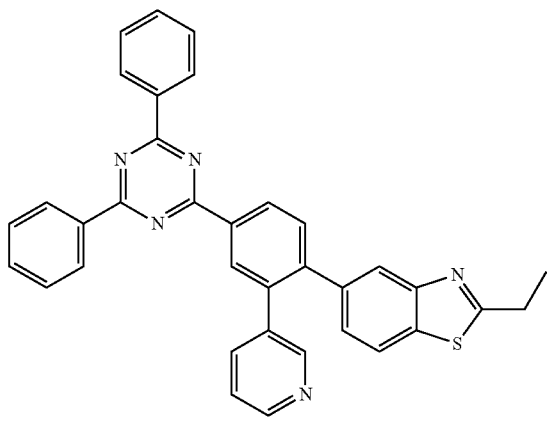

-continued
371
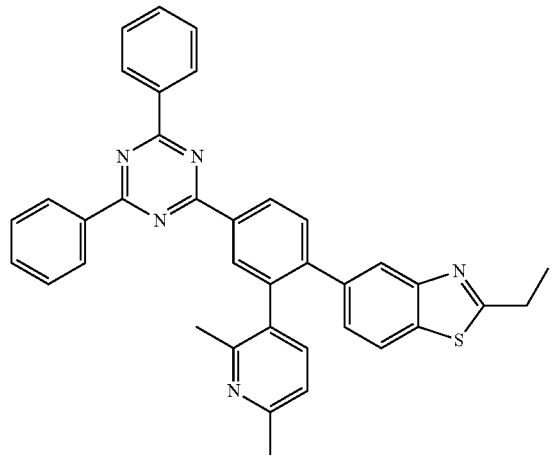
372
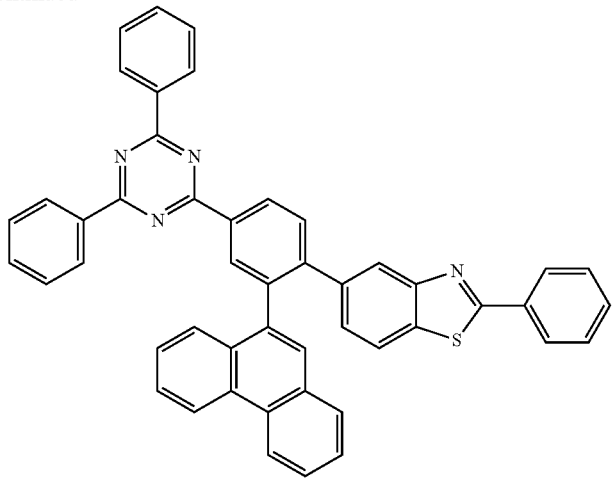
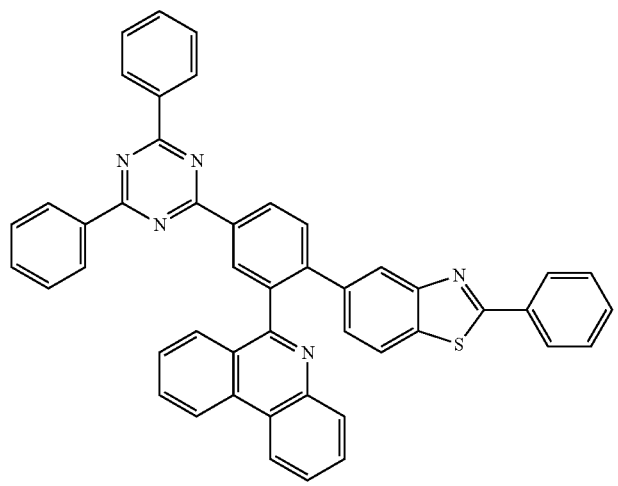
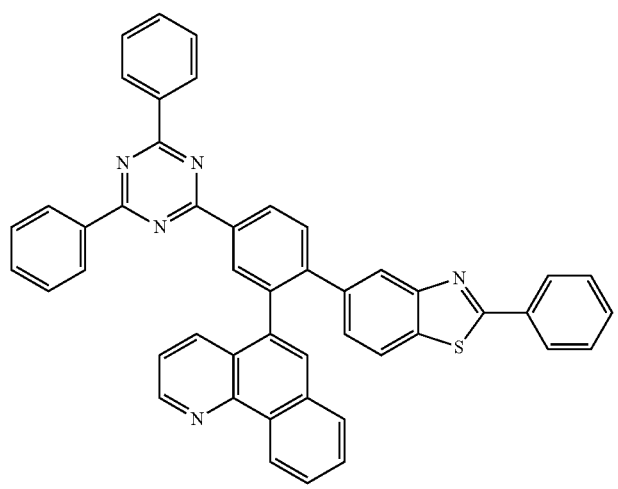

-continued
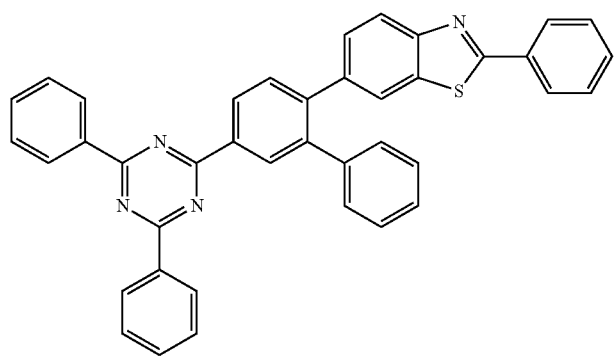
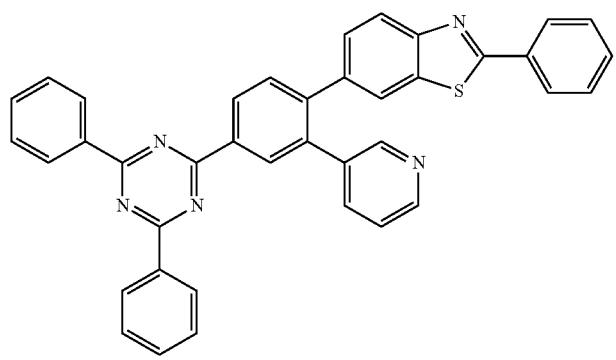
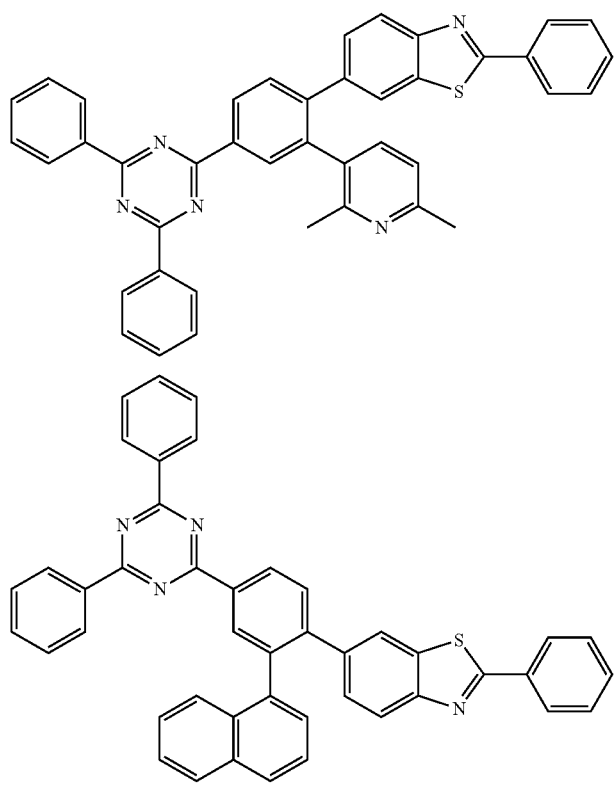

-continued
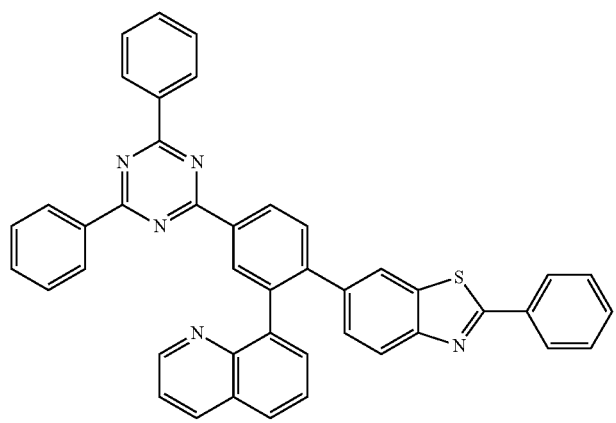
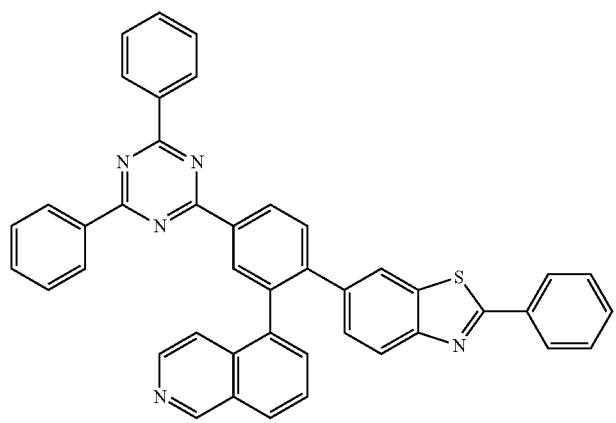
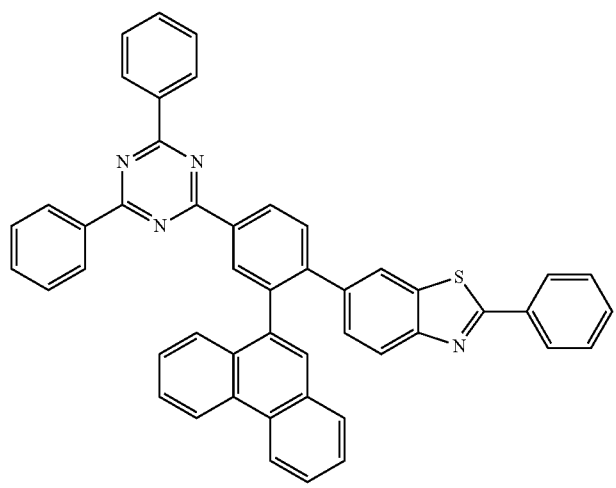

-continued
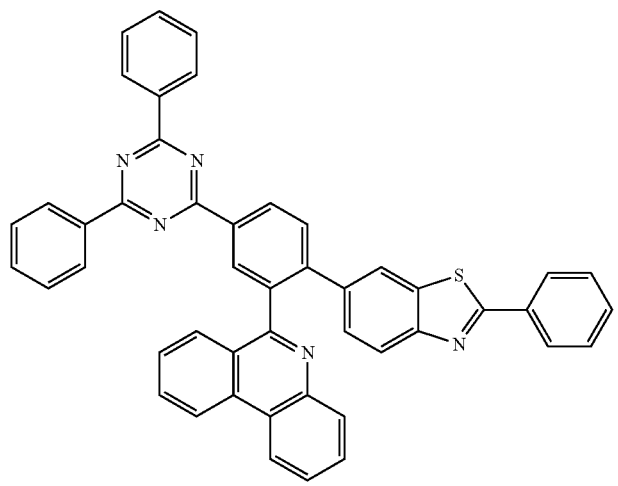
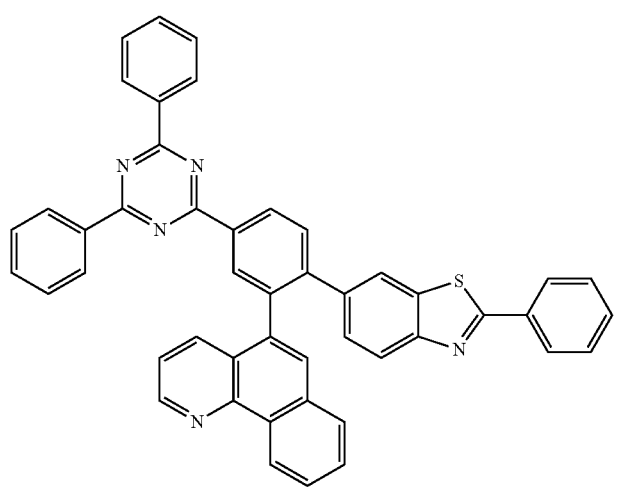
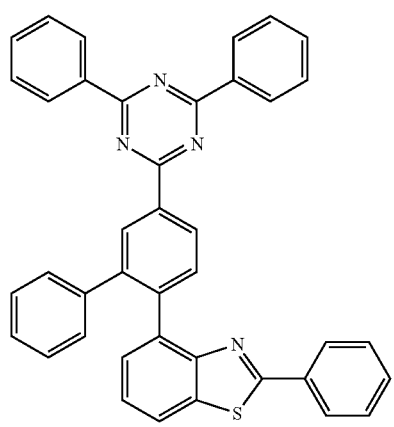 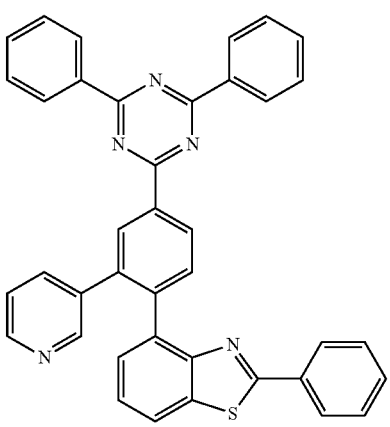

-continued
379
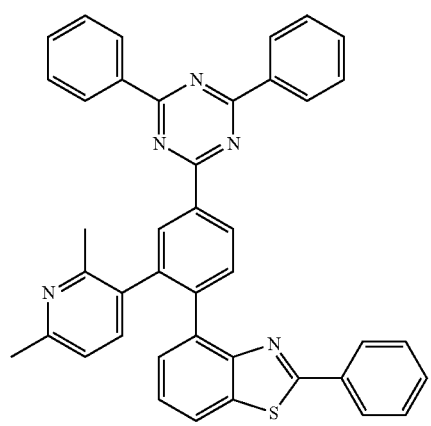
380
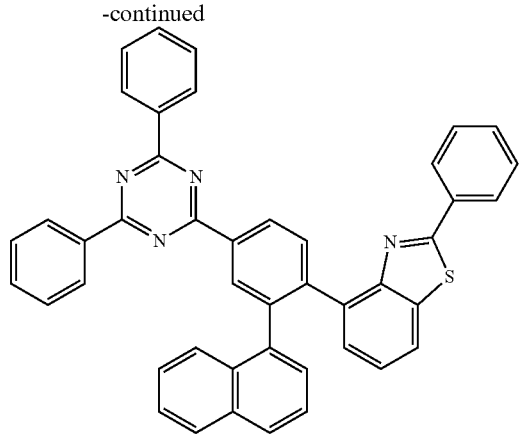
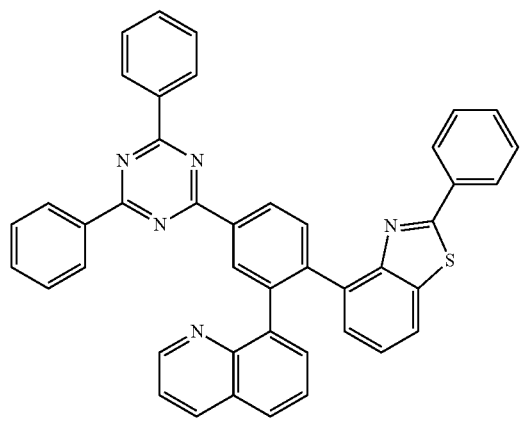
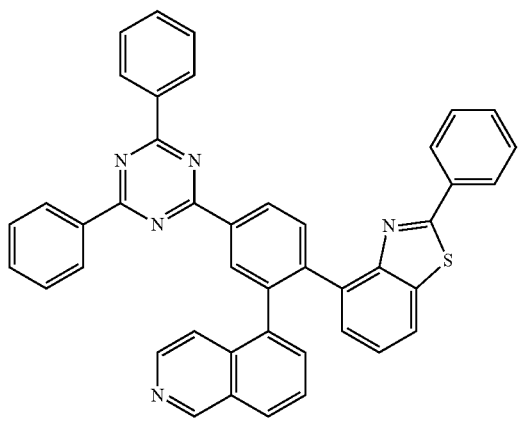
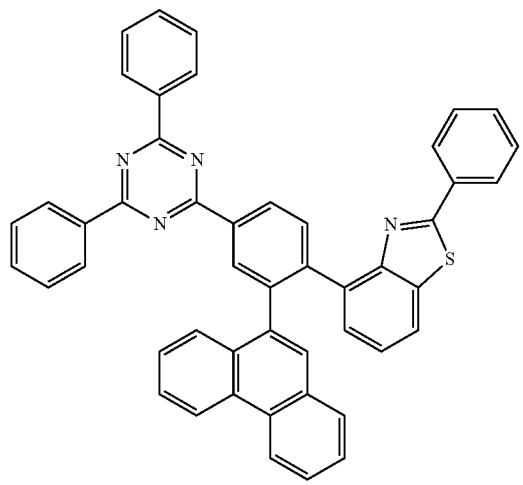
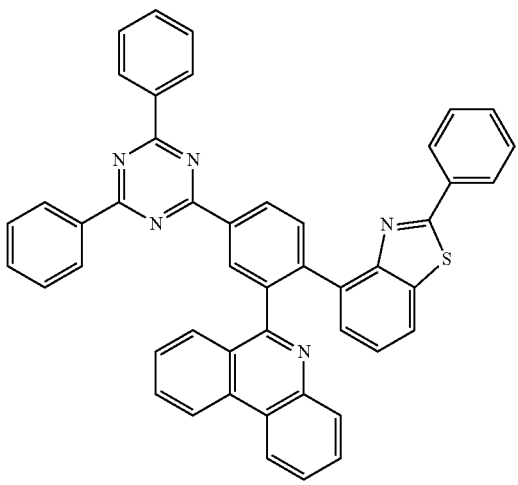

-continued
381
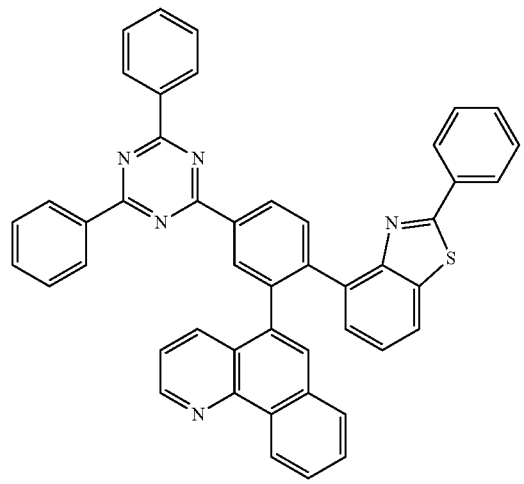
382
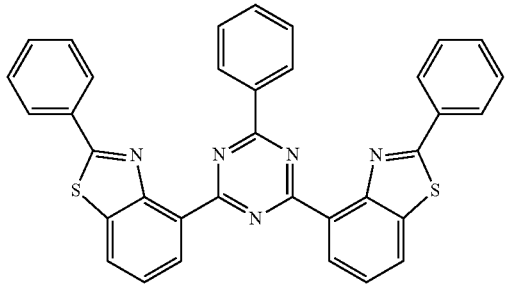
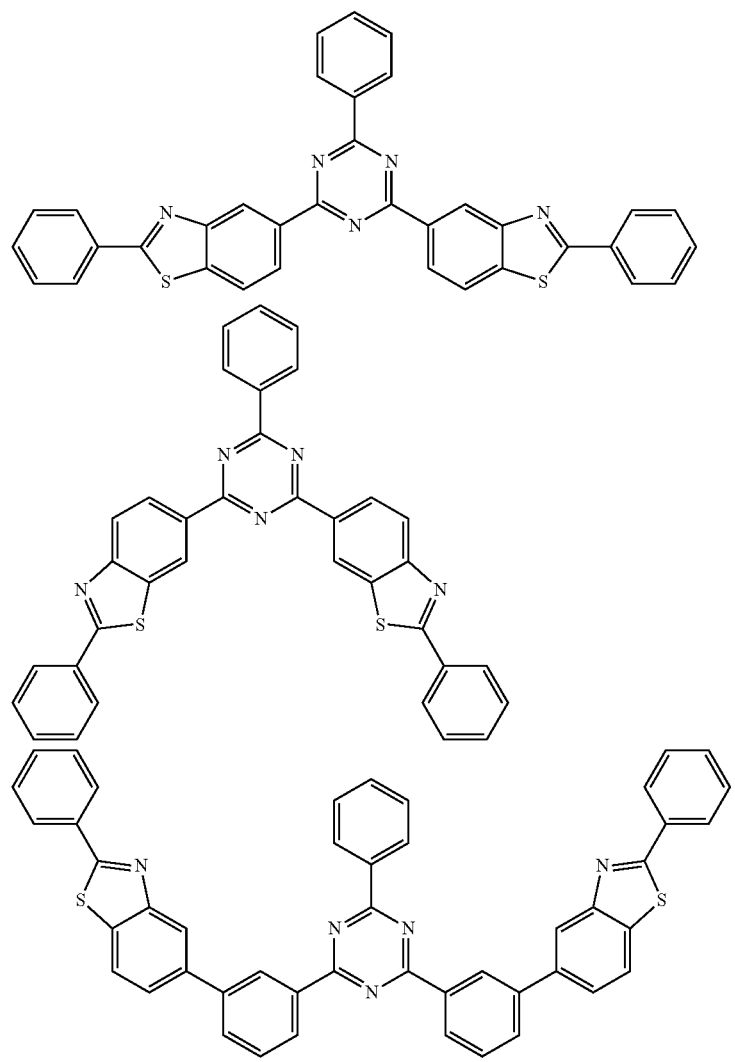

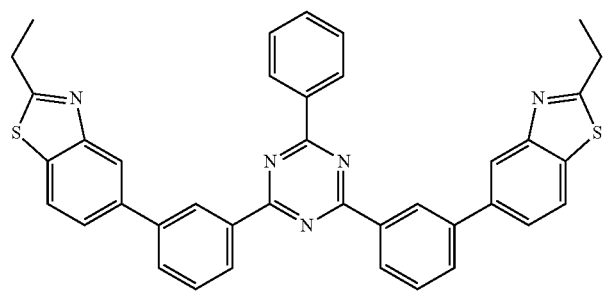
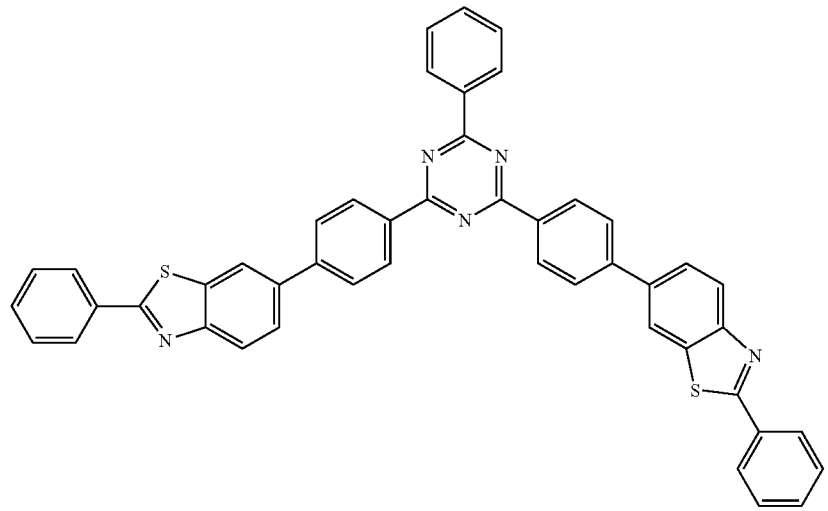
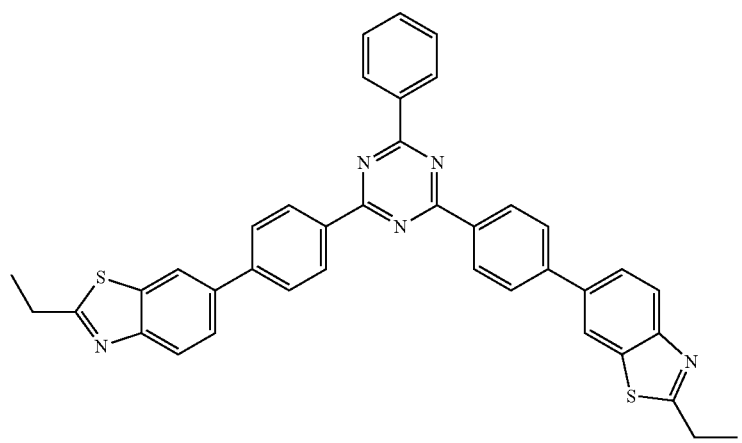
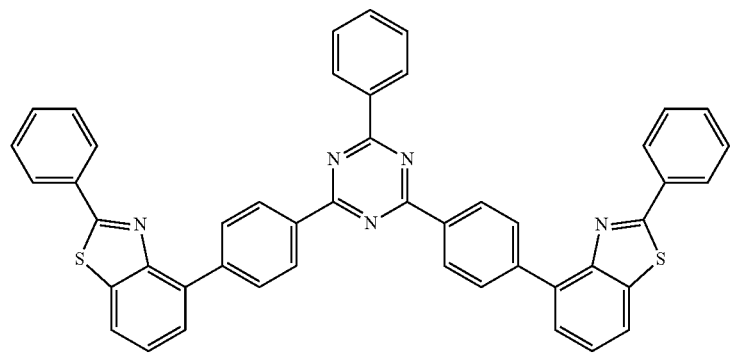

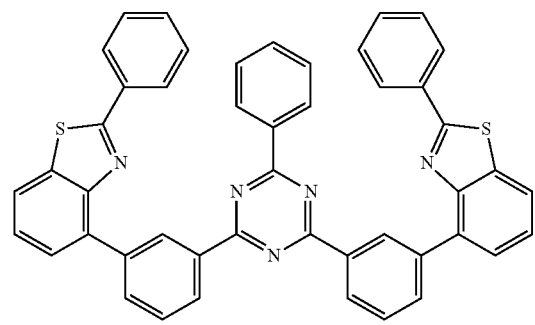
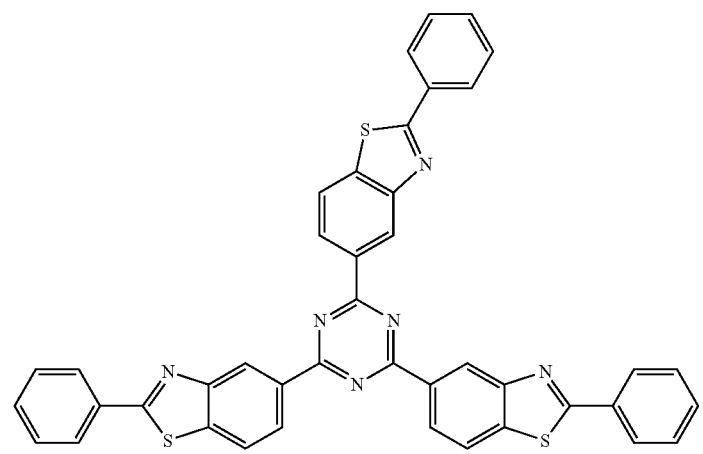
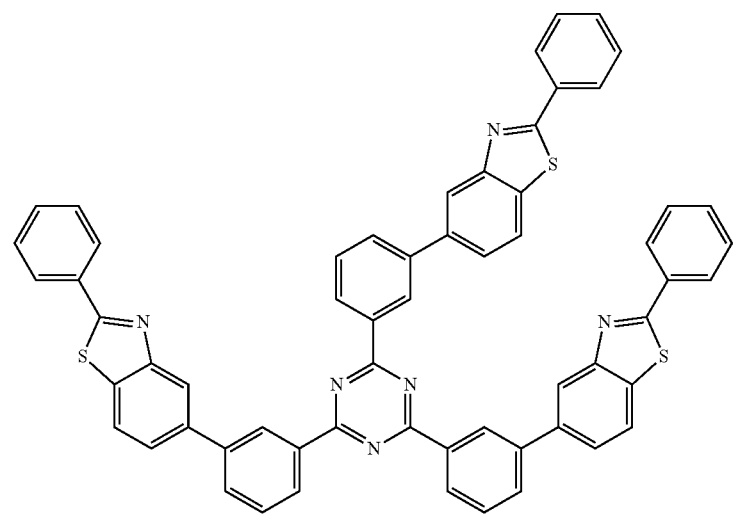

-continued

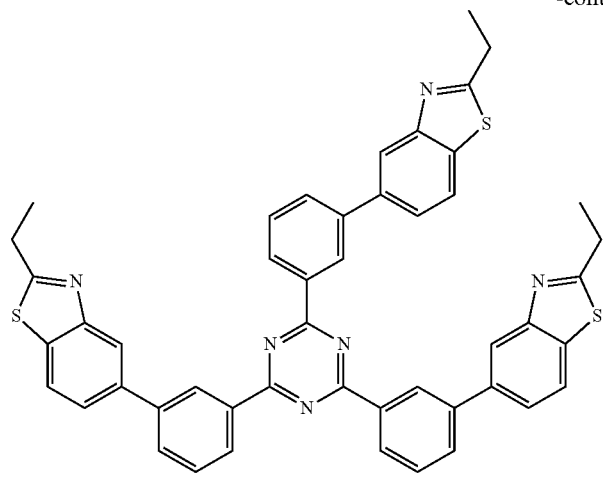

Hereinafter, results of comparative experiments showing that the benzazole derivative having the heteroaryl group contributes to the performance improvement of the organic electroluminescence device will be described. The comparative experiments were carried out by preparing organic electroluminescence devices according to Comparative Examples and organic electroluminescence devices according to Examples in the following manner.

Comparative Example 1

A hole injection layer, a hole transport layer, a light-emission layer, an electron transport layer, an electron injection layer, and a cathode were deposited onto an ITO substrate in an order of following (a) to (e), under about 10-7 torr vacuum, via evaporation from a heated boat, to form an organic electroluminescence device (ITO/HIL/HTL/EML/ETL/EIL/Cathode). Then, the device was transferred from a deposition chamber to a drying box and was subsequently encapsulated using UV cured epoxy and moisture getter.

The ITO substrate was washed with UV ozone before use and then loaded into an evaporation system. Thereafter, the ITO substrate was transferred into a vacuum deposition chamber in which following (a) to (e) were conducted to deposit the hole injection layer, the hole transport layer, the light-emission layer, the electron transport layer, the electron injection layer and the cathode on the ITO substrate in this order.

(a) Hole injection layer (thickness 100 Å): a composition of the hole injection layer material contains 97% of a compound expressed by Chemical Formula (I) and 3% of a compound expressed by Chemical Formula (II):

<Chemical Formula (I)>

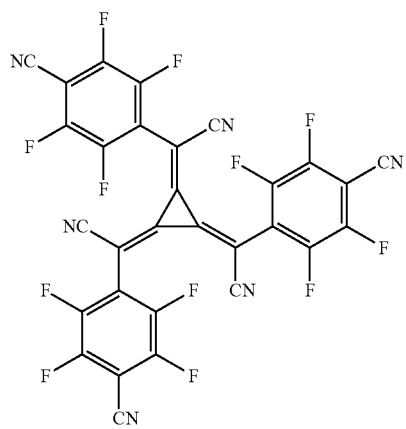

(b) Hole transport layer (thickness 1200 Å): a compound represented by Chemical Formula (II) was used as a hole transport layer material:

<Chemical Formula (II)>

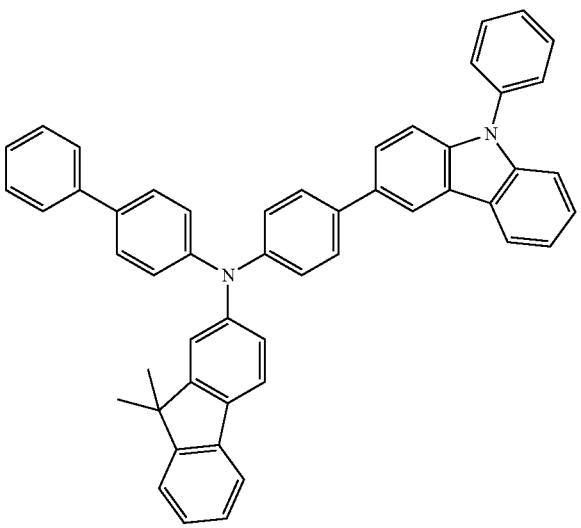

(c) Light-emission layer (thickness 400 Å): a composition of the light-emission layer material contains 85% of a host compound and 15% of a dopant compound. The host compound contains a first host represented by Chemical Formula (III-1) and a second host represented by Chemical Formula (III-2). A compound represented by Chemical Formula (IV) was used as the dopant compound. A composition ratio of the first host and second host was 1:1:

<Chemical Formula (III-1)>

<Chemical Formula (III-2)>

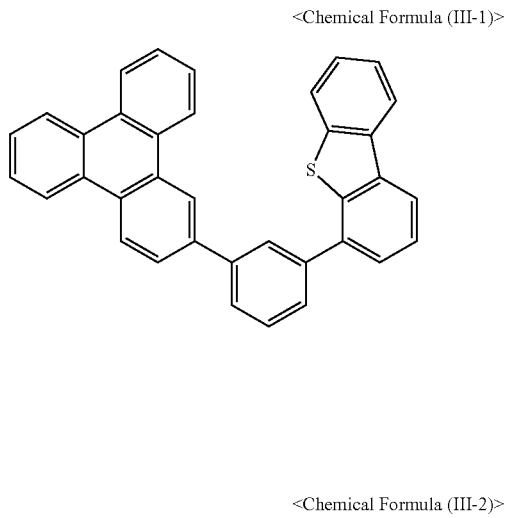

<Chemical Formula (IV)>

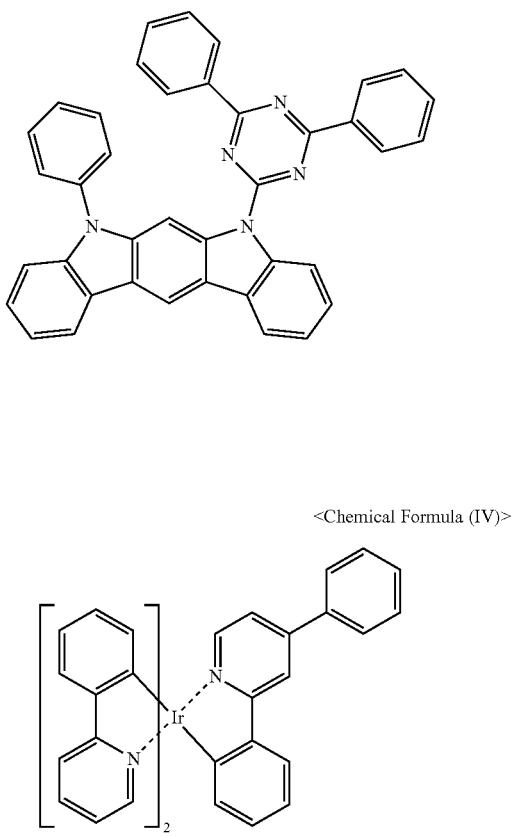

(f) Electron transport layer (thickness 300 Å): a compound represented by Chemical Formula (V) was used as the electron transport layer material:

<Chemical Formula (V)>

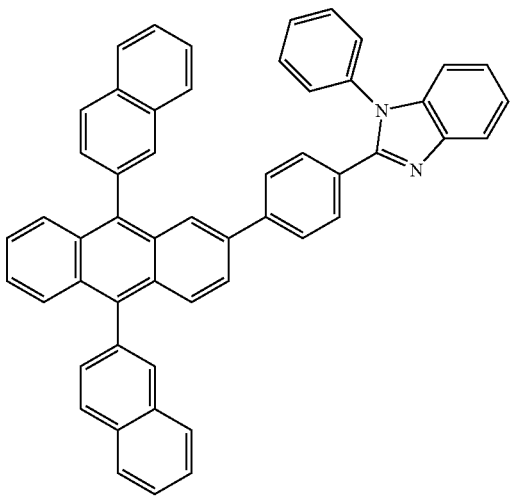

(g) Electron injection layer (thickness 10 Å): the electron injection layer material employs LiF.

(h) Cathode (thickness 500 Å): the cathode employs Al as a material thereof.

Comparative Example 2

An organic electroluminescence device was fabricated in the same manner as in Comparative Example 1 except that a compound represented by Chemical Formula (VI) instead of the compound represented by Chemical Formula (V) in Comparative Example 1 was used as the electron transport layer material to form the electron transport layer:

<Chemical Formula (VI)>

Comparative Example 3

An organic electroluminescence device was fabricated in the same manner as in Comparative Example 1 except that a compound represented by Chemical Formula (VII) instead of the compound represented by Chemical Formula (V) in Comparative Example 1 was used as the electron transport layer material to form the electron transport layer:

<Chemical Formula (VII)>

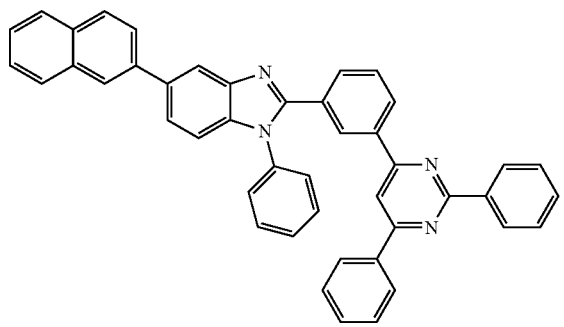

Comparative Example 4

An organic electroluminescence device was fabricated in the same manner as in Comparative Example 1 except that a compound represented by Chemical Formula (VIII) instead of the compound represented by Chemical Formula (V) in Comparative Example 1 was used as the electron transport layer material to form the electron transport layer:

<Chemical Formula (VIII)>

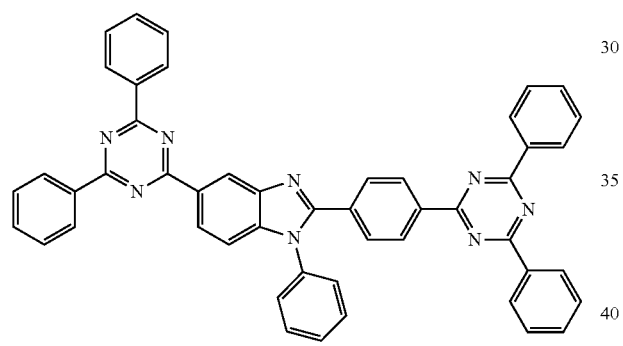

Example 1

An organic electroluminescence device was fabricated in the same manner as in Comparative Example 1 except that the compound LT18-30-129 instead of the compound represented by Chemical Formula (V) in Comparative Example 1 was used as the electron transport layer material to form the electron transport layer:

LT18-30-129

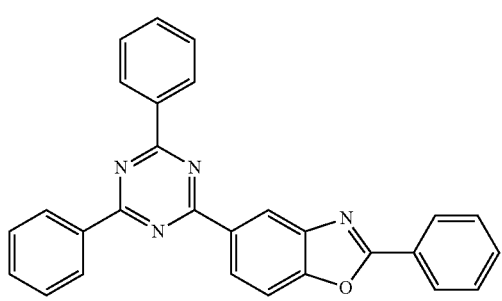

Example 2

An organic electroluminescence device was fabricated in the same manner as in Comparative Example 1 except that the compound LT18-30-033 instead of the compound represented by Chemical Formula (V) in Comparative Example 1 was used as the electron transport layer material to form the electron transport layer:

LT18-30-033

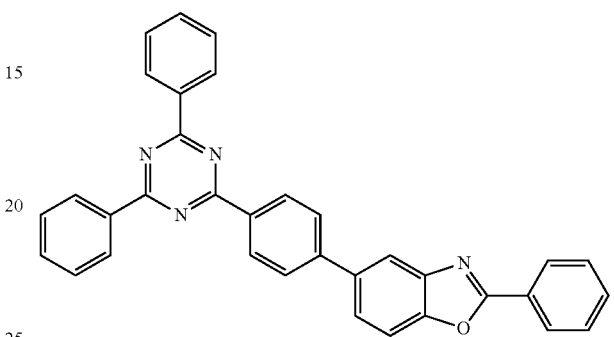

Example 3

An organic electroluminescence device was fabricated in the same manner as in Comparative Example 1 except that the compound LT18-30-022 instead of the compound represented by Chemical Formula (V) in Comparative Example 1 was used as the electron transport layer material to form the electron transport layer:

LT18-30-022

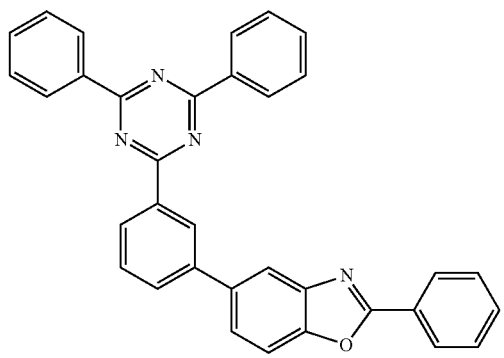

Example 4

An organic electroluminescence device was fabricated in the same manner as in Comparative Example 1 except that the compound LT18-30-141 instead of the compound represented by Chemical Formula (V) in Comparative Example 1 was used as the electron transport layer material to form the electron transport layer:

LT18-30-141

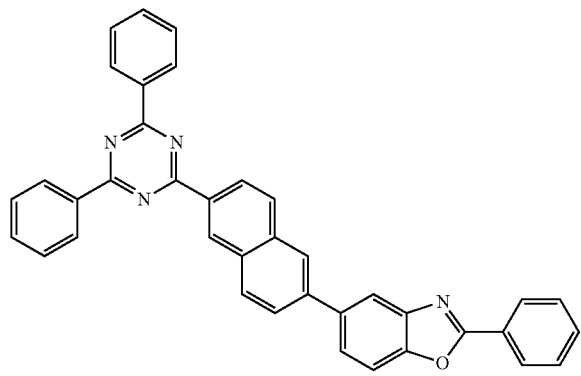

Example 5

An organic electroluminescence device was fabricated in the same manner as in Comparative Example 1 except that the compound LT18-30-201 instead of the compound represented by Chemical Formula (V) in Comparative Example 1 was used as the electron transport layer material to form the electron transport layer:

LT18-30-201

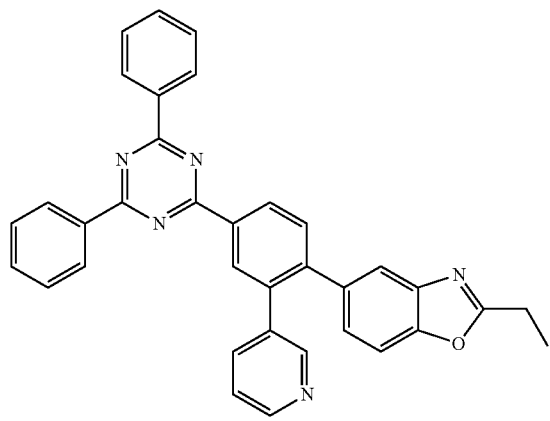

Example 6

An organic electroluminescence device was fabricated in the same manner as in Comparative Example 1 except that the compound LT18-30-065 instead of the compound represented by Chemical Formula (V) in Comparative Example 1 was used as the electron transport layer material to form the electron transport layer:

LT18-30-065

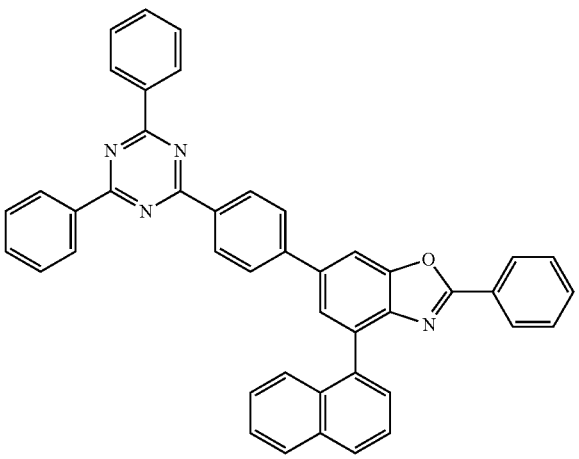

Example 7

An organic electroluminescence device was fabricated in the same manner as in Comparative Example 1 except that the compound LT18-30-023 instead of the compound represented by Chemical Formula (V) in Comparative Example 1 was used as the electron transport layer material to form the electron transport layer:

LT18-30-023

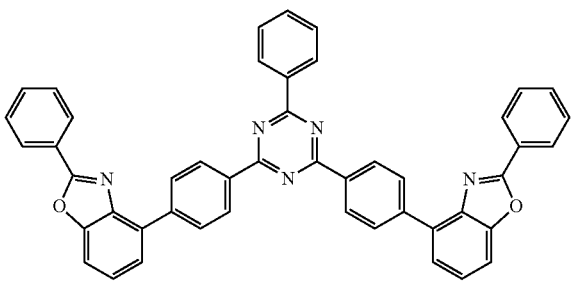

Example 8

An organic electroluminescence device was fabricated in the same manner as in Comparative Example 1 except that the compound LT18-30-054 instead of the compound represented by Chemical Formula (V) in Comparative Example 1 was used as the electron transport layer material to form the electron transport layer:

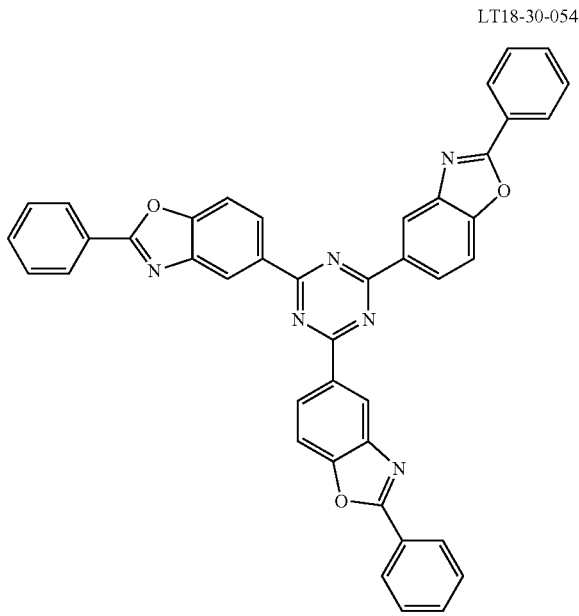 [SMILES: c1ccc(-c2nc3cc(-c4nc(-c5ccc6oc(-c7ccccc7)nc6c5)nc(-c5ccc6oc(-c7ccccc7)nc6c5)n4)ccc3o2)cc1]

FIG. 1 to FIG. 4 show comparison experiment results between organic electroluminescence devices according to the Examples and organic electroluminescence devices according to the Comparative Examples.

FIG. 1 is a graph showing a relationship between current density and driving voltage. FIG. 1 shows that the organic electroluminescence devices according to the Examples are driven at lower driving voltages than those of the organic electroluminescence devices according to the Comparative Examples, at the same current density.

In one example, the organic electroluminescence devices according to the Examples were driven at driving voltages of 4.0 V or lower at the same current density of 50 mA/cm2. In contrast, the organic electroluminescent devices according to the Comparative Examples were driven at driving voltages higher than 4.0 V at the current density of 50 mA/cm2.

Figure 2:
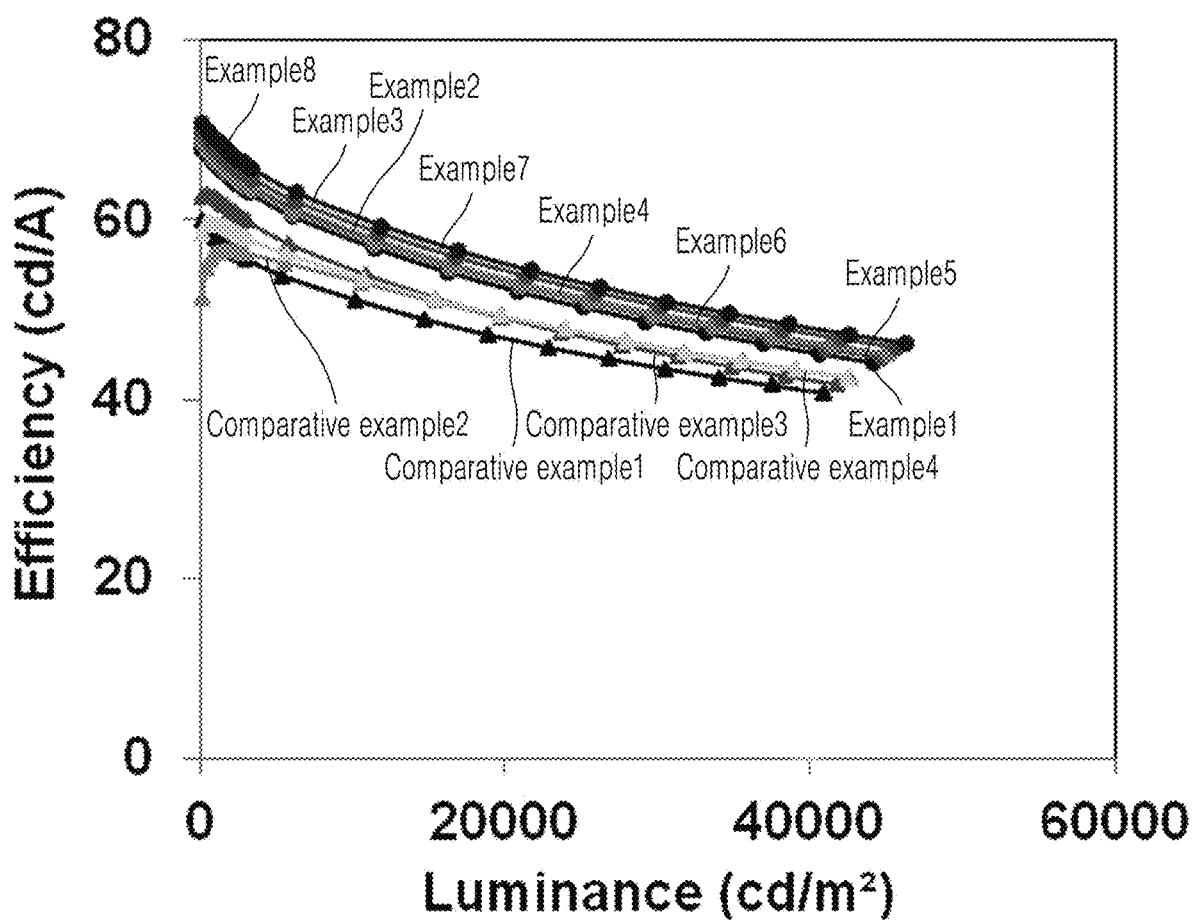

FIG. 2 is a graph showing a relationship between luminance and light-emission efficiency. FIG. 2 shows that the organic electroluminescence devices according to the Examples exhibit relatively higher light-emission efficiencies than those of the organic electroluminescence devices according to the Comparative Examples, at the same luminance.

In one example, the organic electroluminescence devices according to Examples have light-emission efficiencies higher than 50 cd/A at the same luminance of 20000 cd/m2. In contrast, the organic electroluminescence devices according to the Comparative Examples have light-emission efficiencies lower than 50 cd/A at the same luminance of 20000 cd/m2.

Figure 3:
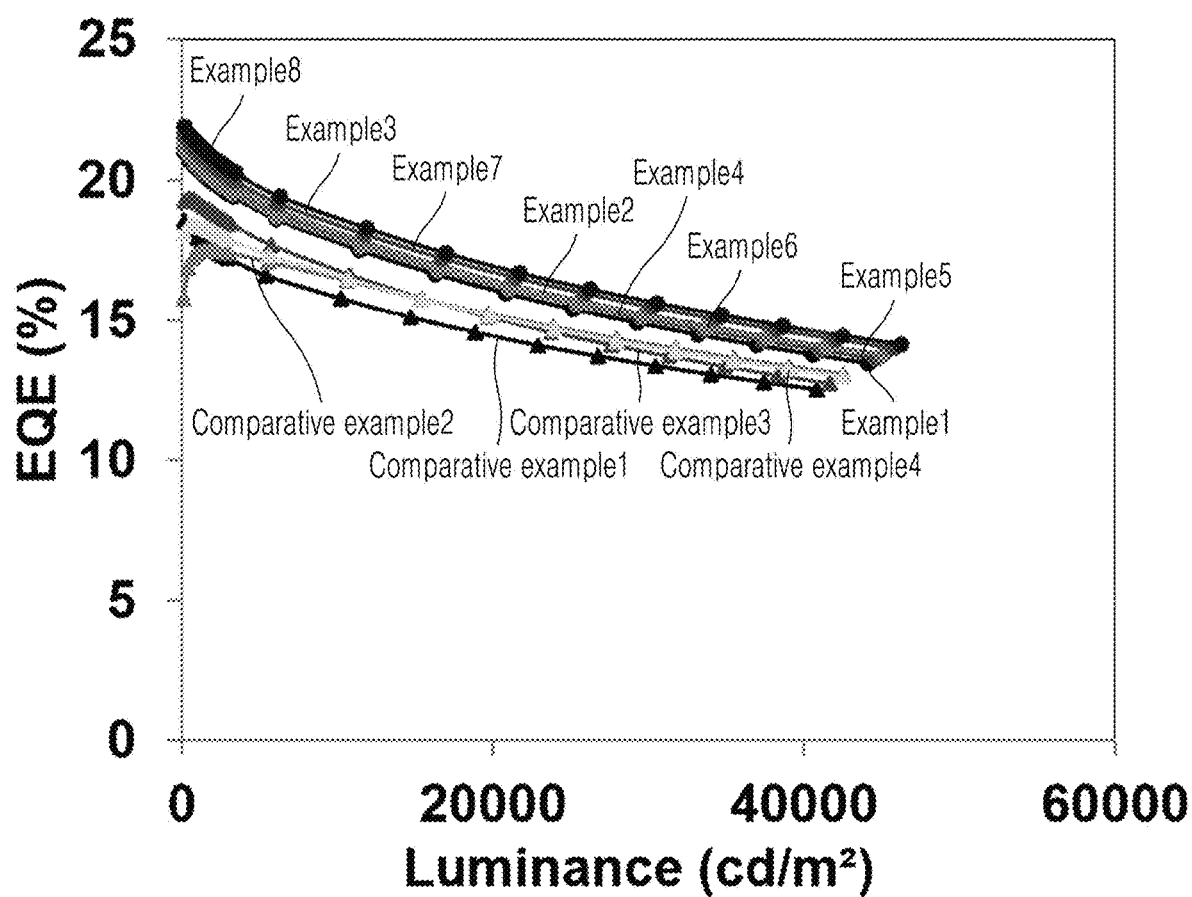

FIG. 3 is a graph showing a relationship between luminance and external quantum efficiency. FIG. 3 shows that the organic electroluminescence devices according to the Examples exhibit relatively higher external quantum efficiencies than those of the organic electroluminescence devices according to the Comparative Examples, at the same luminance.

In one example, the organic electroluminescence devices according to the Examples have external quantum efficiencies (EQEs) higher than 15% at the same luminance of 20000 cd/m2. In contrast, the organic electroluminescence devices according to Comparative Examples have external quantum efficiencies (EQEs) lower than 15% at the same luminance of 20000 cd/m2.

Figure 4:
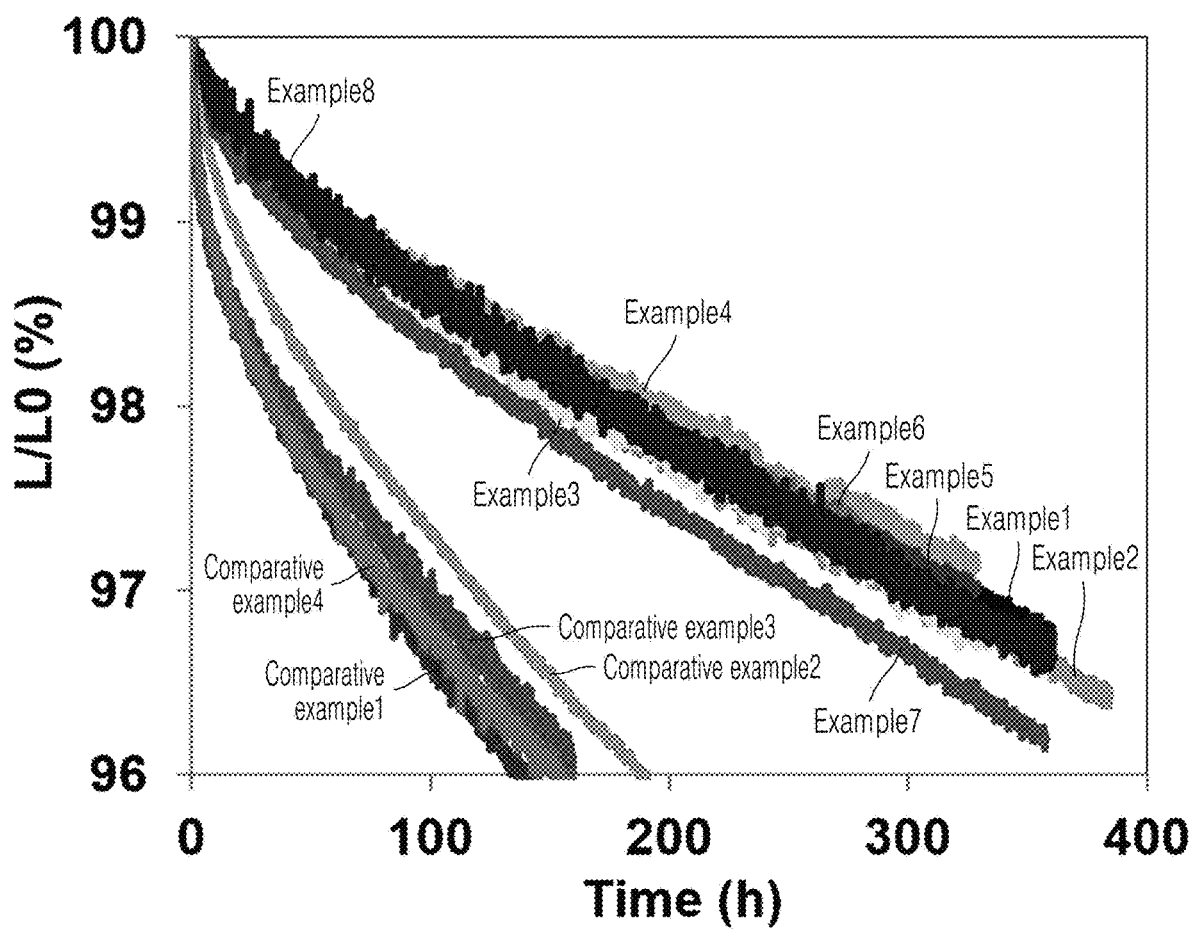

FIG. 4 is a graph of a relationship between driving duration and a ratio L/L0. The L/L0 refers to a ratio of current luminance (L) to initial luminance (L0). FIG. 4 shows that the organic electroluminescence devices according to the Examples have increased the time duration required to experience the luminance reduction compared to the organic electroluminescence devices according to the Comparative Examples. In other words, FIG. 4 shows that the organic electroluminescence devices according to the Examples have improved life-spans compared to those of the organic electroluminescence devices according to the Comparative Examples.

In one example, referring to FIG. 4, in terms of the driving duration to a time when the L/L0 value reaches 98%, the driving duration of the organic electroluminescence devices according to the Examples increased compared to the driving duration of the organic electroluminescence devices according to the Comparative Examples. Specifically, in terms of the driving duration to a time when the L/L0 value reaches 98%, the driving durations of the organic electroluminescence devices according to the Examples exceed 100 hours, whereas the driving durations of the organic electroluminescence devices according to the Comparative Examples are smaller than 100 hours.

As described above with reference to FIG. 1 to FIG. 4, it may be seen that the benzazole derivative having the heteroaryl group according to the present disclosure may improve the performance of the organic electroluminescence device.

Specifically, the organic electroluminescence devices according to the Examples of the present disclosure could be driven at lower driving voltages than those of the organic electroluminescence devices according to the Comparative Examples. Further, the organic electroluminescence devices according to the Examples of the present disclosure have higher light-emission efficiencies, and higher external quantum efficiencies, and longer life-spans compared to the organic electroluminescence devices according to the Comparative Examples.

Although the implementations have been described with reference to the accompanying drawings, the present disclosure is not limited to the implementations, but may be embodied in various forms in combination with contents disclosed in the respective implementations. Those of ordinary skill in the art to which the present disclosure pertains may understand that the present disclosure may be embodied in other specific forms without departing from the spirit or essential characteristics of the present disclosure. It is therefore to be understood that the implementations as described above are intended to be illustrative in all respects and not restrictive.

What is claimed is:
1. An organic electroluminescence device comprising an organic layer,
   wherein the organic layer comprises a light-emission layer and an electron transport layer,
   wherein the electron transport layer comprises a benzazole derivative having a heteroaryl group, and
   wherein the benzazole derivative is a compound selected from one of the compounds represented by one of the following structural formulas:

397
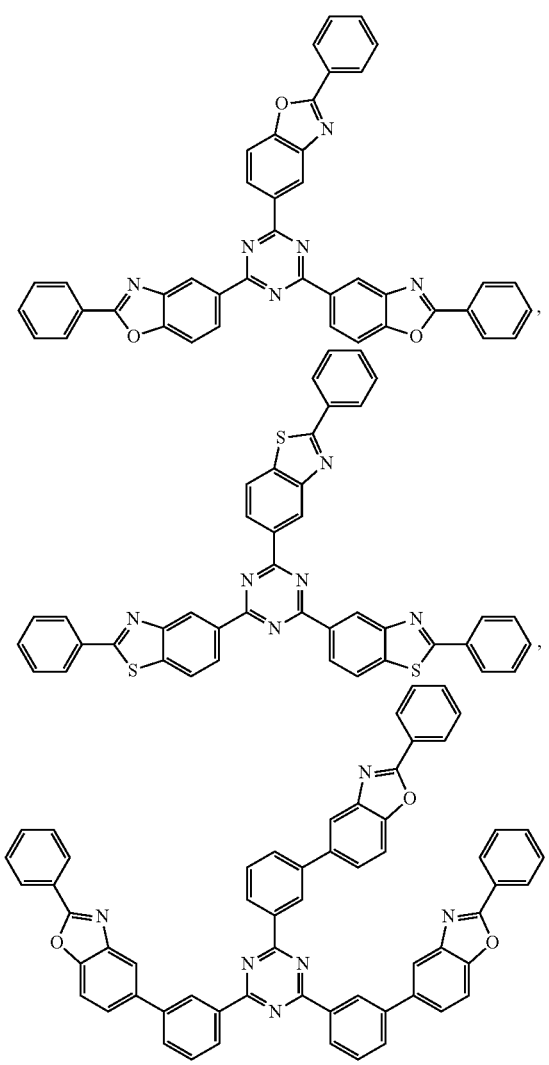
398
-continued
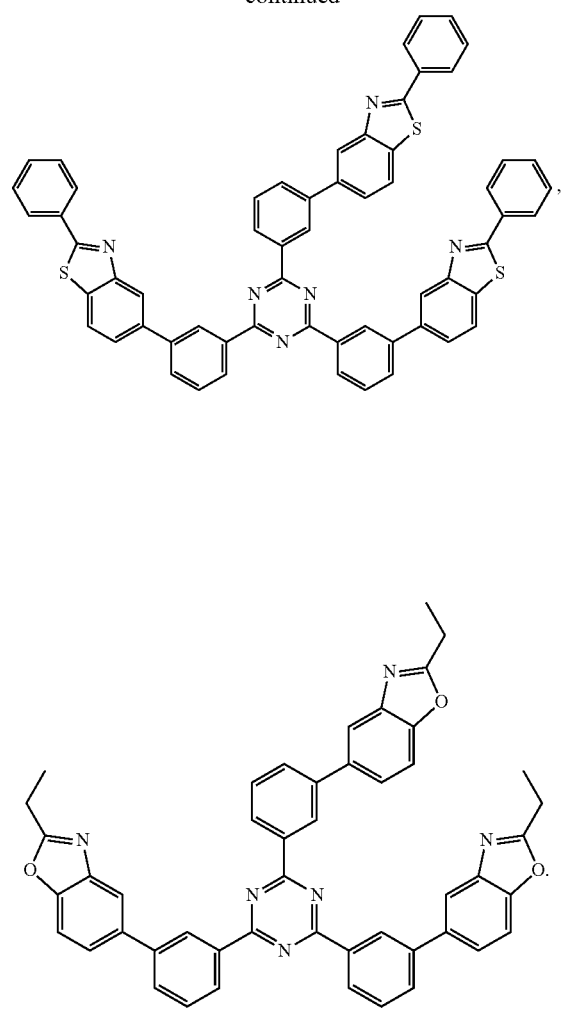
* * * * *